(12) United States Patent
Yoshioka et al.

(10) Patent No.: US 12,250,881 B2
(45) Date of Patent: Mar. 11, 2025

(54) PHOTOELECTRIC CONVERSION ELEMENT, IMAGING ELEMENT, OPTICAL SENSOR, AND COMPOUND

(71) Applicant: FUJIFILM Corporation, Tokyo (JP)

(72) Inventors: Tomoaki Yoshioka, Kanagawa (JP); Tomoyuki Mashiko, Kanagawa (JP); Koichi Iwasaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 843 days.

(21) Appl. No.: 17/145,412

(22) Filed: Jan. 11, 2021

(65) Prior Publication Data

US 2021/0135128 A1 May 6, 2021

Related U.S. Application Data

(63) Continuation of application No. PCT/JP2019/027383, filed on Jul. 10, 2019.

(30) Foreign Application Priority Data

Jul. 13, 2018 (JP) .................................. 2018-133583
Nov. 20, 2018 (JP) .................................. 2018-217630

(51) Int. Cl.
  *H10K 85/60* (2023.01)
  *H10K 30/80* (2023.01)
  *H10K 85/20* (2023.01)

(52) U.S. Cl.
  CPC ......... *H10K 85/6572* (2023.02); *H10K 30/80* (2023.02); *H10K 85/211* (2023.02)

(58) Field of Classification Search
  CPC .... H10K 39/32; H10K 10/464; H10K 10/466; H10K 30/80; H10K 85/211; H10K 85/6572
  See application file for complete search history.

(56) References Cited

U.S. PATENT DOCUMENTS 3,431,111 A * 3/1969 Lare ..................... C07D 209/60
                                                         430/587
8,222,519 B2   7/2012 Nomura et al.
(Continued)

FOREIGN PATENT DOCUMENTS

| JP | 2009167348 | 7/2009 |
| JP | 2011253861 | 12/2011 |
| WO | 2005043630 | 5/2005 |

OTHER PUBLICATIONS

Kulinich, Fluorescent Properties of Merocyanines Based on 1,3-Indandione, Optics and Spectroscopy, 2015, vol. 119, No. 1, pp. 39-48 (Year: 2015).*

(Continued)

*Primary Examiner* — Devina Pillay
(74) *Attorney, Agent, or Firm* — JCIPRNET

(57) ABSTRACT

The present invention is to provide a photoelectric conversion element having excellent heat resistance. In addition, an imaging element and an optical sensor which include the photoelectric conversion element are provided. Furthermore, a compound applied to the photoelectric conversion element is provided. A photoelectric conversion element according to the present invention includes a conductive film, a photoelectric conversion film, and a transparent (Continued)

conductive film, in this order, in which the photoelectric conversion film contains a compound represented by Formula (1).

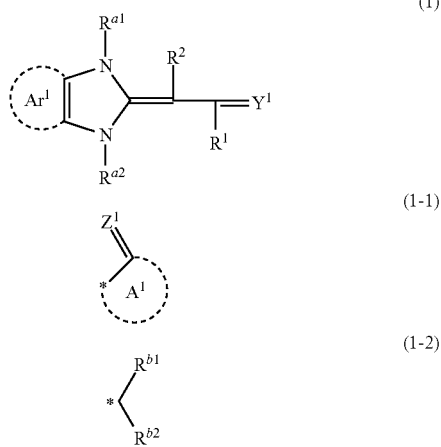

In Formula (1), $Y^1$ represents a group represented by Formula (1-1) or a group represented by Formula (1-2).

12 Claims, 36 Drawing Sheets

(56) References Cited

U.S. PATENT DOCUMENTS

| | | | |
|---|---|---|---|
| 2007/0120111 A1* | 5/2007 | Nakamura | H10K 85/621 257/40 |
| 2009/0050881 A1* | 2/2009 | Hayashi | H10K 30/30 257/E51.001 |
| 2009/0223566 A1 | 9/2009 | Mitsui et al. | |
| 2012/0235015 A1* | 9/2012 | Nomura | C09B 23/105 257/E51.026 |
| 2013/0087682 A1 | 4/2013 | Nomura | |
| 2014/0239284 A1* | 8/2014 | Yoshimura | C08K 3/04 526/240 |
| 2017/0352811 A1 | 12/2017 | Choi et al. | |

OTHER PUBLICATIONS

Office Action of Korea Counterpart Application, with English translation thereof, issued on Jul. 5, 2022, pp. 1-8.
"Office Action of Japan Counterpart Application", issued on Dec. 7, 2021, with English translation thereof, pp. 1-6.
Office Action of Taiwan Counterpart Application, with English translation thereof, issued on Dec. 22, 2022, pp. 1-9.
Andrii V. Kulinich et al., "Merocyanines based on 1,3-indanedione: electronic structure and solvatochromism", Journal of Physical Organic Chemistry, Dec. 13, 2010, pp. 732-742.
"International Search Report (Form PCT/ISA/210) of PCT/JP2019/027383," mailed on Oct. 8, 2019, with English translation thereof, pp. 1-5.
"Written Opinion of the International Searching Authority (Form PCT/ISA/237) of PCT/JP2019/027383," mailed on Oct. 8, 2019, with English translation thereof, pp. 1-9.
A. V. Kulinich et al., "Fluorescent Properties of Merocyanines Based on 1,3-Indandione", Optics and Spectroscopy, Jul. 2015, pp. 39-48.
"Search Report of Europe Counterpart Application", issued on Jul. 23, 2021, pp. 1-8.
"Office Action of China Counterpart Application", issued on Feb. 29, 2024, with English translation thereof, p. 1-p.17.
Search Report of Europe Counterpart Application, issued on Feb. 20, 2024, pp. 1-8.
"Office Action of China Counterpart Application", issued on Sep. 14, 2024, with English translation thereof, p. 1-p. 11.
"Office Action of China Counterpart Application", issued on Nov. 30, 2024, with English translation thereof, p. 1-p. 10.

* cited by examiner

PHOTOELECTRIC CONVERSION ELEMENT, IMAGING ELEMENT, OPTICAL SENSOR, AND COMPOUND

CROSS-REFERENCE TO RELATED APPLICATIONS

This application is a Continuation of PCT International Application No. PCT/JP2019/027383 filed on Jul. 10, 2019, which claims priority under 35 U.S.C. § 119(a) to Japanese Patent Application No. 2018-133583 filed on Jul. 13, 2018 and Japanese Patent Application No. 2018-217630 filed on Nov. 20, 2018. Each of the above applications is hereby expressly incorporated by reference, in its entirety, into the present application.

BACKGROUND OF THE INVENTION

1. Field of the Invention

The present invention relates to a photoelectric conversion element, an imaging element, an optical sensor, and a compound.

2. Description of the Related Art

In recent years, development of an element having a photoelectric conversion film has progressed.

For example, it is disclosed in JP2009-167348A that a compound represented by the following formula is used as a material applied to a photoelectric conversion element (claim 1).

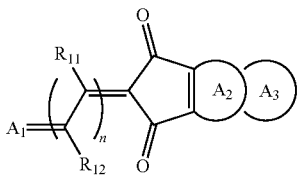

SUMMARY OF THE INVENTION

In recent years, along with the demand for improving the performance of an imaging element, an optical sensor, and the like, further improvements are required for various characteristics required for photoelectric conversion elements used therein.

For example, the photoelectric conversion elements are required to have excellent heat resistance.

The present inventors produced photoelectric conversion elements using the compound disclosed in JP2009-167348A and evaluated the heat resistance of the obtained photoelectric conversion elements. As result, it was found that there was room for improvement.

In view of the above circumstances, an object of the present invention is to provide a photoelectric conversion element having excellent heat resistance.

Another object of the present invention is to provide an imaging element and an optical sensor which include the photoelectric conversion element. Furthermore, an object of the present invention is also to provide a compound applied to the photoelectric conversion element.

The inventors of the present invention have conducted extensive studies on the above-described problems. As a result, the inventors have found that it is possible to solve the above-described problems by applying the compound having a predetermined structure to the photoelectric conversion film, and have completed the present invention.

[1]

A photoelectric conversion element comprising, in the following order: a conductive film; a photoelectric conversion film; and a transparent conductive film,
in which the photoelectric conversion film contains a compound represented by Formula (1) described below.

[2]

The photoelectric conversion element according to [1], in which the compound represented by Formula (1) described below is a compound represented by Formula (2) described below.

[3]

The photoelectric conversion element according to [1] or [2], in which the compound represented by Formula (1) described below is a compound represented by Formula (3) described below.

[4]

The photoelectric conversion element according to [1] or [3], in which the compound represented by Formula (1) described below is a compound represented by Formula (4) described below.

[5]

The photoelectric conversion element according to [1] or [4], in which the compound represented by Formula (1) described below is a compound represented by Formula (5) described below.

[6]

The photoelectric conversion element according to any one of [1] to [5], in which in Formulae (1) to (5) described below, $R^{a1}$ and $R^{a2}$ each independently represent a group represented by Formula (X) described below, $-C(R^{L1})(R^{L2})(R^{L3})$, a polycyclic aryl group which may have a substituent, or a polycyclic heteroaryl group which may have a substituent.

[7]

The photoelectric conversion element according to any one of [1] to [6], in which the photoelectric conversion film further includes an n-type organic semiconductor, and
the photoelectric conversion film has a bulk hetero structure formed in a state where the compound represented by Formula (1) described below and the n-type organic semiconductor are mixed to each other.

[8]

The photoelectric conversion element according to [7], in which the n-type organic semiconductor contains fullerenes selected from the group consisting of a fullerene and a derivative thereof.

[9]

The photoelectric conversion element according to any one of [1] to [8], further comprising one or more interlayers between the conductive film and the transparent conductive film, in addition to the photoelectric conversion film.

[10]

An imaging element comprising the photoelectric conversion element according to any one of [1] to [9].

[11]

The imaging element according to [10], further comprising another photoelectric conversion element that receives light having a wavelength different from a wavelength of light received by the photoelectric conversion element.

[12]

The imaging element according to [11], in which the photoelectric conversion element and the other photoelectric conversion element are laminated, and at least a part of incident light is transmitted through the photoelectric conversion element and then received by the other photoelectric conversion element.

[13]

The imaging element according to [11] or [12], in which the photoelectric conversion element is a green photoelectric conversion element, and the other photoelectric conversion element includes a blue photoelectric conversion element and a red photoelectric conversion element.

[14]

An optical sensor comprising the photoelectric conversion element according to any one of [1] to [9].

[15]

A compound represented by Formula (4-2) described below.

According to the present invention, the photoelectric conversion element having excellent heat resistance can be provided.

In addition, the imaging element and the optical sensor which include the photoelectric conversion element can be provided. Furthermore, the compound applied to the photoelectric conversion element can be provided.

DESCRIPTION OF THE PREFERRED EMBODIMENTS

Hereinafter, suitable embodiments of a photoelectric conversion element of the present invention will be described.

In the present specification, a substituent for which whether it is substituted or unsubstituted is not specified may be further substituted with a substituent (for example, a substituent W described below) within the scope not impairing an intended effect. For example, the expression "alkyl group" corresponds to an alkyl group with which a substituent (for example, the substituent W described below) may be substituted, the alkyl group may have a substituent (for example, the substituent W described below), and may not have a substituent.

In addition, in the present specification, the numerical range represented by "to" means a range including numerical values denoted before and after "to" as a lower limit value and an upper limit value.

In the present specification, in a case where there are plural substituents, linking groups, and the like (hereinafter, referred to as substituents and the like) represented by specific symbols, or a case where a plurality of substituents and the like are specified all together, each of the substituents and the like may be the same or may be different from each other. This also applies to a case of specifying the number of substituents and the like.

In the present specification, a hydrogen atom may be a light hydrogen atom (an ordinary hydrogen atom) or a deuterium atom (a double hydrogen atom and the like).

[Photoelectric Conversion Element]

As a feature of the present invention, compared to the related art, there is a point that a compound represented by Formula (1) described below (hereinafter, also referred to as "specific compound") is used in a photoelectric conversion film.

The present inventors have considered that since a relatively large substituent ($R^{a1}$ and $R^{a2}$ in Formula (1)) is bonded to a predetermined nitrogen atom, it is possible to suppress a specific compound from crystallizing even in a case of being heated because, and to avoid performance deterioration (such as an increase in a dark current) due to heating of a photoelectric conversion element.

Figure 1:
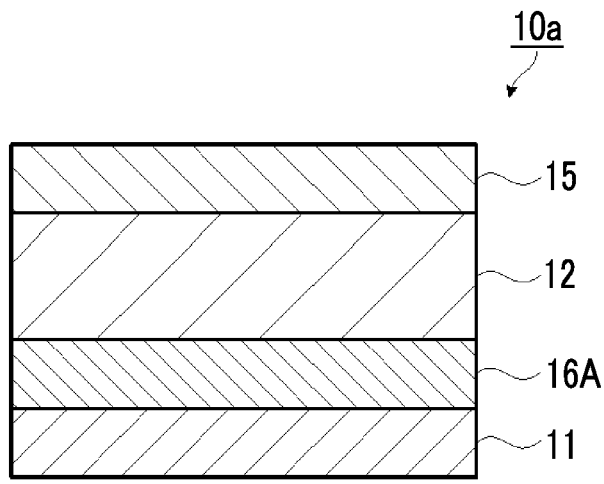
FIG. 1 is a schematic cross-sectional view showing an example of a configuration of a photoelectric conversion element.

FIG. 1 shows a schematic cross-sectional view of one embodiment of a photoelectric conversion element of the present invention.

A photoelectric conversion element 10a shown in FIG. 1 has a configuration in which a conductive film (hereinafter, also referred to as a lower electrode) 11 functioning as the lower electrode, an electron blocking film 16A, a photoelectric conversion film 12 containing the specific compound described below, and a transparent conductive film (hereinafter, also referred to as an upper electrode) 15 functioning as the upper electrode are laminated in this order.

Figure 2:
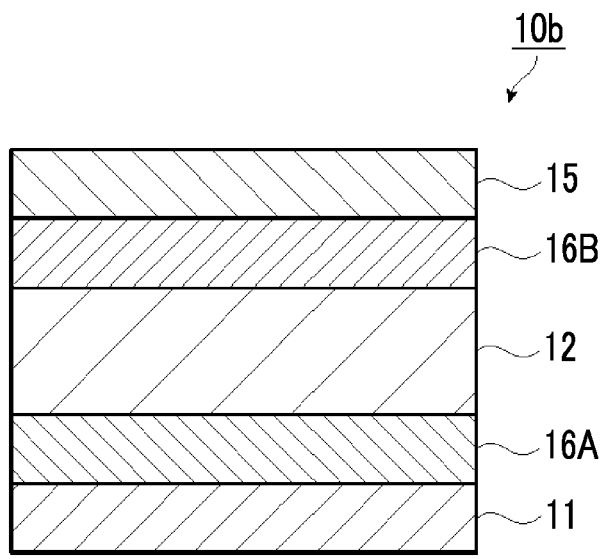
FIG. 2 is a schematic cross-sectional view showing an example of a configuration of a photoelectric conversion element.

FIG. 2 shows a configuration example of another photoelectric conversion element. A photoelectric conversion element 10b shown in FIG. 2 has a configuration in which the electron blocking film 16A, the photoelectric conversion film 12, a positive hole blocking film 16B, and the upper electrode 15 are laminated on the lower electrode 11 in this order. The lamination order of the electron blocking film 16A, the photoelectric conversion film 12, and the positive hole blocking film 16B in FIGS. 1 and 2 may be appropriately changed according to the application and the characteristics.

In the photoelectric conversion element 10a (or 10b), it is preferable that light is incident on the photoelectric conversion film 12 through the upper electrode 15.

In a case where the photoelectric conversion element 10a (or 10b) is used, a voltage can be applied. In this case, it is preferable that the lower electrode 11 and the upper electrode 15 form a pair of electrodes and the voltage of $1 \times 10^{-5}$ to $1 \times 10^7$ V/cm is applied thereto. From the viewpoint of performance and power consumption, the voltage to be applied is more preferably $1 \times 10^{-4}$ to $1 \times 10^7$ V/cm, and still more preferably $1 \times 10^{-3}$ to $5 \times 10^6$ V/cm.

A voltage application method is preferable that the voltage is applied such that the electron blocking film 16A side is a cathode and the photoelectric conversion film 12 side is an anode, in FIGS. 1 and 2. In a case where the photoelectric conversion element 10a (or 10b) is used as an optical sensor, or also in a case where the photoelectric conversion element 10a (or 10b) is incorporated in an imaging element, the voltage can be applied by the same method.

As described in detail below, the photoelectric conversion element 10a (or 10b) can be suitably applied to applications of the imaging element.

Hereinafter, a form of each layer constituting the photoelectric conversion element according to the embodiment of the present invention will be described in detail.

[Photoelectric Conversion Film]

<Specific Compound>

The photoelectric conversion film 12 (or an organic photoelectric conversion film 209) is a film containing a specific compound as a photoelectric conversion material. In a case of using this compound, the photoelectric conversion element having excellent heat resistance can be obtained.

Hereinafter, the specific compound will be described in detail.

Formula (1) includes all geometric isomers that can be distinguished based on the C=C double bond constituted by a carbon atom to which $R^1$ bonds and a carbon atom adjacent thereto in Formula (1). That is, both the cis isomer and the trans isomer which are distinguished based on the C=C double bond are included in the compound represented by Formula (1). This point is the same for Formulae (2) and (3).

In the present specification, unless otherwise specified, examples of a substituent which may be contained in the specific compound include each independently the substituent W described below.

In addition, unless otherwise specified, examples of an alkyl group (including an alkyl group which may have a substituent) that the specific compound may have each independently include an alkyl group AL described below. Examples of an aryl group (including an aryl group which may have a substituent) each independently include an aryl group AR described below, and examples of a heteroaryl group (including a heteroaryl group which may have a substituent) each independently include a heteroaryl group HA described below.

(Formula (1))

The photoelectric conversion film included in the photoelectric conversion element according to the embodiment of the present invention contains the specific compound.

The specific compound is the compound represented by Formula (1).

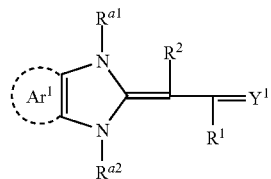

(1)

(1-1)

(1-2)

In Formula (1), $Y^1$ represents a group represented by Formula (1-1) or a group represented by Formula (1-2). Among these, the group represented by Formula (1-1) is preferable from the viewpoint of obtaining an excellent effect of the present invention. In Formulae (1-1) and (1-2), * represents a bonding position, and a carbon atom marked with * and a carbon atom bonded to $R^1$ are bonded to each other to form a double bond.

That is, the compound represented by Formula (1) is a compound represented by Formula (1-1a) or a compound represented by Formula (1-2a).

The symbols used in Formulae (1-1a) and (1-2a) have the same meanings as the corresponding symbols used in Formula (1).

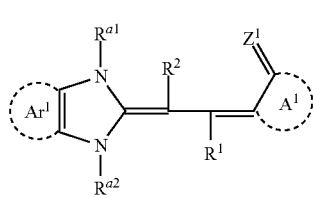

(1-1a)

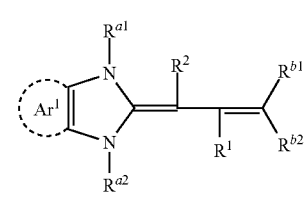

(1-2a)

In Formula (1-1), $A^1$ represents a ring which contains at least two carbon atoms and may have a substituent. The two carbon atoms mean a carbon atom that is bonded to $Z^1$ specified in Formula (1-1), and a carbon atom that is adjacent to the carbon atom bonded to the $Z^1$ and is specified in Formula (1-1) (a carbon atom bonded with the carbon atom bonded to $R^1$ to form a double bond), and any carbon atom is an atom constituting $A^1$.

In addition, in the above ring, carbon atoms constituting the ring may be substituted with another carbonyl carbon (>C=O) and/or another thiocarbonyl carbon (>C=S). The other carbonyl carbon (>C=O) and the other thiocarbonyl carbon (>C=S) as used herein respectively mean a carbonyl carbon and a thiocarbonyl carbon each of which has a carbon atom other than the carbon atom bonded to $Z^1$ among the carbon atoms constituting the ring, as a constituent.

The carbon atoms of $A^1$ are preferably 3 to 30, more preferably 3 to 20, and still more preferably 3 to 15. The number of carbon atoms described above is a number containing two carbon atoms specified in Formula.

$A^1$ may have a hetero atom, and examples thereof preferably include a nitrogen atom, a sulfur atom, an oxygen atom, a selenium atom, a tellurium atom, a phosphorus atom, a silicon atom, and a boron atom.

The number of hetero atoms in $A^1$ is preferably 0 to 10, more preferably 0 to 5, and still more preferably 0 to 2. The number of hetero atoms in which a carbon atom constituting the ring represented by $A^1$ is substituted by the carbonyl carbon (>C=O) or the thiocarbonyl carbon (>C=S) and introduced into the ring (the carbonyl carbon (>C=O) described herein includes the carbonyl carbon specified in Formula (1-1)), and the number of hetero atoms that a substituent of $A^1$ has is not included in the number of hetero atoms.

$A^1$ may have a substituent, and examples of the substituent preferably include a halogen atom (preferably a chlorine atom), an alkyl group (may be any of linear, branched, or cyclic, and preferably has 1 to 10 carbon atoms and more preferably 1 to 6 carbon atoms), an aryl group (preferably has 6 to 18 carbon atoms, and more preferably 6 to 12 carbon atoms), a heteroaryl group (preferably has 5 to 18 carbon atoms, and more preferably 5 to 6 carbon atoms), or a silyl group (for example, an alkylsilyl group is mentioned, the alkyl group in the alkylsilyl group may be any of linear, branched or cyclic, and the silyl group preferably has 1 to 4 carbon atoms, and more preferably one carbon atom).

$A^1$ may or may not indicate aromaticity.

$A^1$ may have a monocyclic structure or a condensed ring structure, but is preferably a 5-membered ring, a 6-membered ring, or a fused ring containing at least any one of a 5-membered ring or a 6-membered ring. The number of rings forming the fused ring is preferably 1 to 4, and more preferably 1 to 3.

The ring represented by $A^1$ is usually preferably a ring used as an acidic nucleus (specifically, an acidic nucleus of a merocyanine coloring agent), and specific examples thereof are as follows:

(a) 1,3-dicarbonyl nuclei: for example, a 1,3-indandione, 1,3-cyclohexanedione, 5,5-dimethyl-1,3-cyclohexanedione, 1,3-dioxane-4,6-dione, and the like;
(b) pyrazolinone nuclei: for example, 1-phenyl-2-pyrazolin-5-one, 3-methyl-1-phenyl-2-pyrazolin-5-one, 1-(2-benzothiazolyl)-3-methyl-2-pyrazolin-5-one, and the like;
(c) isoxazolinone nuclei: for example, 3-phenyl-2-isoxazolin-5-one, 3-methyl-2-isoxazolin-5-one, and the like;
(d) oxindole nuclei: for example, 1-alkyl-2,3-hydro-2-oxindole, and the like;
(e) 2,4,6-trioxohexahydropyrimidine nuclei: for example, barbituric acid or 2-thibarbituric acid and derivatives thereof, and the like, and examples of the derivatives include 1-alkyl compounds such as 1-methyl and 1-ethyl, 1,3-dialkyl compounds such as 1,3-dimethyl, 1,3-diethyl, and 1,3-dibutyl, 1,3-diaryl compounds such as 1,3-diphenyl, 1,3-di(p-chlorophenyl), and 1,3-di(p-ethoxycarbonylphenyl), 1-alkyl-1-aryl compounds such as 1-ethyl-3-phenyl, 1,3-diheteroaryl compounds such as 1,3-di(2-pyridyl), and the like;
(f) 2-thio-2,4-thiazolidinedione nuclei: for example, rhodanine and derivatives thereof, and the like, and examples of the derivatives include 3-aklylrhodanine such as 3-methylrhodanine, 3-ethylrhodanine, and 3-allylrhodanine, 3-arylrhodanine such as 3-phenylrhodanine, 3-heteroarylrhodanine such as 3-(2-pyridyl)rhodanine, and the like;
(g) 2-thio-2,4-oxazolidinedione nuclei (2-thio-2,4-(3H,5H)-oxazoledione nuclei): for example, 3-ethyl-2-thio-2,4-oxazolidinedione, and the like;
(h) thianaphthenone nuclei: for example, 3(2H)-thianaphthenone-1,1-dioxide, and the like;
(i) 2-thio-2,5-thiazolidinedione nuclei: for example, 3-ethyl-2-thio-2,5-thiazolidinedione, and the like;
(j) 2,4-thiazolidinedione nuclei: for example, 2,4-thiazolidinedione, 3-ethyl-2,4-thiazolidinedione, 3-phenyl-2,4-thiazolidinedione, and the like;
(k) thiazolin-4-one nuclei: for example, 4-thiazolinone, 2-ethyl-4-thiazolinone, and the like;
(l) 2,4-imidazolidinedione (hydantoin) nuclei: for example, 2,4-imidazolidinedione, 3-ethyl-2,4-imidazolidinedione, and the like;
(m) 2-thio-2,4-imidazolidinedione (2-thiohydantoin) nuclei: for example, 2-thio-2,4-imidazolidinedione, 3-ethyl-2-thio-2,4-imidazolidinedione, and the like;
(n) imidazolin-5-one nuclei: for example, 2-propylmercapto-2-imidazolin-5-one, and the like;
(o) 3,5-pyrazolidinedione nuclei: for example, 1,2-diphenyl-3,5-pyrazolidinedione, 1,2-dimethyl-3,5-pyrazolidinedione, and the like;
(p) benzothiophen-3(2H)-one nuclei: for example, benzothiophen-3(2H)-one, oxobenzothiophen-3(2H)-one, dioxobenzothiophen-3(2H)-one, and the like;
(q) indanone nuclei: for example, 1-indanone, 3-phenyl-1-indanone, 3-methyl-1-indanone, 3,3-diphenyl-1-indanone, 3,3-dimethyl-1-indanone, and the like;
(r) benzofuran-3-(2H)-one nucleus: for example, benzofuran-3-(2H)-one, and the like; and
(s) 2,2-dihydrophenalene-1,3-dione nucleus, and the like.

$A^1$ may be a ring having a group represented by Formula (AW).

$$\text{*1-L-Y—Z-*2} \qquad (AW)$$

In Formula (AW), *1 represents a bonding position with the carbon atom in —C(=$Z^1$)— which is specified in Formula (1-1) (or Formula (1-1a)). *2 represents a bonding position with a carbon atom marked with * in Formula (1-1) (in other words, *2 represents a bonding position with a carbon atom bonded to the carbon atom, to which $R^1$ in Formula (1) is directly bonded to form a double bond).

That is, in a case where $A^1$ is a ring having a group represented by Formula (AW), a compound represented by Formula (1), in which $Y^1$ is a group represented by Formula (1-1), (or a compound represented by Formula (1-1a) is a compound represented by Formula (1-1b). The symbols used in Formulae (1-1b) have the same meanings as the corresponding symbols used in Formula (1).

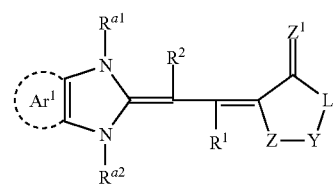

(1-1b)

In Formula (AW), L represents a single bond or —NR$^L$—.

R$^L$ represents a hydrogen atom or a substituent. Among these, R$^L$ is preferably an alkyl group, an aryl group, or a heteroaryl group, and more preferably an alkyl group or an aryl group.

L is preferably a single bond.

Y represents —CR$^{Y1}$=CR$^{Y2}$—, —CS—NR$^{Y3}$—, —CO—, —CS—, —NR$^{Y4}$—, —N=CR$^{Y5}$—, or 1,8-naphthalenediyl group which may have a substituent, and among these, —CR$^{Y1}$=CR$^{Y2}$— is preferable.

R$^{Y1}$ to R$^{Y5}$ each independently represent a hydrogen atom or a substituent. Among these, R$^{Y1}$ to R$^{Y5}$ each are independently preferably an alkyl group, an aryl group, or a heteroaryl group.

In addition, in a case where Y represents —CR$^{Y1}$=CR$^{Y2}$—, R$^{Y1}$ and R$^{Y2}$ are preferably bonded to each other to form a ring. Examples of the ring formed by bonding R$^{Y1}$ and R$^{Y2}$ to each other include an aromatic ring (such as an aromatic hydrocarbon ring and an aromatic heterocycle), and specific examples thereof include a benzene ring and a pyridine ring. The ring formed by bonding R$^{Y1}$ and R$^{Y2}$ to each other may further have a substituent, and furthermore, such substituents may be bonded to each other to form a ring.

Z represents a single bond, —CO—, —S—, —SO$_2$— or —CR$^{Z1}$=CR$^{Z2}$—, and among these, —CO— is preferable.

R$^{Z1}$ and R$^{Z2}$ each independently represent a hydrogen atom or a substituent.

The combination of L, Y, and Z described above is preferably a combination in which a ring formed by bonding -L-Y-Z- to two carbon atoms specified in Formula (1-1) is a 5-membered ring or a 6-membered ring. However, as described above, the 5-membered ring or the 6-membered ring may be condensed with a different ring (preferably a benzene ring) to form a condensed ring structure.

Among these, A$^1$ is preferably a ring having a group represented by Formula (AX) from the viewpoint that the heat resistance of the photoelectric conversion element is more excellent.

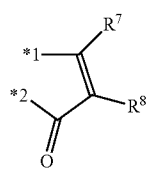

(AX)

In Formula (AX), *1 and *2 have the same meanings as *1 and *2 in Formula (AW), respectively.

R$^7$ to R$^8$ each independently represent a hydrogen atom or a substituent.

R$^7$ and R$^8$ are preferably bonded to each other to form a ring. Examples of the ring formed by bonding R$^7$ and R$^8$ to each other include aromatic rings (such as an aromatic hydrocarbon ring and an aromatic heterocycle), and specific examples thereof include a benzene ring, a pyrazine ring, and a pyridine ring.

The ring formed by bonding R$^7$ and R$^8$ to each other preferably further has a substituent. As the substituent, a halogen atom is preferable, and a chlorine atom is more preferable.

In addition, the substituents contained in the ring formed by bonding R$^7$ and R$^8$ to each other may further be bonded to each other to form a ring (benzene ring or the like).

The group represented by Formula (AX) is preferably a group represented by Formula (AY) from the viewpoint that the heat resistance of the photoelectric conversion element is more excellent.

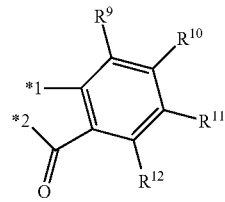

(AY)

In Formula (AY), *1 and *2 have the same meanings as *1 and *2 in Formula (AX), respectively.

R$^9$ to R$^{12}$ each independently represent a hydrogen atom or a substituent. Among these, R$^9$ to R$^{12}$ each are independently preferably a hydrogen atom or a halogen atom, and more preferably a hydrogen atom or a chlorine atom.

R$^9$ and R$^{10}$ may be bonded to each other to form a ring, R$^{10}$ and R$^{11}$ may be bonded to each other to form a ring, and R$^{11}$ and R$^{12}$ may be bonded to each other to form a ring. Examples of the ring, which is formed by bonding R$^9$ and R$^{10}$, R$^{10}$ and R$^{11}$, and R$^{11}$ and R$^{12}$ to each other respectively, include an aromatic ring (aromatic hydrocarbon ring and aromatic heterocycle), and a specific example preferably includes a benzene ring.

Among these, it is preferable that R$^{10}$ and R$^{11}$ are bonded to each other to form a ring.

The ring, which is formed by bonding R$^9$ and R$^{10}$, R$^{10}$ and R$^{11}$, and R$^{11}$ and R$^{12}$ to each other respectively, may be further substituted with a substituent. Such substituents contained in the ring may be bonded to each other to form a ring. In addition, in an available case, the substituents contained in the ring and one or more of R$^9$ to R$^{12}$ may be bonded to each other to form one or more rings.

A group may be formed by bonding the substituents contained in the ring to each other to form a single bond.

In Formula (1-1), Z$^1$ represents an oxygen atom, a sulfur atom, =NR$^{Z1}$, or =CR$^{Z2}$R$^{Z3}$.

R$^{Z1}$ represents a hydrogen atom or a substituent. R$^{Z2}$ and R$^{Z3}$ each independently represent a cyano group or —COOR$^{Z4}$. R$^{Z4}$ represents an alkyl group which may have a substituent, an aryl group which may have a substituent, or a heteroaryl group which may have a substituent.

Z$^1$ is preferably an oxygen atom.

In Formula (1-2), R$^{b1}$ and R$^{b2}$ each independently represent a cyano group or —COOR$^{b3}$.

R$^{b3}$ represents an alkyl group which may have a substituent, an aryl group (phenyl group or the like) which may have a substituent, or a heteroaryl group which may have a substituent.

In Formula (1), R$^1$ and R$^2$ each independently represent a hydrogen atom or a substituent.

R$^1$ and R$^2$ each independently preferably represent a hydrogen atom.

In Formula (1), R$^{a1}$ and R$^{a2}$ each independently represent an aryl group which may have a substituent, —C(R$^{L1}$)(R$^{L2}$)(R$^{L3}$), or a heteroaryl group which may have a substituent.

The aryl group is preferably a phenyl group, a naphthyl group, or a fluorenyl group, and more preferably a phenyl group or a naphthyl group.

In a case where the aryl group is a phenyl group, the phenyl group preferably has a substituent, and the substituent is independently preferably an alkyl group (preferably having 1 to 3 carbon atoms).

In a case where the aryl group is a phenyl group, the number of substituents contained in the phenyl group is preferably 1 to 5, and more preferably 2 or 3.

In —C($R^{L1}$)($R^{L2}$)($R^{L3}$), $R^{L1}$ to $R^{L3}$ each independently represent an alkyl group which may have a substituent, an aryl group which may have a substituent, a heteroaryl group which may have a substituent, or a hydrogen atom, and at least two of $R^{L1}$, $R^{L2}$, or $R^{L3}$ each independently represent an alkyl group which may have a substituent, an aryl group which may have a substituent, or a heteroaryl group which may have a substituent. An alkyl group which may have a substituent, an aryl group which may have a substituent, and a heteroaryl group which may have a substituent, which are represented by $R^{L1}$ to $R^{L3}$, may be bonded to each other to form a ring.

For example, the alkyl groups which may have a substituent may be bonded to each other to form a ring. A substituent in the aryl group which may have a substituent and the alkyl group which may have a substituent may be bonded to each other to form a ring. A substituent in the heteroaryl group which may have a substituent and the alkyl group which may have a substituent may be bonded to each other to form a ring. A substituent in the aryl group which may have a substituent and a substituent in another aryl group which may have a substituent may be bonded to each other to form a ring. A substituent in the aryl group which may have a substituent and a substituent in the heteroaryl group which may have a substituent may be bonded to each other to form a ring. A substituent in the heteroaryl group which may have a substituent and a substituent in another heteroaryl group which may have a substituent may be bonded to each other to form a ring.

A substituent in the ring formed as described above, and another alkyl group which may have a substituent, a substituent in another aryl group which may have a substituent, or a substituent in another heteroaryl group which may have a substituent may be bonded to form a ring.

As described above, a group may be formed by bonding the substituent and the substituent (for example, the substituent in the aryl group which may have a substituent and the substituent in the heteroaryl group which may have a substituent) to form a single bond.

In a case where the alkyl group which may have a substituent, the aryl group which may have a substituent, and the heteroaryl group which may have a substituent, which are represented by $R^{L1}$ to $R^{L3}$, may be bonded to each other to form a ring, —C($R^{L1}$)($R^{L2}$)($R^{L3}$) is preferably a group other than the aryl group and the heteroaryl group.

The alkyl groups represented by $R^{L1}$ to $R^{L3}$ each may be independently linear, branched, or cyclic. In the alkyl groups represented by $R^{L1}$ to $R^{L3}$, it is preferable that two alkyl groups are bonded to each other to form a ring.

More specifically, for example, the alkyl group represented by $R^{L1}$ and the alkyl group represented by $R^{L2}$ may be bonded to each other to form a ring. Furthermore, a substituent contained in a ring (a monocyclic cycloalkane ring or the like), which is formed by bonding the alkyl group represented by $R^{L1}$ and the alkyl group represented by $R^{L2}$ to each other, and an alkyl group represented by $R^{L3}$ may be bonded to each other to form a polycycle (a polycyclic cycloalkane ring or the like).

That is, —C($R^{L1}$)($R^{L2}$)($R^{L3}$) may be a cycloalkyl group (preferably a cyclohexyl group) which may have a substituent. The number of membered rings of the cycloalkyl group is preferably 3 to 12, more preferably 5 to 8, and still more preferably 6.

The cycloalkyl group may be monocyclic (a cyclohexyl group or the like) or polycyclic (1-adamantyl group or the like).

The cycloalkyl group preferably has a substituent. In a case where the cycloalkyl group has a substituent, a carbon atom adjacent to a carbon atom directly bonded to the nitrogen atom specified in General Formula (1) (that is, the "C" atom specified in "—C($R^{L1}$)($R^{L2}$)($R^{L3}$)") preferably has a substituent.

An example of a substituent which may be contained in the cycloalkyl group includes an alkyl group (preferably having 1 to 3 carbon atoms).

Substituents contained in the cycloalkyl group may be bonded to each other to form a ring, and the ring formed by bonding the substituents to each other may be a ring other than a cycloalkane ring.

$R^{a1}$ and $R^{a2}$ each independently preferably represent a group represented by Formula (X), —C($R^{L1}$)($R^{L2}$)($R^{L3}$), a polycyclic aryl group which may have a substituent, or a polycyclic heteroaryl group which may have a substituent, from the viewpoint that the heat resistance of the photoelectric conversion element is more excellent.

Among these, $R^{a1}$ and $R^{a2}$ each are preferably independently a group represented by Formula (X), —C($R^{L1}$)($R^{L2}$)($R^{L3}$), or a polycyclic aryl group which may have a substituent, from the viewpoint that an absorption peak of the photoelectric conversion element has a narrow half-width. The group represented by Formula (X) is preferably a group represented by Formula (Z) described below, and more preferably a group represented by Formula (ZB) described below.

In a laminated imaging element formed by laminating a plurality of photoelectric conversion elements that receive different types of light, in a case where light is incident on the imaging element, a part of the incident light is absorbed by the photoelectric conversion elements arranged on the incident side, and the transmitted light is absorbed by the photoelectric conversion elements arranged further inside. In such an imaging element, since colors are easily separated, it is preferable that the absorption peak of each photoelectric conversion element has a narrow half-width.

The group represented by Formula (X) is a group shown below.

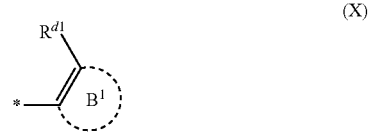

In Formula (X), $B^1$ represents a monocyclic aromatic ring which may have a substituent other than $R^{d1}$.

$R^{d1}$ represents an alkyl group, a silyl group, an alkoxy group, an alkylthio group, a cyano group, a halogen atom, an aryl group, a heteroaryl group, an alkenyl group, or an alkynyl group.

These groups may further have a substituent as much as possible.

Examples of the monocyclic aromatic ring include a monocyclic aromatic hydrocarbon ring and a monocyclic aromatic heterocycle. An example of the aromatic hydrocarbon ring includes a benzene ring. Examples of the aromatic heterocycle include a pyrrole ring, a furan ring, a thiophene ring, an imidazole ring, and an oxazole ring.

Among these, the aromatic hydrocarbon ring is preferable, and the benzene ring is more preferable, from the viewpoint that the heat resistance of the photoelectric conversion element is more excellent.

The alkyl group represented by $R^{d1}$ preferably has 1 to 12 carbon atoms, more preferably has 1 to 6 carbon atoms, and still more preferably has 1 to 3 carbon atoms. In addition, the alkyl group is preferably —CH($R^{d3}$)($R^{d4}$), or —C($R^{d3}$)($R^{d4}$)($R^{d5}$). $R^{d3}$ to $R^{d5}$ each independently represent an aryl group, an alkyl group (preferably having 1 to 3 carbon atoms) or a heteroaryl group, and an alkyl group is preferable.

The silyl group represented by $R^{d1}$ is preferably, for example, a group represented by —Si($R^p$)($R^q$)($R^r$). $R^p$ to $R^r$ each independently represent a hydrogen atom or a substituent. Examples of the substituents represented by $R^p$ to $R^r$ include an alkyl group (the alkyl group may be any of linear, branched, or cyclic, preferably has 1 to 4 carbon atoms, and more preferably has one carbon atom), an aryl group, and a heteroaryl group. These groups may further have a substituent.

The alkoxy group represented by $R^{d1}$ preferably has 1 to 12 carbon atoms, more preferably has 1 to 6 carbon atoms, and still more preferably has 1 to 3 carbon atoms.

The alkylthio group represented by $R^{d1}$ preferably has 1 to 12 carbon atoms, more preferably has 1 to 6 carbon atoms, and still more preferably has 1 to 3 carbon atoms.

Examples of the halogen atom represented by $R^{d1}$ include a fluorine atom, an iodine atom, a bromine atom, a chlorine atom, and the like.

An example of the aryl group represented by $R^{d1}$ includes an aryl group AR described below.

An example of the heteroaryl group represented by $R^{d1}$ includes a heteroaryl group HA described below.

The alkenyl group represented by $R^{d1}$ preferably has 2 to 12 carbon atoms, more preferably has 2 to 6 carbon atoms, and still more preferably has 2 to 3 carbon atoms.

The alkynyl group represented by $R^{d1}$ preferably has 2 to 12 carbon atoms, more preferably has 2 to 6 carbon atoms, and still more preferably has 2 to 3 carbon atoms.

Substituents which contained in $R^{d1}$ and $B^1$ may be bonded to each other to form a non-aromatic ring.

* represents a bonding position. The aromatic ring of $B^1$ is directly bonded to the nitrogen atom specified in Formula (1).

As the group represented by Formula (X), the group represented by Formula (Z) is preferable.

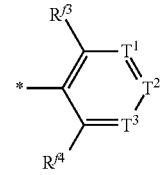

(Z)

In Formula (Z), $T^1$ to $T^4$ each independently represent —$CR^{e12}$= or a nitrogen atom (=N—). $R^{e12}$ represents a hydrogen atom or a substituent.

It is preferable that "at least one of $T^1$, $T^2$, $T^3$, or $T^4$ represents —$CR^{e12}$= and at least one of $R^{e12}$ represents a substituent", more preferable that "at least $T^4$ represents —$CR^{e12}$=, and $R^{e12}$ represents an alkyl group, an aryl group, or a heteroaryl group", and still more preferable that "at least $T^4$ represents —$CR^{e12}$=, and $R^{e12}$ is —CH($R^{d3}$)($R^{d4}$), or —C($R^{d3}$)($R^{d4}$)($R^{d5}$)".

The —CH($R^{d3}$)($R^{d4}$) and the —C($R^{d3}$)($R^{d4}$)($R^{d5}$) will be described below.

The definition of the substituent is the same as the substituent W described below. Examples of the substituent include an alkyl group, an aryl group, a heteroaryl group, a silyl group, a halogen atom, a cyano group, and the like. In addition, these groups may further have a substituent (for example, a halogen atom such as a fluorine atom).

The alkyl group represented by $R^{e12}$ preferably has 1 to 12 carbon atoms, more preferably has 1 to 6 carbon atoms, and still more preferably has 1 to 3 carbon atoms. In addition, the alkyl group is preferably —CH($R^{d3}$)($R^{d4}$), or —C($R^{d3}$)($R^{d4}$)($R^{d5}$). $R^{d3}$ to $R^{d5}$ each independently represent an aryl group, an alkyl group (preferably having 1 to 3 carbon atoms) or a heteroaryl group, and an alkyl group is preferable.

An example of the aryl group represented by $R^{e12}$ includes an aryl group AR described below.

An example of the heteroaryl group represented by $R^{e12}$ includes a heteroaryl group HA described below.

An example of the silyl group represented by $R^{e12}$ includes the silyl group described as the silyl group represented by $R^{d1}$.

Examples of the halogen atom represented by $R^{e12}$ include a fluorine atom, an iodine atom, a bromine atom, and a chlorine atom.

In addition, in a case where a plurality of $R^{e12}$'s exist in Formula (Z), $R^{e12}$, s may be the same or different from each other.

In Formula (Z), $R^{f2}$ represents an alkyl group, a silyl group, an alkoxy group, an alkylthio group, a cyano group, a halogen atom, an aryl group, a heteroaryl group, an alkenyl group, or an alkynyl group, and has the same meaning as $R^{d1}$ in Formula (X) and preferred conditions are also the same.

In addition, $R^{f2}$ and $R^{e12}$ in $T^1$ may be bonded to each other to form a non-aromatic ring.

As the group represented by Formula (X), the group represented by Formula (ZB) is more preferable.

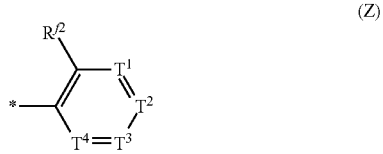

(ZB)

In Formula (ZB), $T^1$ to $T^3$ each independently represent —$CR^{e12}$= or a nitrogen atom. $R^{e12}$ represents a hydrogen atom or a substituent.

$R^{e12}$ in Formula (ZB) is the same as $R^{e12}$ in Formula (Z).

In Formula (ZB), $R^{f3}$ and $R^{f4}$ each independently represent an alkyl group, an aryl group, or a heteroaryl group. One or both of $R^{f3}$ and $R^{f4}$ are preferably —CH($R^{d3}$)($R^{d4}$), —C($R^{d3}$)($R^{d4}$)($R^{d5}$), an aryl group, or a heteroaryl group. $R^{d3}$ to $R^{d5}$ each independently represent an aryl group, an alkyl group (preferably having 1 to 3 carbon atoms) or a heteroaryl group, and an alkyl group is preferable.

These groups may further have a substituent as much as possible.

* represents a bonding position.

The number of rings constituting the polycyclic aryl group which may have a substituent and the polycyclic heteroaryl group which may have a substituent is 2 or more, preferably 2 to 4, more preferably 2 to 3, and still more preferably 2.

The polycyclic aryl group which may have a substituent and a substituent which may be contained in the polycyclic heteroaryl group which may have a substituent may contain a non-aromatic ring.

As the polycyclic aryl group which may have a substituent, for example, a naphthyl group which may have a substituent is preferable.

In Formula (1), $Ar^1$ represents an aromatic ring which may have a substituent.

The aromatic ring may be monocyclic or polycyclic.

Examples of the aromatic ring include an aromatic hydrocarbon ring and an aromatic heterocycle. Examples of the aromatic hydrocarbon ring include a benzene ring, a naphthalene ring, an anthracene ring, and a phenanthrene ring. Examples of the aromatic heterocycle include a quinoxaline ring, a pyrazine ring, a pyrrole ring, a furan ring, a thiophene ring, an imidazole ring, and an oxazole ring. These rings may be further condensed with another ring (which may be a non-aromatic ring).

Among these, $Ar^1$ is preferably an aromatic heterocycle, and more preferably a quinoxaline ring or a pyrazine ring.

A substituent contained in an aromatic ring represented by $Ar^1$ is preferably an alkyl group.

(Formula (2))

The specific compound is preferably a compound represented by Formula (2) from the viewpoint that the heat resistance of the photoelectric conversion element is more excellent.

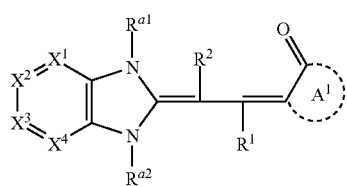

(2)

$A^1$ in Formula (2) has the same meaning as $A^1$ in Formula (1-1) (or Formula (1-1a)) and preferred conditions are also the same.

$R^1$ and $R^2$ in Formula (2) have the same meanings as $R^1$ and $R^2$ in Formula (1) and preferred conditions are also the same.

$R^{a1}$ and $R^{a2}$ in Formula (2) have the same meanings as $R^{a1}$ and $R^{a2}$ in Formula (1) and preferred conditions are also the same.

$X^1$ to $X^4$ each independently represent a nitrogen atom (—N=) or —$CR^{c1}$=.

$R^{c1}$ represents a hydrogen atom or a substituent.

At least two of $X^1$, $X^2$, $X^3$, or $X^4$ are preferably nitrogen atoms, more preferably at least $X^1$ and $X^4$ are nitrogen atoms, and still more preferably only $X^1$ and $X^4$ are nitrogen atoms.

In a case where a plurality of $R^{c1}$'s exist, the plurality of $R^{c1}$'s may be bonded to each other to form a ring. The ring formed by bonding the plurality of $R^{c1}$'s to each other is preferably an aromatic ring, and more preferably a benzene ring or a pyridine ring. The ring formed by bonding the plurality of $R^{c1}$'s to each other may further have a substituent.

(Formula (3))

The specific compound is more preferably a compound represented by Formula (3) from the viewpoint that the heat resistance of the photoelectric conversion element is more excellent.

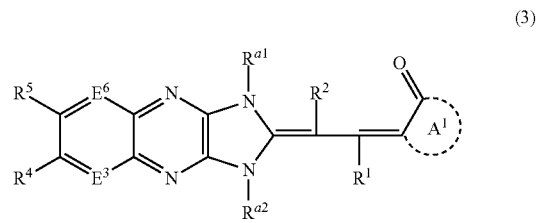

(3)

$A^1$ in Formula (3) has the same meaning as $A^1$ in Formula (1-1) (or Formula (1-1a)) and preferred conditions are also the same.

$R^1$ and $R^2$ in Formula (3) have the same meanings as $R^1$ and $R^2$ in Formula (1) and preferred conditions are also the same.

$E^3$ represents a nitrogen atom (—N=) or —$CR^3$=.
$E^6$ represents a nitrogen atom (—N=) or —$CR^6$=.
$E^3$ and $E^6$ preferably have "a form in which $E^3$ is —$CR^3$=, $E^6$ is —$CR^6$=", "a form in which $E^3$ is —N= and $E^6$ is —$CR^6$=", or "a form in which $E^3$ is —$CR^3$= and $E^6$ is —N=", and more preferably have "a form in which $E^3$ is —$CR^3$= and $E^6$ is —$CR^6$=".

$R^3$ to $R^6$ each independently represent a hydrogen atom or a substituent.

$R^3$ to $R^6$ each are independently preferably a hydrogen atom, an alkoxy group, a silyl group, or an alkyl group, and more preferably a hydrogen atom, an alkoxy group containing an alkyl group moiety having 1 to 3 carbon atoms, or an alkyl group having 1 to 4 carbon atoms. In $R^3$ to $R^6$, the number of $R^3$ to $R^6$ representing a substituent is preferably 0 to 2. In a case where one or more of $R^3$ to $R^6$ represent a substituent, it is preferable that $R^4$ and/or $R^5$ represent a substituent.

$R^3$ and $R^4$, and $R^4$ and $R^5$ in a case where $E^3$ is —$CR^3$=, and $R^5$ and $R^6$ in a case where $E^6$ is —$CR^6$= may be independently bonded to each other to form a ring, respectively. The rings, which are formed by bonding $R^3$ and $R^4$, $R^4$ and $R^5$, and $R^5$ and $R^6$ to each other respectively, may be monocyclic or polycyclic, may be aromatic or non-aromatic, and may have a substituent.

$R^{a1}$ and $R^{a2}$ in Formula (3) have the same meanings as $R^{a1}$ and $R^{a2}$ in Formula (1) and preferred conditions are also the same.

(Formula (4))

The specific compound is more preferably a compound represented by Formula (4) from the viewpoint that the heat resistance of the photoelectric conversion element is more excellent.

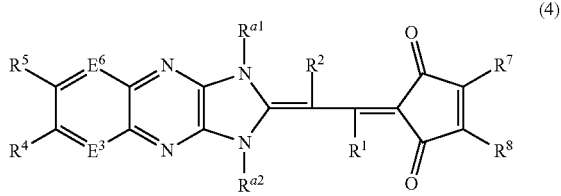

(4)

$R^1$ and $R^2$ in Formula (4) have the same meanings as $R^1$ and $R^2$ in Formula (1) and preferred conditions are also the same.

$E^3$ and $E^6$ in Formula (4) have the same meanings as $E^3$ and $E^6$ in Formula (3) and preferred conditions are also the same.

$R^3$ to $R^6$ in Formula (4) have the same meanings as $R^3$ to $R^6$ in Formula (3) and preferred conditions are also the same.

$R^7$ and $R^8$ in Formula (4) have the same meanings as $R^7$ and $R^8$ in Formula (AX) and preferred conditions are also the same.

$R^{a1}$ and $R^{a2}$ in Formula (4) have the same meanings as $R^{a1}$ and $R^{a2}$ in Formula (1) and preferred conditions are also the same.

(Formula (4-2))

An example of a suitable form of the compound represented by Formula (4) includes a compound represented by Formula (4-2).

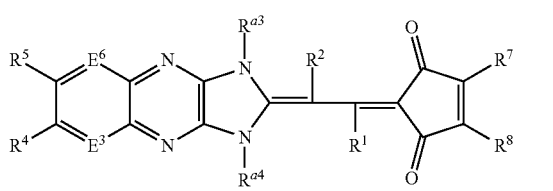

(4-2)

$R^1$ and $R^2$ in Formula (4-2) have the same meanings as $R^1$ and $R^2$ in Formula (1) and preferred conditions are also the same.

$E^3$ and $E^6$ in Formula (4-2) have the same meanings as $E^3$ and $E^6$ in Formula (3) and preferred conditions are also the same.

$R^3$ to $R^6$ in Formula (4-2) have the same meanings as $R^3$ to $R^6$ in Formula (3) and preferred conditions are also the same.

$R^7$ and $R^8$ in Formula (4-2) have the same meanings as $R^7$ and $R^8$ in Formula (AX) and preferred conditions are also the same.

$R^{a3}$ and $R^{a4}$ in Formula (4-2) each independently represent a group represented by Formula (X), —C($R^{L1}$)($R^{L2}$)($R^{L3}$), a polycyclic aryl group which may have a substituent, or a polycyclic heteroaryl group which may have a substituent.

The group represented by Formula (X), —C($R^{L1}$)($R^{L2}$)($R^{L3}$), the polycyclic aryl group which may have a substituent, and the polycyclic heteroaryl group which may have a substituent in $R^{a3}$ and $R^{a4}$ in Formula (4-2) have the same meanings as the group represented by Formula (X) described for $R^{a1}$ and $R^{a2}$ in Formula (1), —C($R^{L1}$)($R^{L2}$)($R^{L3}$), the polycyclic aryl group which may have a substituent, and the polycyclic heteroaryl group which may have a substituent, respectively, and preferred conditions are also the same.

(Formula (5))

The specific compound is particularly preferably a compound represented by Formula (5) from the viewpoint that the heat resistance of the photoelectric conversion element is more excellent.

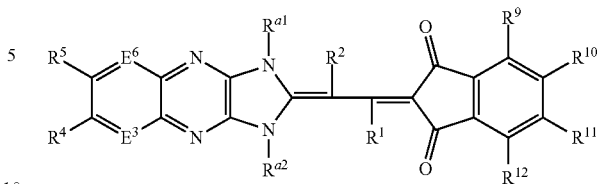

(5)

$R^1$ and $R^2$ in Formula (5) have the same meanings as $R^1$ and $R^2$ in Formula (1) and preferred conditions are also the same.

$E^3$ and $E^6$ in Formula (5) have the same meanings as $E^3$ and $E^6$ in Formula (3) and preferred conditions are also the same.

$R^3$ to $R^6$ in Formula (5) have the same meanings as $R^3$ to $R^6$ in Formula (3) and preferred conditions are also the same.

$R^9$ to $R^{12}$ in Formula (5) have the same meanings as $R^9$ to $R^{12}$ in Formula (AY) and preferred conditions are also the same.

$R^{a1}$ and $R^{a2}$ in Formula (5) have the same meanings as $R^{a1}$ and $R^{a2}$ in Formula (1) and preferred conditions are also the same.

(Substituent W)

The substituent W in the present specification will be described below.

Examples of the substituent W include a halogen atom (such as a fluorine atom, a chlorine atom, a bromine atom, and an iodine atom), an alkyl group, an alkenyl group (including a cycloalkenyl group and a bicycloalkenyl group), an alkynyl group, an aryl group, a heterocycle group (the heterocycle group may be referred to as a heterocyclic group, and a heteroaryl group is included), a cyano group, a hydroxy group, a nitro group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclic thio group, a sulfamoyl group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, a boronic acid group (—B(OH)$_2$), a sulfo group, a carboxy group, a phosphate group, a phosphonyl group, a phosphoryl group, a monosulfate ester group, a monophosphate ester group, a phosphonic acid group, a phosphinic acid group, a boronic acid group, and other known substituents.

In addition, the substituent W may be further substituted with the substituent W. For example, an alkyl group may be substituted with a halogen atom.

The details of the substituent W are described in paragraph [0023] of JP2007-234651A.

(Alkyl Group AL)

The alkyl group AL preferably has, for example, 1 to 15 carbon atoms, more preferably has 1 to 10 carbon atoms, and still more preferably has 1 to 6 carbon atoms. The alkyl group may be any of linear, branched, or cyclic.

Examples of the alkyl group include a methyl group, an ethyl group, an n-propyl group, an i-propyl group, an n-butyl group, a t-butyl group, an n-hexyl group, a cyclopentyl group, and the like.

In addition, the alkyl group may be, for example, a cycloalkyl group, a bicycloalkyl group, or a tricycloalkyl group, and may have a cyclic structure thereof as a partial structure.

A substituent which may be contained in the alkyl group is not particularly limited, an example thereof includes the substituent W, and an aryl group (preferably having 6 to 18 carbon atoms, and more preferably having 6 carbon atoms), and a heteroaryl group (preferably having 5 to 18 carbon atoms, and more preferably having 5 to 6 carbon atoms), or a halogen atom (preferably a fluorine atom or a chlorine atom) is preferable.

(Aryl Group AR)

An example of the aryl group AR includes an aryl group having 6 to 18 carbon atoms.

The aryl group may be monocyclic or polycyclic.

The aryl group is, for example, preferably a phenyl group, a naphthyl group, an anthryl group, or a fluorenyl group, and more preferably a phenyl group.

A substituent which may be contained in the aryl group is not particularly limited, and an example thereof includes the substituent W. Among these, as the substituent, an alkyl group which may further have a substituent (preferably having 1 to 10 carbon atoms) is preferable, and a methyl group or an i-propyl group is more preferable.

(Heteroaryl Group HA)

An example of the heteroaryl group HA includes a heteroaryl group having a monocyclic or polycyclic ring structure containing a hetero atom such as a sulfur atom, an oxygen atom, or a nitrogen atom.

The number of carbon atoms of the heteroaryl group is not particularly limited, but the heteroaryl group preferably has 3 to 18 carbon atoms, and more preferably has 3 to 5 carbon atoms.

The number of hetero atoms of the heteroaryl group is not particularly limited, but is preferably 1 to 10, more preferably 1 to 4, and still more preferably 1 to 2.

The number of ring members of the heteroaryl group is not particularly limited, but is preferably 3 to 8, more preferably 5 to 7, and still more preferably 5 to 6.

Examples of the heteroaryl group include a furyl group, a pyridyl group, a quinolyl group, an isoquinolyl group, an acridinyl group, a phenanthridinyl group, a pteridinyl group, a pyrazinyl group, a quinoxalinyl group, a pyrimidinyl group, a quinazolyl group, a pyridazinyl group, a cinnolinyl group, a phthalazinyl group, a triazinyl group, an oxazolyl group, a benzoxazolyl group, a thiazolyl group, a benzothiazolyl group, an imidazolyl group, a benzimidazolyl group, a pyrazolyl group, an indazolyl group, an isoxazolyl group, a benzisoxazolyl group, an isothiazolyl group, a benzisothiazolyl group, an oxadiazolyl group, a thiadiazolyl group, a triazolyl group, a tetrazolyl group, a benzofuryl group, a thienyl group, a benzothienyl group, a dibenzofuryl group, a dibenzothienyl group, a pyrrolyl group, an indolyl group, an imidazopyridinyl group, a carbazolyl group, and the like.

A substituent which may be contained in the heteroaryl group is not particularly limited, and an example thereof includes the substituent W.

Specific compounds are exemplified below.

In a case where the specific compounds exemplified below were applied to Formula (1), the specific compounds exemplified below include all geometric isomers that can be distinguished based on the C=C double bond constituted by a carbon atom to which $R^1$ bonds and a carbon atom adjacent thereto. That is, both the cis isomer and the trans isomer which are distinguished based on the C=C double bond are included in the specific compounds exemplified below, respectively.

In the following examples, Me represents a methyl group and Ph represents a phenyl group.

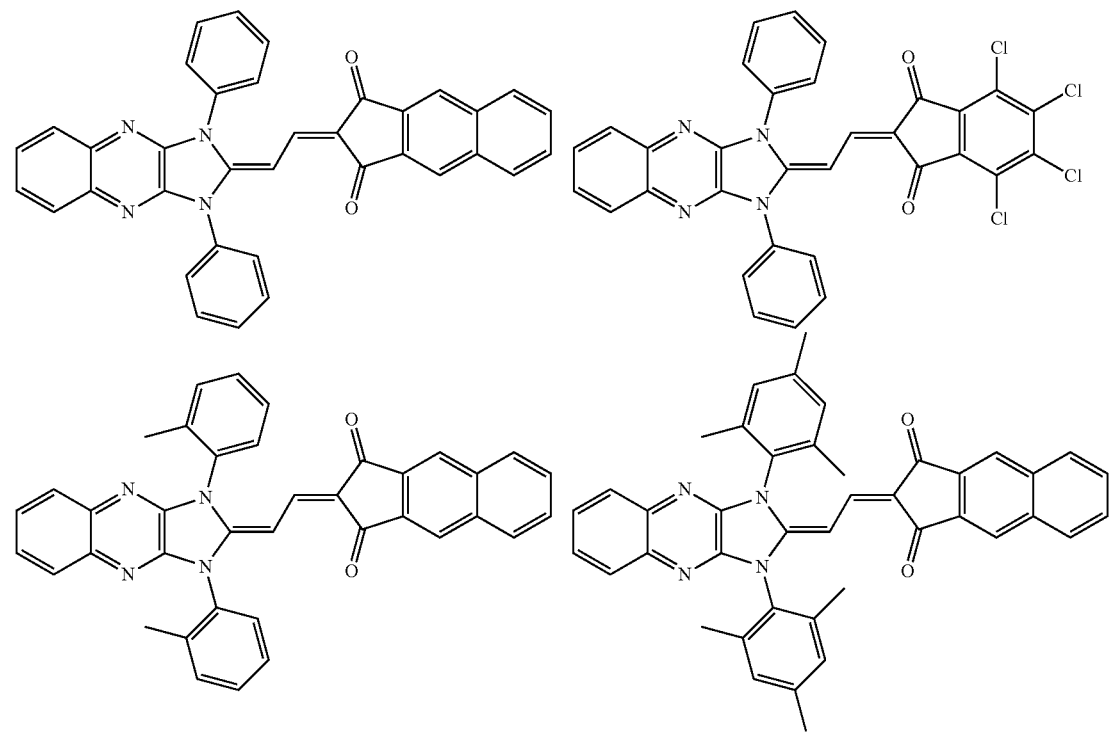

21 22
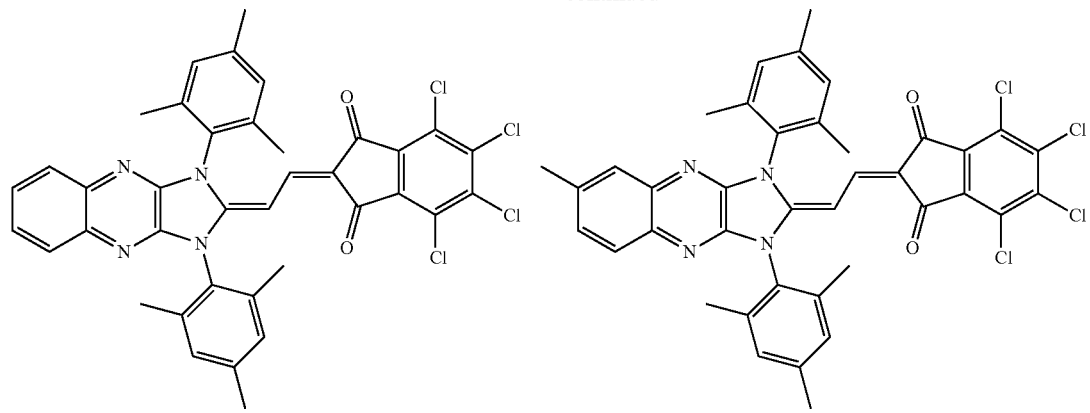
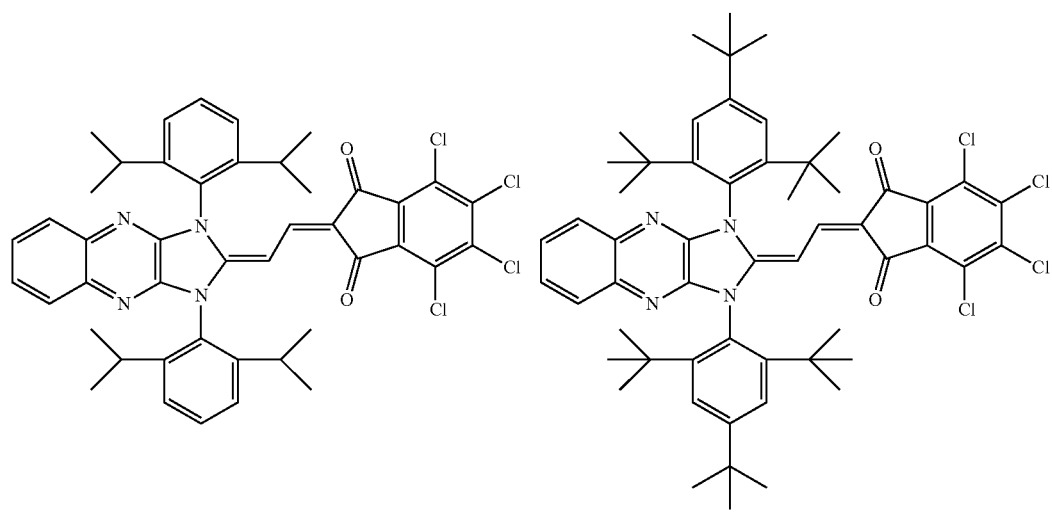
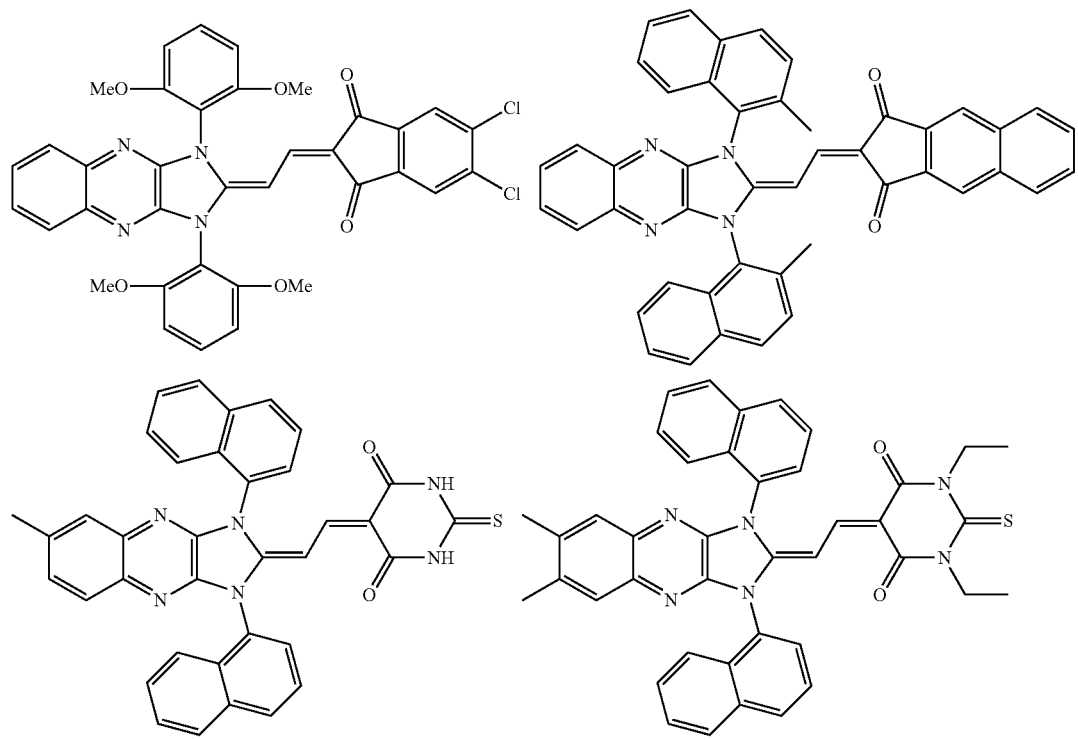

23 24
-continued
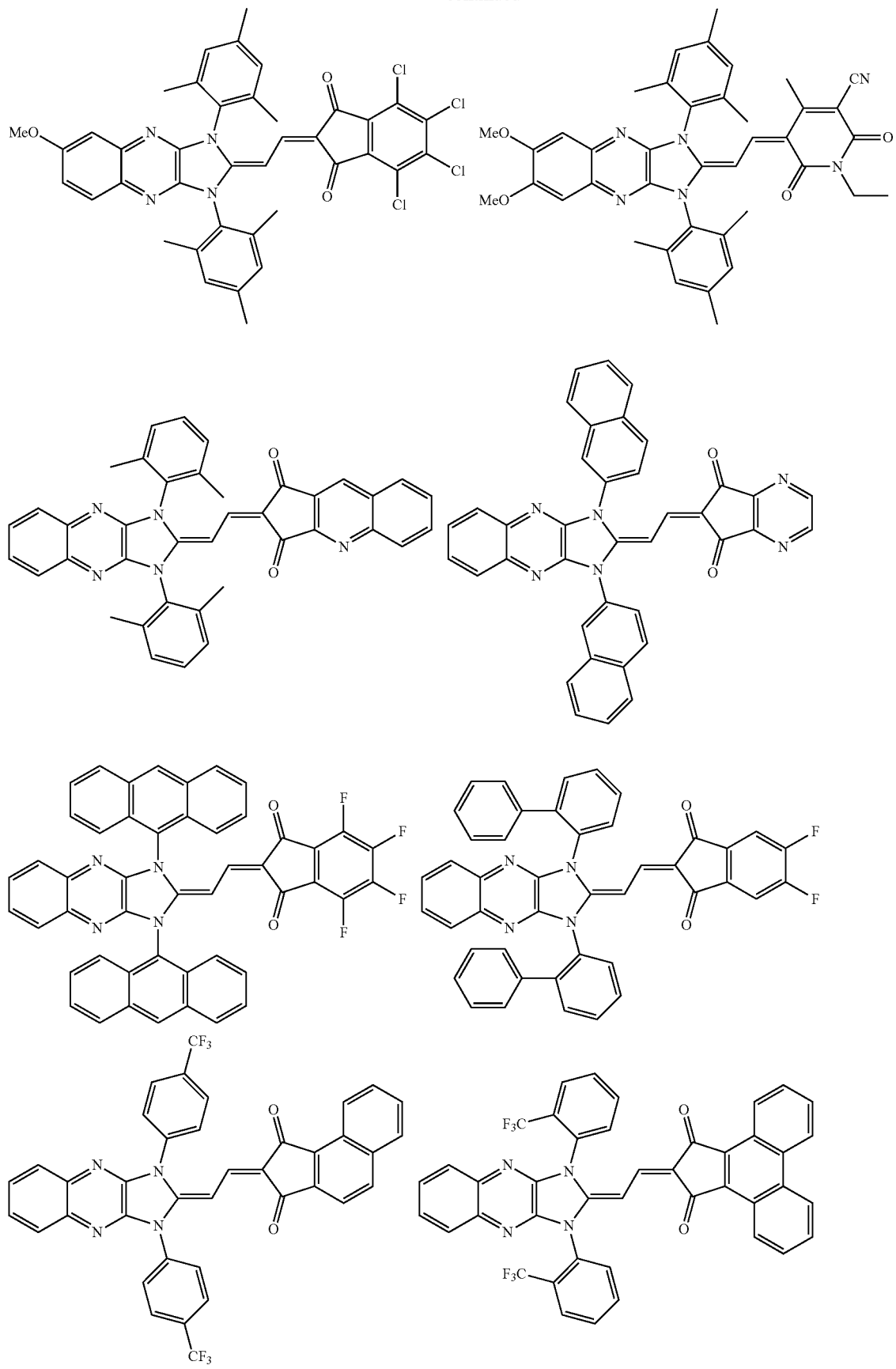

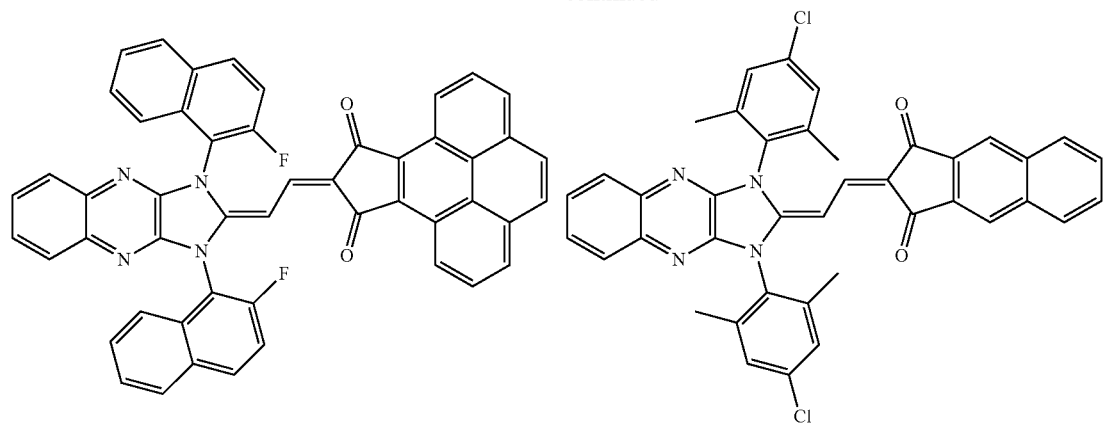
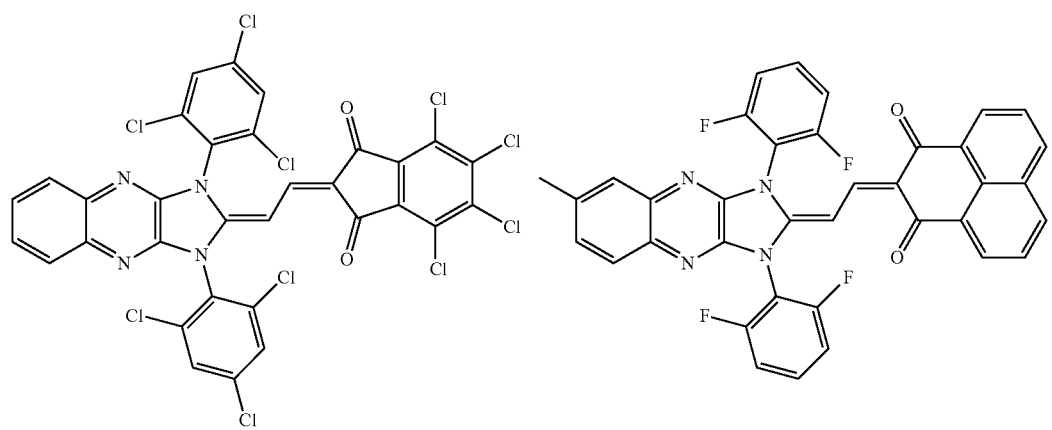
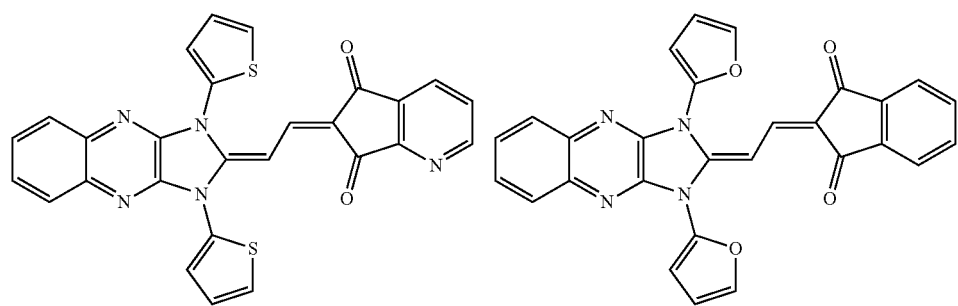
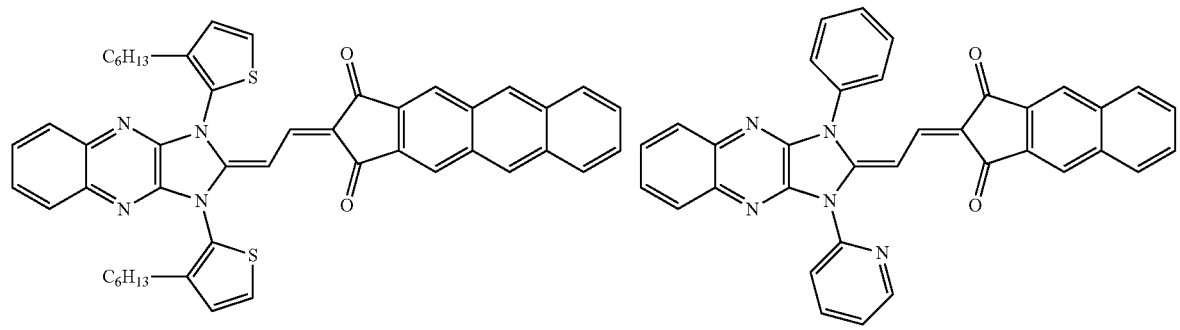

-continued
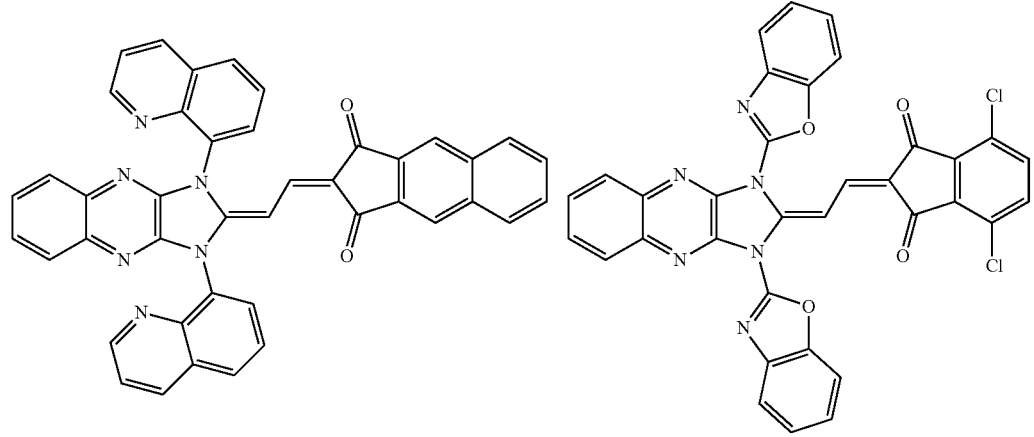
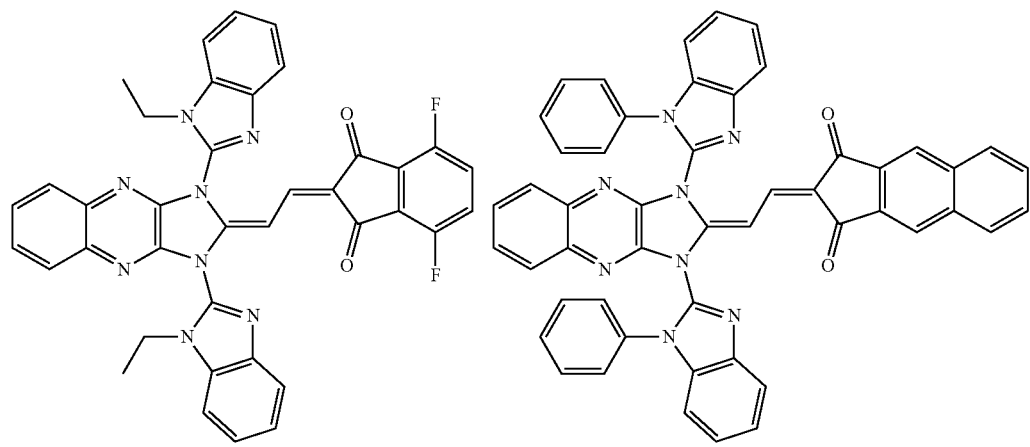
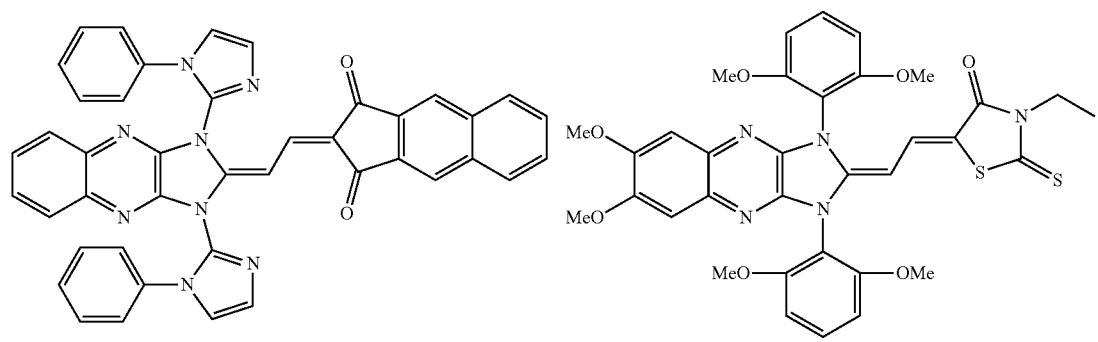
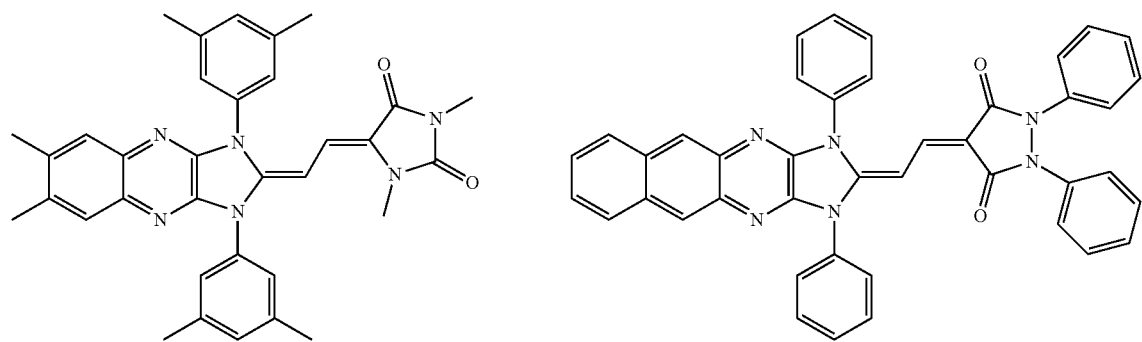

-continued
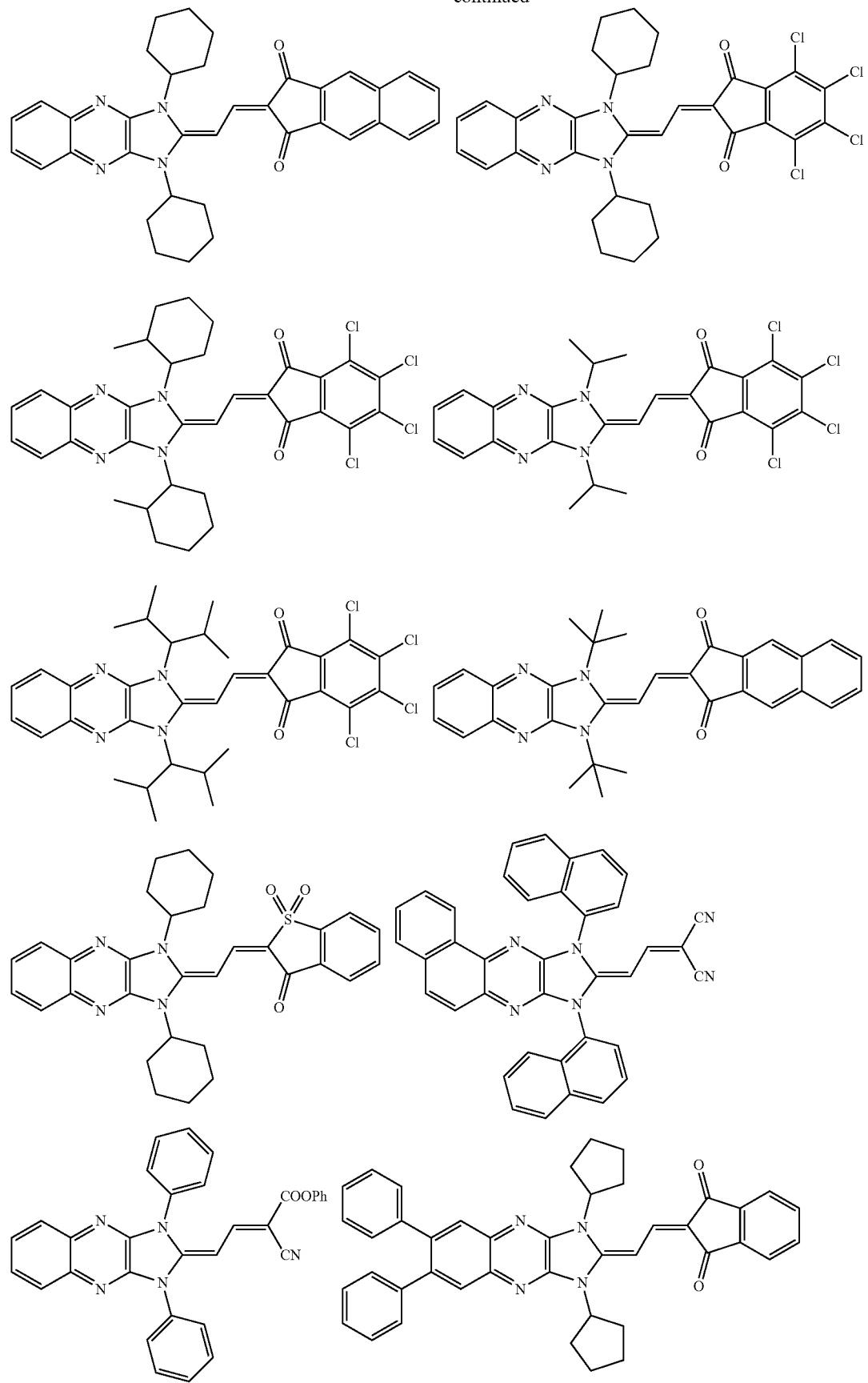

-continued
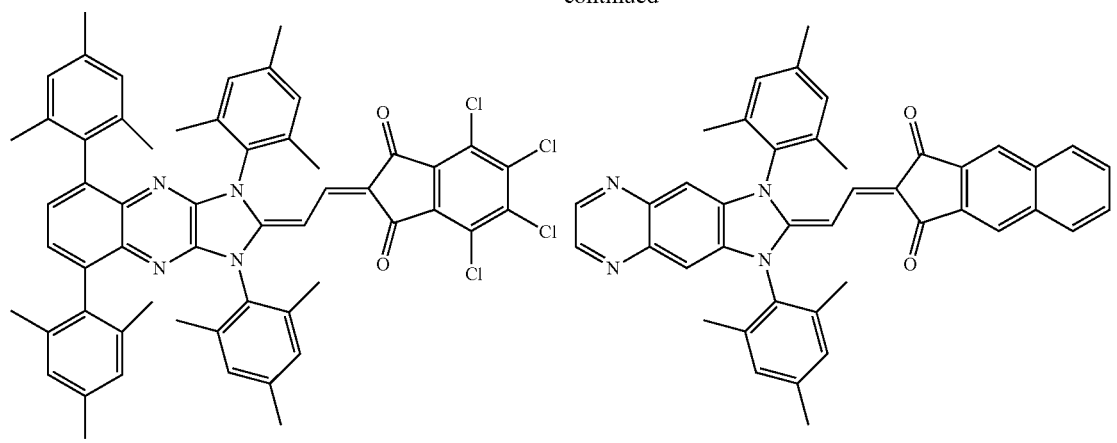
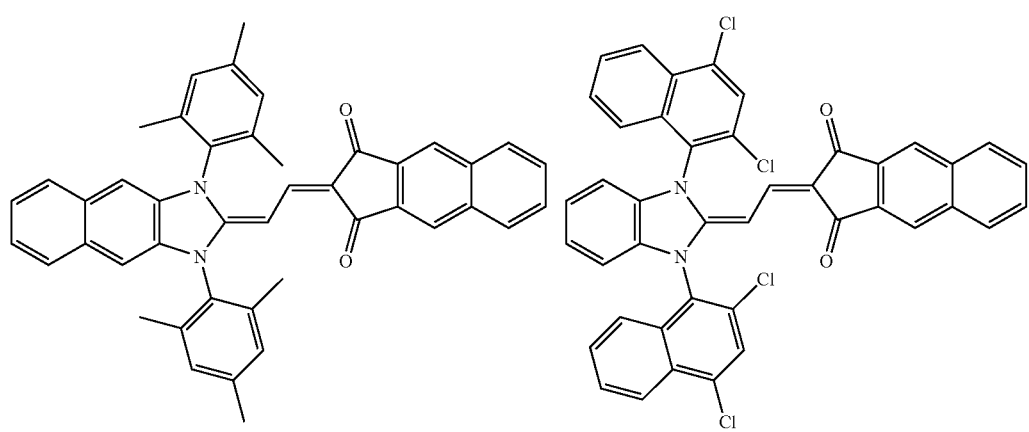
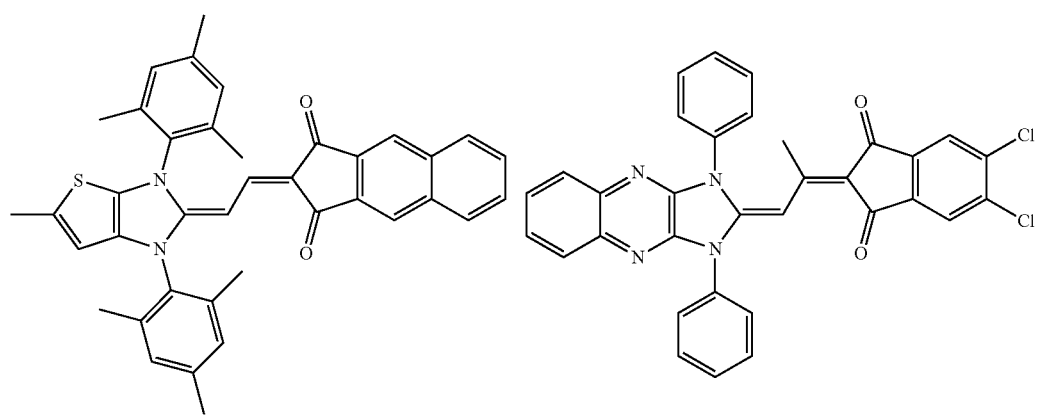
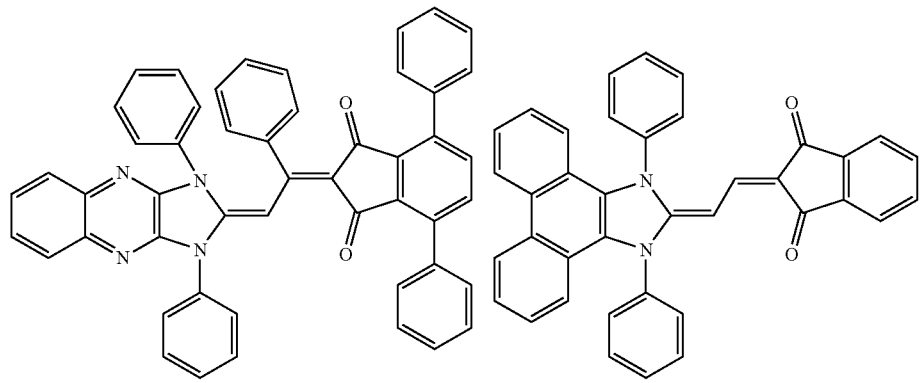

33 34
-continued
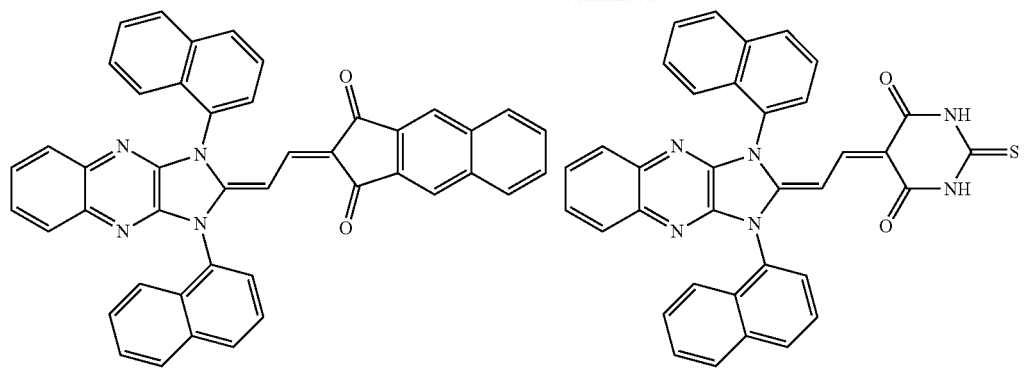
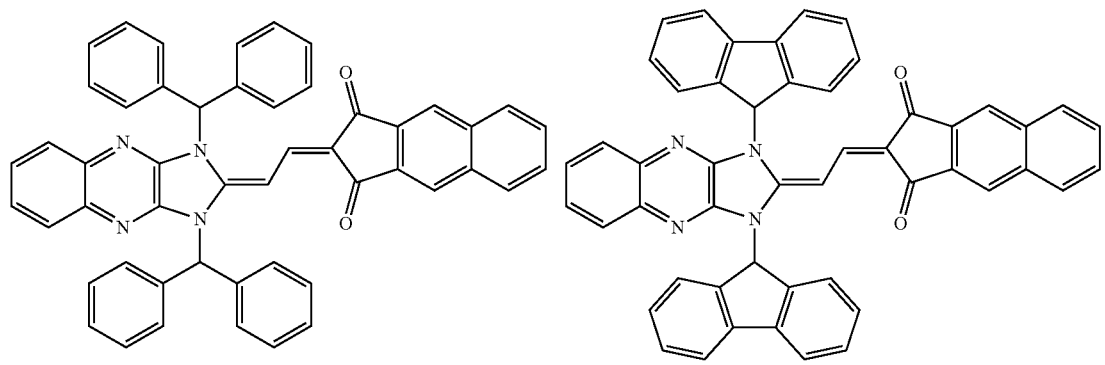
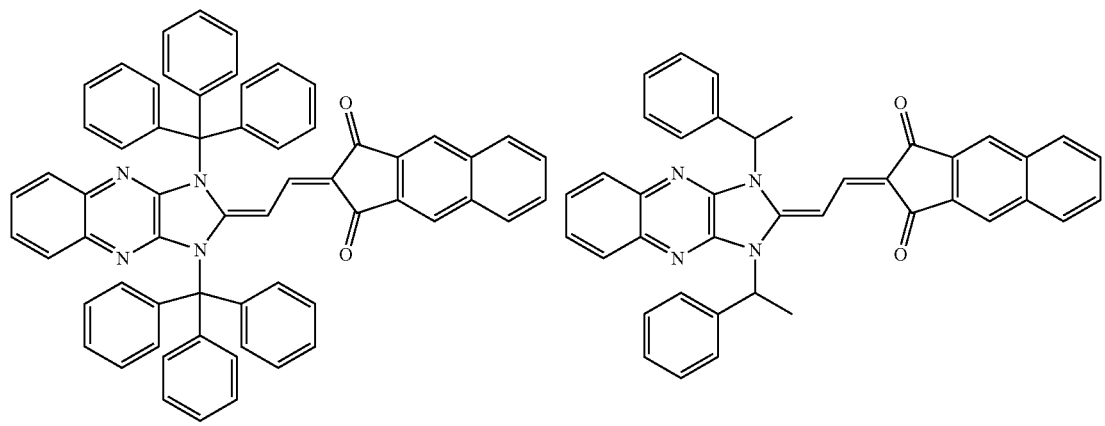
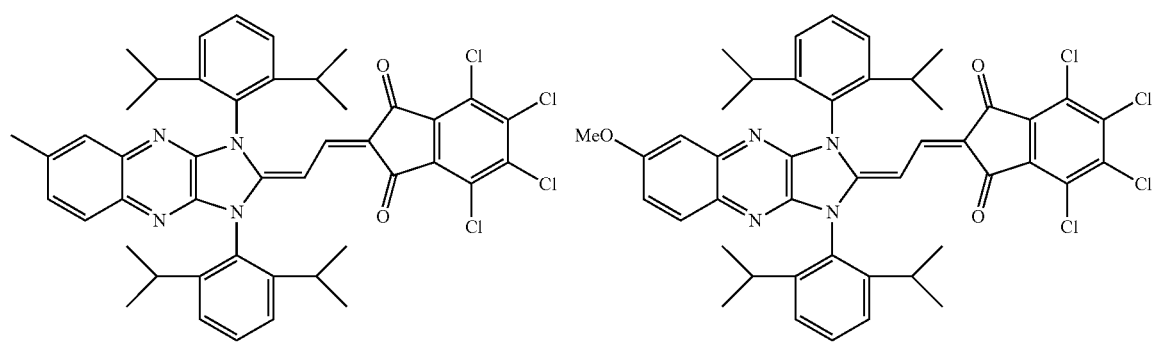

-continued
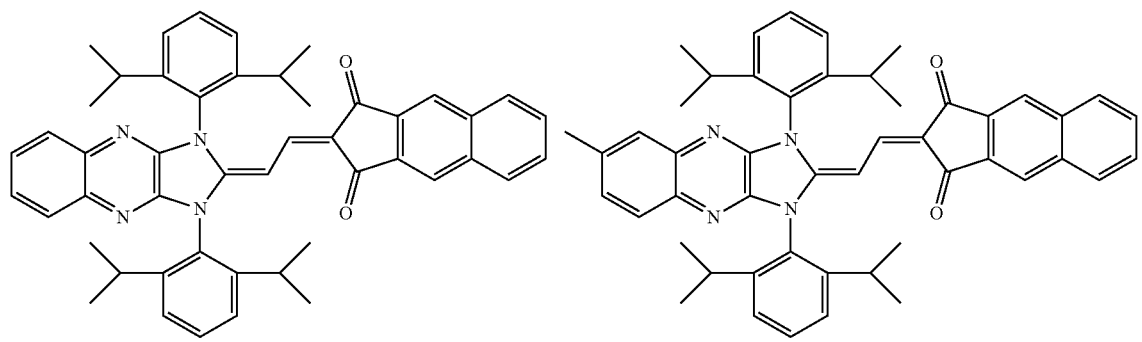
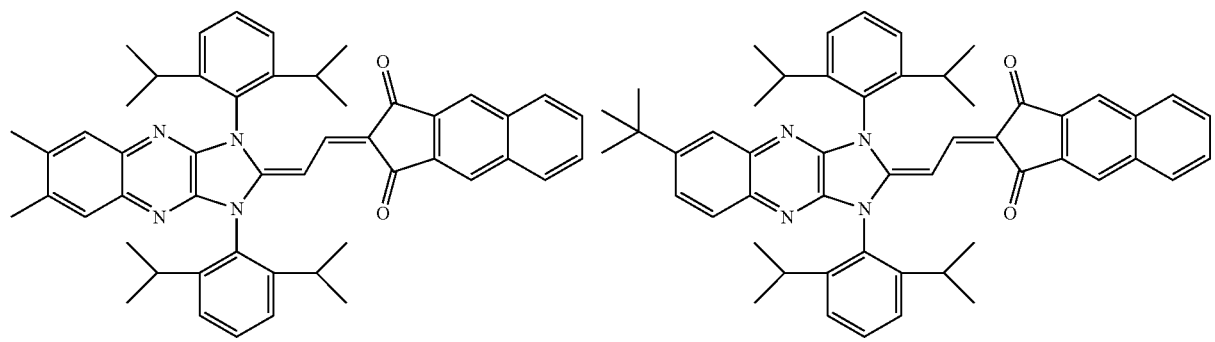
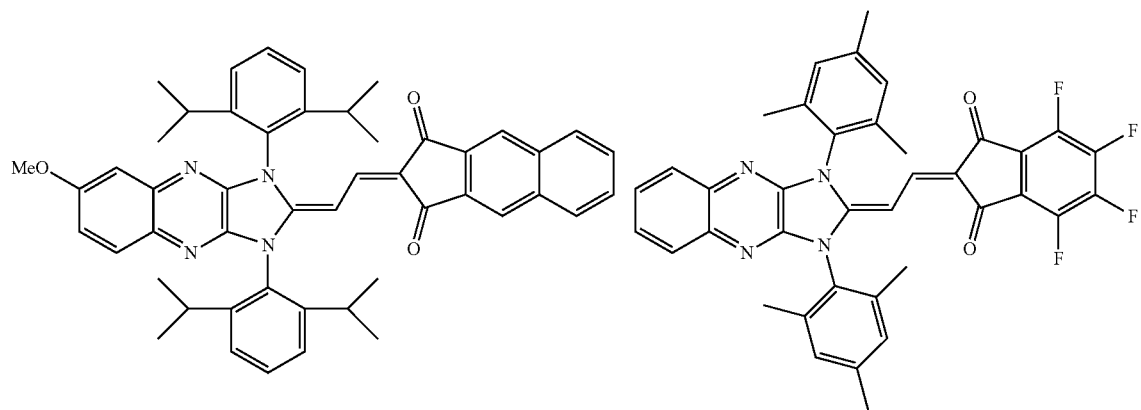
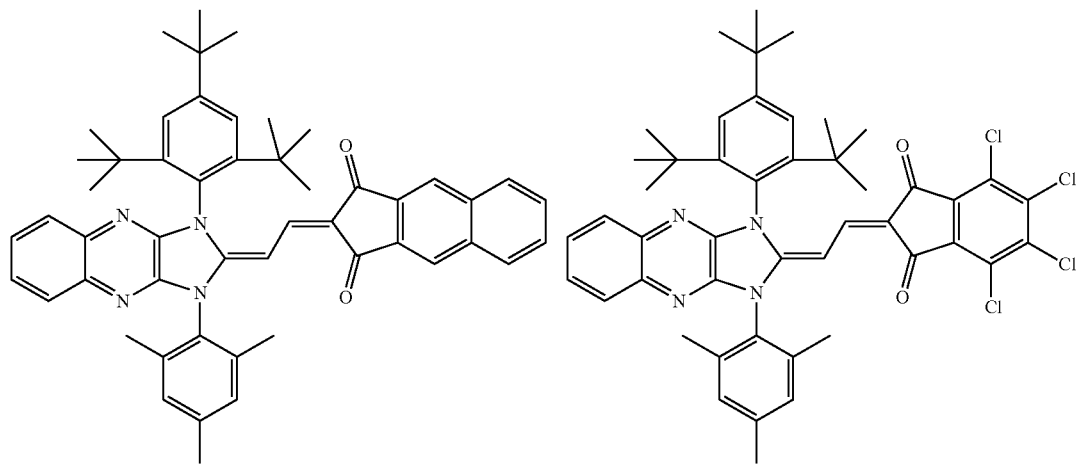

37 38
-continued
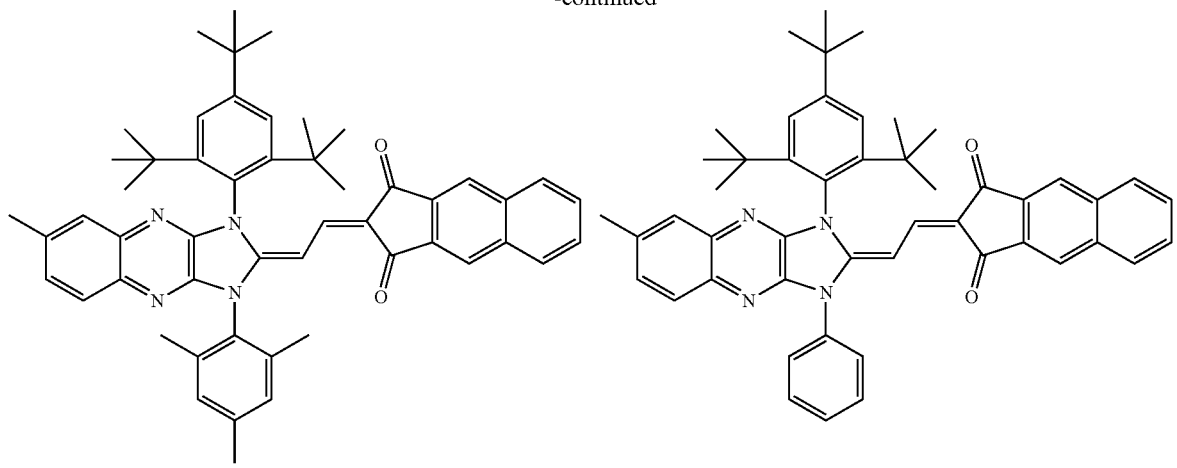
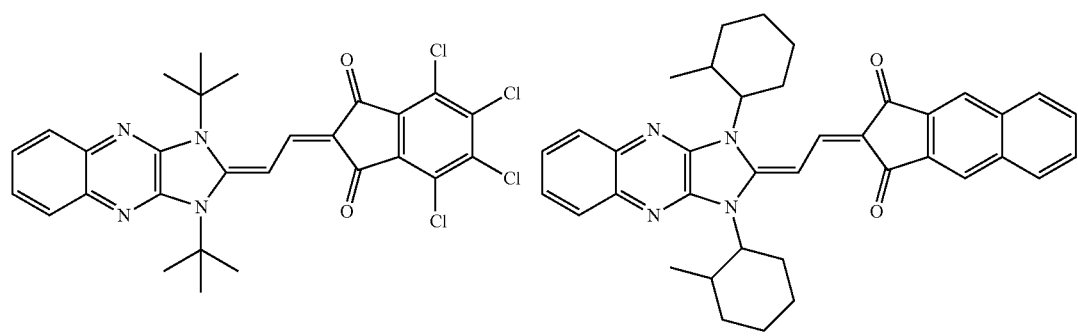
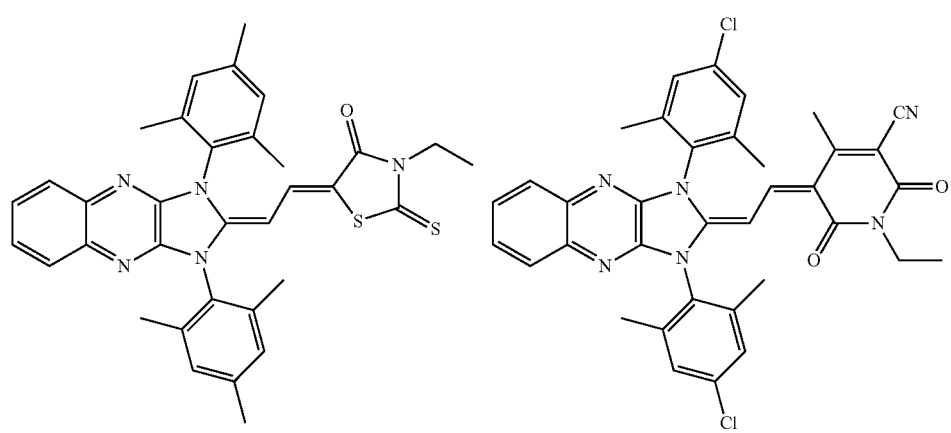
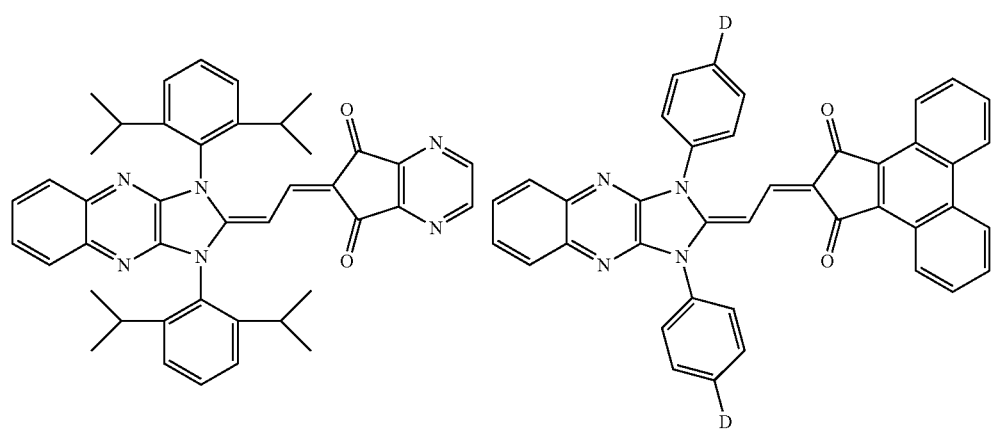

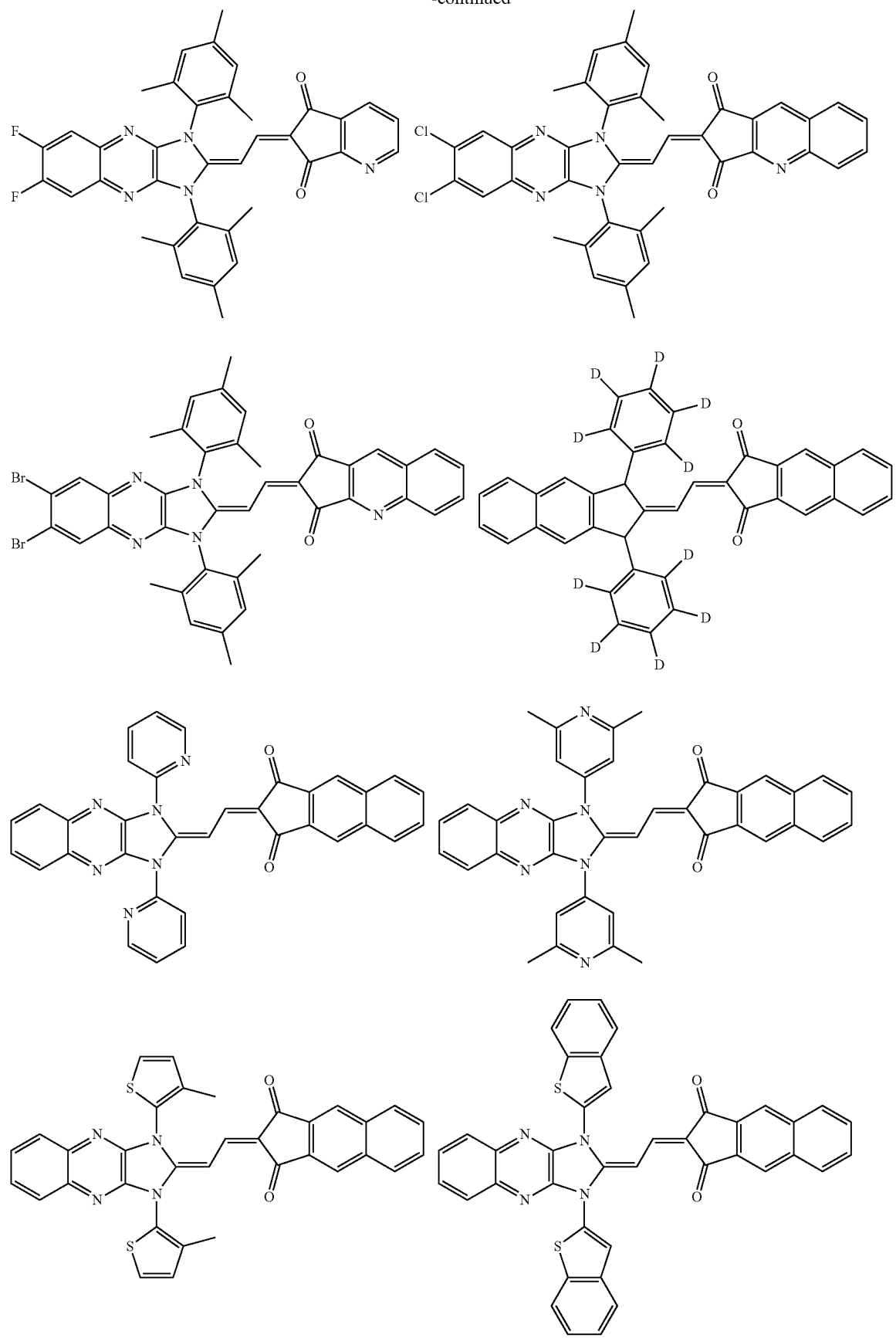

-continued
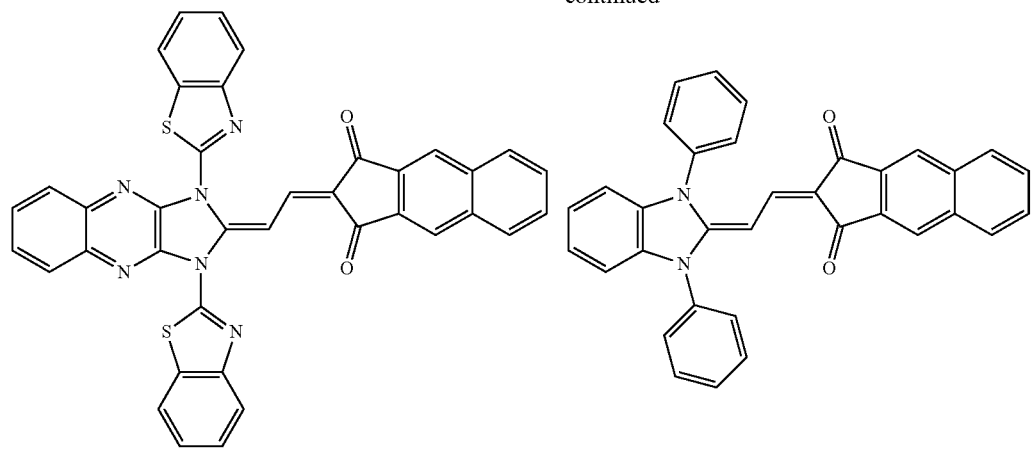
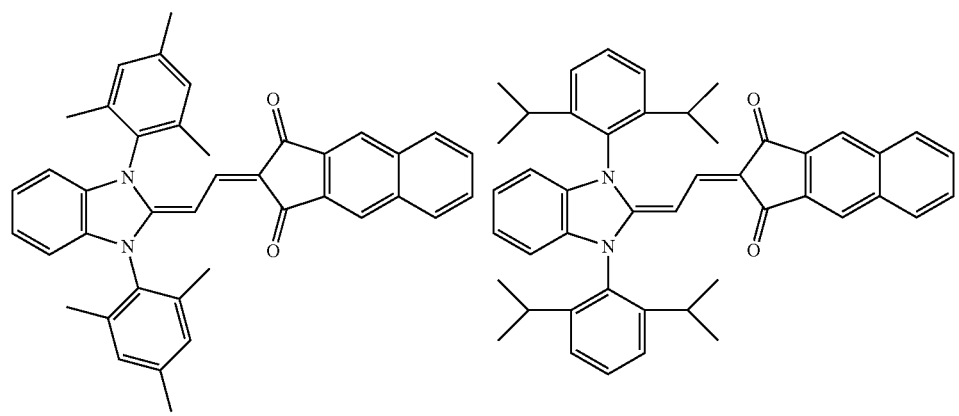
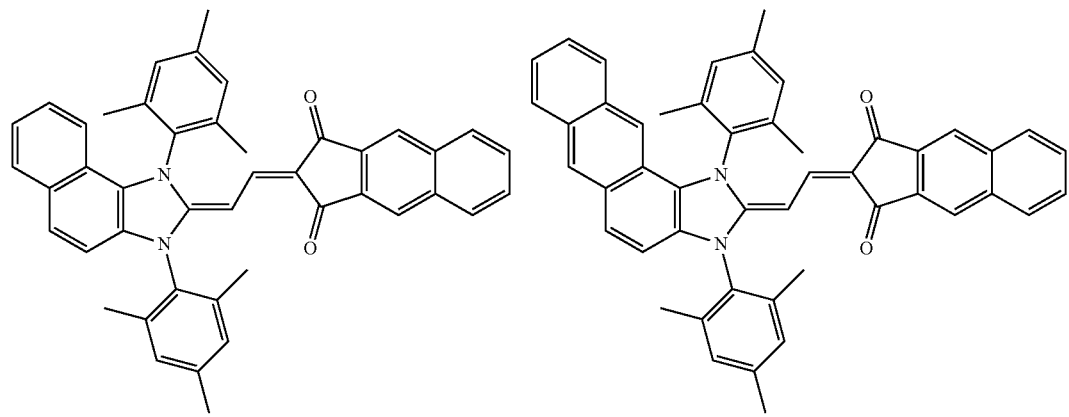
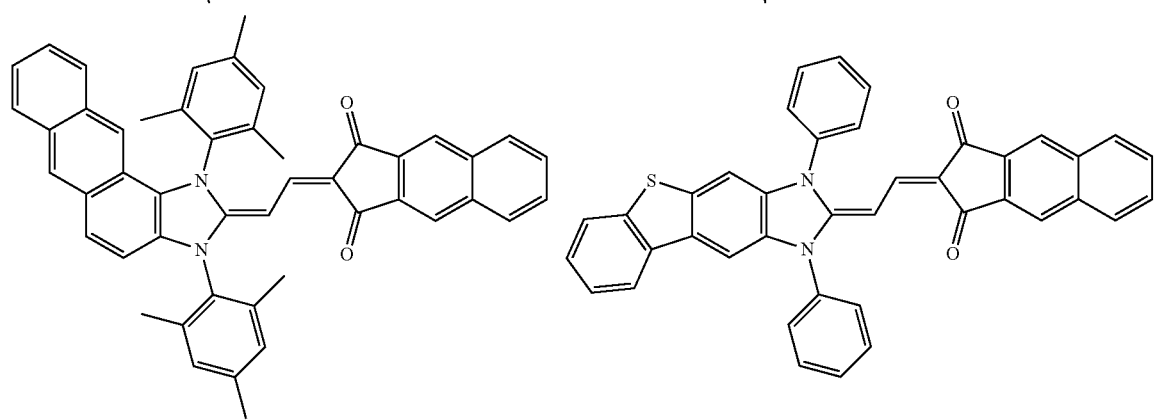

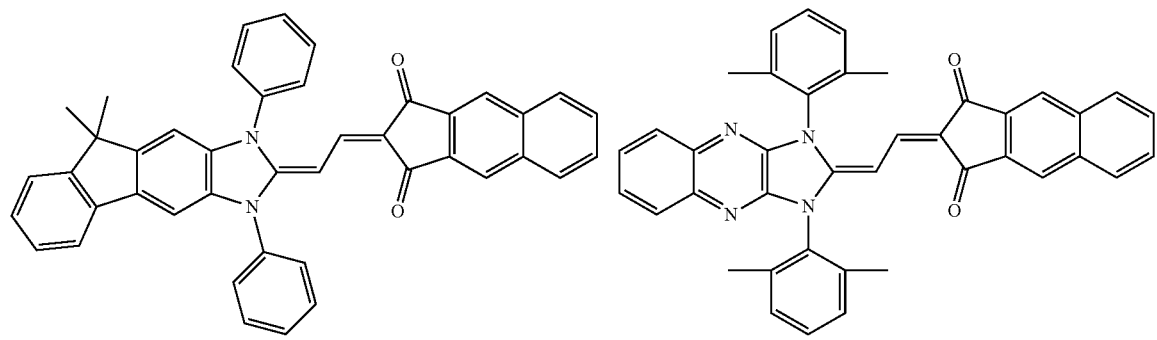
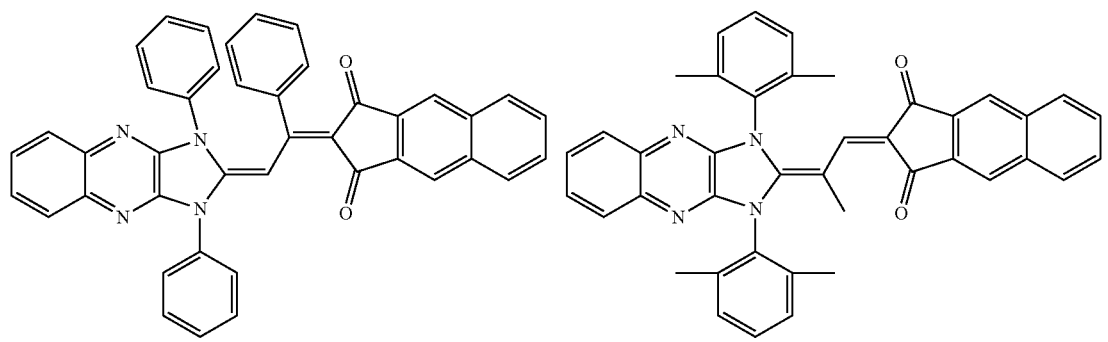
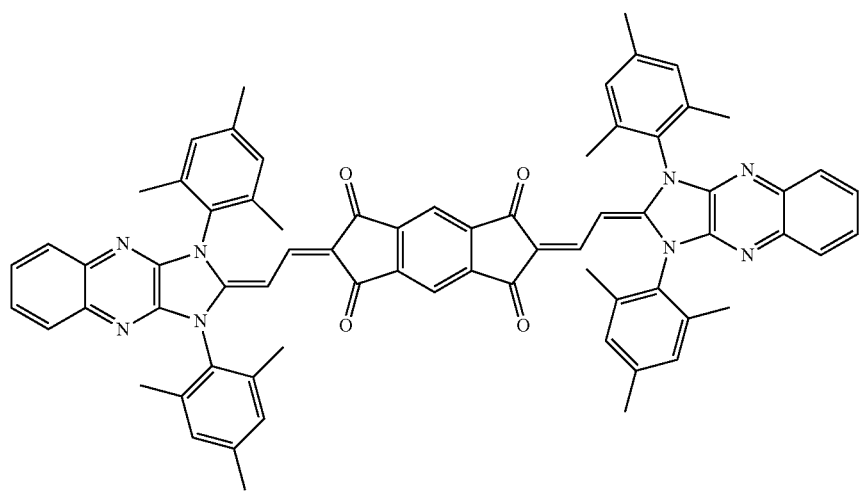
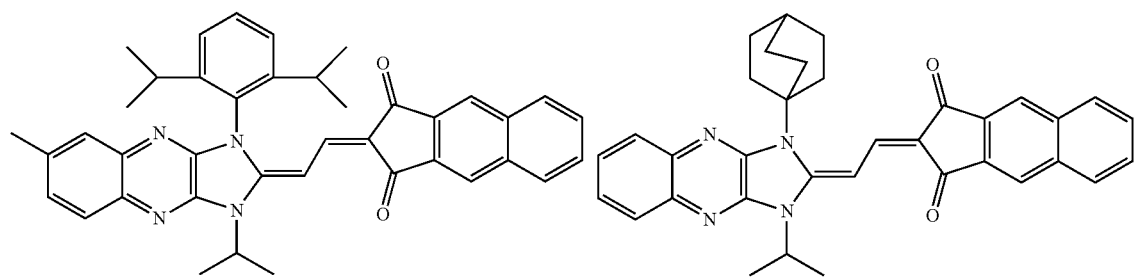

-continued
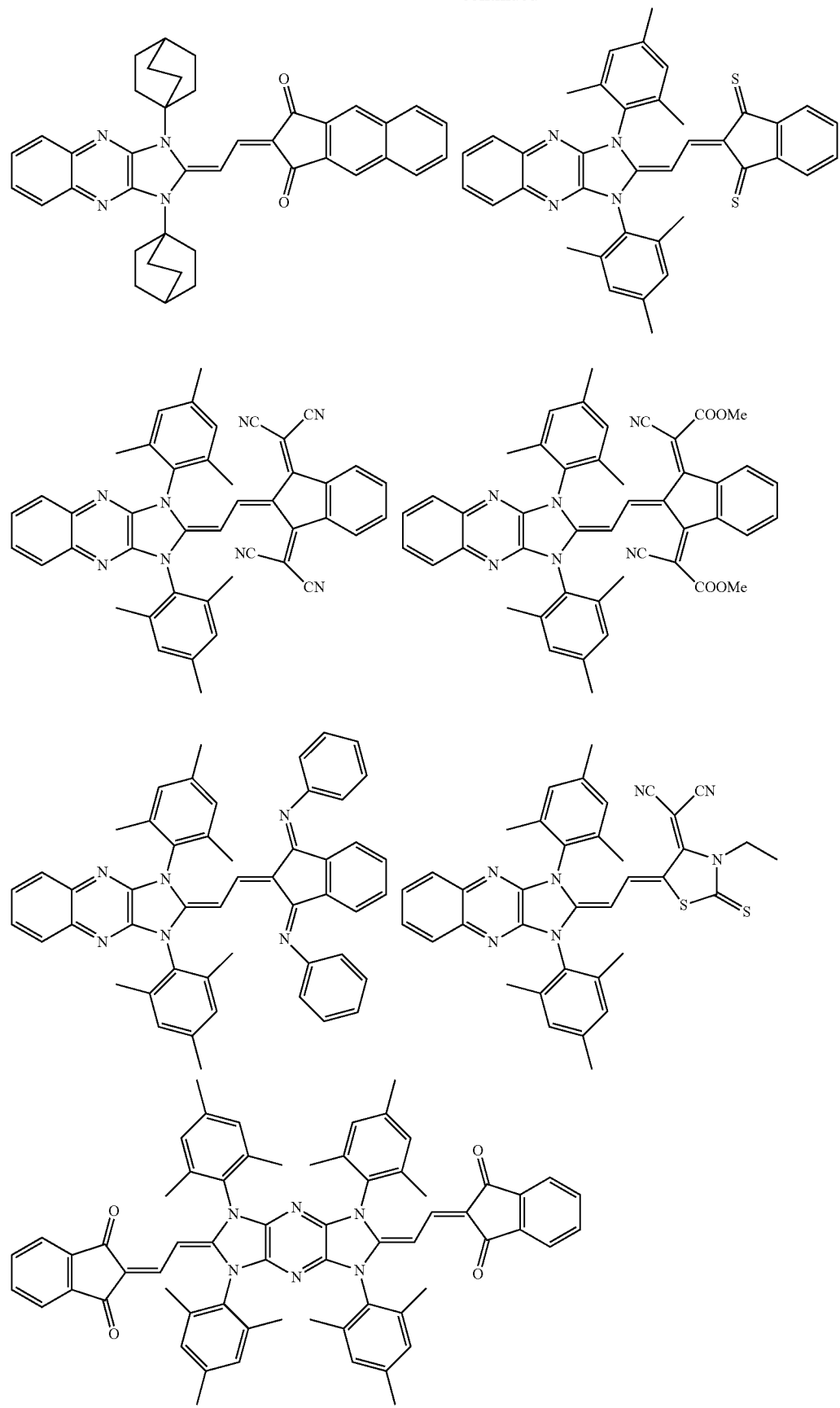

47
48
-continued
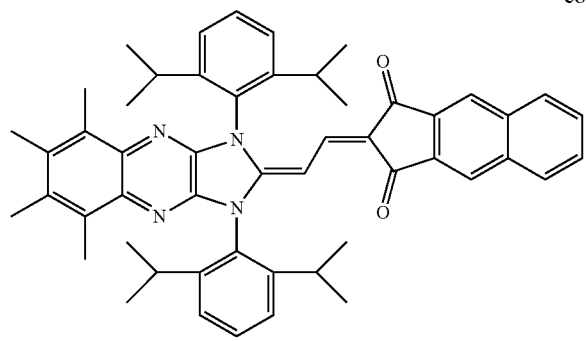
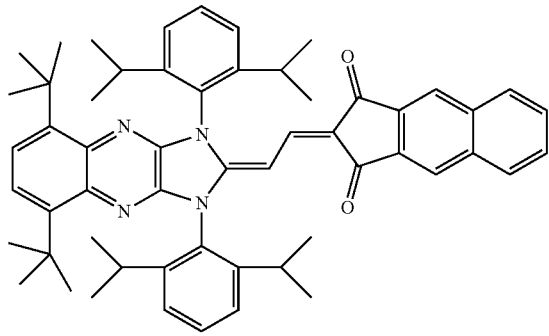
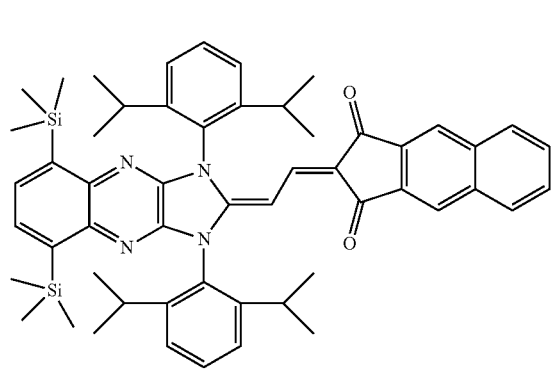
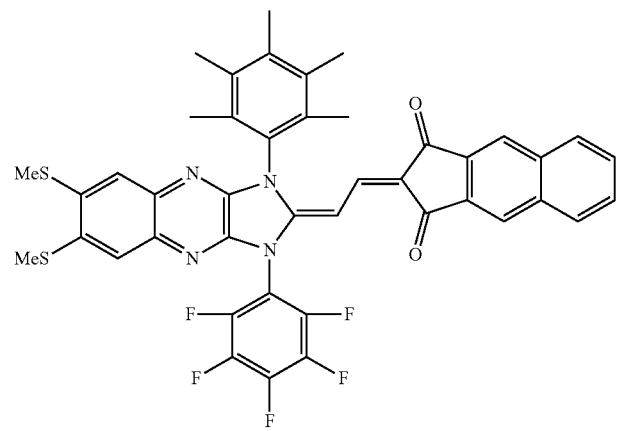
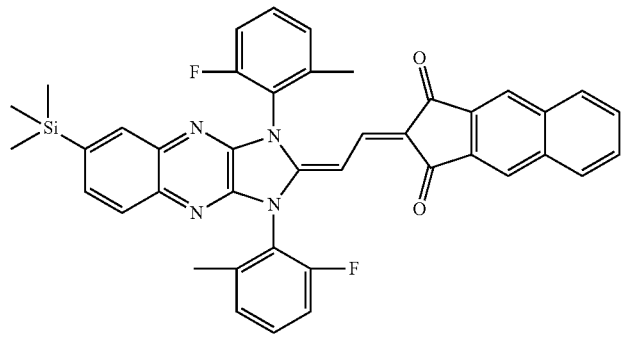
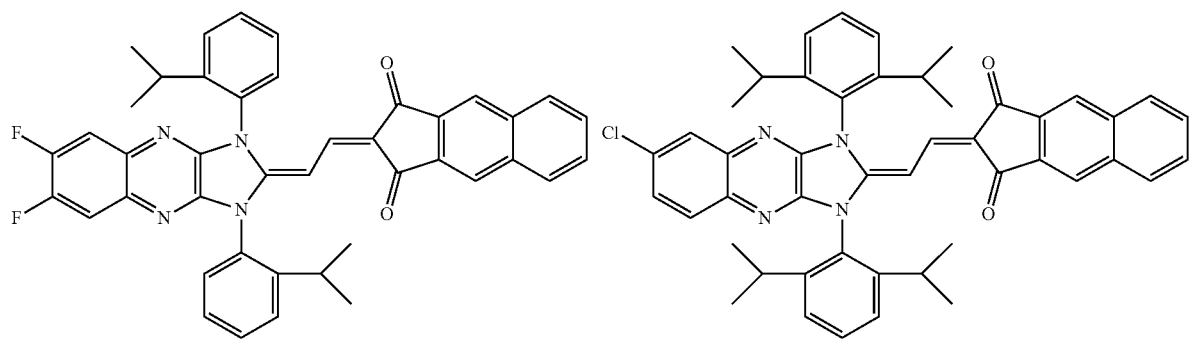

49 50
-continued
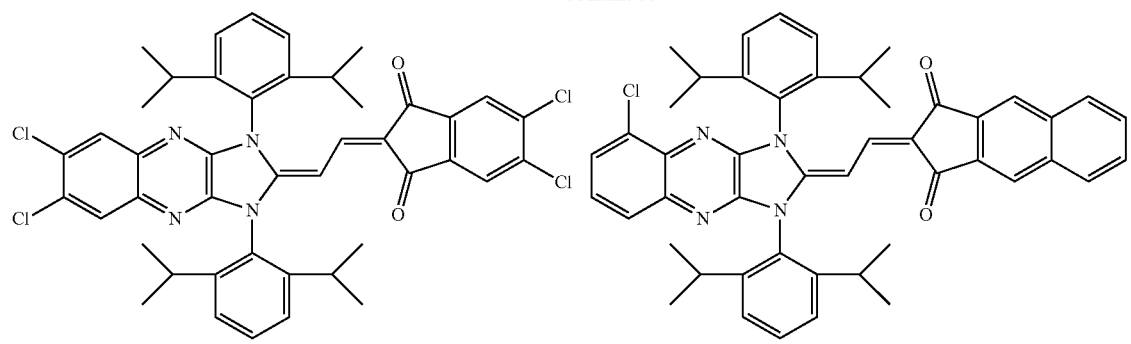
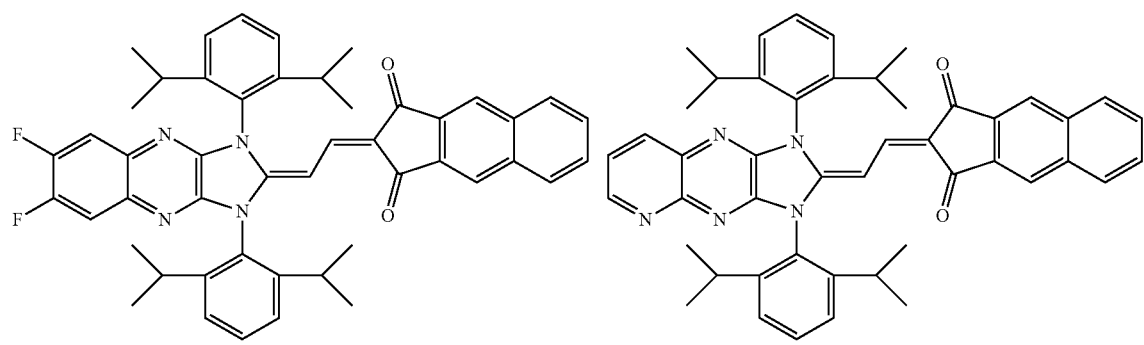
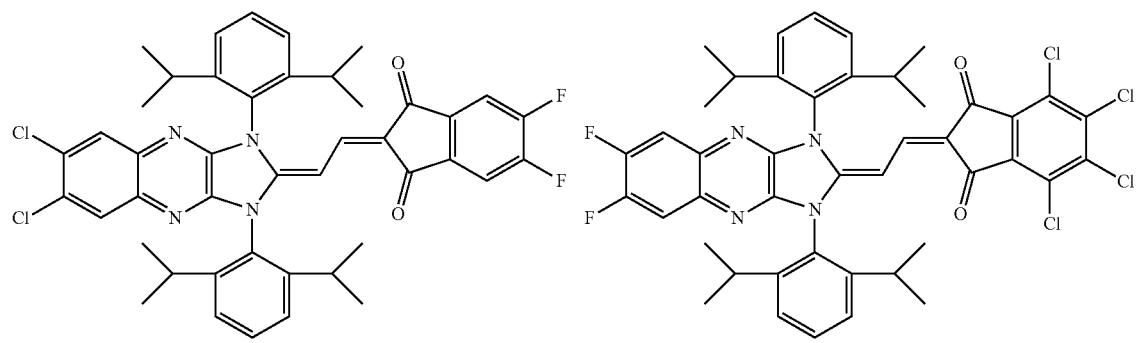
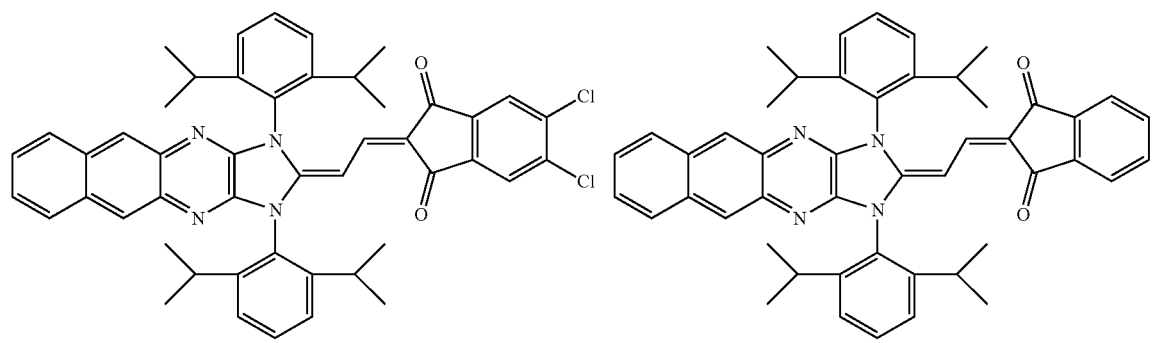

-continued
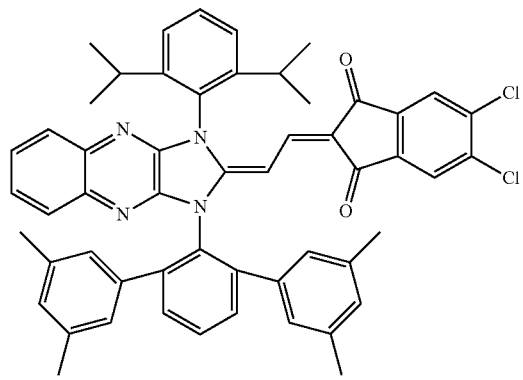
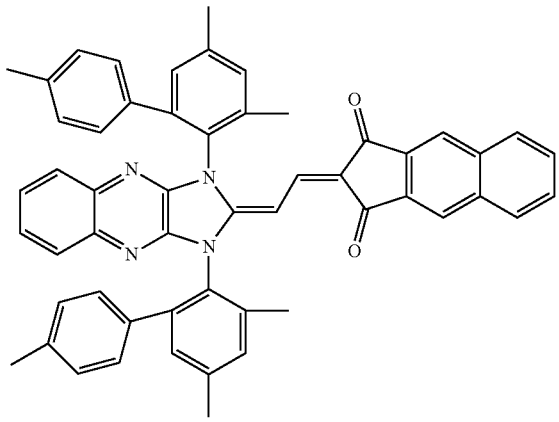
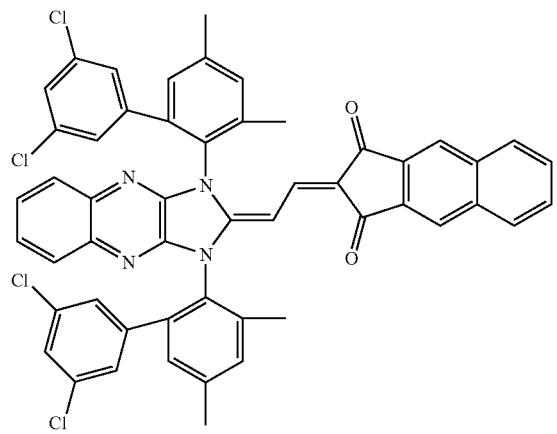
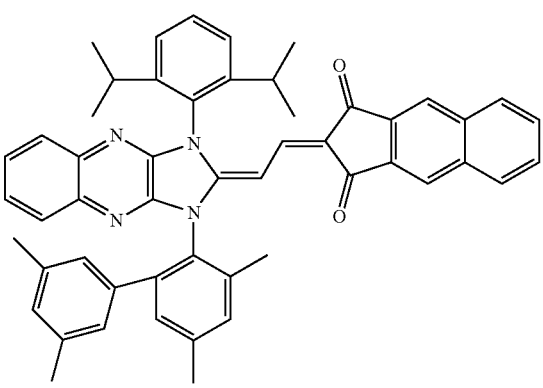
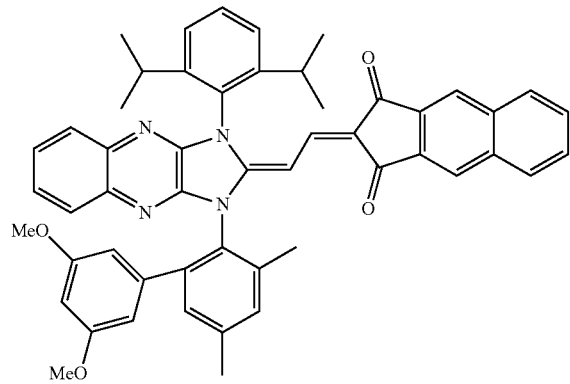
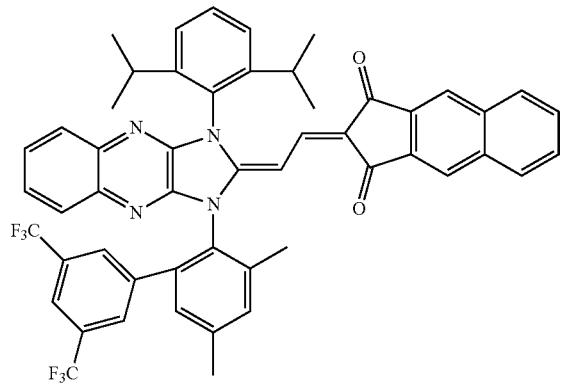
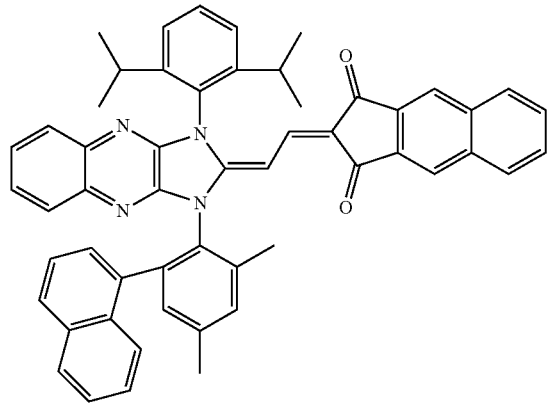
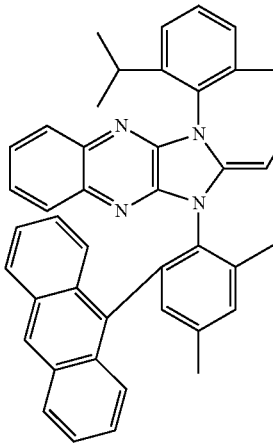

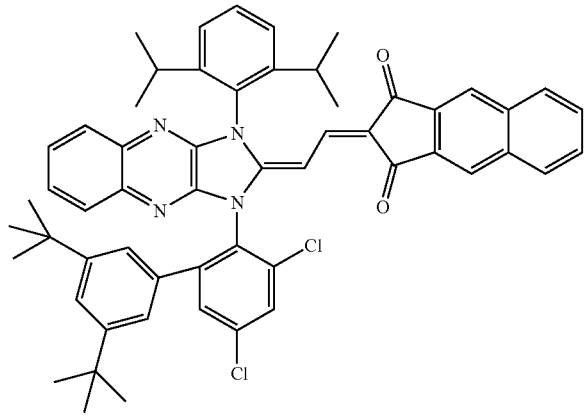
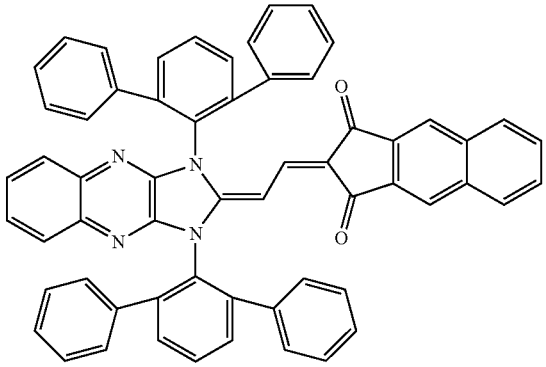
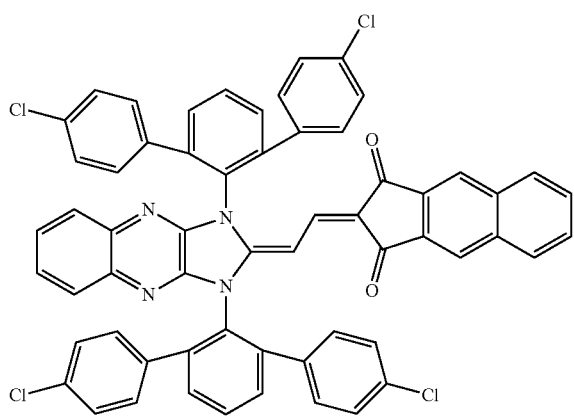
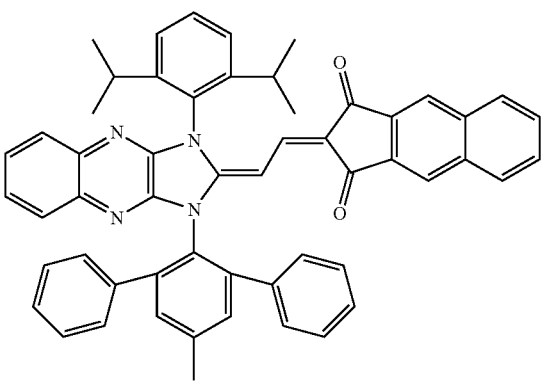
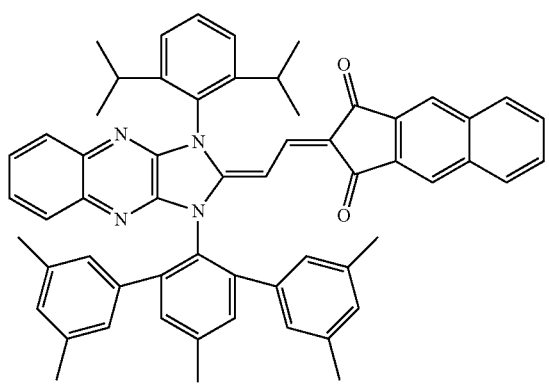
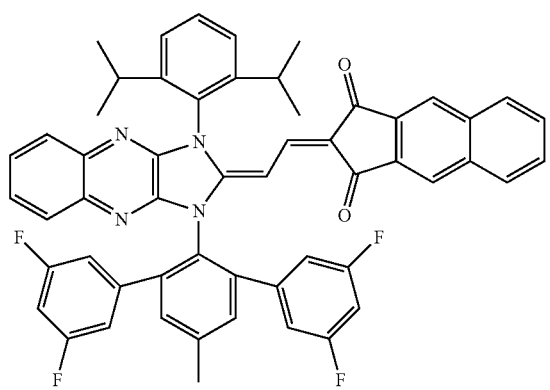
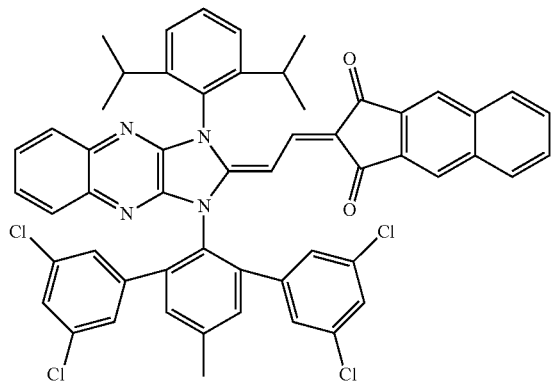
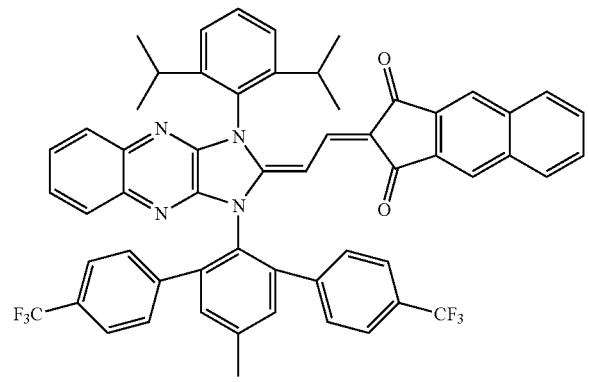

-continued
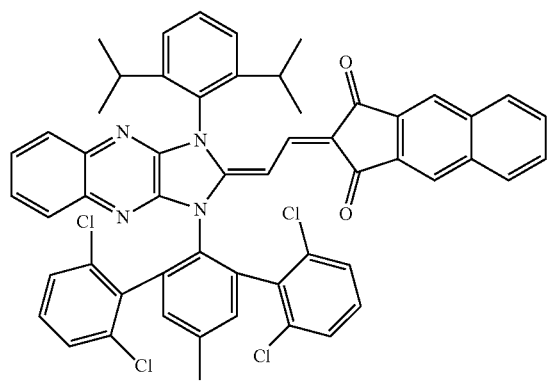 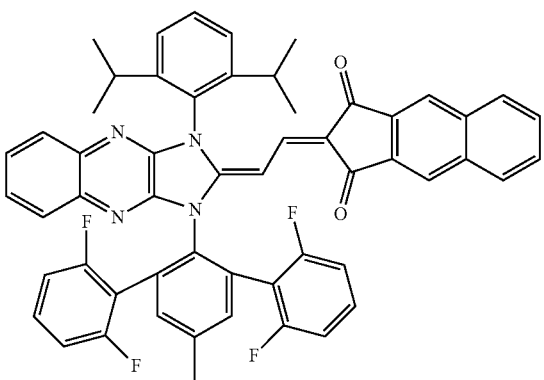
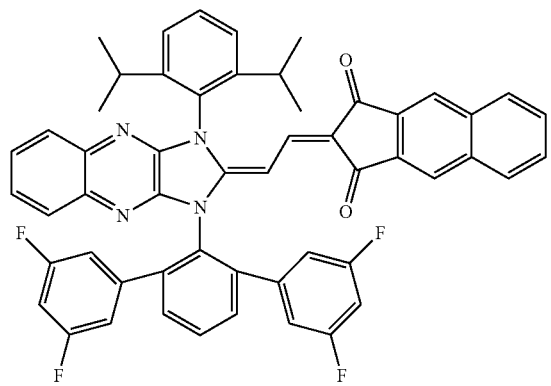 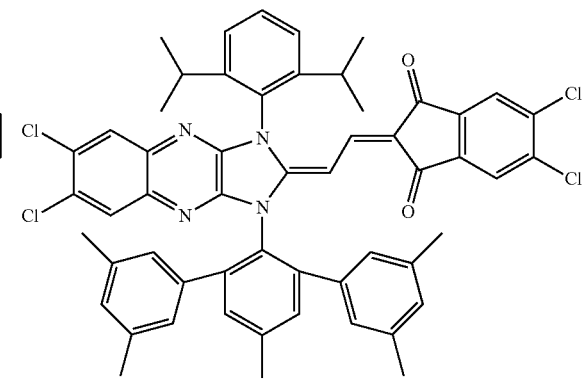
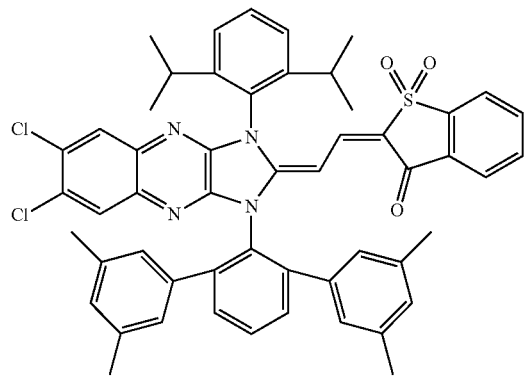 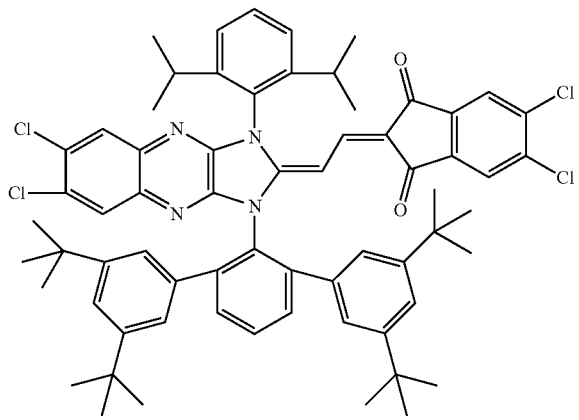
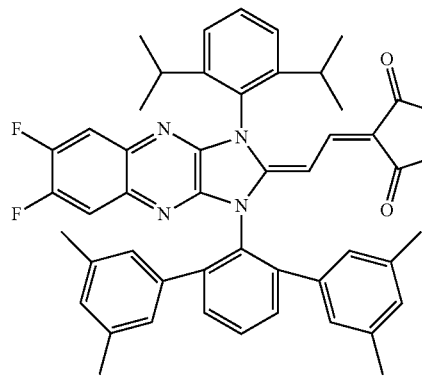 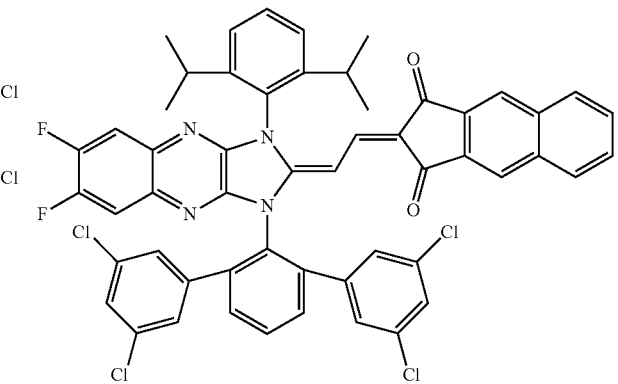

-continued
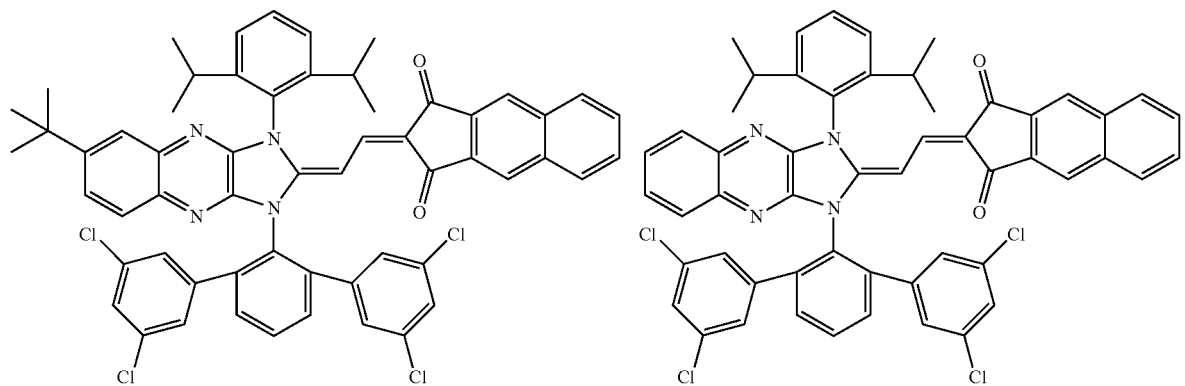
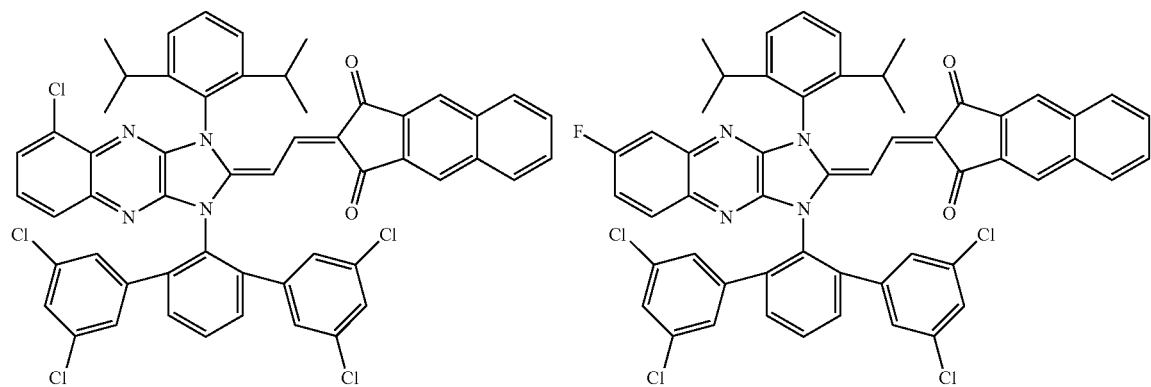
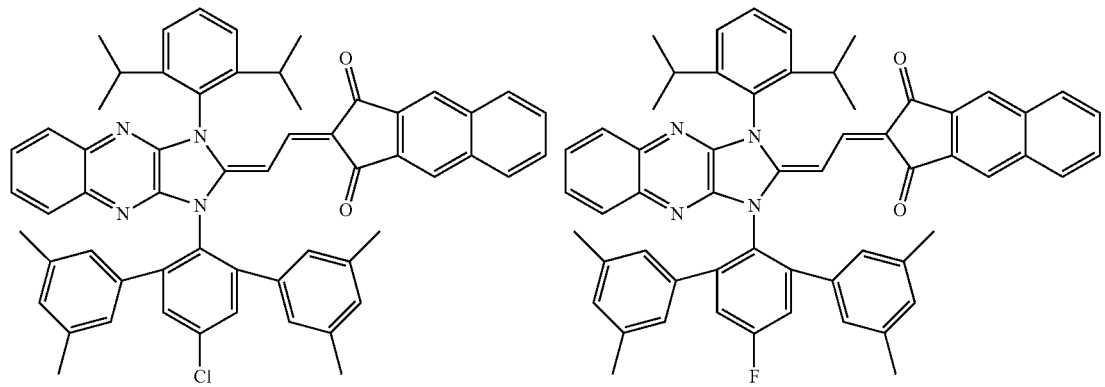
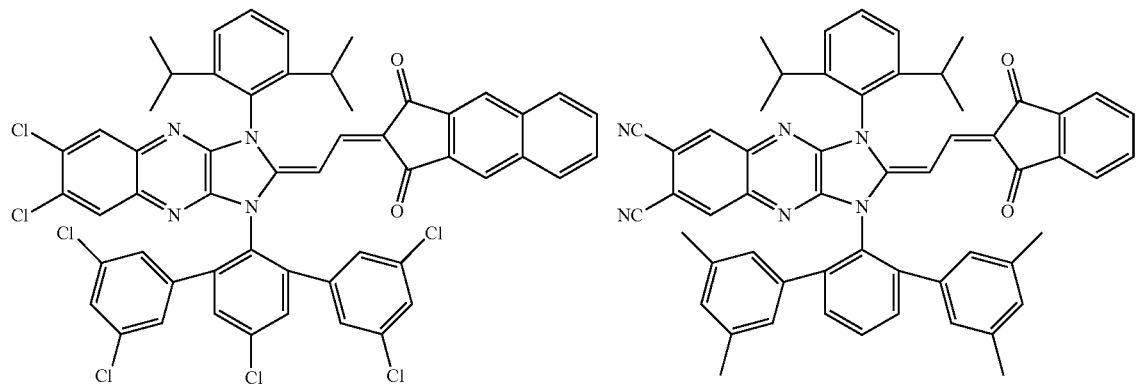

-continued
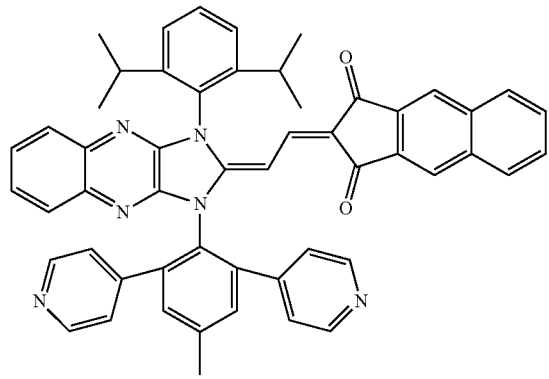
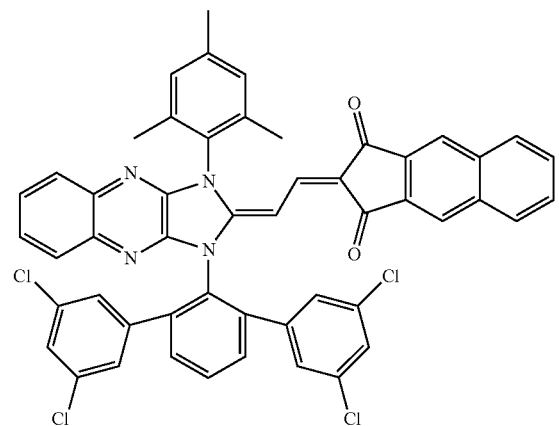
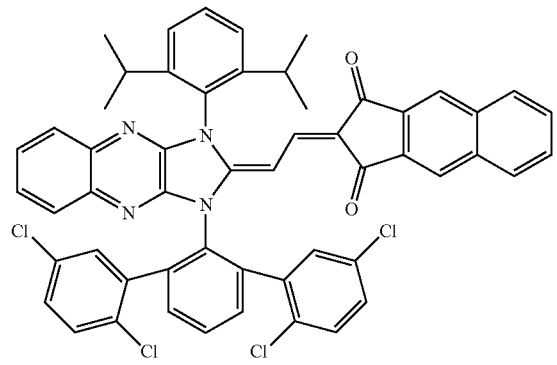
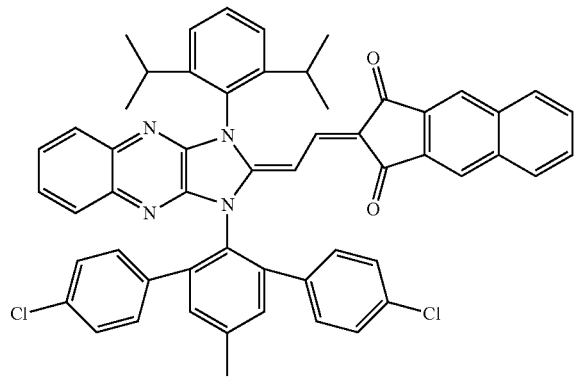
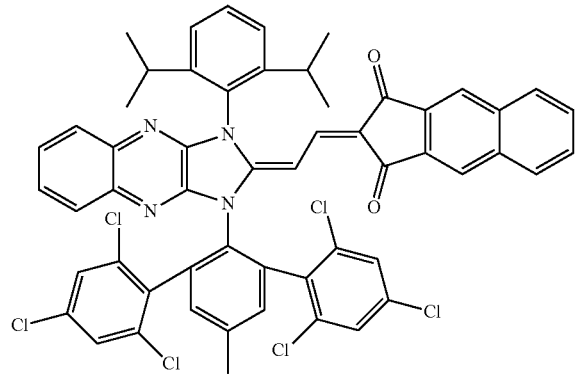
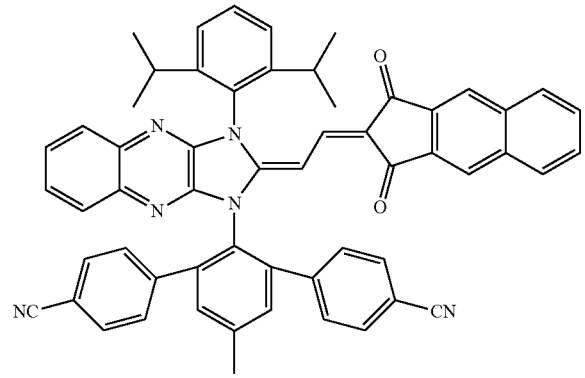
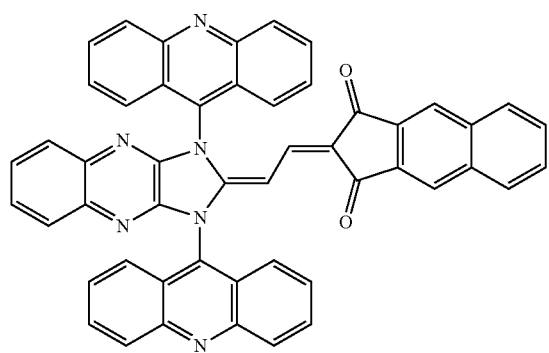
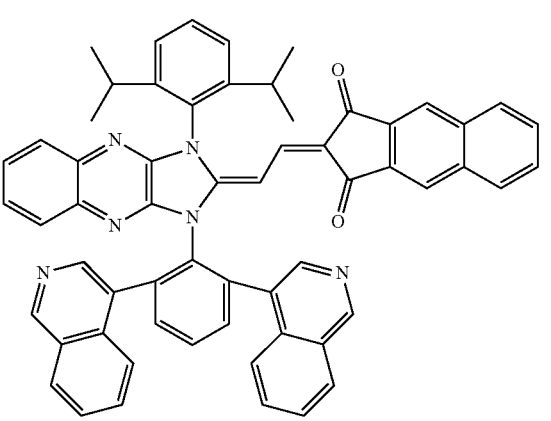

-continued
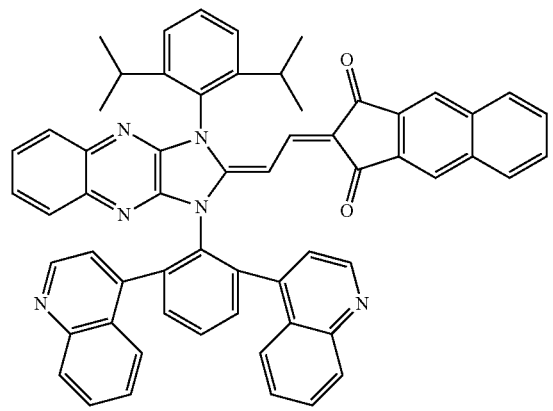
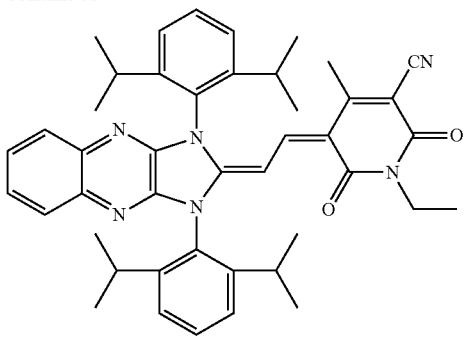
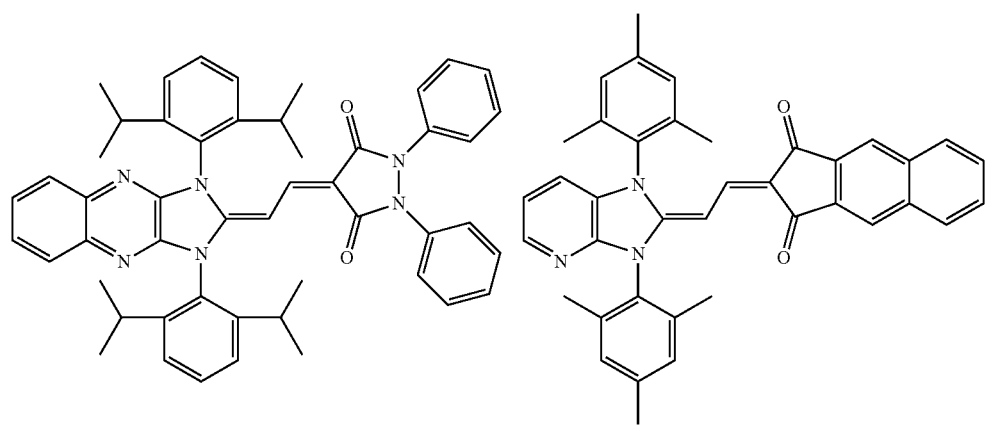
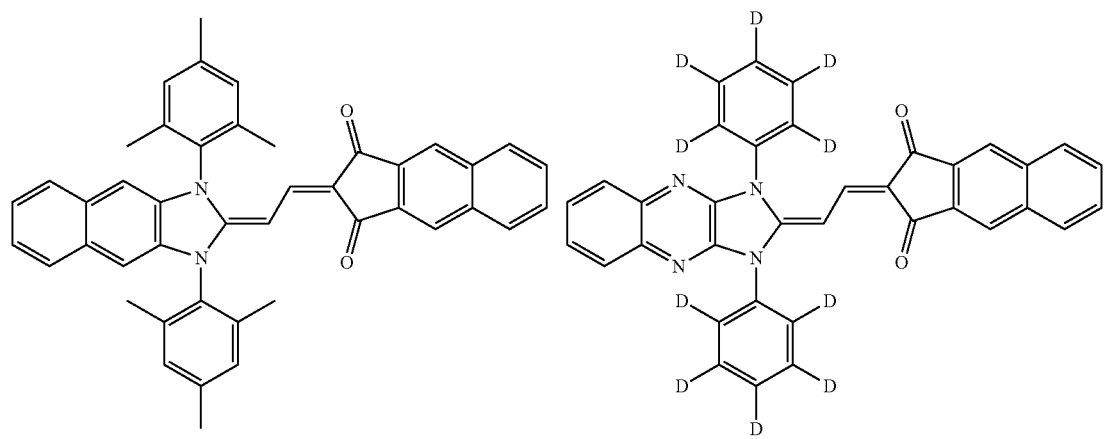
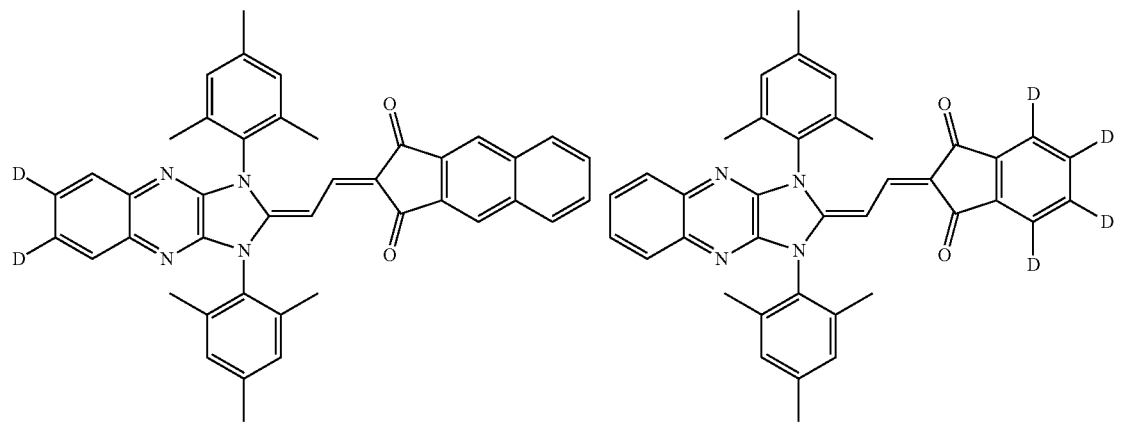

-continued
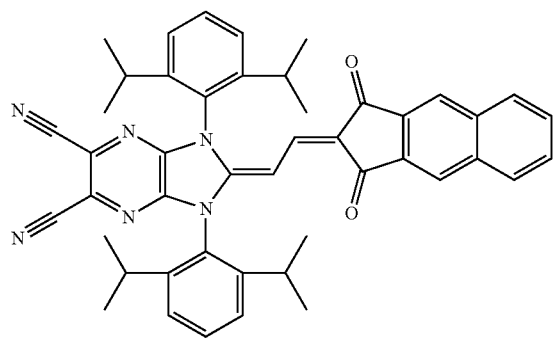
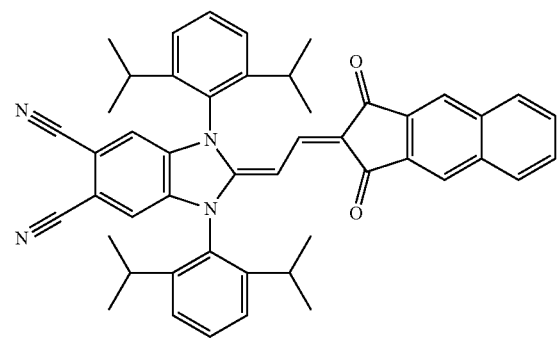
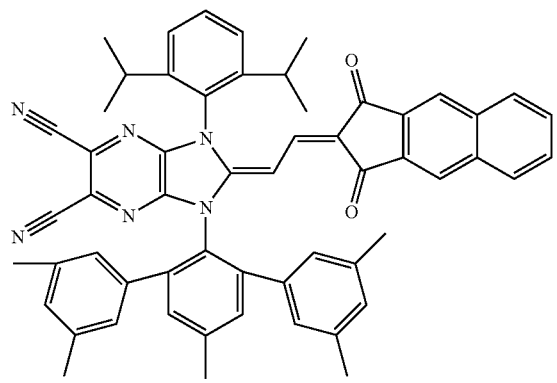
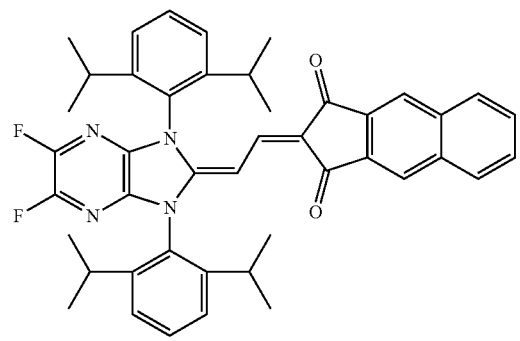
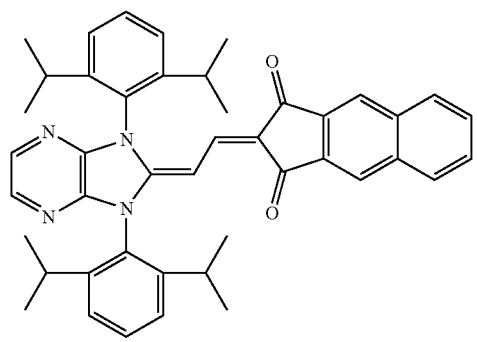
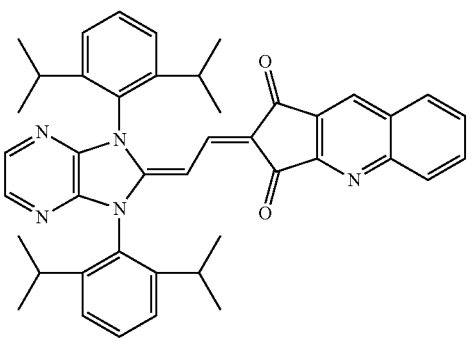
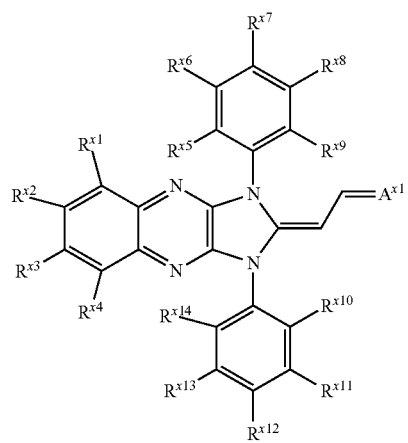

It is shown below that examples of combinations of forms that each group of $R^{X1}$ to $R^{X14}$, and $A^{x1}$ bonded to basic structural moieties in the specific compounds shown in the upper row may have.

In Tables, Me represents a methyl group, MeO represents a methoxy group, Et represents an ethyl group, iPr represents an isopropyl group, and tBu represents a tert-butyl group.

In addition, in Tables, the details of the groups denoted by "A-number" or "S-number" will be explained later.

TABLE 1

| No | $R^{x1}$ | $R^{x2}$ | $R^{x3}$ | $R^{x4}$ | $R^{x5}$ | $R^{x6}$ | $R^{x7}$ | $R^{x8}$ | $R^{x9}$ | $R^{x10}$ | $R^{x11}$ | $R^{x12}$ | $R^{x13}$ | $R^{x14}$ | $A^{x1}$ |
|---|---|---|---|---|---|---|---|---|---|---|---|---|---|---|---|
| 1 | H | H | H | H | Me | H | H | H | Me | Me | H | H | H | Me | A-2 |
| 2 | H | H | H | H | Me | H | Me | H | Me | Me | H | Me | H | Me | A-2 |
| 3 | H | H | H | H | Me | Me | Me | Me | Me | Me | Me | Me | Me | Me | A-2 |
| 4 | H | H | H | H | Et | H | H | H | Et | Et | H | H | H | Et | A-2 |
| 5 | H | H | H | H | Me | H | H | H | tBu | Me | H | H | H | tBu | A-2 |
| 6 | H | H | H | H | Et | H | Me | H | Et | Et | H | Me | H | Et | A-2 |
| 7 | H | H | H | H | tBu | H | tBu | H | tBu | tBu | H | tBu | H | tBu | A-2 |
| 8 | H | H | H | H | Me | H | Cl | H | Me | Me | H | Cl | H | Me | A-2 |
| 9 | H | H | H | H | Me | H | Br | H | Me | Me | H | Br | H | Me | A-2 |
| 10 | H | H | H | H | Me | H | S-1 | H | Me | Me | H | S-1 | H | Me | A-2 |
| 11 | H | H | H | H | iPr | H | H | H | iPr | iPr | H | H | H | iPr | A-2 |
| 12 | F | H | H | H | iPr | H | H | H | iPr | iPr | H | H | H | iPr | A-2 |
| 13 | H | F | H | H | iPr | H | H | H | iPr | iPr | H | H | H | iPr | A-2 |
| 14 | H | F | F | H | iPr | H | H | H | iPr | iPr | H | H | H | iPr | A-2 |
| 15 | Me | F | H | H | iPr | H | H | H | iPr | iPr | H | H | H | iPr | A-2 |
| 16 | H | F | Me | H | iPr | H | H | H | iPr | iPr | H | H | H | iPr | A-2 |
| 17 | H | F | H | Me | iPr | H | H | H | iPr | iPr | H | H | H | iPr | A-2 |
| 18 | H | F | Cl | H | iPr | H | H | H | iPr | iPr | H | H | H | iPr | A-2 |
| 19 | F | H | Cl | H | iPr | H | H | H | iPr | iPr | H | H | H | iPr | A-2 |
| 20 | Cl | H | H | H | iPr | H | H | H | iPr | iPr | H | H | H | iPr | A-2 |
| 21 | H | Cl | H | H | iPr | H | H | H | iPr | iPr | H | H | H | iPr | A-2 |
| 22 | H | Cl | Cl | H | iPr | H | H | H | iPr | iPr | H | H | H | iPr | A-2 |
| 23 | H | Me | H | H | iPr | H | H | H | iPr | iPr | H | H | H | iPr | A-2 |
| 24 | Me | H | H | H | iPr | H | H | H | iPr | iPr | H | H | H | iPr | A-2 |
| 25 | H | Me | Me | H | iPr | H | H | H | iPr | iPr | H | H | H | iPr | A-2 |
| 26 | H | MeO | H | H | iPr | H | H | H | iPr | iPr | H | H | H | iPr | A-2 |
| 27 | H | tBu | H | H | iPr | H | H | H | iPr | iPr | H | H | H | iPr | A-2 |
| 28 | H | S-1 | H | H | iPr | H | H | H | iPr | iPr | H | H | H | iPr | A-2 |
| 29 | H | S-8 | H | H | iPr | H | H | H | iPr | iPr | H | H | H | iPr | A-2 |
| 30 | H | S-14 | H | H | iPr | H | H | H | iPr | iPr | H | H | H | iPr | A-2 |
| 31 | H | S-31 | H | H | iPr | H | H | H | iPr | iPr | H | H | H | iPr | A-2 |
| 32 | H | S-44 | H | H | iPr | H | H | H | iPr | iPr | H | H | H | iPr | A-2 |
| 33 | H | S-47 | H | H | iPr | H | H | H | iPr | iPr | H | H | H | iPr | A-2 |
| 34 | H | S-61 | H | H | iPr | H | H | H | iPr | iPr | H | H | H | iPr | A-2 |
| 35 | H | S-79 | H | H | iPr | H | H | H | iPr | iPr | H | H | H | iPr | A-2 |
| 36 | H | S-81 | H | H | iPr | H | H | H | iPr | iPr | H | H | H | iPr | A-2 |
| 37 | H | S-95 | H | H | iPr | H | H | H | iPr | iPr | H | H | H | iPr | A-2 |
| 38 | H | S-98 | H | H | iPr | H | H | H | iPr | iPr | H | H | H | iPr | A-2 |
| 39 | H | S-102 | H | H | iPr | H | H | H | iPr | iPr | H | H | H | iPr | A-2 |
| 40 | S-1 | H | H | H | iPr | H | H | H | iPr | iPr | H | H | H | iPr | A-2 |

TABLE 2

| No | $R^{x1}$ | $R^{x2}$ | $R^{x3}$ | $R^{x4}$ | $R^{x5}$ | $R^{x6}$ | $R^{x7}$ | $R^{x8}$ | $R^{x9}$ | $R^{x10}$ | $R^{x11}$ | $R^{x12}$ | $R^{x13}$ | $R^{x14}$ | $A^{x1}$ |
|---|---|---|---|---|---|---|---|---|---|---|---|---|---|---|---|
| 41 | S-8 | H | H | H | iPr | H | H | H | iPr | iPr | H | H | H | iPr | A-2 |
| 42 | S-14 | H | H | H | iPr | H | H | H | iPr | iPr | H | H | H | iPr | A-2 |
| 43 | S-31 | H | H | H | iPr | H | H | H | iPr | iPr | H | H | H | iPr | A-2 |
| 44 | S-44 | H | H | H | iPr | H | H | H | iPr | iPr | H | H | H | iPr | A-2 |
| 45 | S-47 | H | H | H | iPr | H | H | H | iPr | iPr | H | H | H | iPr | A-2 |
| 46 | S-61 | H | H | H | iPr | H | H | H | iPr | iPr | H | H | H | iPr | A-2 |
| 47 | S-79 | H | H | H | iPr | H | H | H | iPr | iPr | H | H | H | iPr | A-2 |
| 48 | S-81 | H | H | H | iPr | H | H | H | iPr | iPr | H | H | H | iPr | A-2 |
| 49 | S-95 | H | H | H | iPr | H | H | H | iPr | iPr | H | H | H | iPr | A-2 |
| 50 | S-98 | H | H | H | iPr | H | H | H | iPr | iPr | H | H | H | iPr | A-2 |
| 51 | S-102 | H | H | H | iPr | H | H | H | iPr | iPr | H | H | H | iPr | A-2 |
| 52 | H | H | H | H | iPr | H | H | H | iPr | iPr | H | H | H | iPr | A-1 |
| 53 | H | H | H | H | iPr | H | H | H | iPr | iPr | H | H | H | iPr | A-3 |
| 54 | H | H | H | H | iPr | H | H | H | iPr | iPr | H | H | H | iPr | A-4 |
| 55 | H | H | H | H | iPr | H | H | H | iPr | iPr | H | H | H | iPr | A-5 |
| 56 | H | H | H | H | iPr | H | H | H | iPr | iPr | H | H | H | iPr | A-6 |

TABLE 2-continued

| No | $R^{x1}$ | $R^{x2}$ | $R^{x3}$ | $R^{x4}$ | $R^{x5}$ | $R^{x6}$ | $R^{x7}$ | $R^{x8}$ | $R^{x9}$ | $R^{x10}$ | $R^{x11}$ | $R^{x12}$ | $R^{x13}$ | $R^{x14}$ | $A^{x1}$ |
|---|---|---|---|---|---|---|---|---|---|---|---|---|---|---|---|
| 57 | H | H | H | H | iPr | H | H | H | iPr | iPr | H | H | H | iPr | A-7 |
| 58 | H | H | H | H | iPr | H | H | H | iPr | iPr | H | H | H | iPr | A-8 |
| 59 | H | H | H | H | iPr | H | H | H | iPr | iPr | H | H | H | iPr | A-9 |
| 60 | H | H | H | H | iPr | H | H | H | iPr | iPr | H | H | H | iPr | A-10 |
| 61 | H | H | H | H | iPr | H | H | H | iPr | iPr | H | H | H | iPr | A-11 |
| 62 | H | H | H | H | iPr | H | H | H | iPr | iPr | H | H | H | iPr | A-12 |
| 63 | H | H | H | H | iPr | H | H | H | iPr | iPr | H | H | H | iPr | A-13 |
| 64 | H | H | H | H | iPr | H | H | H | iPr | iPr | H | H | H | iPr | A-14 |
| 65 | H | H | H | H | iPr | H | H | H | iPr | iPr | H | H | H | iPr | A-15 |
| 66 | H | H | H | H | iPr | H | H | H | iPr | iPr | H | H | H | iPr | A-16 |
| 67 | H | H | H | H | iPr | H | H | H | iPr | iPr | H | H | H | iPr | A-17 |
| 68 | H | H | H | H | iPr | H | H | H | iPr | iPr | H | H | H | iPr | A-18 |
| 69 | H | H | H | H | iPr | H | H | H | iPr | iPr | H | H | H | iPr | A-19 |
| 70 | H | H | H | H | iPr | H | H | H | iPr | iPr | H | H | H | iPr | A-20 |
| 71 | H | H | H | H | iPr | H | H | H | iPr | iPr | H | H | H | iPr | A-21 |
| 72 | H | H | H | H | iPr | H | H | H | iPr | iPr | H | H | H | iPr | A-22 |
| 73 | H | H | H | H | iPr | H | H | H | iPr | iPr | H | H | H | iPr | A-23 |
| 74 | H | H | H | H | iPr | H | H | H | iPr | iPr | H | H | H | iPr | A-24 |
| 75 | H | H | H | H | iPr | H | H | H | iPr | iPr | H | H | H | iPr | A-25 |
| 76 | H | H | H | H | iPr | H | H | H | iPr | iPr | H | H | H | iPr | A-26 |
| 77 | H | H | H | H | iPr | H | H | H | iPr | iPr | H | H | H | iPr | A-27 |
| 78 | H | H | H | H | iPr | H | H | H | iPr | iPr | H | H | H | iPr | A-28 |
| 79 | H | H | H | H | iPr | H | H | H | iPr | iPr | H | H | H | iPr | A-29 |
| 80 | H | H | H | H | iPr | H | H | H | iPr | iPr | H | H | H | iPr | A-36 |

TABLE 3

| No | $R^{x1}$ | $R^{x2}$ | $R^{x3}$ | $R^{x4}$ | $R^{x5}$ | $R^{x6}$ | $R^{x7}$ | $R^{x8}$ | $R^{x9}$ | $R^{x10}$ | $R^{x11}$ | $R^{x12}$ | $R^{x13}$ | $R^{x14}$ | $A^{x1}$ |
|---|---|---|---|---|---|---|---|---|---|---|---|---|---|---|---|
| 81 | H | H | H | H | iPr | H | H | H | iPr | iPr | H | H | H | iPr | A-37 |
| 82 | H | H | H | H | iPr | H | H | H | iPr | iPr | H | H | H | iPr | A-40 |
| 83 | H | Cl | H | H | iPr | H | H | H | iPr | iPr | H | H | H | iPr | A-5 |
| 84 | H | Cl | H | H | iPr | H | H | H | iPr | iPr | H | H | H | iPr | A-6 |
| 85 | H | Cl | H | H | iPr | H | H | H | iPr | iPr | H | H | H | iPr | A-7 |
| 86 | H | Cl | H | H | iPr | H | H | H | iPr | iPr | H | H | H | iPr | A-8 |
| 87 | H | Cl | H | H | iPr | H | H | H | iPr | iPr | H | H | H | iPr | A-10 |
| 88 | H | Cl | H | H | iPr | H | H | H | iPr | iPr | H | H | H | iPr | A-11 |
| 89 | H | Cl | H | H | iPr | H | H | H | iPr | iPr | H | H | H | iPr | A-12 |
| 90 | H | Cl | H | H | iPr | H | H | H | iPr | iPr | H | H | H | iPr | A-28 |
| 91 | H | Cl | H | H | iPr | H | H | H | iPr | iPr | H | H | H | iPr | A-31 |
| 92 | H | Cl | Cl | H | iPr | H | H | H | iPr | iPr | H | H | H | iPr | A-8 |
| 93 | H | Cl | Cl | H | iPr | H | H | H | iPr | iPr | H | H | H | iPr | A-12 |
| 94 | H | Cl | Cl | H | iPr | H | H | H | iPr | iPr | H | H | H | iPr | A-17 |
| 95 | H | Me | H | H | iPr | H | H | H | iPr | iPr | H | H | H | iPr | A-5 |
| 96 | H | Me | H | H | iPr | H | H | H | iPr | iPr | H | H | H | iPr | A-6 |
| 97 | H | Me | H | H | iPr | H | H | H | iPr | iPr | H | H | H | iPr | A-8 |
| 98 | H | Me | H | H | iPr | H | H | H | iPr | iPr | H | H | H | iPr | A-12 |
| 99 | H | Me | H | H | iPr | H | H | H | iPr | iPr | H | H | H | iPr | A-17 |
| 100 | H | tBu | H | H | iPr | H | H | H | iPr | iPr | H | H | H | iPr | A-5 |
| 101 | H | tBu | H | H | iPr | H | H | H | iPr | iPr | H | H | H | iPr | A-6 |
| 102 | H | tBu | H | H | iPr | H | H | H | iPr | iPr | H | H | H | iPr | A-8 |
| 103 | H | tBu | H | H | iPr | H | H | H | iPr | iPr | H | H | H | iPr | A-10 |
| 104 | H | tBu | H | H | iPr | H | H | H | iPr | iPr | H | H | H | iPr | A-17 |
| 105 | H | Me | Me | H | iPr | H | H | H | iPr | iPr | H | H | H | iPr | A-5 |
| 106 | H | Me | Me | H | iPr | H | H | H | iPr | iPr | H | H | H | iPr | A-6 |
| 107 | H | Me | Me | H | iPr | H | H | H | iPr | iPr | H | H | H | iPr | A-8 |
| 108 | H | Me | Me | H | iPr | H | H | H | iPr | iPr | H | H | H | iPr | A-10 |
| 109 | H | Me | Me | H | iPr | H | H | H | iPr | iPr | H | H | H | iPr | A-17 |
| 110 | H | F | F | H | iPr | H | H | H | iPr | iPr | H | H | H | iPr | A-1 |
| 111 | H | F | F | H | iPr | H | H | H | iPr | iPr | H | H | H | iPr | A-5 |
| 112 | H | F | F | H | iPr | H | H | H | iPr | iPr | H | H | H | iPr | A-6 |
| 113 | H | F | F | H | iPr | H | H | H | iPr | iPr | H | H | H | iPr | A-7 |
| 114 | H | F | F | H | iPr | H | H | H | iPr | iPr | H | H | H | iPr | A-8 |
| 115 | H | F | F | H | iPr | H | H | H | iPr | iPr | H | H | H | iPr | A-10 |
| 116 | H | F | F | H | iPr | H | H | H | iPr | iPr | H | H | H | iPr | A-11 |
| 117 | H | F | F | H | iPr | H | H | H | iPr | iPr | H | H | H | iPr | A-12 |
| 118 | H | F | F | H | iPr | H | H | H | iPr | iPr | H | H | H | iPr | A-17 |
| 119 | H | H | H | H | iPr | H | H | H | iPr | S-1 | H | Me | H | S-1 | A-5 |
| 120 | H | H | H | H | iPr | H | H | H | iPr | S-2 | H | Me | H | S-2 | A-5 |

TABLE 4

| No | $R^{x1}$ | $R^{x2}$ | $R^{x3}$ | $R^{x4}$ | $R^{x5}$ | $R^{x6}$ | $R^{x7}$ | $R^{x8}$ | $R^{x9}$ | $R^{x10}$ | $R^{x11}$ | $R^{x12}$ | $R^{x13}$ | $R^{x14}$ | $A^{x1}$ |
|---|---|---|---|---|---|---|---|---|---|---|---|---|---|---|---|
| 121 | H | H | H | H | iPr | H | H | H | iPr | S-3 | H | Me | H | S-3 | A-5 |
| 122 | H | H | H | H | iPr | H | H | H | iPr | S-4 | H | Me | H | S-4 | A-5 |
| 123 | H | H | H | H | iPr | H | H | H | iPr | S-5 | H | Me | H | S-5 | A-5 |
| 124 | H | H | H | H | iPr | H | H | H | iPr | S-6 | H | Me | H | S-6 | A-5 |
| 125 | H | H | H | H | iPr | H | H | H | iPr | S-7 | H | Me | H | S-7 | A-5 |
| 126 | H | F | F | H | iPr | H | H | H | iPr | S-8 | H | Me | H | S-8 | A-5 |
| 127 | H | F | F | H | iPr | H | H | H | iPr | S-9 | H | Me | H | S-9 | A-5 |
| 128 | H | F | F | H | iPr | H | H | H | iPr | S-10 | H | Me | H | S-10 | A-5 |
| 129 | H | F | F | H | iPr | H | H | H | iPr | S-11 | H | Me | H | S-11 | A-5 |
| 130 | H | F | F | H | iPr | H | H | H | iPr | S-12 | H | Me | H | S-12 | A-5 |
| 131 | H | F | F | H | iPr | H | H | H | iPr | S-13 | H | Me | H | S-13 | A-5 |
| 132 | H | H | H | H | iPr | H | H | H | iPr | S-14 | H | Me | H | S-14 | A-5 |
| 133 | H | H | H | H | iPr | H | H | H | iPr | S-15 | H | Me | H | S-15 | A-5 |
| 134 | H | H | H | H | iPr | H | H | H | iPr | S-16 | H | Me | H | S-16 | A-5 |
| 135 | H | H | H | H | iPr | H | H | H | iPr | S-17 | H | Me | H | S-17 | A-5 |
| 136 | H | H | H | H | iPr | H | H | H | iPr | S-18 | H | Me | H | S-18 | A-5 |
| 137 | H | H | H | H | iPr | H | H | H | iPr | S-19 | H | Me | H | S-19 | A-5 |
| 138 | H | H | H | H | iPr | H | H | H | iPr | S-20 | H | Me | H | S-20 | A-5 |
| 139 | H | Cl | Cl | H | iPr | H | H | H | iPr | S-21 | H | Me | H | S-21 | A-5 |
| 140 | H | Cl | Cl | H | iPr | H | H | H | iPr | S-22 | H | Me | H | S-22 | A-10 |
| 141 | H | Cl | Cl | H | iPr | H | H | H | iPr | S-23 | H | Me | H | S-23 | A-10 |
| 142 | H | H | H | H | iPr | H | H | H | iPr | S-24 | H | Me | H | S-24 | A-10 |
| 143 | H | H | H | H | iPr | H | H | H | iPr | S-25 | H | Me | H | S-25 | A-10 |
| 144 | H | Cl | Cl | H | iPr | H | H | H | iPr | S-26 | H | Me | H | S-26 | A-10 |
| 145 | H | H | H | H | iPr | H | H | H | iPr | S-27 | H | Me | H | S-27 | A-5 |
| 146 | H | H | H | H | iPr | H | H | H | iPr | S-28 | H | Me | H | S-28 | A-5 |
| 147 | H | H | H | H | iPr | H | H | H | iPr | S-29 | H | Me | H | S-29 | A-5 |
| 148 | H | H | H | H | iPr | H | H | H | iPr | S-30 | H | Me | H | S-30 | A-5 |
| 149 | H | H | H | H | iPr | H | H | H | iPr | S-31 | H | Me | H | S-31 | A-2 |
| 150 | H | H | H | H | iPr | H | H | H | iPr | S-32 | H | Me | H | S-32 | A-2 |
| 151 | H | H | H | H | iPr | H | H | H | iPr | S-33 | H | Me | H | S-33 | A-2 |
| 152 | H | H | H | H | iPr | H | H | H | iPr | S-34 | H | Me | H | S-34 | A-2 |
| 153 | H | H | H | H | iPr | H | H | H | iPr | S-35 | H | Me | H | S-35 | A-2 |
| 154 | H | H | H | H | iPr | H | H | H | iPr | S-36 | H | Me | H | S-36 | A-2 |
| 155 | H | H | H | H | iPr | H | H | H | iPr | S-37 | H | Me | H | S-37 | A-2 |
| 156 | H | H | H | H | iPr | H | H | H | iPr | S-38 | H | Me | H | S-38 | A-2 |
| 157 | H | H | H | H | iPr | H | H | H | iPr | S-39 | H | Me | H | S-39 | A-2 |
| 158 | H | H | H | H | iPr | H | H | H | iPr | S-40 | H | Me | H | S-40 | A-2 |
| 159 | H | H | H | H | iPr | H | H | H | iPr | S-41 | H | Me | H | S-41 | A-2 |
| 160 | H | H | H | H | iPr | H | H | H | iPr | S-42 | H | Me | H | S-42 | A-2 |

TABLE 5

| No | $R^{x1}$ | $R^{x2}$ | $R^{x3}$ | $R^{x4}$ | $R^{x5}$ | $R^{x6}$ | $R^{x7}$ | $R^{x8}$ | $R^{x9}$ | $R^{x10}$ | $R^{x11}$ | $R^{x12}$ | $R^{x13}$ | $R^{x14}$ | $A^{x1}$ |
|---|---|---|---|---|---|---|---|---|---|---|---|---|---|---|---|
| 161 | H | H | H | H | iPr | H | H | H | iPr | S-43 | H | Me | H | S-43 | A-2 |
| 162 | H | H | H | H | iPr | H | H | H | iPr | S-44 | H | Me | H | S-44 | A-2 |
| 163 | H | H | H | H | iPr | H | H | H | iPr | S-45 | H | Me | H | S-45 | A-2 |
| 164 | H | H | H | H | iPr | H | H | H | iPr | S-46 | H | Me | H | S-46 | A-2 |
| 165 | H | H | H | H | iPr | H | H | H | iPr | S-47 | H | Me | H | S-47 | A-2 |
| 166 | H | H | H | H | iPr | H | H | H | iPr | S-48 | H | Me | H | S-48 | A-2 |
| 167 | H | H | H | H | iPr | H | H | H | iPr | S-49 | H | Me | H | S-49 | A-2 |
| 168 | H | H | H | H | iPr | H | H | H | iPr | S-50 | H | Me | H | S-50 | A-2 |
| 169 | H | H | H | H | iPr | H | H | H | iPr | S-51 | H | Me | H | S-51 | A-2 |
| 170 | H | H | H | H | iPr | H | H | H | iPr | S-52 | H | Me | H | S-52 | A-2 |
| 171 | H | H | H | H | iPr | H | H | H | iPr | S-53 | H | Me | H | S-53 | A-2 |
| 172 | H | H | H | H | iPr | H | H | H | iPr | S-54 | H | Me | H | S-54 | A-2 |
| 173 | H | H | H | H | iPr | H | H | H | iPr | S-55 | H | Me | H | S-55 | A-2 |
| 174 | H | H | H | H | iPr | H | H | H | iPr | S-56 | H | Me | H | S-56 | A-2 |
| 175 | H | H | H | H | iPr | H | H | H | iPr | S-57 | H | Me | H | S-57 | A-2 |
| 176 | H | H | H | H | iPr | H | H | H | iPr | S-58 | H | Me | H | S-58 | A-2 |
| 177 | H | H | H | H | iPr | H | H | H | iPr | S-59 | H | Me | H | S-59 | A-2 |
| 178 | H | H | H | H | iPr | H | H | H | iPr | S-60 | H | Me | H | S-60 | A-2 |
| 179 | H | H | H | H | iPr | H | H | H | iPr | S-61 | H | Me | H | S-61 | A-2 |
| 180 | H | H | H | H | iPr | H | H | H | iPr | S-62 | H | Me | H | S-62 | A-2 |
| 181 | H | H | H | H | iPr | H | H | H | iPr | S-63 | H | Me | H | S-63 | A-2 |
| 182 | H | H | H | H | iPr | H | H | H | iPr | S-64 | H | Me | H | S-64 | A-2 |
| 183 | H | H | H | H | iPr | H | H | H | iPr | S-65 | H | Me | H | S-65 | A-2 |
| 184 | H | H | H | H | iPr | H | H | H | iPr | S-66 | H | Me | H | S-66 | A-2 |
| 185 | H | H | H | H | iPr | H | H | H | iPr | S-67 | H | Me | H | S-67 | A-2 |
| 186 | H | H | H | H | iPr | H | H | H | iPr | S-68 | H | Me | H | S-68 | A-2 |
| 187 | H | H | H | H | iPr | H | H | H | iPr | S-69 | H | Me | H | S-69 | A-2 |
| 188 | H | H | H | H | iPr | H | H | H | iPr | S-70 | H | Me | H | S-70 | A-2 |
| 189 | H | H | H | H | iPr | H | H | H | iPr | S-71 | H | Me | H | S-71 | A-2 |

TABLE 5-continued

| No | $R^{x1}$ | $R^{x2}$ | $R^{x3}$ | $R^{x4}$ | $R^{x5}$ | $R^{x6}$ | $R^{x7}$ | $R^{x8}$ | $R^{x9}$ | $R^{x10}$ | $R^{x11}$ | $R^{x12}$ | $R^{x13}$ | $R^{x14}$ | $A^{x1}$ |
|---|---|---|---|---|---|---|---|---|---|---|---|---|---|---|---|
| 190 | H | H | H | H | iPr | H | H | H | iPr | S-72 | H | Me | H | S-72 | A-2 |
| 191 | H | H | H | H | iPr | H | H | H | iPr | S-73 | H | Me | H | S-73 | A-2 |
| 192 | H | H | H | H | iPr | H | H | H | iPr | S-74 | H | Me | H | S-74 | A-2 |
| 193 | H | H | H | H | iPr | H | H | H | iPr | S-75 | H | Me | H | S-75 | A-2 |
| 194 | H | H | H | H | iPr | H | H | H | iPr | S-76 | H | Me | H | S-76 | A-2 |
| 195 | H | H | H | H | iPr | H | H | H | iPr | S-77 | H | Me | H | S-77 | A-2 |
| 196 | H | H | H | H | iPr | H | H | H | iPr | S-78 | H | Me | H | S-78 | A-2 |
| 197 | H | H | H | H | iPr | H | H | H | iPr | S-79 | H | Me | H | S-79 | A-2 |
| 198 | H | H | H | H | iPr | H | H | H | iPr | S-80 | H | Me | H | S-80 | A-2 |
| 199 | H | Cl | Cl | H | iPr | H | H | H | iPr | S-81 | H | Me | H | S-81 | A-10 |
| 200 | H | Cl | Cl | H | iPr | H | H | H | iPr | S-82 | H | Me | H | S-82 | A-10 |

TABLE 6

| No | $R^{x1}$ | $R^{x2}$ | $R^{x3}$ | $R^{x4}$ | $R^{x5}$ | $R^{x6}$ | $R^{x7}$ | $R^{x8}$ | $R^{x9}$ | $R^{x10}$ | $R^{x11}$ | $R^{x12}$ | $R^{x13}$ | $R^{x14}$ | $A^{x1}$ |
|---|---|---|---|---|---|---|---|---|---|---|---|---|---|---|---|
| 201 | H | F | F | H | iPr | H | H | H | iPr | S-83 | H | Me | H | S-83 | A-5 |
| 202 | H | F | F | H | iPr | H | H | H | iPr | S-84 | H | Me | H | S-84 | A-5 |
| 203 | H | F | F | H | iPr | H | H | H | iPr | S-85 | H | Me | H | S-85 | A-5 |
| 204 | H | Cl | H | H | iPr | H | H | H | iPr | S-86 | H | Me | H | S-86 | A-6 |
| 205 | H | Cl | H | H | iPr | H | H | H | iPr | S-87 | H | Me | H | S-87 | A-10 |
| 206 | H | Cl | H | H | iPr | H | H | H | iPr | S-88 | H | Me | H | S-88 | A-11 |
| 207 | H | Cl | H | H | iPr | H | H | H | iPr | S-89 | H | Me | H | S-89 | A-12 |
| 208 | H | H | H | H | iPr | H | H | H | iPr | S-90 | H | Me | H | S-90 | A-2 |
| 209 | H | H | H | H | iPr | H | H | H | iPr | S-91 | H | Me | H | S-91 | A-2 |
| 210 | H | H | H | H | iPr | H | H | H | iPr | S-92 | H | Me | H | S-92 | A-2 |
| 211 | H | H | H | H | iPr | H | H | H | iPr | S-93 | H | Me | H | S-93 | A-2 |
| 212 | H | H | H | H | iPr | H | H | H | iPr | S-94 | H | Me | H | S-94 | A-2 |
| 213 | H | H | H | H | iPr | H | H | H | iPr | S-95 | H | Me | H | S-95 | A-2 |
| 214 | H | H | H | H | iPr | H | H | H | iPr | S-96 | H | Me | H | S-96 | A-2 |
| 215 | H | H | H | H | iPr | H | H | H | iPr | S-97 | H | Me | H | S-97 | A-2 |
| 216 | H | H | H | H | iPr | H | H | H | iPr | S-98 | H | Me | H | S-98 | A-2 |
| 217 | H | H | H | H | iPr | H | H | H | iPr | S-99 | H | Me | H | S-99 | A-2 |
| 218 | H | H | H | H | iPr | H | H | H | iPr | S-100 | H | Me | H | S-100 | A-2 |
| 219 | H | H | H | H | iPr | H | H | H | iPr | S-101 | H | Me | H | S-101 | A-5 |
| 220 | H | H | H | H | iPr | H | H | H | iPr | S-102 | H | Me | H | S-102 | A-6 |
| 221 | H | H | H | H | iPr | H | H | H | iPr | S-103 | H | Me | H | S-103 | A-8 |
| 222 | H | H | H | H | iPr | H | H | H | iPr | S-104 | H | Me | H | S-104 | A-8 |
| 223 | Cl | H | H | H | iPr | H | H | H | iPr | S-105 | H | Me | H | S-105 | A-17 |
| 224 | F | H | F | H | iPr | H | H | H | iPr | S-106 | H | Me | H | S-106 | A-5 |
| 225 | Cl | H | H | H | iPr | H | H | H | iPr | S-107 | H | Me | H | S-107 | A-6 |
| 226 | Cl | H | H | H | iPr | H | H | H | iPr | S-108 | H | Me | H | S-108 | A-8 |
| 227 | H | H | H | H | iPr | H | H | H | iPr | S-109 | H | Me | H | S-109 | A-10 |
| 228 | H | H | H | H | iPr | H | H | H | iPr | S-110 | H | Me | H | S-110 | A-11 |
| 229 | H | H | H | H | iPr | H | H | H | iPr | S-111 | H | Me | H | S-111 | A-2 |
| 230 | H | H | H | H | iPr | H | H | H | iPr | S-112 | H | Me | H | S-112 | A-2 |
| 231 | H | H | H | H | iPr | H | H | H | iPr | S-113 | H | Me | H | S-113 | A-2 |
| 232 | H | H | H | H | iPr | H | H | H | iPr | S-114 | H | Me | H | S-114 | A-2 |
| 233 | H | H | H | H | iPr | H | H | H | iPr | S-115 | H | Me | H | S-115 | A-2 |
| 234 | H | H | H | H | iPr | H | H | H | iPr | S-116 | H | Me | H | S-116 | A-2 |
| 235 | H | H | H | H | iPr | H | H | H | iPr | S-117 | H | Me | H | S-117 | A-2 |
| 236 | H | H | H | H | iPr | H | H | H | iPr | S-118 | H | Me | H | S-118 | A-4 |
| 237 | H | Cl | H | H | iPr | H | H | H | iPr | S-119 | H | Me | H | S-119 | A-9 |
| 238 | H | Cl | Cl | H | iPr | H | H | H | iPr | S-120 | H | Me | H | S-120 | A-1 |
| 239 | H | Me | H | H | iPr | H | H | H | iPr | S-1 | H | H | H | S-1 | A-5 |
| 240 | H | Me | H | H | iPr | H | H | H | iPr | S-4 | H | H | H | S-4 | A-5 |

TABLE 7

| No | $R^{x1}$ | $R^{x2}$ | $R^{x3}$ | $R^{x4}$ | $R^{x5}$ | $R^{x6}$ | $R^{x7}$ | $R^{x8}$ | $R^{x9}$ | $R^{x10}$ | $R^{x11}$ | $R^{x12}$ | $R^{x13}$ | $R^{x14}$ | $A^{x1}$ |
|---|---|---|---|---|---|---|---|---|---|---|---|---|---|---|---|
| 241 | H | Me | Me | H | iPr | H | H | H | iPr | S-4 | H | H | H | S-4 | A-5 |
| 242 | H | tBu | H | H | iPr | H | H | H | iPr | S-1 | H | H | H | S-1 | A-5 |
| 243 | H | tBu | H | H | iPr | H | H | H | iPr | S-4 | H | H | H | S-4 | A-5 |
| 244 | H | Cl | Cl | H | iPr | H | H | H | iPr | S-28 | H | H | H | S-28 | A-5 |
| 245 | H | H | H | H | iPr | H | H | H | iPr | S-37 | H | H | H | S-37 | A-2 |
| 246 | H | H | H | H | iPr | H | H | H | iPr | S-40 | H | H | H | S-40 | A-2 |
| 247 | H | H | H | H | iPr | H | H | H | iPr | S-47 | H | H | H | S-47 | A-2 |
| 248 | H | H | H | H | iPr | H | H | H | iPr | S-57 | H | H | H | S-57 | A-2 |

TABLE 7-continued

| No | $R^{x1}$ | $R^{x2}$ | $R^{x3}$ | $R^{x4}$ | $R^{x5}$ | $R^{x6}$ | $R^{x7}$ | $R^{x8}$ | $R^{x9}$ | $R^{x10}$ | $R^{x11}$ | $R^{x12}$ | $R^{x13}$ | $R^{x14}$ | $A^{x1}$ |
|---|---|---|---|---|---|---|---|---|---|---|---|---|---|---|---|
| 249 | H | H | H | H | iPr | H | H | H | iPr | S-61 | H | H | H | S-61 | A-2 |
| 250 | H | H | H | H | iPr | H | H | H | iPr | S-63 | H | H | H | S-63 | A-2 |
| 251 | H | Cl | Cl | H | iPr | H | H | H | iPr | S-81 | H | H | H | S-81 | A-5 |
| 252 | H | Cl | Cl | H | iPr | H | H | H | iPr | S-82 | H | H | H | S-82 | A-5 |
| 253 | H | H | H | H | iPr | H | H | H | iPr | S-90 | H | H | H | S-90 | A-2 |
| 254 | H | H | H | H | iPr | H | H | H | iPr | S-95 | H | H | H | S-95 | A-2 |
| 255 | H | H | H | H | iPr | H | H | H | iPr | S-97 | H | H | H | S-97 | A-2 |
| 256 | H | H | H | H | iPr | H | H | H | iPr | S-111 | H | H | H | S-111 | A-2 |
| 257 | H | H | H | H | iPr | H | H | H | iPr | S-1 | H | F | H | S-1 | A-2 |
| 258 | H | H | H | H | iPr | H | H | H | iPr | S-1 | H | Cl | H | S-1 | A-2 |
| 259 | H | H | H | H | iPr | H | H | H | iPr | S-3 | H | F | H | S-3 | A-2 |
| 260 | H | H | H | H | iPr | H | H | H | iPr | S-3 | H | Cl | H | S-3 | A-2 |
| 261 | H | H | H | H | iPr | H | H | H | iPr | S-4 | H | F | H | S-4 | A-2 |
| 262 | H | H | H | H | iPr | H | H | H | iPr | S-4 | H | Cl | H | S-4 | A-2 |
| 263 | H | H | H | H | iPr | H | H | H | iPr | S-4 | H | $CF_3$ | H | S-4 | A-2 |
| 264 | H | H | H | H | iPr | H | H | H | iPr | S-8 | H | F | H | S-8 | A-2 |
| 265 | H | H | H | H | iPr | H | H | H | iPr | S-8 | H | Cl | H | S-8 | A-5 |
| 266 | H | H | H | H | iPr | H | H | H | iPr | S-4 | H | Me | H | S-4 | A-2 |
| 267 | H | H | H | H | iPr | H | H | H | iPr | S-4 | H | Me | H | S-4 | A-5 |
| 268 | H | H | H | H | iPr | H | H | H | iPr | S-4 | H | Me | H | S-4 | A-8 |
| 269 | H | H | H | H | iPr | H | H | H | iPr | S-4 | H | Me | H | S-4 | A-10 |
| 270 | H | H | H | H | iPr | H | H | H | iPr | S-4 | H | Me | H | S-4 | A-12 |
| 271 | H | H | H | H | iPr | H | H | H | iPr | S-4 | H | Me | H | S-4 | A-17 |
| 272 | H | Cl | Cl | H | iPr | H | H | H | iPr | S-4 | H | Me | H | S-4 | A-10 |
| 273 | H | Cl | Cl | H | iPr | H | H | H | iPr | S-20 | H | Me | H | S-20 | A-5 |
| 274 | H | Cl | Cl | H | iPr | H | H | H | iPr | S-47 | H | Me | H | S-47 | A-10 |
| 275 | H | Cl | Cl | H | iPr | H | H | H | iPr | S-47 | H | Me | H | S-47 | A-5 |
| 276 | H | Cl | Cl | H | iPr | H | H | H | iPr | S-63 | H | Me | H | S-63 | A-5 |
| 277 | H | Cl | Cl | H | iPr | H | H | H | iPr | S-63 | H | Me | H | S-63 | S-8 |
| 278 | H | F | F | H | iPr | H | H | H | iPr | S-4 | H | Me | H | S-4 | A-5 |
| 279 | H | F | F | H | iPr | H | H | H | iPr | S-4 | H | Me | H | S-4 | A-6 |
| 280 | H | F | F | H | iPr | H | H | H | iPr | S-4 | H | Me | H | S-4 | A-12 |

TABLE 8

| No | $R^{x1}$ | $R^{x2}$ | $R^{x3}$ | $R^{x4}$ | $R^{x5}$ | $R^{x6}$ | $R^{x7}$ | $R^{x8}$ | $R^{x9}$ | $R^{x10}$ | $R^{x11}$ | $R^{x12}$ | $R^{x12}$ | $R^{x13}$ | $A^{x1}$ |
|---|---|---|---|---|---|---|---|---|---|---|---|---|---|---|---|
| 281 | H | F | F | H | iPr | H | H | H | iPr | S-20 | H | Me | H | S-20 | A-10 |
| 282 | H | F | F | H | iPr | H | H | H | iPr | S-28 | H | Me | H | S-28 | A-5 |
| 283 | H | F | F | H | iPr | H | H | H | iPr | S-28 | H | Me | H | S-28 | A-10 |
| 284 | H | F | F | H | iPr | H | H | H | iPr | S-37 | H | Me | H | S-37 | A-2 |
| 285 | H | F | F | H | iPr | H | H | H | iPr | S-47 | H | Me | H | S-47 | A-2 |
| 286 | H | F | F | H | iPr | H | H | H | iPr | S-63 | H | Me | H | S-63 | A-2 |
| 287 | H | Cl | H | H | iPr | H | H | H | iPr | S-55 | H | Me | H | S-55 | A-2 |
| 288 | Cl | H | H | H | iPr | H | H | H | iPr | S-55 | H | Me | H | S-55 | A-2 |
| 289 | H | Me | H | H | iPr | H | H | H | iPr | S-55 | H | Me | H | S-55 | A-2 |
| 290 | Me | H | H | H | iPr | H | H | H | iPr | S-55 | H | Me | H | S-55 | A-2 |
| 291 | H | tBu | H | H | iPr | H | H | H | iPr | S-31 | H | Me | H | S-31 | A-2 |
| 292 | H | tBu | H | H | iPr | H | H | H | iPr | S-37 | H | Me | H | S-37 | A-2 |
| 293 | H | tBu | H | H | iPr | H | H | H | iPr | S-40 | H | Me | H | S-40 | A-2 |
| 294 | H | tBu | H | H | iPr | H | H | H | iPr | S-47 | H | Me | H | S-47 | A-2 |
| 295 | H | tBu | H | H | iPr | H | H | H | iPr | S-63 | H | Me | H | S-63 | A-2 |
| 296 | H | tBu | H | H | iPr | H | H | H | iPr | S-90 | H | Me | H | S-90 | A-2 |
| 297 | H | tBu | H | H | iPr | H | H | H | iPr | S-94 | H | Me | H | S-94 | A-2 |
| 298 | H | tBu | H | H | iPr | H | H | H | iPr | S-95 | H | Me | H | S-95 | A-2 |
| 299 | H | tBu | H | H | iPr | H | H | H | iPr | S-100 | H | Me | H | S-100 | A-2 |
| 300 | H | H | H | H | iPr | H | H | H | iPr | S-1 | H | Me | H | S-3 | A-2 |
| 301 | H | H | H | H | iPr | H | H | H | iPr | S-1 | H | Me | H | S-4 | A-2 |
| 302 | H | H | H | H | iPr | H | H | H | iPr | S-1 | H | Me | H | S-20 | A-2 |
| 303 | H | H | H | H | iPr | H | H | H | iPr | S-1 | H | Me | H | S-47 | A-2 |
| 304 | H | H | H | H | iPr | H | H | H | iPr | S-1 | H | Me | H | S-63 | A-2 |
| 305 | H | H | H | H | iPr | H | H | H | iPr | S-4 | H | Me | H | S-63 | A-2 |
| 306 | H | H | H | H | iPr | H | H | H | iPr | S-47 | H | Me | H | S-63 | A-2 |
| 307 | H | H | H | H | iPr | H | H | H | iPr | Me | H | Me | H | S-1 | A-2 |
| 308 | H | H | H | H | iPr | H | H | H | iPr | Me | H | Me | H | S-4 | A-2 |
| 309 | H | H | H | H | iPr | H | H | H | iPr | Me | H | Me | H | S-20 | A-2 |
| 310 | H | H | H | H | iPr | H | H | H | iPr | Me | H | Me | H | S-24 | A-2 |
| 311 | H | H | H | H | iPr | H | H | H | iPr | Me | H | Me | H | S-34 | A-2 |
| 312 | H | H | H | H | iPr | H | H | H | iPr | Me | H | Me | H | S-47 | A-2 |
| 313 | H | H | H | H | iPr | H | H | H | iPr | Me | H | Me | H | S-63 | A-2 |
| 314 | H | H | H | H | iPr | H | H | H | iPr | Me | H | Me | H | S-81 | A-2 |
| 315 | H | H | H | H | iPr | H | H | H | iPr | Me | H | Me | H | S-82 | A-2 |
| 316 | H | H | H | H | iPr | H | H | H | iPr | Me | H | Me | H | S-86 | A-2 |
| 317 | H | H | H | H | iPr | H | H | H | iPr | Me | H | Me | H | S-88 | A-2 |

TABLE 8-continued

| No | $R^{x1}$ | $R^{x2}$ | $R^{x3}$ | $R^{x4}$ | $R^{x5}$ | $R^{x6}$ | $R^{x7}$ | $R^{x8}$ | $R^{x9}$ | $R^{x10}$ | $R^{x11}$ | $R^{x12}$ | $R^{x12}$ | $R^{x13}$ | $A^{x1}$ |
|---|---|---|---|---|---|---|---|---|---|---|---|---|---|---|---|
| 318 | H | H | H | H | iPr | H | H | H | iPr | Me | H | Me | H | S-98 | A-2 |
| 319 | H | H | H | H | iPr | H | H | H | iPr | Me | H | Me | H | S-101 | A-2 |
| 320 | H | H | H | H | iPr | H | H | H | iPr | Me | H | Cl | H | S-1 | A-2 |

TABLE 9

| No | $R^{x1}$ | $R^{x2}$ | $R^{x3}$ | $R^{x4}$ | $R^{x5}$ | $R^{x6}$ | $R^{x7}$ | $R^{x8}$ | $R^{x9}$ | $R^{x10}$ | $R^{x11}$ | $R^{x12}$ | $R^{x13}$ | $R^{x14}$ | $A^{x1}$ |
|---|---|---|---|---|---|---|---|---|---|---|---|---|---|---|---|
| 321 | H | H | H | H | iPr | H | H | H | iPr | Me | H | Cl | H | S-21 | A-2 |
| 322 | H | H | H | H | iPr | H | H | H | iPr | Me | H | Cl | H | S-87 | A-2 |
| 323 | H | H | H | H | iPr | H | H | H | iPr | Me | H | Cl | H | S-111 | A-2 |
| 324 | H | H | H | H | iPr | H | H | H | iPr | Cl | H | Cl | H | S-1 | A-2 |
| 325 | H | H | H | H | Me | H | Me | H | S-1 | Me | H | Me | H | S-1 | A-2 |
| 326 | H | H | H | H | Me | H | Me | H | S-3 | Me | H | Me | H | S-3 | A-2 |
| 327 | H | H | H | H | Me | H | Me | H | S-20 | Me | H | Me | H | S-20 | A-2 |
| 328 | H | H | H | H | Me | H | Me | H | S-47 | Me | H | Me | H | S-47 | A-2 |
| 329 | H | H | H | H | S-1 | H | H | H | S-1 | S-1 | H | H | H | S-1 | A-2 |
| 330 | H | H | H | H | S-1 | H | H | H | S-1 | S-1 | H | H | H | S-1 | A-4 |
| 331 | H | H | H | H | S-1 | H | H | H | S-1 | S-1 | H | H | H | S-1 | A-5 |
| 332 | H | H | H | H | S-1 | H | H | H | S-1 | S-1 | H | H | H | S-1 | A-6 |
| 333 | H | H | H | H | S-1 | H | H | H | S-1 | S-1 | H | H | H | S-1 | A-7 |
| 334 | H | H | H | H | S-1 | H | H | H | S-1 | S-1 | H | H | H | S-1 | A-8 |
| 335 | H | H | H | H | S-1 | H | H | H | S-1 | S-1 | H | H | H | S-1 | A-9 |
| 336 | H | H | H | H | S-1 | H | H | H | S-1 | S-1 | H | H | H | S-1 | A-10 |
| 337 | H | H | H | H | S-1 | H | H | H | S-1 | S-1 | H | H | H | S-1 | A-11 |
| 338 | H | H | H | H | S-1 | H | H | H | S-1 | S-1 | H | H | H | S-1 | A-12 |
| 339 | H | H | H | H | S-1 | H | H | H | S-1 | S-1 | H | H | H | S-1 | A-30 |
| 340 | H | H | H | H | S-1 | H | H | H | S-1 | S-1 | H | Me | H | S-1 | A-2 |
| 341 | H | H | H | H | S-3 | H | H | H | S-3 | S-3 | H | H | H | S-3 | A-5 |
| 342 | H | H | H | H | S-4 | H | H | H | S-4 | S-4 | H | H | H | S-4 | A-5 |
| 343 | H | H | H | H | S-40 | H | H | H | S-40 | S-40 | H | H | H | S-40 | A-5 |
| 344 | H | H | H | H | S-47 | H | H | H | S-47 | S-47 | H | H | H | S-47 | A-5 |
| 345 | H | H | H | H | Me | H | H | H | S-1 | S-1 | H | H | H | S-1 | A-2 |
| 346 | H | H | H | H | Me | H | H | H | S-1 | S-1 | H | H | H | S-1 | A-5 |
| 347 | H | H | H | H | Me | H | S-1 | H | S-1 | S-1 | H | S-1 | H | S-1 | A-1 |
| 348 | H | H | H | H | S-1 | H | S-1 | H | S-1 | S-1 | H | S-1 | H | S-1 | A-1 |
| 349 | H | S-1 | S-1 | H | S-1 | H | S-1 | H | S-1 | S-1 | H | S-1 | H | S-1 | A-1 |
| 350 | S-1 | H | H | S-1 | S-1 | H | S-1 | H | S-1 | S-1 | H | S-1 | H | S-1 | A-1 |

Hereinbelow, the groups represented by "S-number" (S-1 and the like) are shown below.

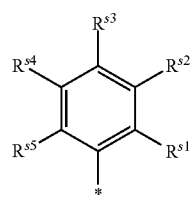

TABLE 10

| Substituent name | $R^{s1}$ | $R^{s2}$ | $R^{s3}$ | $R^{s4}$ | $R^{s5}$ |
|---|---|---|---|---|---|
| S-1 | H | H | H | H | H |
| S-2 | Me | H | H | H | H |
| S-3 | H | H | Me | H | H |
| S-4 | H | Me | H | Me | H |
| S-5 | H | Me | H | H | H |
| S-6 | Me | H | Me | H | H |
| S-7 | Me | H | H | Me | H |
| S-8 | Me | H | H | H | Me |
| S-9 | Me | H | Me | H | Me |
| S-10 | H | Me | Me | H | H |
| S-11 | Et | H | H | H | H |

TABLE 10-continued

| Substituent name | $R^{s1}$ | $R^{s2}$ | $R^{s3}$ | $R^{s4}$ | $R^{s5}$ |
|---|---|---|---|---|---|
| S-12 | iPr | H | H | H | H |
| S-13 | H | H | iPr | H | H |
| S-14 | iPr | H | H | H | iPr |
| S-15 | iPr | H | iPr | H | iPr |
| S-16 | tBu | H | H | H | H |
| S-17 | H | tBu | H | H | H |
| S-18 | H | H | tBu | H | H |
| S-19 | tBu | H | tBu | H | tBu |
| S-20 | H | tBu | H | tBu | H |
| S-21 | H | H | nBu | H | H |
| S-22 | MeO | H | H | H | H |
| S-23 | H | H | MeO | H | H |
| S-24 | H | MeO | H | MeO | H |
| S-25 | MeO | H | H | H | MeO |
| S-26 | H | Me | MeO | Me | H |
| S-27 | SiMe$_3$ | H | H | H | H |
| S-28 | H | H | SiMe$_3$ | H | H |
| S-29 | MeS | H | H | H | H |
| S-30 | H | H | MeS | H | H |
| S-31 | CF$_3$ | H | H | H | H |
| S-32 | H | H | CF$_3$ | H | H |
| S-33 | CF$_3$ | H | CF$_3$ | H | H |
| S-34 | H | CF$_3$ | H | CF$_3$ | H |
| S-35 | CN | H | H | H | H |
| S-36 | H | CN | H | H | H |
| S-37 | H | H | CN | H | H |
| S-38 | Cl | H | H | H | H |

TABLE 10-continued

| Substituent name | $R^{s1}$ | $R^{s2}$ | $R^{s3}$ | $R^{s4}$ | $R^{s5}$ |
|---|---|---|---|---|---|
| S-39 | H | Cl | H | H | H |
| S-40 | H | H | Cl | H | H |
| S-41 | Cl | Cl | H | H | H |
| S-42 | Cl | H | Cl | H | H |
| S-43 | Cl | H | H | Cl | H |
| S-44 | Cl | H | H | H | Cl |
| S-45 | Cl | H | Cl | H | Cl |
| S-46 | H | Cl | Cl | H | H |
| S-47 | H | Cl | H | Cl | H |
| S-48 | Cl | Cl | H | Cl | H |
| S-49 | Cl | H | Me | H | H |
| S-50 | Cl | H | H | Me | H |
| S-51 | Me | H | Cl | H | H |
| S-52 | Cl | H | $CF_3$ | H | H |
| S-53 | MeO | H | H | Cl | H |
| S-54 | H | H | Br | H | H |
| S-55 | F | H | H | H | H |
| S-56 | H | F | H | H | H |
| S-57 | H | H | F | H | H |
| S-58 | F | F | H | H | H |
| S-59 | F | H | F | H | H |
| S-60 | F | H | H | F | H |
| S-61 | F | H | H | H | F |
| S-62 | F | H | F | H | F |
| S-63 | H | F | H | F | H |
| S-64 | F | F | F | H | H |
| S-65 | H | F | F | F | H |
| S-66 | F | H | F | F | H |
| S-67 | H | F | H | Cl | H |
| S-68 | F | H | Cl | H | H |
| S-69 | Cl | H | F | H | H |
| S-70 | H | F | Cl | H | H |
| S-71 | F | H | Me | H | H |
| S-72 | Me | H | F | H | H |
| S-73 | Me | H | H | F | H |
| S-74 | MeO | H | F | H | H |
| S-75 | MeO | H | H | F | H |
| S-76 | MeO | H | H | H | F |
| S-77 | $CF_3$ | H | F | H | H |
| S-78 | F | H | H | CN | H |
| S-79 | H | F | CN | H | H |
| S-80 | H | CN | F | H | H |

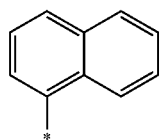

(S-81)

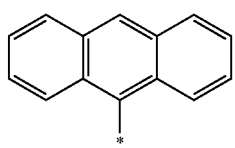

(S-82)

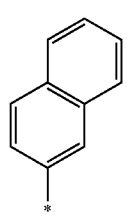

(S-83)

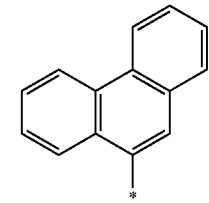

(S-84)

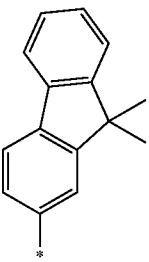

(S-85)

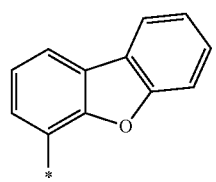

(S-86)

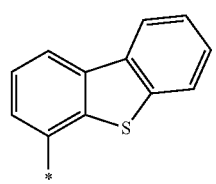

(S-87)

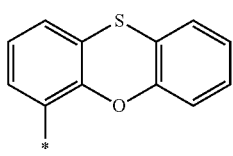

(S-88)

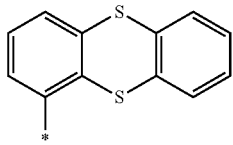

(S-89)

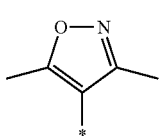

(S-90)

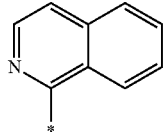

(S-91)

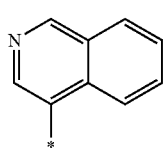

(S-92)

-continued
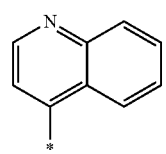 (S-93)
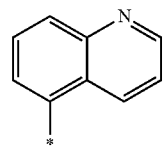 (S-94)
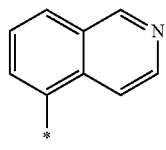 (S-95)
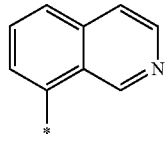 (S-96)
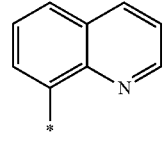 (S-97)
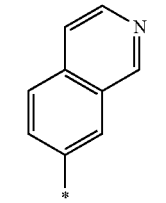 (S-98)
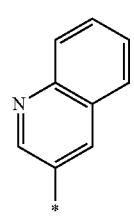 (S-99)
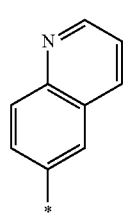 (S-100)
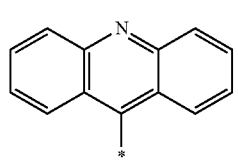 (S-101)
-continued
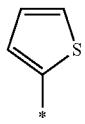 (S-102)
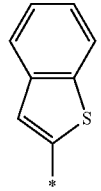 (S-103)
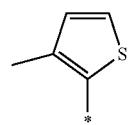 (S-104)
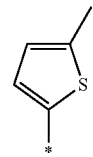 (S-105)
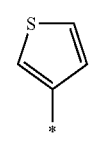 (S-106)
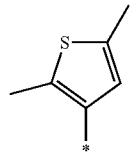 (S-107)
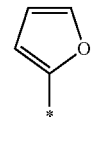 (S-108)
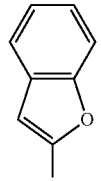 (S-109)
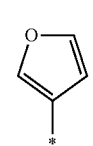 (S-110)
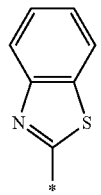 (S-111)

(S-112)
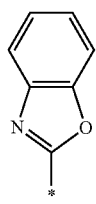
(S-113)
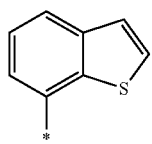
(S-114)
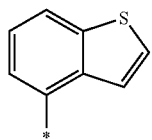
(S-115)
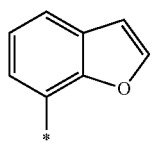
(S-116)
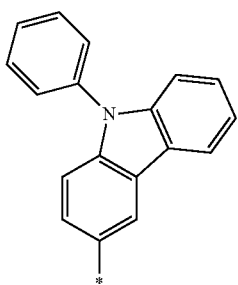
(S-117)
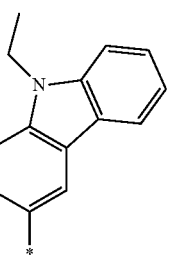
(S-118)
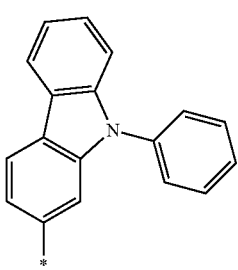
(S-119)
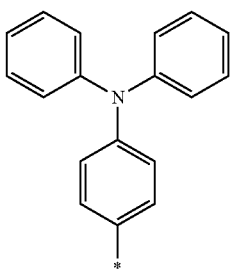
(S-120)
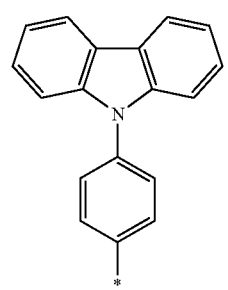
Hereinbelow, the groups represented by "A-number" (A-1 and the like) are shown below.
In A-1 to A-40, atoms marked with * are carbon atoms (=C<) which are directly bonded to basic structural moieties.
(A-1)
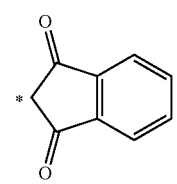
(A-2)
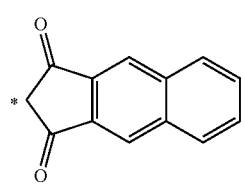
(A-3)
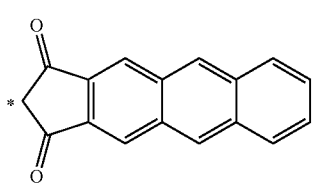
(A-4)
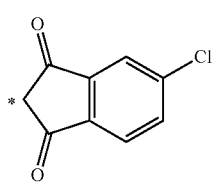

-continued (A-5) (A-13) (A-6) (A-14) (A-7) (A-15) (A-8) (A-16) (A-9) (A-17) (A-10) (A-18) (A-11) (A-19) (A-12) (A-20)

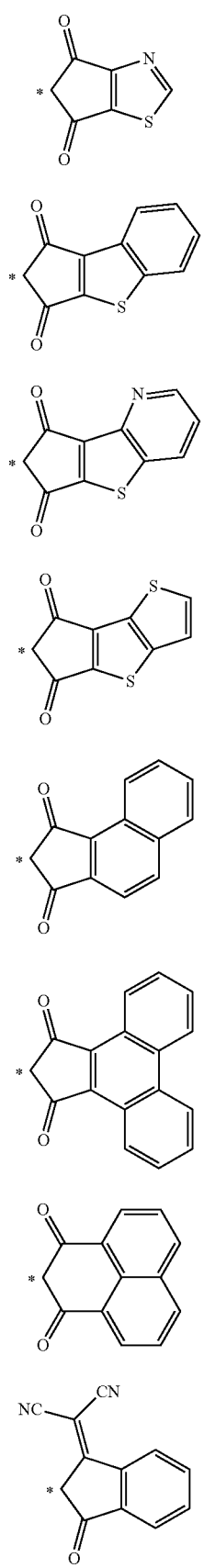
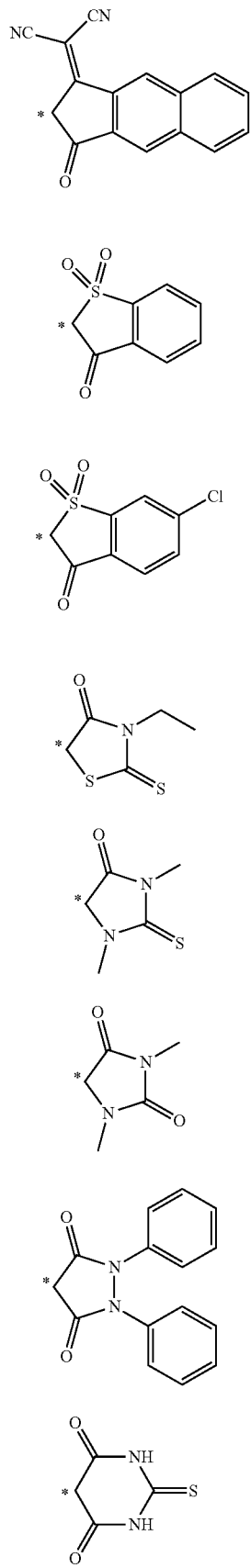

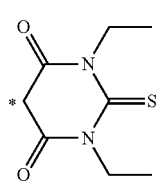

(A-37)

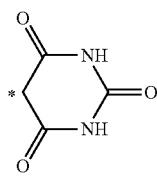

(A-38)

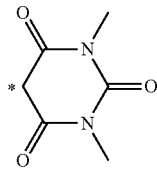

(A-39)

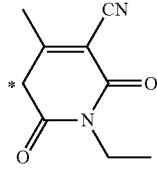

(A-40)

A molecular weight of the specific compound is not particularly limited, but is preferably 400 to 1200. In a case where the molecular weight is 1200 or less, a vapor deposition temperature is not increased, and the compound is not easily degraded. In a case where the molecular weight of the compound is 400 or more, a glass transition point of a vapor deposition film is not lowered, and the heat resistance of the photoelectric conversion element is improved.

The specific compound is particularly useful as a material of the photoelectric conversion film used for the imaging element, the optical sensor, or a photoelectric cell. In addition, the specific compound usually functions as the p-type organic semiconductor in the photoelectric conversion film in many cases. The specific compound can also be used as a coloring material, a liquid crystal material, an organic semiconductor material, a charge transport material, a pharmaceutical material, and a fluorescent diagnostic material.

The specific compound is preferably a compound in which an ionization potential in a single film is −5.0 to −6.0 eV from the viewpoints of stability in a case of using the compound as the p-type organic semiconductor and matching of energy levels between the compound and the n-type organic semiconductor.

The maximum absorption wavelength of the specific compound is not particularly limited, but is preferably in the range of 500 to 600 nm, and more preferably in the range of 520 to 570 nm in that the photoelectric conversion film in the photoelectric conversion element according to the embodiment of the present invention is suitably used as an organic photoelectric conversion film that receives (absorbs) green light and performs photoelectrically conversion.

An absorption half-width of the specific compound is not particularly limited, but is preferably 120 nm or less, more preferably 95 nm or less, still more preferably 90 nm or less, and particularly preferably 85 nm or less in that the photoelectric conversion film in the photoelectric conversion element according to the embodiment of the present invention is suitably used as an organic photoelectric conversion film that receives (absorbs) green light and is photoelectrically converted. The lower limit is not particularly limited, but is often 60 nm or more.

The maximum absorption wavelength and the absorption half-width are values measured in a film state of the specific compound (for example, a vapor deposition film of the specific compound).

The maximum absorption wavelength of the photoelectric conversion film is not particularly limited, but is preferably in the range of 500 to 600 nm, and more preferably in the range of 520 to 570 nm in that the photoelectric conversion film in the photoelectric conversion element according to the embodiment of the present invention is suitably used as an organic photoelectric conversion film that receives (absorbs) green light and is photoelectrically converted.

<n-Type Organic Semiconductor>

It is preferable that the photoelectric conversion film contains the n-type organic semiconductor as a component other than the specific compound.

The n-type organic semiconductor is an acceptor-property organic semiconductor material (a compound), and refers to an organic compound having a property of easily accepting an electron. More specifically, the n-type organic semiconductor refers to an organic compound having a large electron affinity of two organic compounds used in contact with each other. Therefore, any organic compound having an electron accepting property can be used as the acceptor type organic semiconductor.

Examples of the n-type organic semiconductor include fullerenes selected from the group consisting of a fullerene and derivatives thereof, fused aromatic carbocyclic compounds (for example, a naphthalene derivative, an anthracene derivative, a phenanthrene derivative, a tetracene derivative, a pyrene derivative, a perylene derivative, and a fluoranthene derivative); a heterocyclic compound having a 5- to 7-membered ring having at least one of a nitrogen atom, an oxygen atom, or a sulfur atom (for example, pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, and thiazole); polyarylene compounds; fluorene compounds; cyclopentadiene compounds; silyl compounds; 1,4,5,8-naphthalenetetracarboxylic acid anhydride; 1,4,5,8-naphthalenetetracarboxylic acid anhydride imide derivative; oxadiazole derivative; anthraquinodimethane derivatives; diphenylquinone derivatives; bathocuproine, bathophenanthroline, and derivatives thereof; triazole compounds; a distyrylarylene derivative; a metal complex having a nitrogen-containing heterocyclic compound as a ligand; a silole compound; and compounds disclosed in paragraphs [0056] to [0057] of JP2006-100767A.

Among these, it is preferable that examples of the n-type organic semiconductor (compound) include fullerenes selected from the group consisting of a fullerene and derivatives thereof.

Examples of fullerene include fullerene C60, fullerene C70, fullerene C76, fullerene C78, fullerene C80, fullerene C82, fullerene C84, fullerene C90, fullerene C96, fullerene C240, fullerene C540, and mixed fullerene.

Examples of fullerene derivatives include compounds in which a substituent is added to the above fullerenes. As the substituent, an alkyl group, an aryl group, or a heterocyclic group is preferable. As the fullerene derivative, the compounds described in JP2007-123707A are preferable.

An organic coloring agent may be used as the n-type organic semiconductor. Examples of the organic coloring agent include a cyanine coloring agent, a styryl coloring agent, a hemicyanine coloring agent, a merocyanine coloring agent (including zeromethine merocyanine (simple merocyanine)), a rhodacyanine coloring agent, an allopolar coloring agent, an oxonol coloring agent, a hemioxonol coloring agent, a squarylium coloring agent, a croconium coloring agent, an azamethine coloring agent, a coumarin coloring agent, an arylidene coloring agent, an anthraquinone coloring agent, a triphenylmethane coloring agent, an azo coloring agent, an azomethine coloring agent, a metallocene coloring agent, a fluorenone coloring agent, a flugide coloring agent, a perylene coloring agent, a phenazine coloring agent, a phenothiazine coloring agent, a quinone coloring agent, a diphenylmethane coloring agent, a polyene coloring agent, an acridine coloring agent, an acridinone coloring agent, a diphenylamine coloring agent, a quinophthalone coloring agent, a phenoxazine coloring agent, a phthaloperylene coloring agent, a dioxane coloring agent, a porphyrin coloring agent, a chlorophyll coloring agent, a phthalocyanine coloring agent, a subphthalocyanine coloring agent, and a metal complex coloring agent.

The molecular weight of the n-type organic semiconductor is preferably 200 to 1200, and more preferably 200 to 900.

From the point that the photoelectric conversion film in the photoelectric conversion element according to the embodiment of the present invention is suitably used as an organic photoelectric conversion film that receives (absorbs) green light and is photoelectrically converted, it is preferable that the n-type organic semiconductor is colorless or has a maximum absorption wavelength and/or an absorption waveform close to that of the specific compound, and as the specific value, the maximum absorption wavelength of the n-type organic semiconductor is preferably 400 nm or less or in the range of 500 to 600 nm.

It is preferable that the photoelectric conversion film has a bulk hetero structure formed in a state in which the specific compound and the n-type organic semiconductor are mixed. The bulk hetero structure refers to a layer in which the specific compound and the n-type organic semiconductor are mixed and dispersed in the photoelectric conversion film. The photoelectric conversion film having the bulk hetero structure can be formed by either a wet method or a dry method. The bulk hetero structure is described in detail in, for example, paragraphs [0013] to [0014] of the description of JP2005-303266A.

From the viewpoint of responsiveness of the photoelectric conversion element, the content of the specific compound to the total content of the specific compound and the n-type organic semiconductor (=film thickness in terms of single layer of specific compound/(film thickness in terms of single layer of specific compound+film thickness in terms of single layer of n-type organic semiconductor)×100) is preferably 20% to 80% by volume, and more preferably 40% to 80% by volume.

Also, in a case where the photoelectric conversion film contains a p-type organic semiconductor described below, the content of the specific compound to the total content of the specific compound and the n-type organic semiconductor (=film thickness in terms of single layer of specific compound/(film thickness in terms of single layer of specific compound+film thickness in terms of single layer of n-type organic semiconductor+film thickness in terms of single layer of p-type organic semiconductor)×100) is preferably 15% to 75% by volume, and more preferably 35% to 75% by volume.

It is preferable that the photoelectric conversion film is substantially formed of the specific compound, the n-type organic semiconductor, and the p-type organic semiconductor included as desired. The term "substantially" means that a total content of the specific compound, the n-type organic semiconductor, and the p-type organic semiconductor included as desired is 95% by mass or more with respect to a total mass of the photoelectric conversion film.

The n-type organic semiconductor contained in the photoelectric conversion film may be used alone or in combination of two or more.

In addition to the specific compound and the n-type organic semiconductor, the photoelectric conversion film may further contain the p-type organic semiconductor. Examples of the p-type organic semiconductor include the compounds shown below.

The p-type organic semiconductor here means a p-type organic semiconductor which is a compound different from the specific compound. In a case where the photoelectric conversion film contains the p-type organic semiconductor, the p-type organic semiconductor may be used alone or in combination of two or more.

<p-Type Organic Semiconductor>

The p-type organic semiconductor is a donor organic semiconductor material (a compound), and refers to an organic compound having a property of easily donating an electron. More specifically, the p-type organic semiconductor means an organic compound having a smaller ionization potential in a case where two organic compounds are used in contact with each other.

Examples of p-type organic semiconductors include triarylamine compounds (for example, N, N'-bis (3-methylphenyl)-(1,1'-biphenyl)-4,4'-diamine (TPD), 4,4'-bis [N-(naphthyl)-N-Phenyl-amino] biphenyl (α-NPD), the compounds disclosed in paragraphs [0128] to [0148] of JP2011-228614A, the compounds disclosed in paragraphs [0052] to [0063] of JP2011-176259A, the compounds disclosed in paragraphs [0119] to [0158] of JP2011-225544A, the compounds disclosed in paragraphs [0044] to [0051] of JP2015-153910A, and the compounds disclosed in paragraphs [0086] to [0090] of JP2012-094660A, pyrazoline compounds, styrylamine compounds, hydrazone compounds, polysilane compounds, thiophene compounds (for example, a thienothiophene derivative, a dibenzothiophene derivative, a benzodithiophene derivative, a dithienothiophene derivative, a [1] benzothieno [3,2-b] thiophene (BTBT) derivative, a thieno [3,2-f: 4,5-f] bis [1]benzothiophene (TBBT) derivative, the compounds disclosed in paragraphs [0031] to [0036] of JP2018-014474A, the compounds disclosed in paragraphs [0043] to [0045] of WO2016-194630A, the compounds disclosed in paragraphs [0025] to [0037], and [0099] to [0109] of WO2017-159684A, the compounds disclosed in paragraphs [0029] to [0034] of JP2017-076766A, the compounds disclosed in paragraphs [0015] to [0025] of WO2018-207722A, the compounds disclosed in paragraphs [0045] to [0053] of JP2019-054228A, the compounds disclosed in paragraphs [0045] to [0055] of WO2019-058995A, the compounds disclosed in paragraphs [0063] to [0089] of WO2019-081416A, the compounds disclosed in paragraphs [0033] to [0036] of JP2019-080052A, the compounds disclosed in paragraphs [0044] to [0054] of WO2019-054125A, the compounds disclosed in paragraphs [0041] to [0046] of WO2019-093188A, and the like), a cyanine compound, an oxonol compound, a polyamine compound, an indole compound, a pyrrole compound, a pyrazole compound, a polyarylene compound, a fused aromatic carbocyclic compound (for example, a naphthalene derivative, an anthracene derivative, a phenanthrene derivative, a tetracene derivative, a pentacene derivative, a pyrene derivative, a perylene derivative, and a fluoranthene derivative), a porphyrin compound, a phthalocyanine compound, a triazole compound, an oxadiazole compound, an imidazole compound, a polyarylalkane compound, a pyrazolone compound, an amino-substituted chalcone compound, an oxazole compound, a fluorenone compound, a silazane compound, and a metal complex having nitrogen-containing heterocyclic compounds as ligands.

Examples of the p-type organic semiconductor include compounds having an ionization potential smaller than that of the n-type organic semiconductor, and in a case where this condition is satisfied, the organic coloring agents exemplified as the n-type organic semiconductor can be used.

The compounds that can be used as the p-type semiconductor compound are exemplified below.

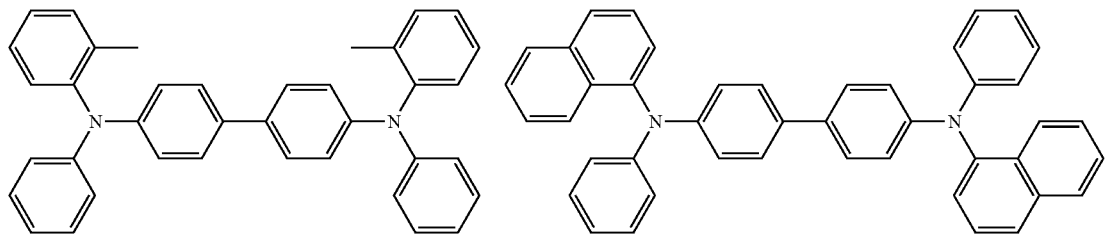

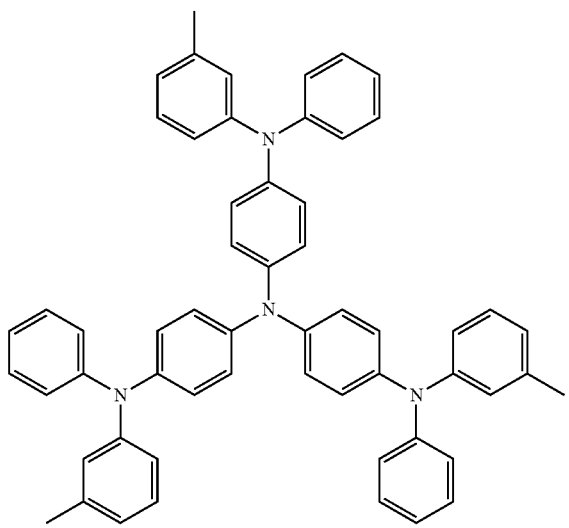

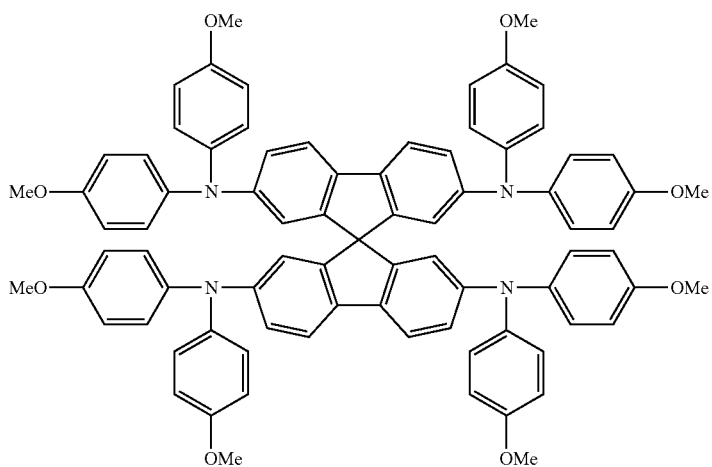

-continued
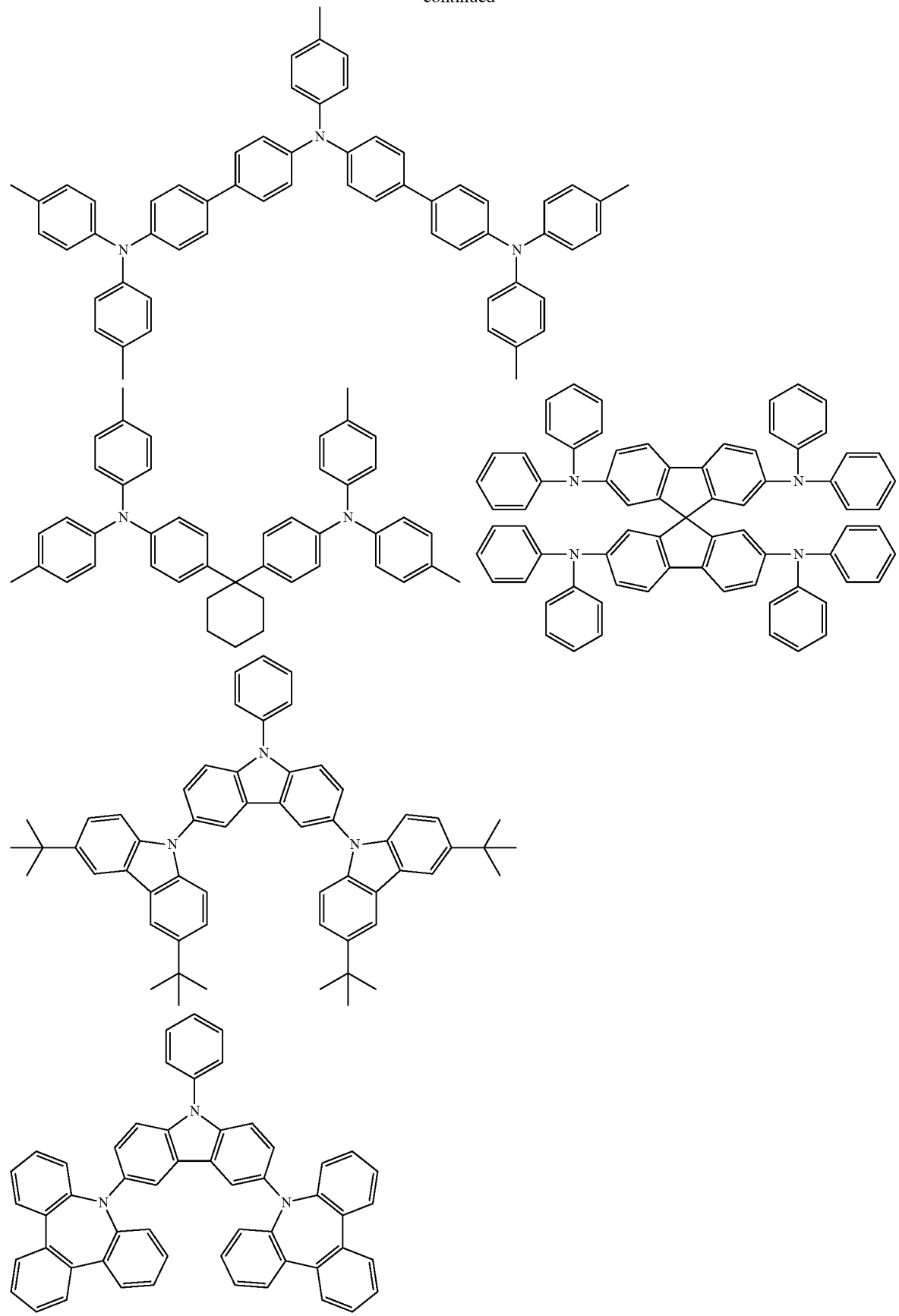

-continued
95
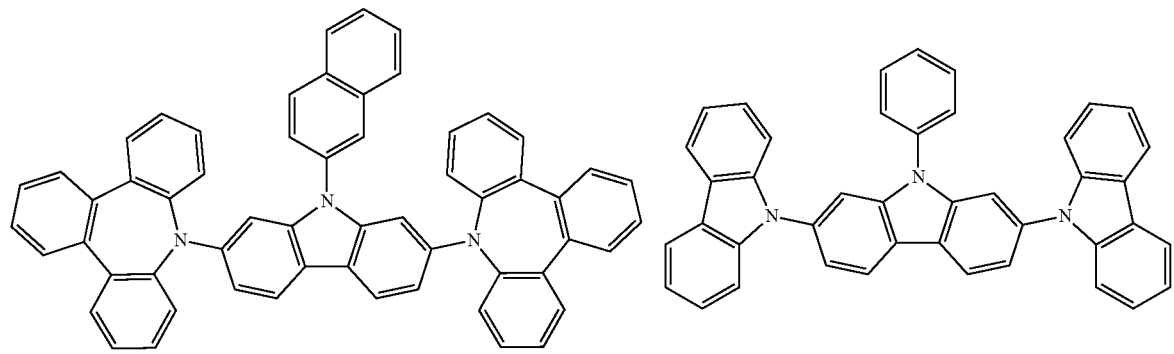
96
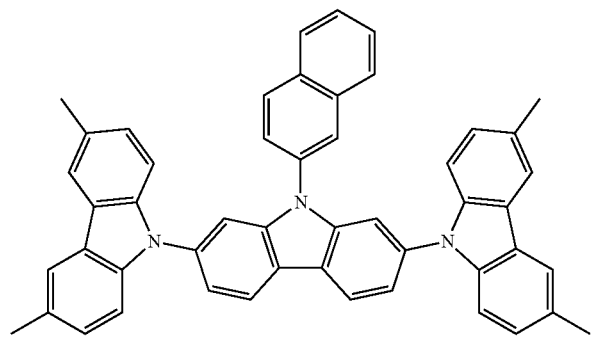
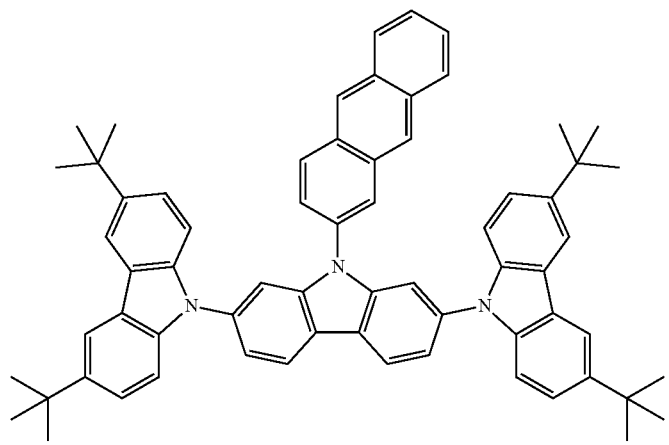
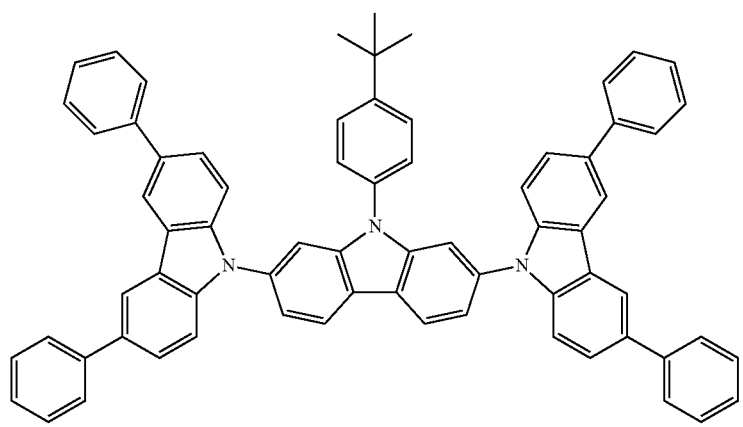

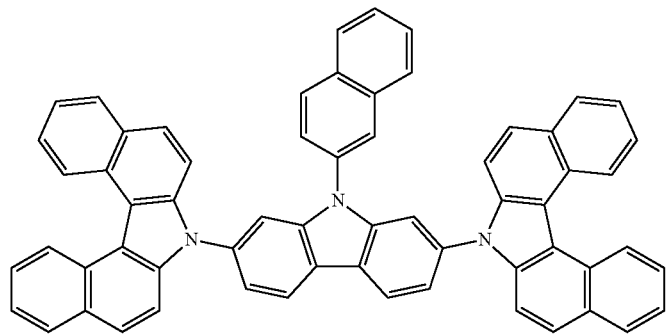
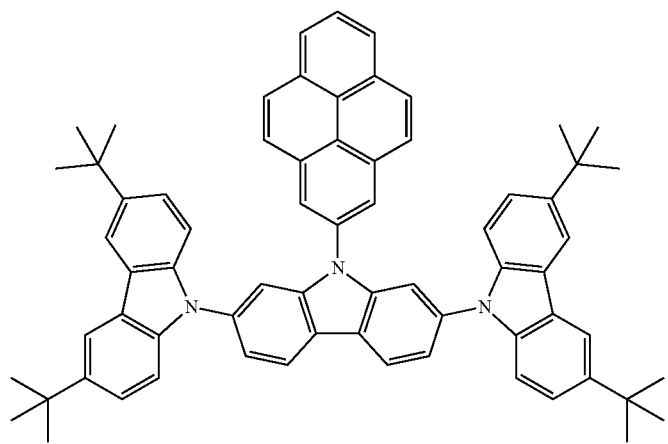
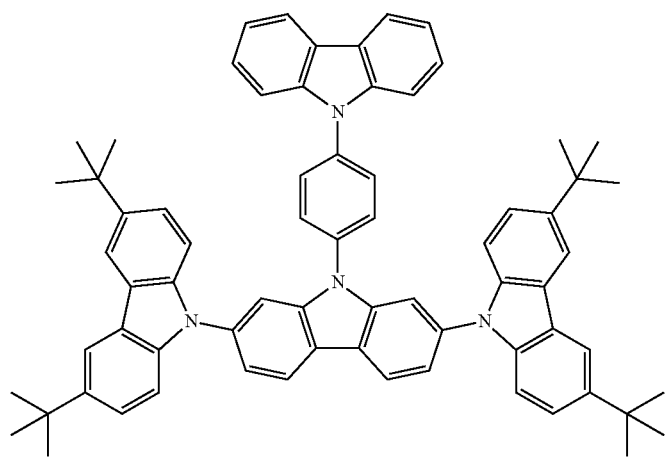
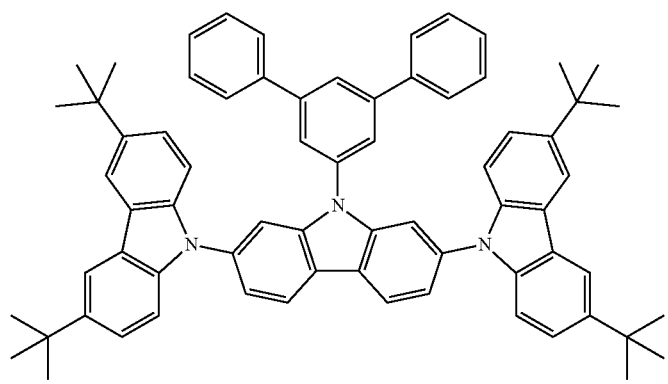

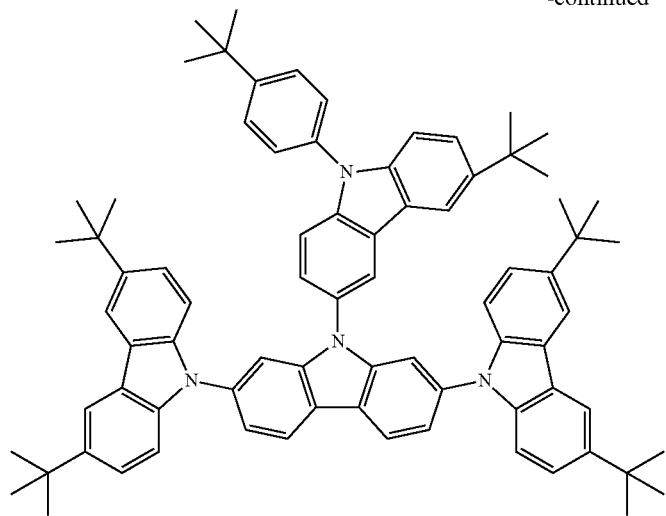
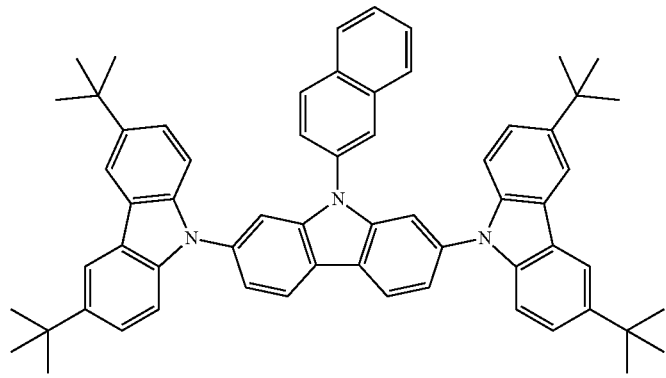
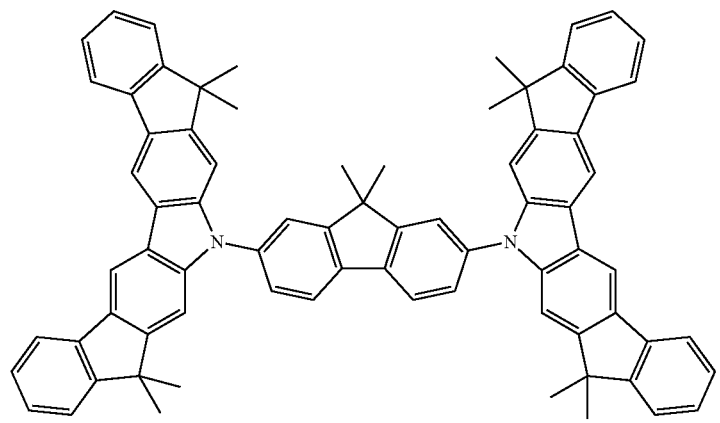
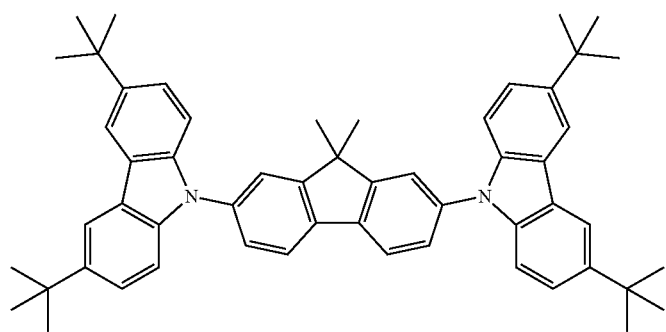

-continued
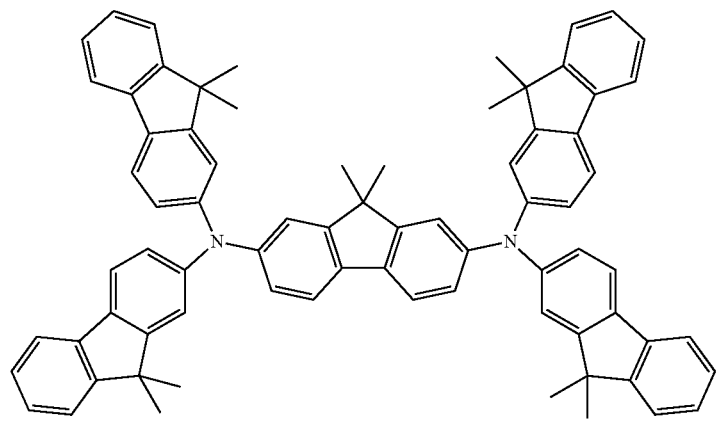
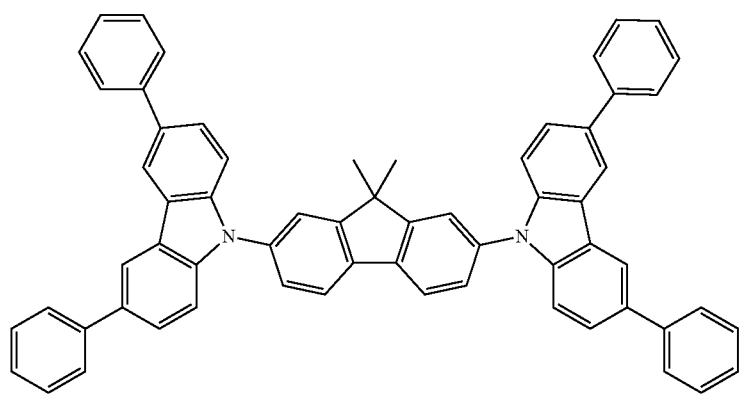
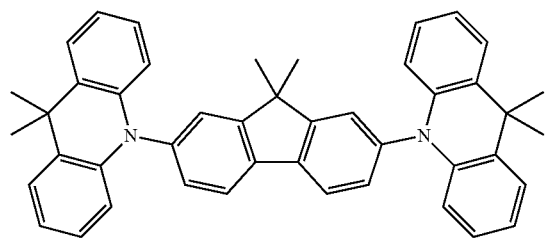
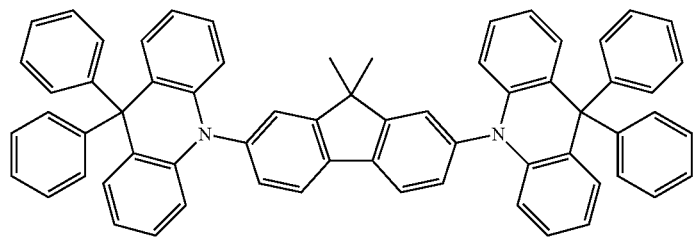
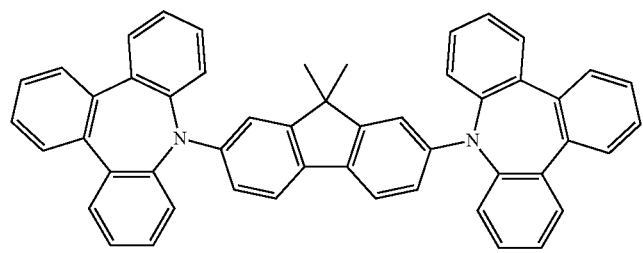

-continued
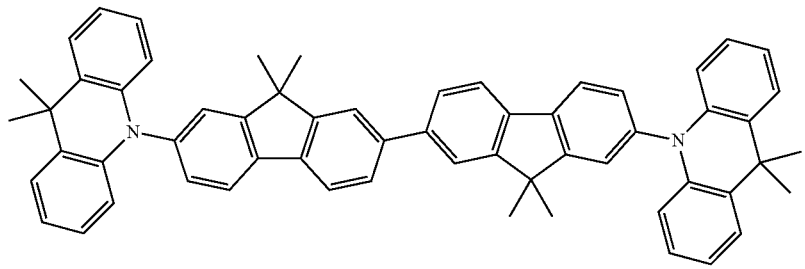
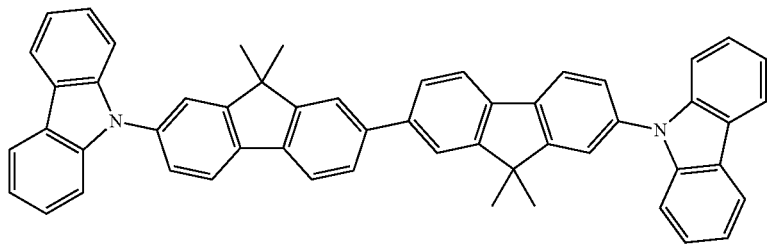
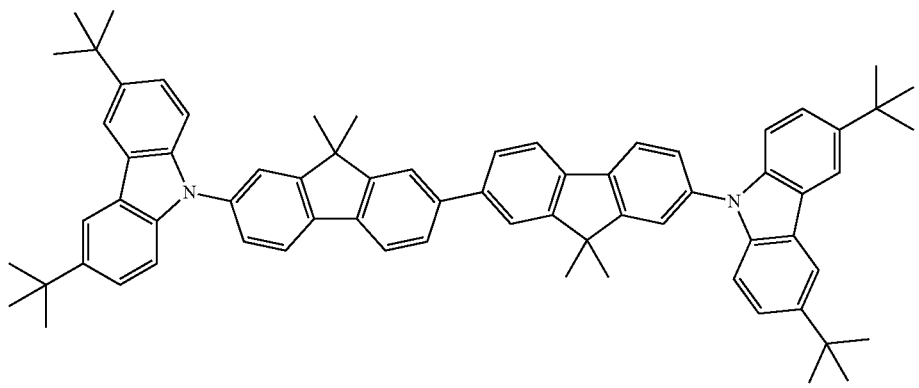
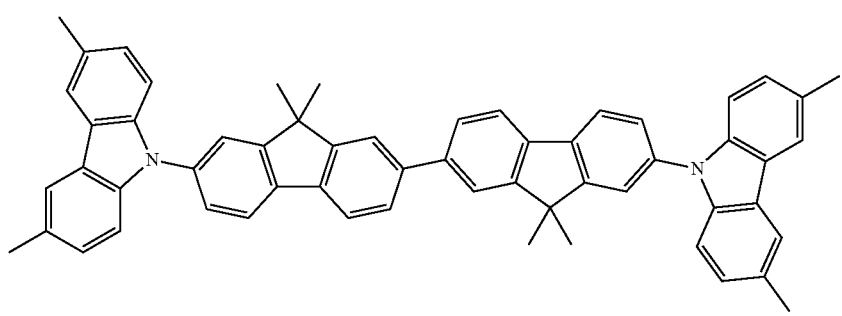
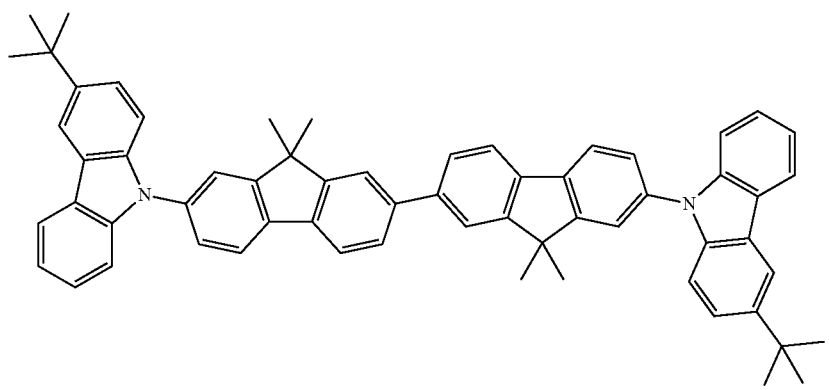

-continued
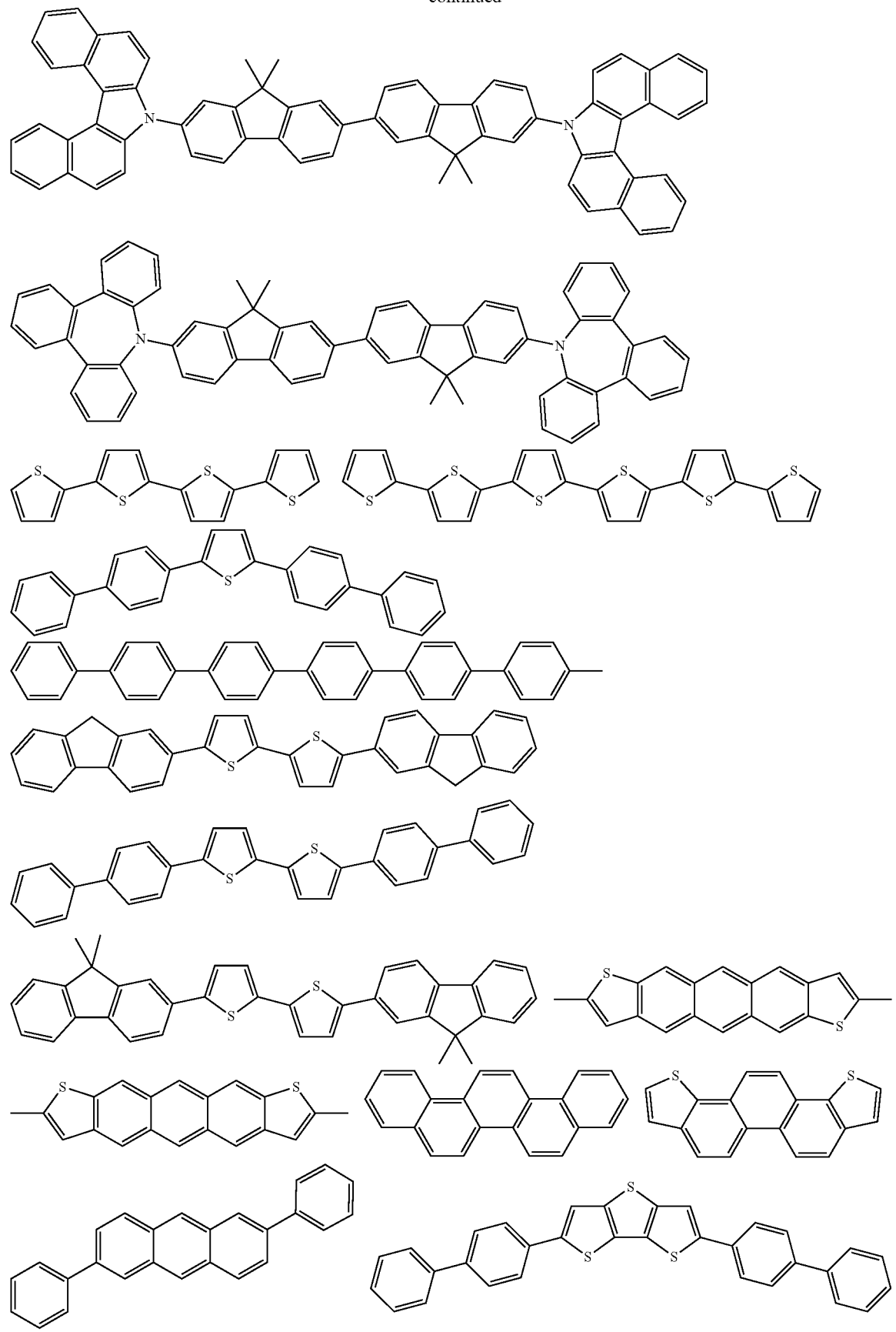

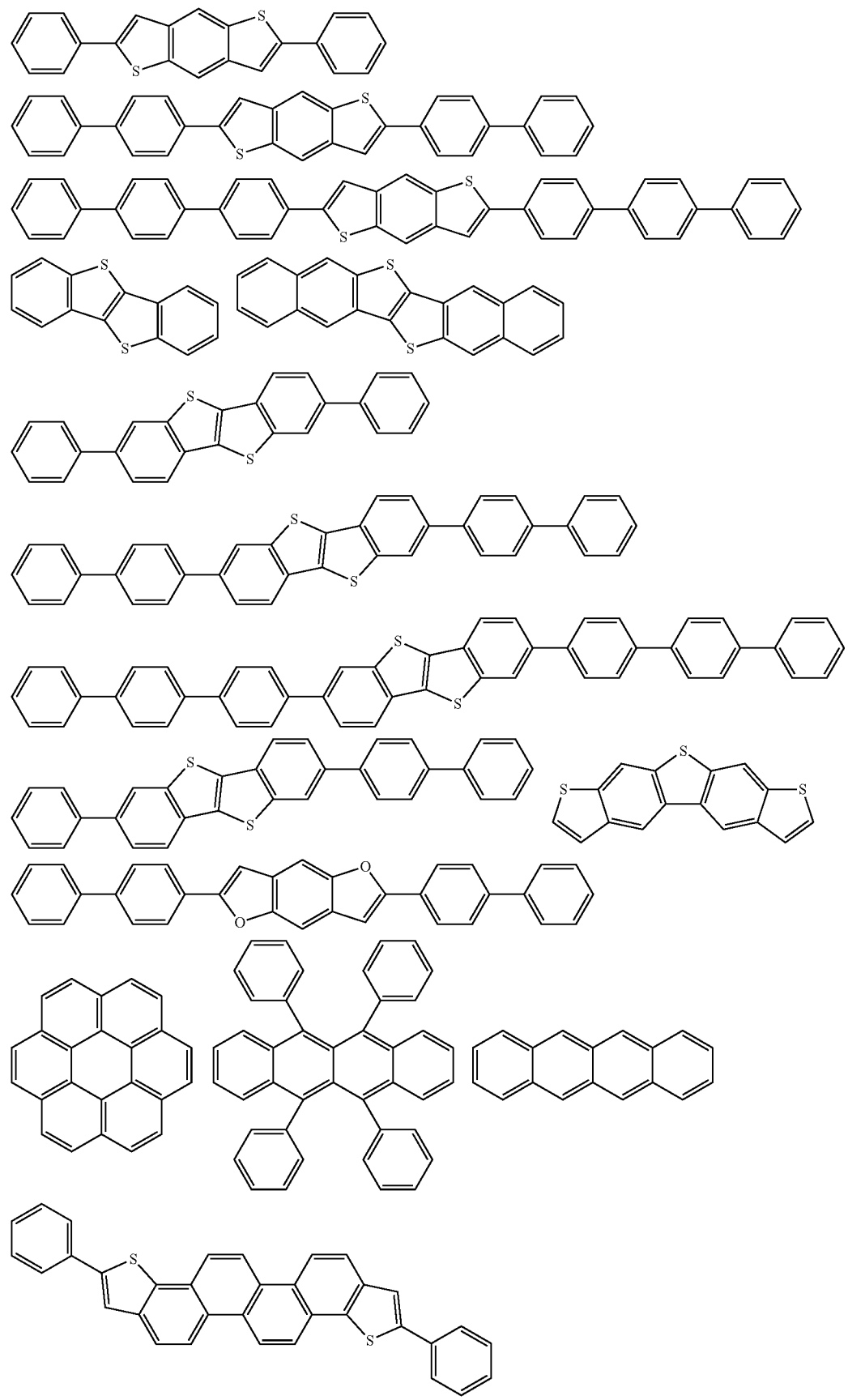

-continued
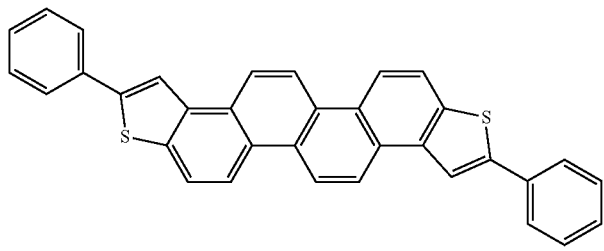
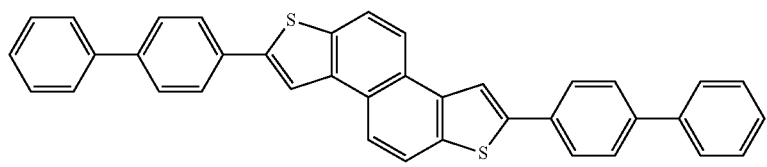
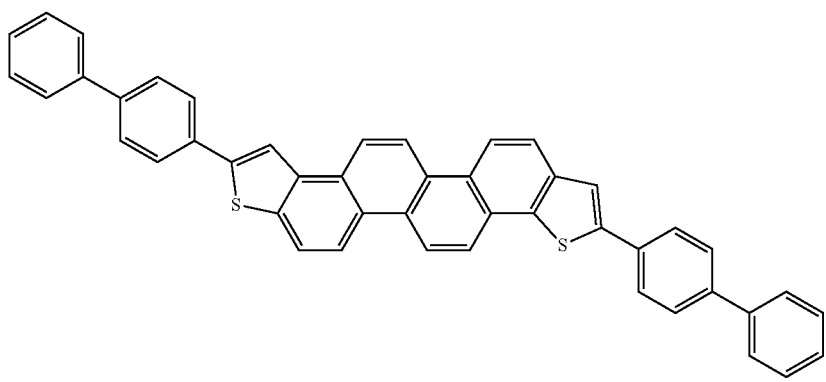
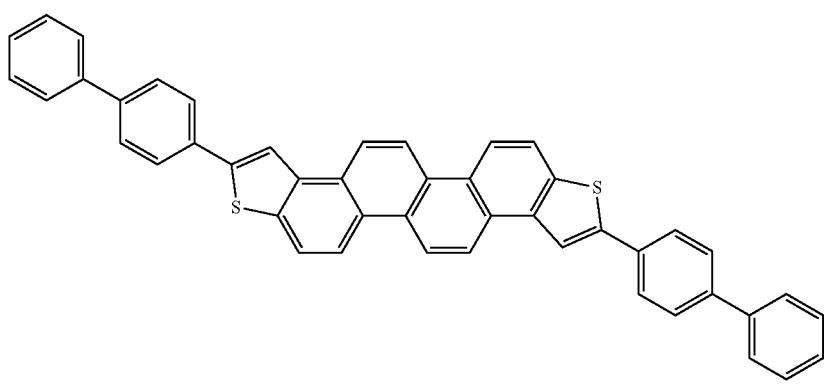
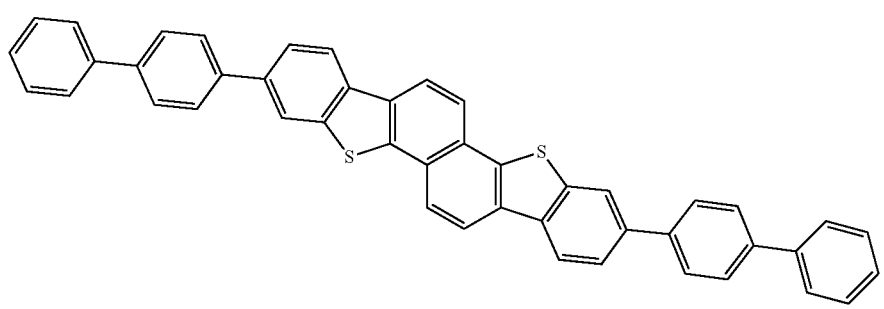

-continued
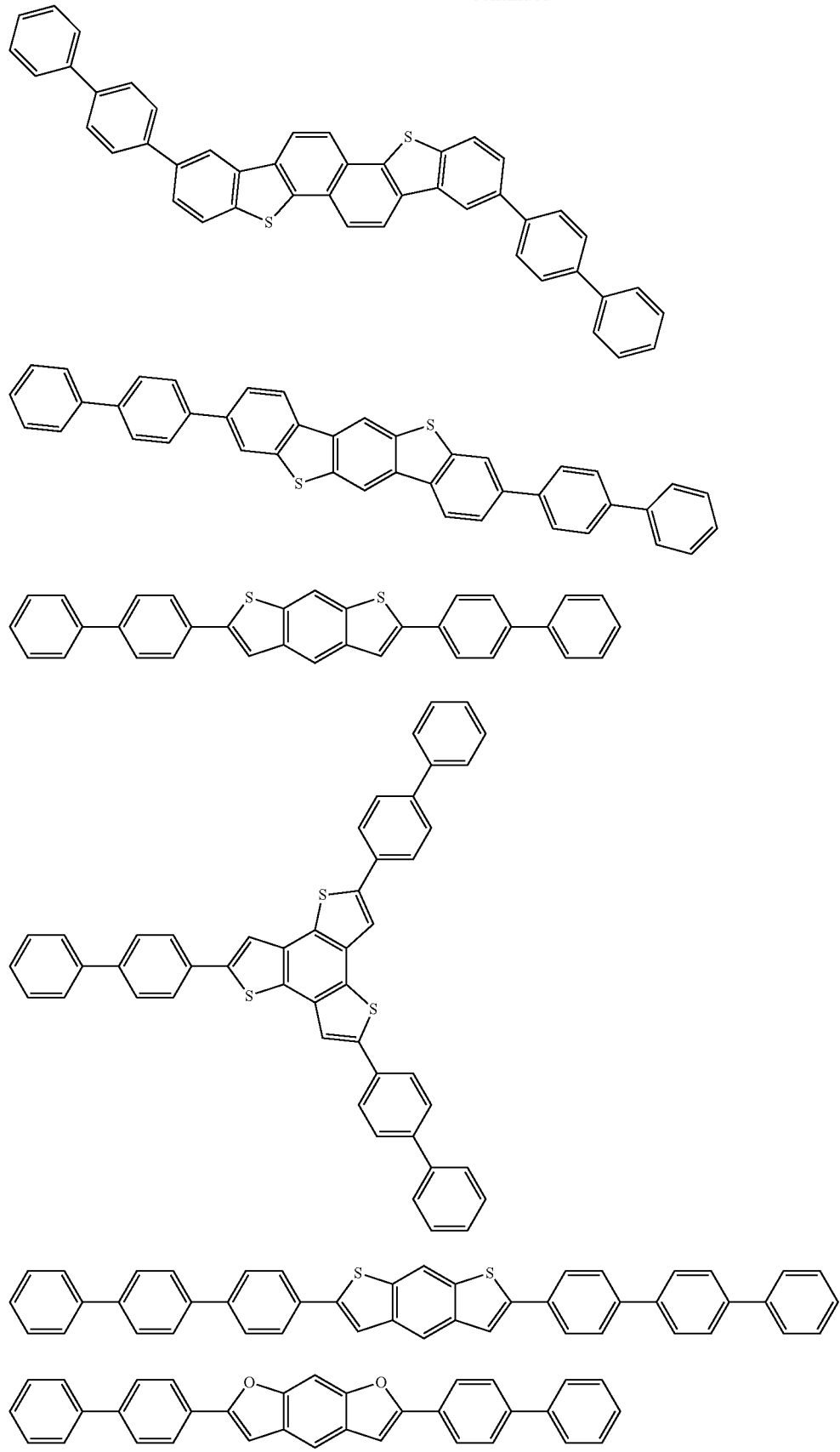

The photoelectric conversion film containing the specific compound is a non-luminescent film, and has a feature different from an organic light emitting diode (OLED). The non-luminescent film means a film having a luminescence quantum efficiency of 1% or less, and the luminescence quantum efficiency is preferably 0.5% or less, and more preferably 0.1% or less.

<Film Formation Method>

The photoelectric conversion film can be formed mostly by a dry film formation method. Examples of the dry film formation method include a physical vapor deposition method such as a vapor deposition method (in particular, a vacuum evaporation method), a sputtering method, an ion plating method, and molecular beam epitaxy (MBE), and chemical vapor deposition (CVD) such as plasma polymerization. Among these, the vacuum evaporation method is preferable. In a case where the photoelectric conversion film is formed by the vacuum evaporation method, producing conditions such as a degree of vacuum and a vapor deposition temperature can be set according to the normal method.

The thickness of the photoelectric conversion film is preferably 10 to 1000 nm, more preferably 50 to 800 nm, still more preferably 50 to 500 nm, and particularly preferably 50 to 300 nm.

<Electrode>

The electrode (the upper electrode (the transparent conductive film) 15 and the lower electrode (the conductive film) 11) is formed of a conductive material. Examples of the conductive material include metals, alloys, metal oxides, electrically conductive compounds, and mixtures thereof.

Since light is incident through the upper electrode 15, the upper electrode 15 is preferably transparent to light to be detected. Examples of the material forming the upper electrode 15 include conductive metal oxides such as tin oxide (antimony tin oxide (ATO), fluorine doped tin oxide (FTO)) doped with antimony, fluorine, or the like, tin oxide, zinc oxide, indium oxide, indium tin oxide (ITO), and indium zinc oxide (IZO); metal thin films such as gold, silver, chromium, and nickel; mixtures or laminates of these metals and the conductive metal oxides; and organic conductive materials such as polyaniline, polythiophene, and polypyrrole. Among these, conductive metal oxides are preferable from the viewpoints of high conductivity, transparency, and the like.

In general, in a case where the conductive film is made to be thinner than a certain range, a resistance value is rapidly increased. However, in the solid-state imaging element into which the photoelectric conversion element according to the present embodiment is incorporated, the sheet resistance is preferably 100 to 10000Ω/□, and the degree of freedom of the range of the film thickness that can be thinned is large. In addition, as the thickness of the upper electrode (the transparent conductive film) 15 is thinner, the amount of light that the upper electrode absorbs becomes smaller, and the light transmittance usually increases. The increase in the light transmittance causes an increase in light absorbance in the photoelectric conversion film and an increase in the photoelectric conversion ability, which is preferable. Considering the suppression of leakage current, an increase in the resistance value of the thin film, and an increase in transmittance accompanied by the thinning, the film thickness of the upper electrode 15 is preferably 5 to 100 nm, and more preferably 5 to 20 nm.

There is a case where the lower electrode 11 has transparency or an opposite case where the lower electrode does not have transparency and reflects light, depending on the application. Examples of a material constituting the lower electrode 11 include conductive metal oxides such as tin oxide (ATO, FTO) doped with antimony, fluorine, or the like, tin oxide, zinc oxide, indium oxide, indium tin oxide (ITO), and indium zinc oxide (IZO); metals such as gold, silver, chromium, nickel, titanium, tungsten, and aluminum, conductive compounds (for example, titanium nitride (TiN)) such as oxides or nitrides of these metals; mixtures or laminates of these metals and conductive metal oxides; and organic conductive materials such as polyaniline, polythiophene, and polypyrrole.

The method of forming electrodes is not particularly limited, and can be appropriately selected in accordance with the electrode material. Specific examples thereof include a wet method such as a printing method and a coating method; a physical method such as a vacuum evaporation method, a sputtering method, and an ion plating method; and a chemical method such as a CVD method and a plasma CVD method.

In a case where the material of the electrode is ITO, examples thereof include an electron beam method, a sputtering method, a resistance thermal vapor deposition method, a chemical reaction method (such as a sol-gel method), and a coating method with a dispersion of indium tin oxide.

<Charge Blocking Film: Electron Blocking Film and Positive Hole Blocking Film>

It is also preferable that the photoelectric conversion element according to the embodiment of the present invention has one or more interlayers between the conductive film and the transparent conductive film, in addition to the photoelectric conversion film. Example of the interlayer includes the charge blocking film. In a case where the photoelectric conversion element has this film, the characteristics (such as photoelectric conversion efficiency and responsiveness) of the photoelectric conversion element to be obtained is more excellent. Examples of the charge blocking film include the electron blocking film and the positive hole blocking film. Hereinafter, the films will be described in detail.

(Electron Blocking Film)

The electron blocking film is a donor organic semiconductor material (a compound), and the p-type organic semiconductor described above can be used.

A polymer material can also be used as the electron blocking film.

Specific examples of a polymer material include a polymer such as phenylenevinylene, fluorene, carbazole, indole, pyrene, pyrrole, picoline, thiophene, acetylene, and diacetylene, and a derivative thereof.

The electron blocking film may be configured by a plurality of films.

The electron blocking film may be formed of an inorganic material. In general, an inorganic material has a dielectric constant larger than that of an organic material. Therefore, in a case where the inorganic material is used in the electron blocking film, a large voltage is applied to the photoelectric conversion film. Therefore, the photoelectric conversion efficiency increases. Examples of the inorganic material that can be used in the electron blocking film include calcium oxide, chromium oxide, copper chromium oxide, manganese oxide, cobalt oxide, nickel oxide, copper oxide, copper gallium oxide, copper strontium oxide, niobium oxide, molybdenum oxide, copper indium oxide, silver indium oxide, and iridium oxide.

(Positive Hole Blocking Film)

A positive hole blocking film is an acceptor-property organic semiconductor material (a compound), and the n-type organic semiconductor described above can be used.

The method of producing the charge blocking film is not particularly limited, but a dry film formation method and a wet film formation method are exemplified. Examples of the dry film formation method include a vapor deposition method and a sputtering method. The vapor deposition method may be any of physical vapor deposition (PVD) method and chemical vapor deposition (CVD) method, and physical vapor deposition method such as vacuum evaporation method is preferable. Examples of the wet film formation method include an inkjet method, a spray method, a nozzle printing method, a spin coating method, a dip coating method, a casting method, a die coating method, a roll coating method, a bar coating method, and a gravure coating method, and an inkjet method is preferable from the viewpoint of high precision patterning.

Each thickness of the charge blocking films (the electron blocking film and the positive hole blocking film) is preferably 3 to 200 nm, more preferably 5 to 100 nm, and still more preferably 5 to 30 nm.

<Substrate>

The photoelectric conversion element may further include a substrate. The type of substrate to be used is not particularly limited, but a semiconductor substrate, a glass substrate, and a plastic substrate are exemplified.

The position of the substrate is not particularly limited, but in general, the conductive film, the photoelectric conversion film, and the transparent conductive film are laminated on the substrate in this order.

<Sealing Layer>

The photoelectric conversion element may further include a sealing layer. The performance of the photoelectric conversion material may deteriorate noticeably due to the presence of deterioration factors such as water molecules. The deterioration can be prevented by sealing and coating the entirety of the photoelectric conversion film with the sealing layer such as diamond-like carbon (DLC) or ceramics such as metal oxide, or metal nitride, and metal nitride oxide which are dense and into which water molecules do not permeate.

The material of the sealing layer may be selected and the sealing layer may be produced according to the description in paragraphs [0210] to [0215] of JP2011-082508A.

[Imaging Element]

An example of the application of the photoelectric conversion element includes an imaging element. The imaging element is an element that converts optical information of an image into an electric signal, and usually, a plurality of photoelectric conversion elements are arranged in a matrix on the same plane, and an optical signal is converted into the electric signal in each photoelectric conversion element (pixels) to sequentially output the electric signal to the outside of the imaging element for each pixel. Therefore, each pixel is composed of one or more photoelectric conversion elements and one or more transistors.

Figure 3:
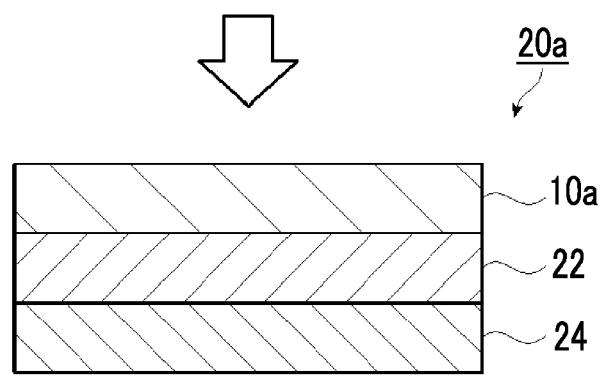
FIG. 3 is a schematic cross-sectional view of one embodiment of an imaging element.
Figure 4:
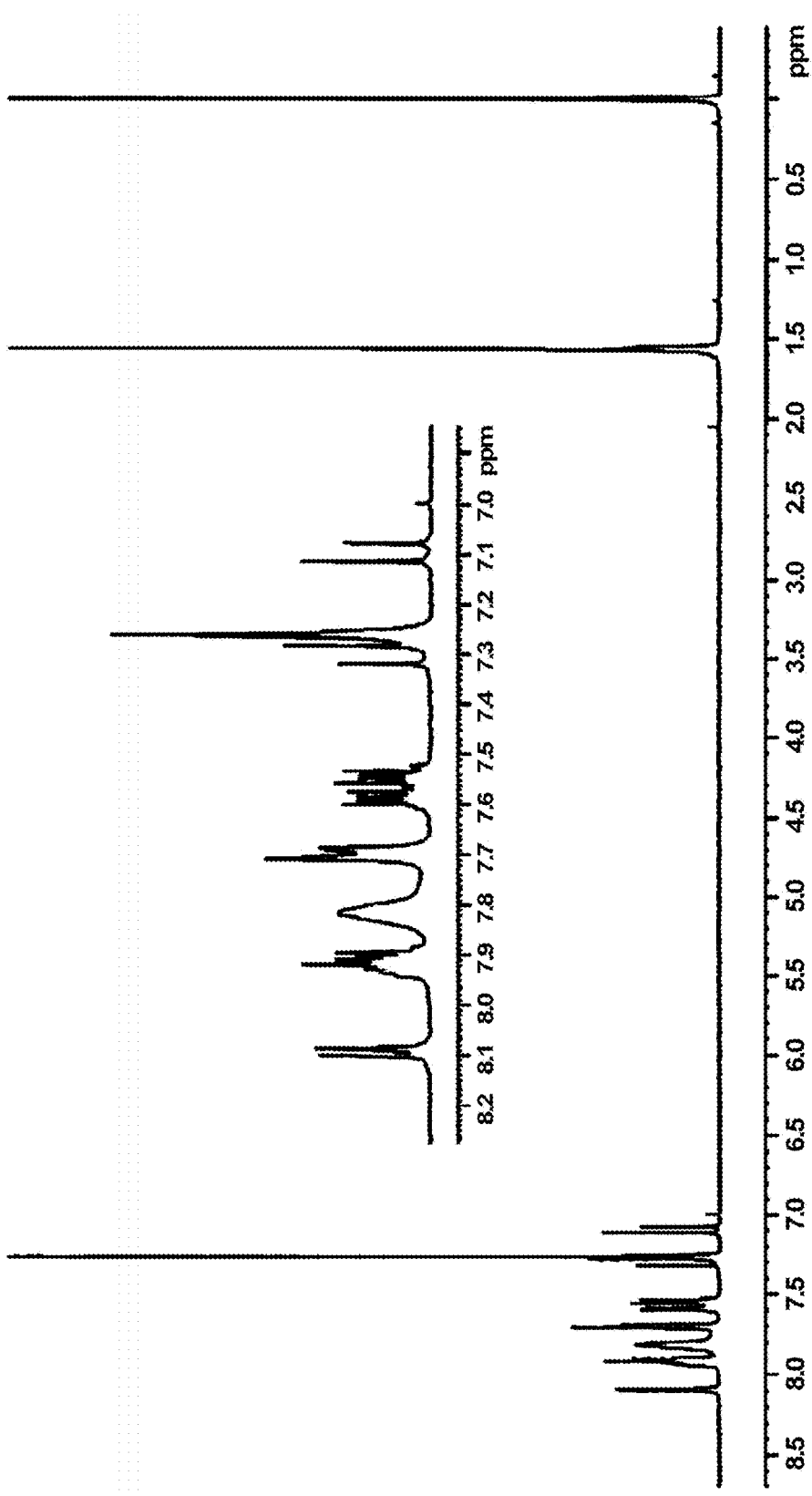
FIG. 4 is a $^1$H NMR (Nuclear Magnetic Resonance) chart of a compound (D-1).

FIG. 3 is a schematic cross-sectional view showing a schematic configuration of an imaging element for describing an embodiment of the present invention. This imaging element is mounted on an imaging element such as a digital camera and a digital video camera, an electronic endoscope, and imaging modules such as a cellular phone.

An imaging element 20a shown in FIG. 3 includes a photoelectric conversion element 10a according to the embodiment of the present invention, a blue photoelectric conversion element 22, and a red photoelectric conversion element 24, which are laminated along the light incident direction. As described above, the photoelectric conversion element 10a can mainly function as a green photoelectric conversion element capable of receiving green light.

The imaging element 20a is a so-called laminated type color separation imaging element. The photoelectric conversion element 10a, the blue photoelectric conversion element 22, and the red photoelectric conversion element 24 have different wavelength spectra to be detected. That is, the blue photoelectric conversion element 22 and the red photoelectric conversion element 24 correspond to photoelectric conversion elements that receive (absorb) light having a wavelength different from a wavelength of the light received by the photoelectric conversion element 10a. The photoelectric conversion element 10a can mainly receive green light, the blue photoelectric conversion element 22 can mainly receive blue light, and the red photoelectric conversion element can mainly receive red light.

Green light means light in the wavelength range of 500 to 600 nm, blue light means light in the wavelength range of 400 to 500 nm, and red light means light in the wavelength range of 600 to 700 nm.

In a case where light is incident on the imaging element 20a in the direction of the arrow, first, green light is mainly absorbed by the photoelectric conversion element 10a, but blue light and red light are transmitted through the photoelectric conversion element 10a. In a case where the light transmitted through the photoelectric conversion element 10a travels to the blue photoelectric conversion element 22, the blue light is mainly absorbed, but the red light is transmitted through the blue photoelectric conversion element 22. Then, light transmitted through the blue photoelectric conversion element 22 is absorbed by the red photoelectric conversion element 24. As described above, in the imaging element 20a, which is a laminated type color separation imaging element, one pixel can be configured with three light receiving sections of green, blue, and red, and a large area of the light receiving section can be taken.

In particular, the photoelectric conversion element 10a according to the embodiment of the present invention has a narrow absorption peak half-width, and thus absorptions of blue light and red light do not occur, and it is difficult to affect the detectability of the blue photoelectric conversion element 22 and the red photoelectric conversion element 24.

The configurations of the blue photoelectric conversion element 22 and the red photoelectric conversion element 24 are not particularly limited.

For example, the photoelectric conversion element having a configuration in which colors are separated by using silicon using a difference in light absorption length may be used. As a more specific example, both the blue photoelectric conversion element 22 and the red photoelectric conversion element 24 may be made of silicon. In this case, as for the light including the blue light, the green light, and the red light that has entered the imaging element 20a in the direction of the arrow, the photoelectric conversion element 10a mainly receives the green light having the center wavelength, and the remaining blue light and red light are easily separated. Blue light and red light have different light absorption lengths for silicon (wavelength dependence of absorption coefficient for silicon), blue light is easily absorbed near the surface of silicon, and red light can penetrate deeper into the silicon. Based on such a difference in light absorption length, blue light is mainly received by the blue photoelectric conversion element 22 existing in a shallower position, and red light is mainly received by the red photoelectric conversion element 24 existing in a deeper position.

Furthermore, the blue photoelectric conversion element 22 and the red photoelectric conversion element 24 may be the photoelectric conversion element (the blue photoelectric conversion element 22 or the red photoelectric conversion element 24) having a configuration including a conductive film, an organic photoelectric conversion film having an absorption maximum for blue light or red light, and the transparent conductive film in this order.

In FIG. 3, the photoelectric conversion element according to the embodiment of the present invention, the blue photoelectric conversion element, and the red photoelectric conversion element are arranged in this order from the light incident side, but the arrangement is not limited to the aspect, and may be another aspect. For example, the blue photoelectric conversion element, the photoelectric conversion element according to the embodiment of the present invention, and the red photoelectric conversion element may be arranged in this order from the light incident side.

As described above, the configuration in which the photoelectric conversion elements of the three primary colors of blue, green, and red are laminated as the imaging element is described, but the configuration may be two layers (two colors) or four layers (four colors) or more.

For example, an aspect in which the photoelectric conversion element 10a according to the embodiment of the present invention may be arranged on the arrayed blue photoelectric conversion element 22 and red photoelectric conversion element 24 may be employed. As needed, a color filter that absorbs light of a predetermined wavelength may be arranged on the light incident side.

The form of the imaging element is not limited to the forms shown in FIG. 3 and may be other forms.

For example, an aspect in which the photoelectric conversion element according to the embodiment of the present invention, the blue photoelectric conversion element, and the red photoelectric conversion element may be arranged in the same plane position may be employed.

Alternatively, the photoelectric conversion element may be used in a single layer. For example, blue, red, and green color filters may be arranged on the photoelectric conversion element 10a according to the embodiment of the present invention to separate colors.

[Optical Sensor]

Examples of another application of the photoelectric conversion element include the photoelectric cell and the optical sensor, but the photoelectric conversion element according to the embodiment of the present invention is preferably used as the optical sensor. The photoelectric conversion element may be used alone as the optical sensor. Alternately, the photoelectric conversion element may be used as a line sensor in which the photoelectric conversion elements are linearly arranged or as a two-dimensional sensor in which the photoelectric conversion elements are arranged on a plane.

[Compound]

The present invention further includes the invention of compounds. A compound according to the embodiment of the present invention is the same as the compound represented by Formula (4-2).

EXAMPLES

Examples will be shown below, but the present invention is not limited thereto.

[Compound Used for Photoelectric Conversion Film]

<Synthesis of Compound (D-1)>

A compound (D-1) was synthesized according to the following scheme.

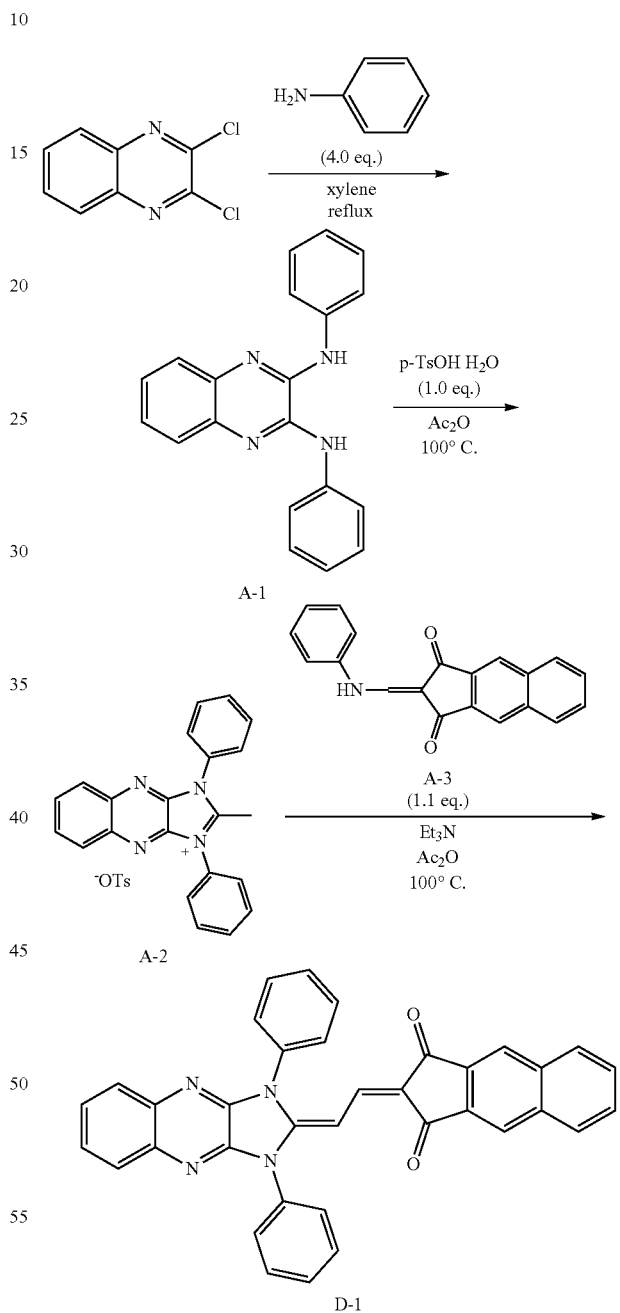

2,3-Dichloroquinoxaline (5.00 g, 25.1 mmol) and aniline (9.31 g, 100 mmol) were added to xylene (20 mL) in a flask to obtain a reaction solution. The obtained reaction solution was heated under reflux and reacted for 6 hours. Methanol (80 mL) was added to the reaction solution after cooled, the resultant mixture was stirred at room temperature for 30 minutes, and a solid was deposited. Thereafter, the solid obtained by filtering the deposited solid was washed with methanol to obtain a compound (A-1) (3.20 g, 10.2 mmol, yield 41%).

The compound (A-1) (3.00 g, 9.60 mmol) was added to acetic anhydride (Ac₂O) (18 mL) in a flask, and p-toluene-sulfonic acid monohydrate (p-TsOH·H₂O) (1.83 g, 9.60 mmol) was added to the flask to obtain a reaction solution. The obtained reaction solution was reacted at 100° C. for 7 hours. Water (50 mL) and ethyl acetate (30 mL) were added to the reaction solution after cooled, the resultant mixture was stirred at room temperature for 30 minutes, and a solid was deposited. Thereafter, the solid obtained by filtering the deposited solid was washed with ethyl acetate to obtain a compound (A-2) (2.10 g, 4.13 mmol, yield 43%).

The compound (A-2) (509 mg, 1.00 mmol) and the compound (A-3) (329 mg, 1.1 mmol) were placed in a flask, and acetic anhydride (Ac₂O) (5.0 mL) and triethylamine (Et₃N) (0.50 mL) were added to the flask to obtain a reaction solution. The obtained reaction solution was reacted at 100° C. for 5 hours. Water (15 mL) and methanol (15 mL) were added to the reaction solution after cooled, the resultant mixture was stirred at room temperature for 30 minutes, and a solid was deposited. Thereafter, the solid obtained by filtering the deposited solid was washed with methanol to obtain a crude. The obtained crude was purified by silica gel column chromatography (eluent: mixed solution of ethyl acetate/chloroform=1/9 (mass ratio)), and then was recrystallized from methanol to obtain a compound (D-1) (220 mg, 0.41 mmol, yield 41%).

The obtained compound (D-1) was identified by nuclear magnetic resonance (NMR) and mass spectrometry (MS).

Figure 5:
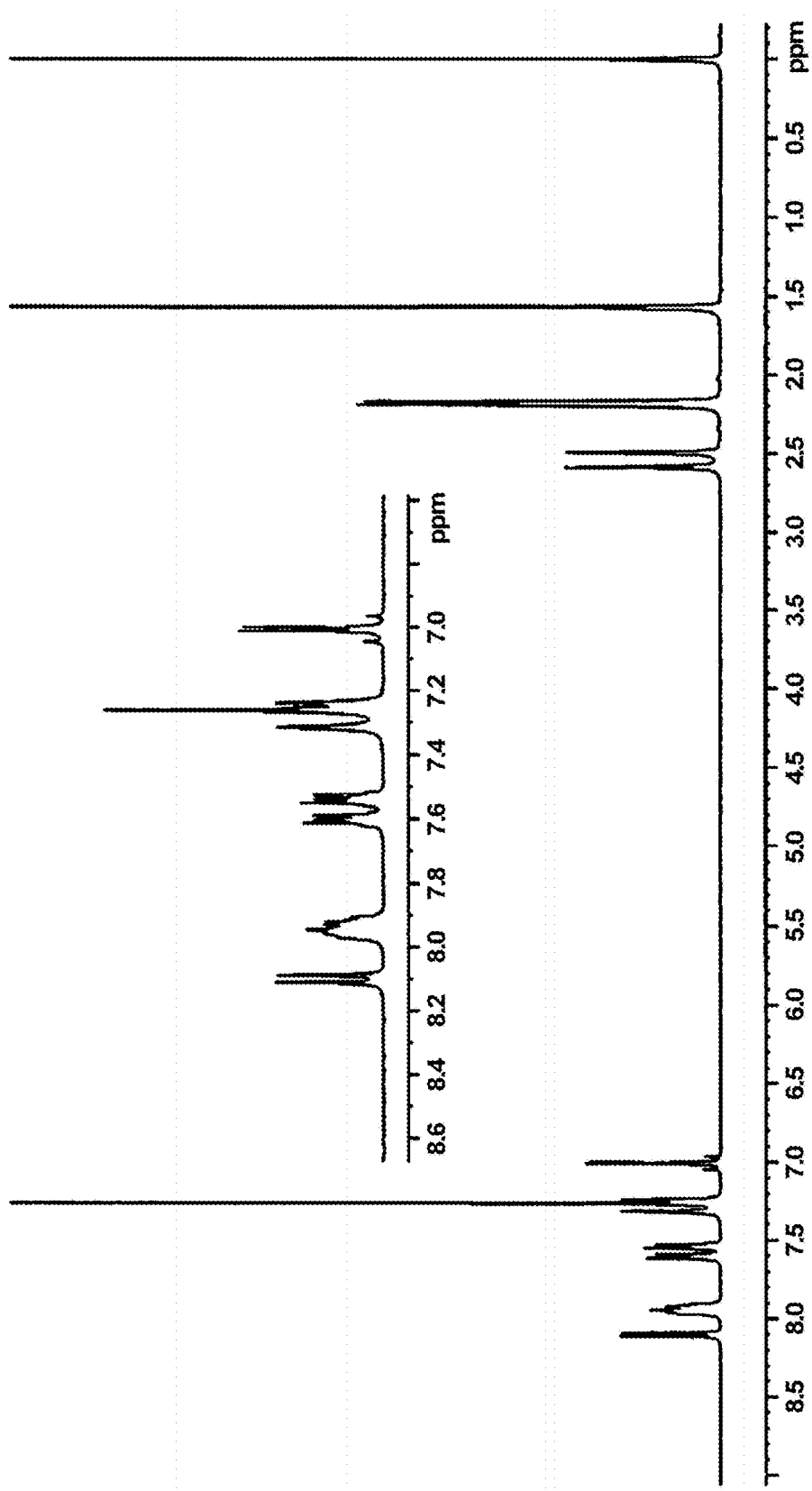
FIG. 5 is a $^1$H NMR chart of a compound (D-2).
Figure 6:
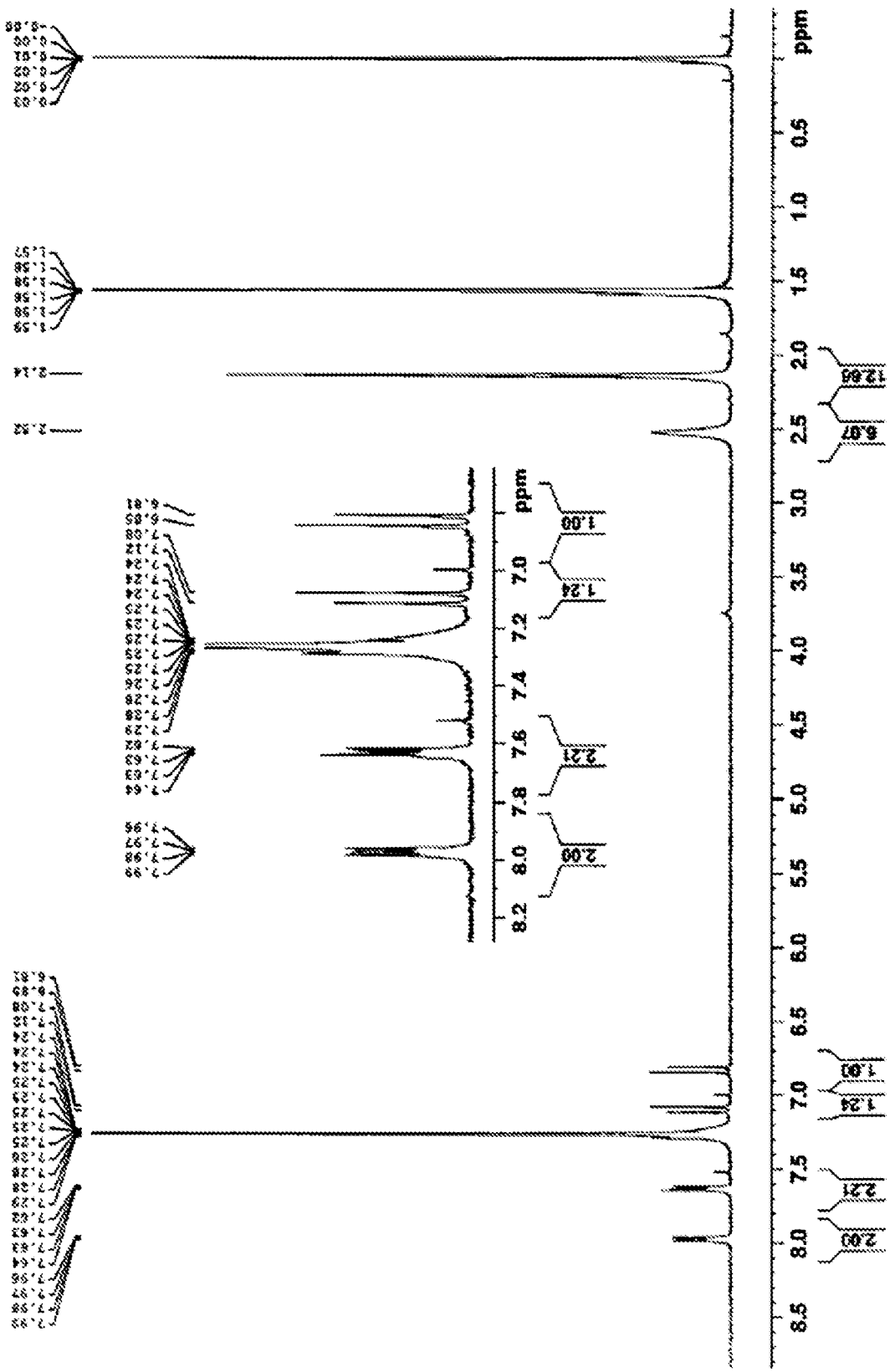
FIG. 6 is a $^1$H NMR chart of a compound (D-3).
Figure 7:
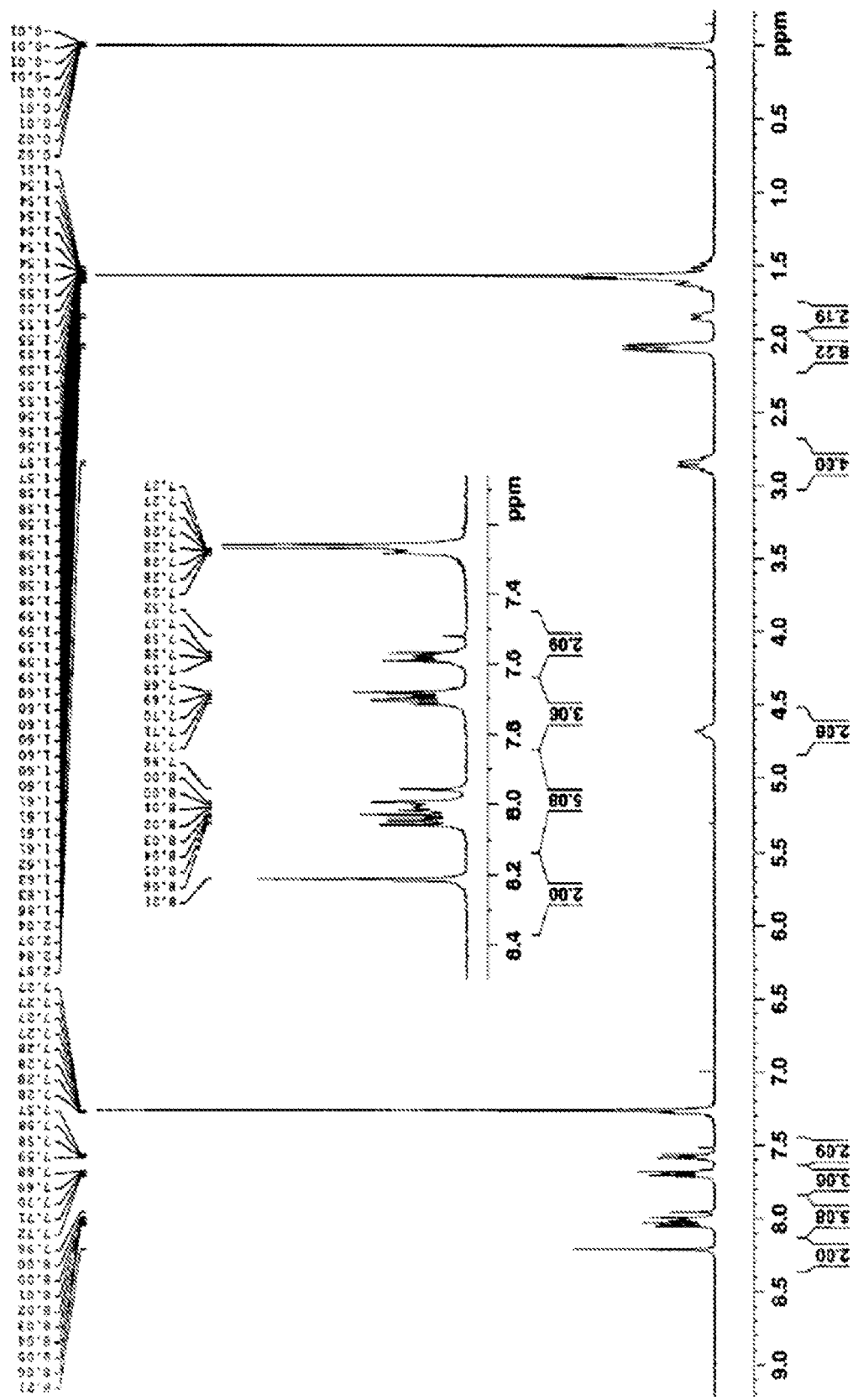
FIG. 7 is a $^1$H NMR chart of a compound (D-4).
Figure 8:
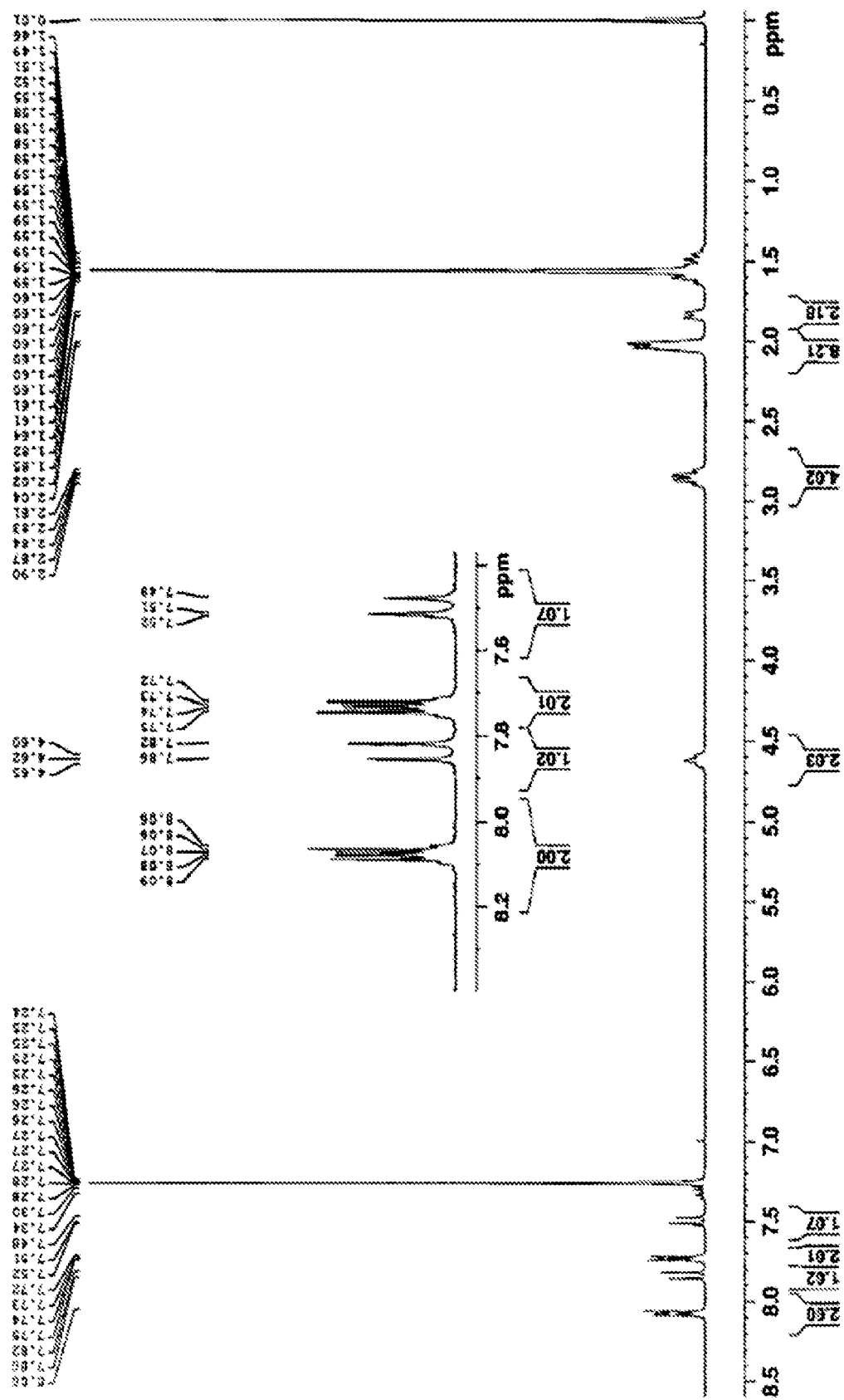
FIG. 8 is a $^1$H NMR chart of a compound (D-5).
Figure 9:
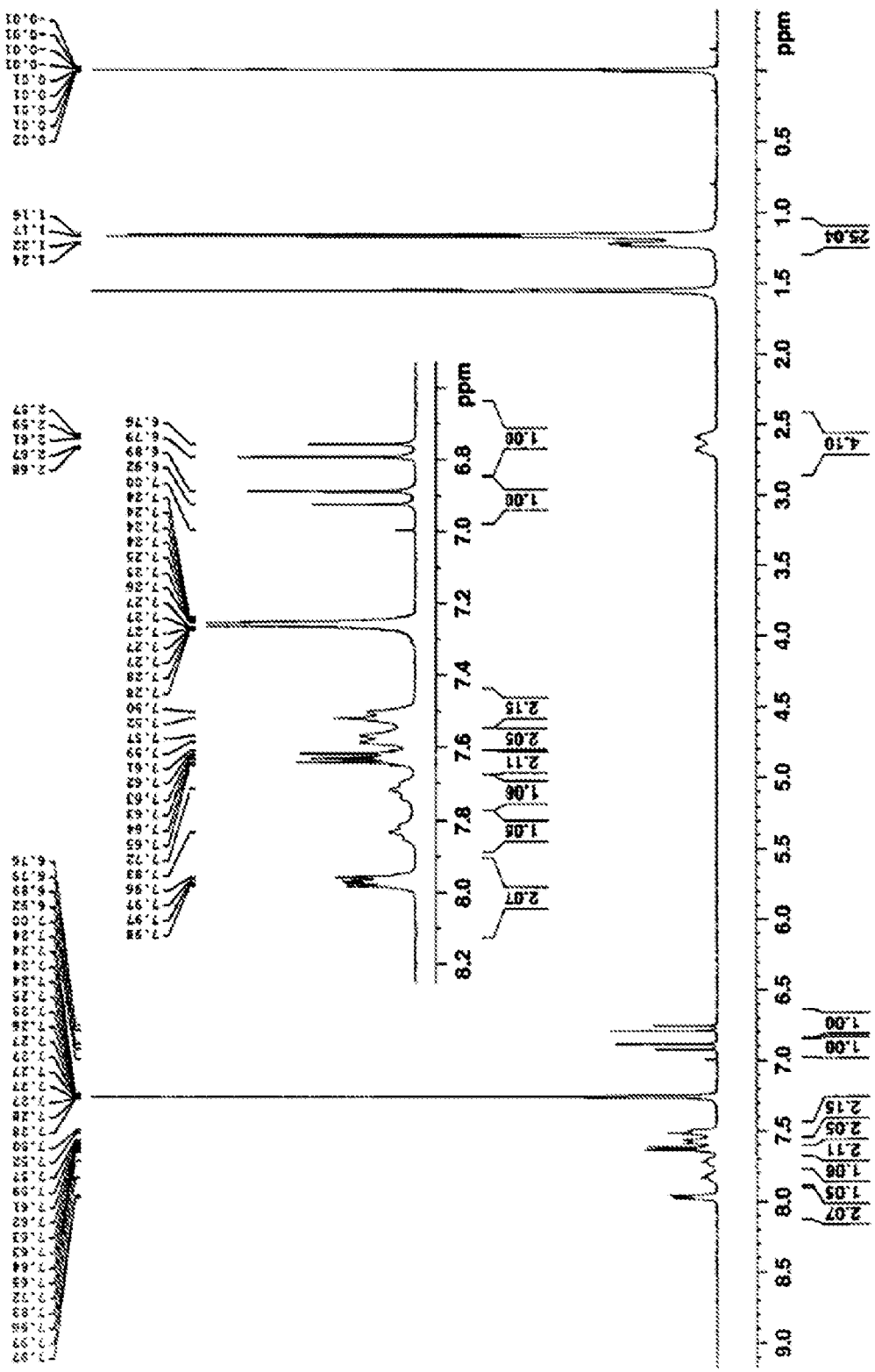
FIG. 9 is a $^1$H NMR chart of a compound (D-7).
Figure 10:
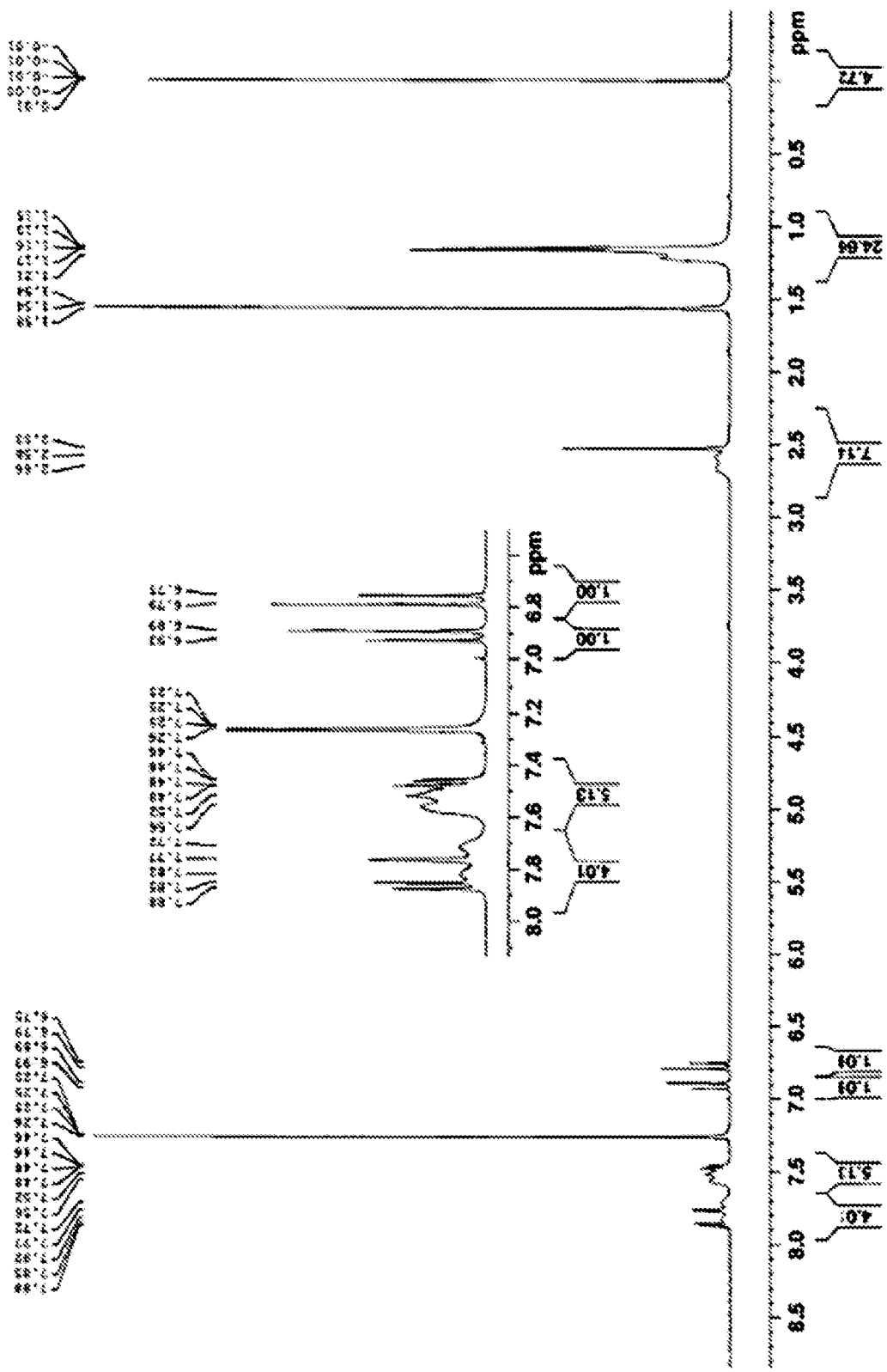
FIG. 10 is a $^1$H NMR chart of a compound (D-10).
Figure 11:
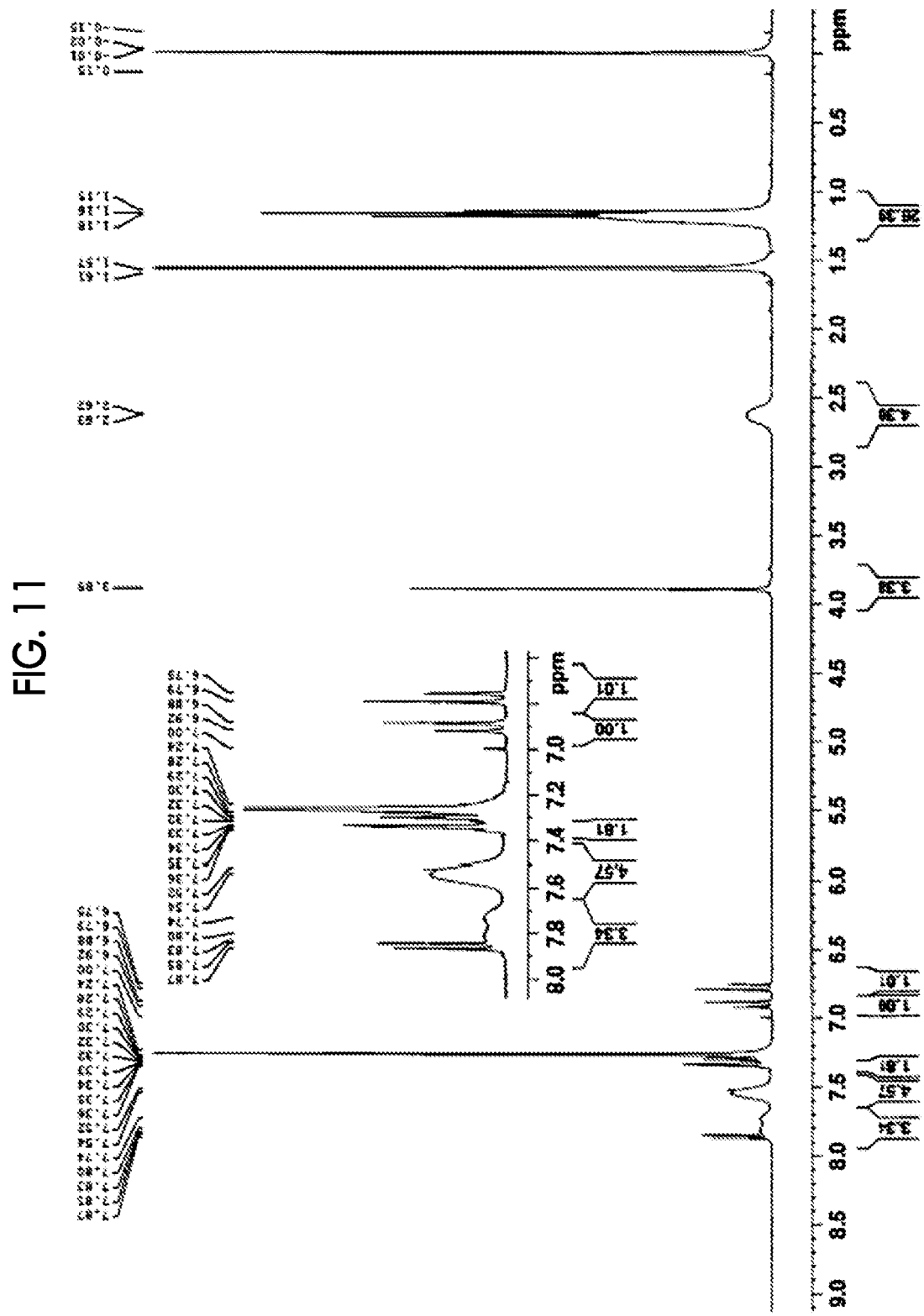
FIG. 11 is a $^1$H NMR chart of a compound (D-11).
Figure 12:
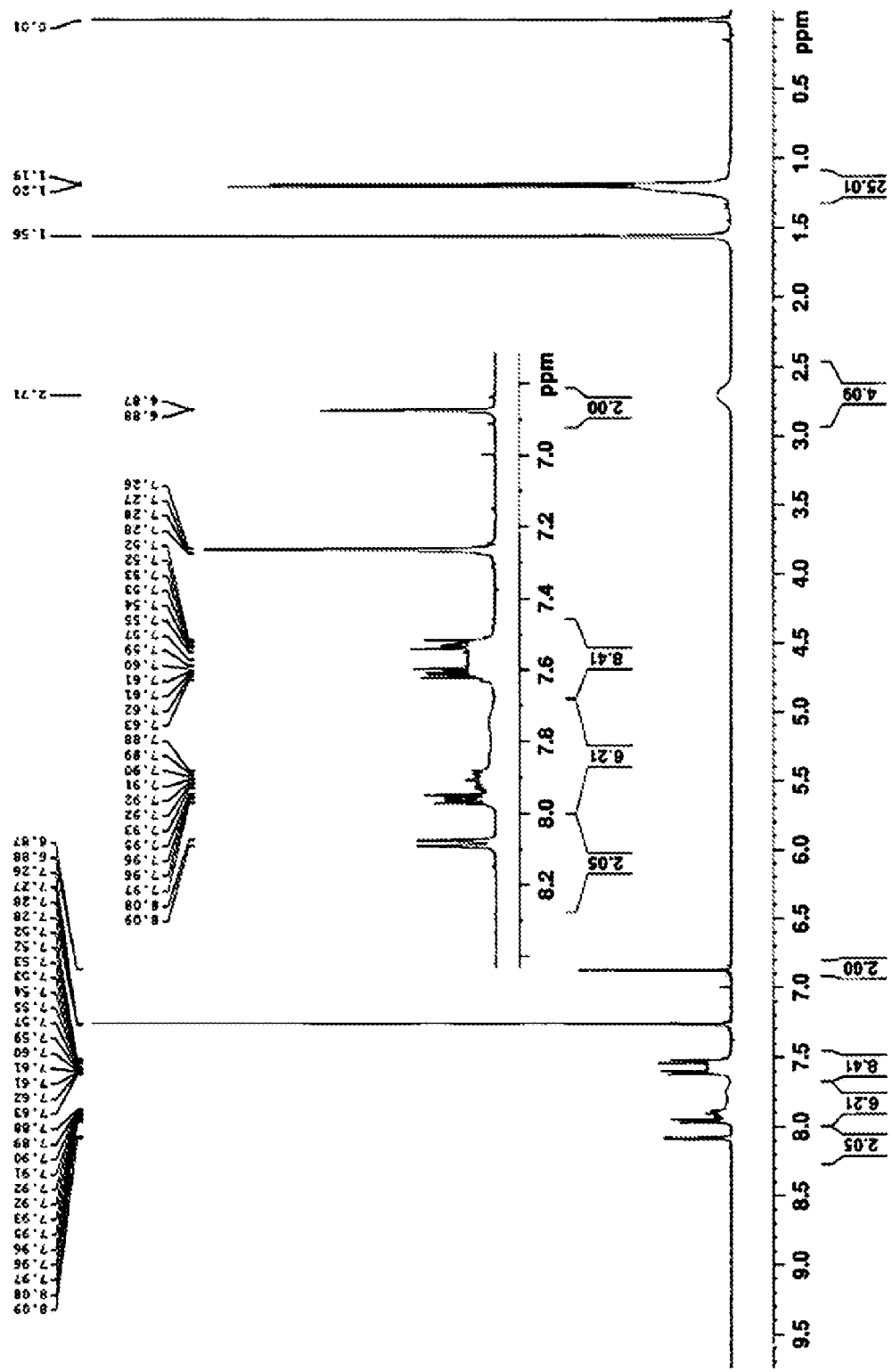
FIG. 12 is a $^1$H NMR chart of a compound (D-12).
Figure 13:
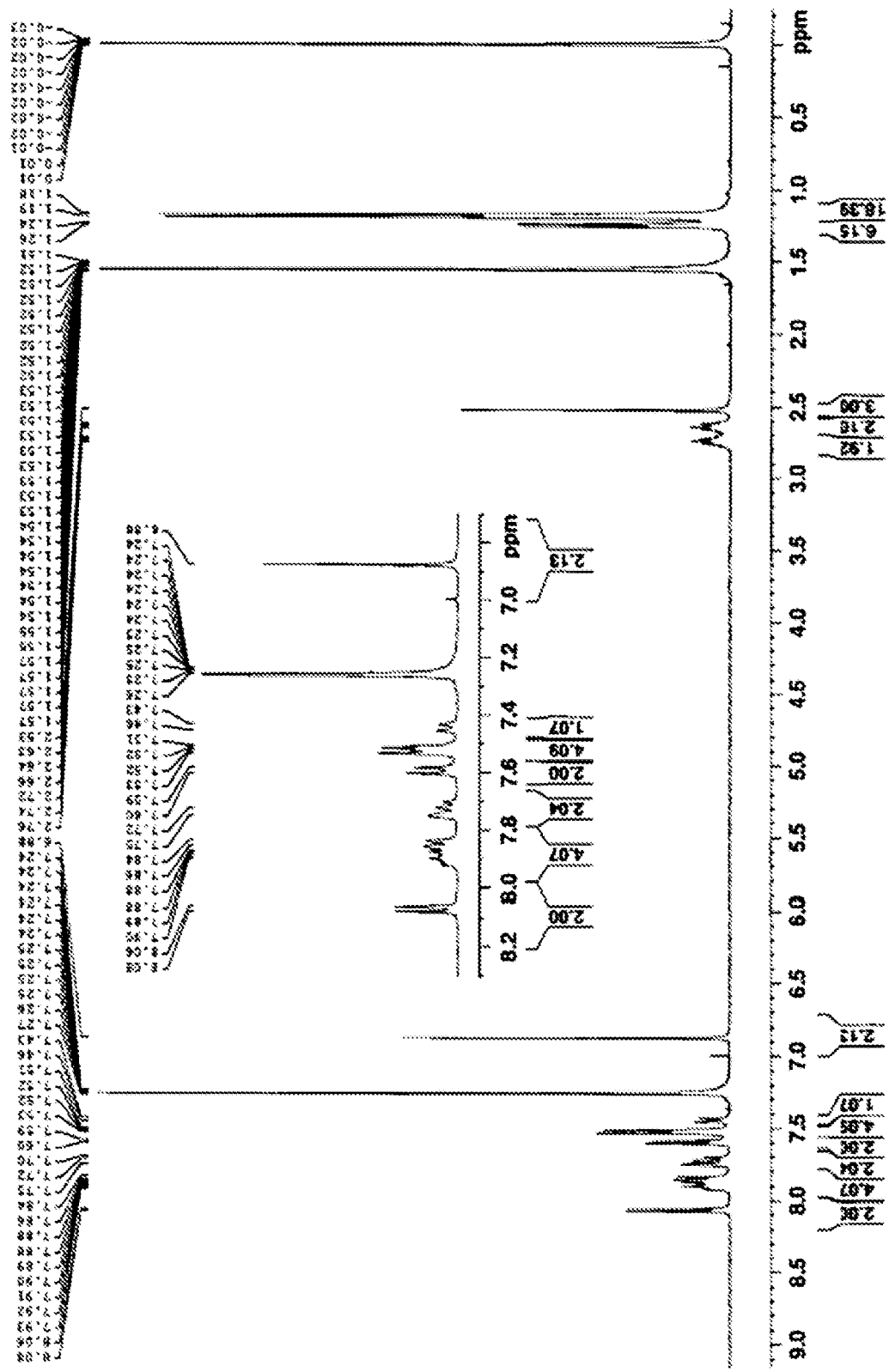
FIG. 13 is a $^1$H NMR chart of a compound (D-13).
Figure 14:
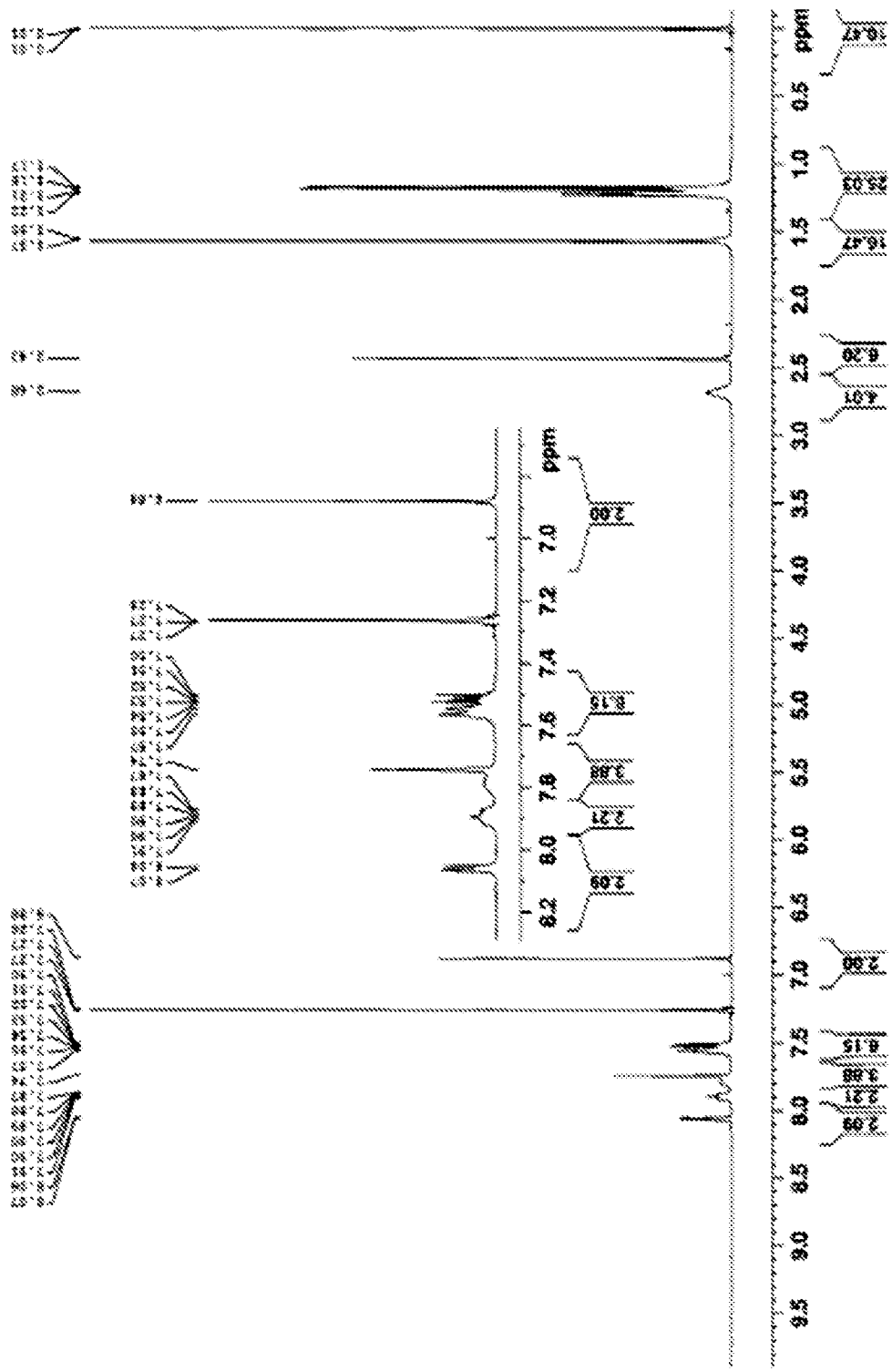
FIG. 14 is a $^1$H NMR chart of a compound (D-14).
Figure 15:
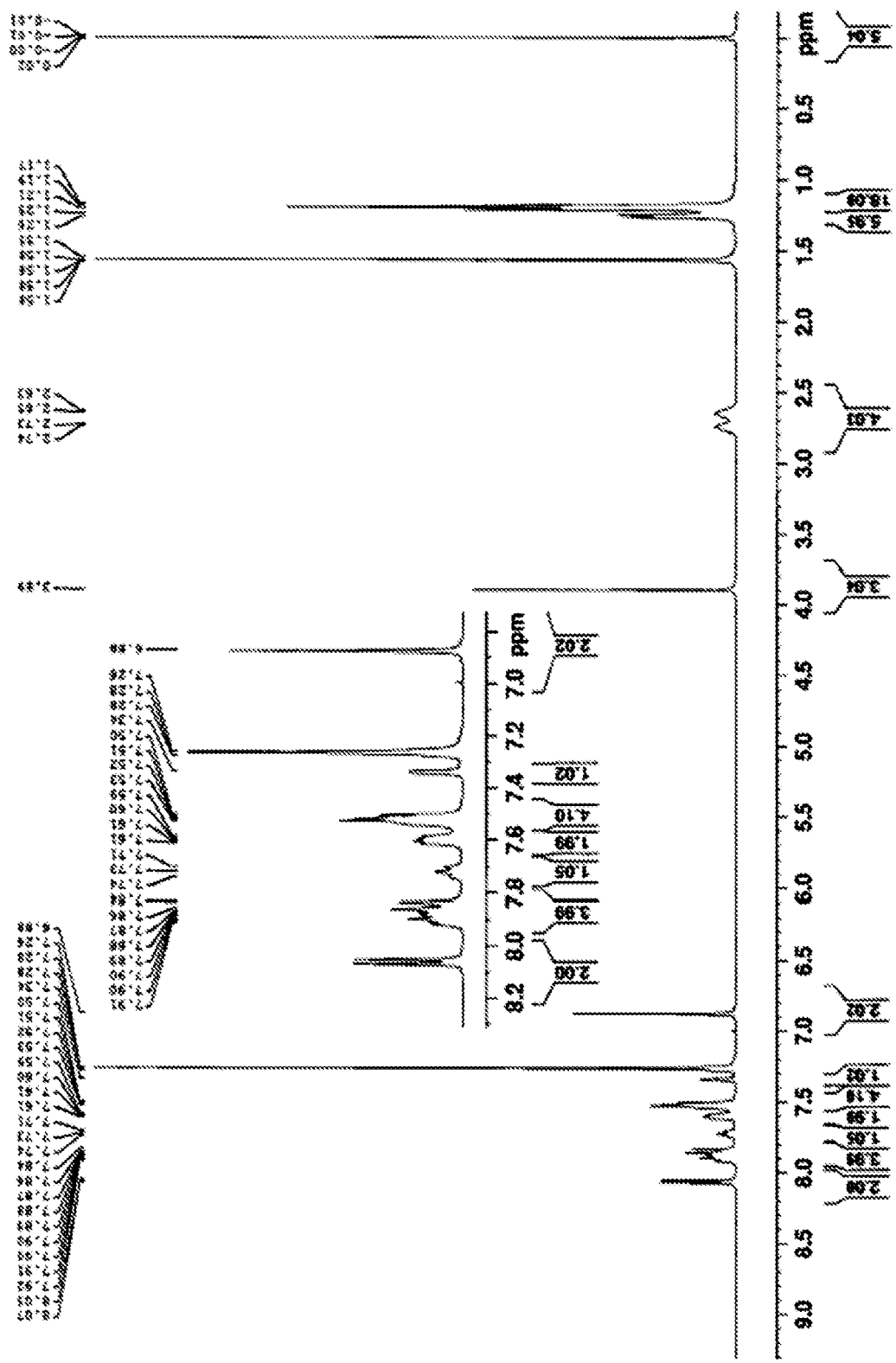
FIG. 15 is a $^1$H NMR chart of a compound (D-16).
Figure 16:
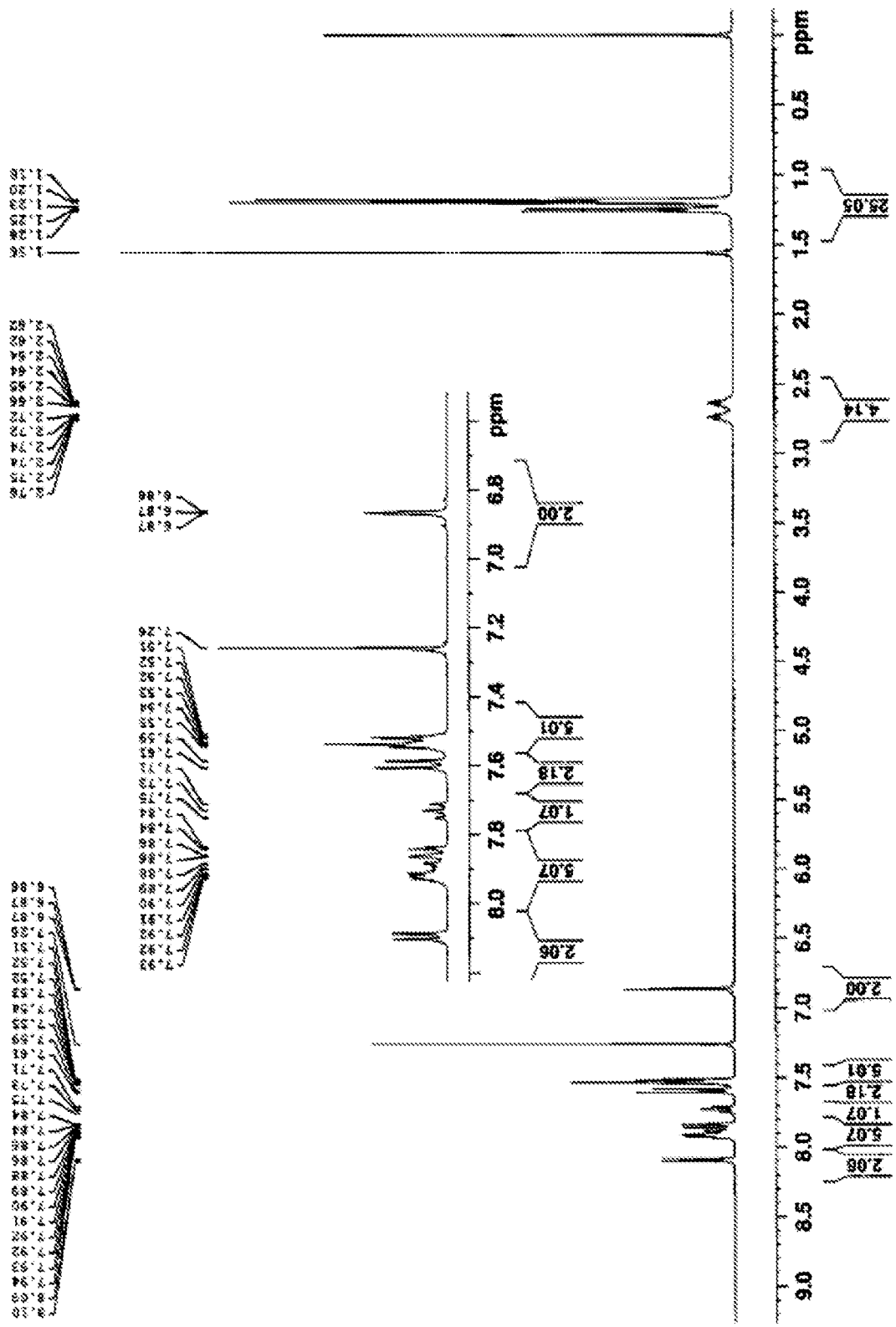
FIG. 16 is a $^1$H NMR chart of a compound (D-25).
Figure 17:
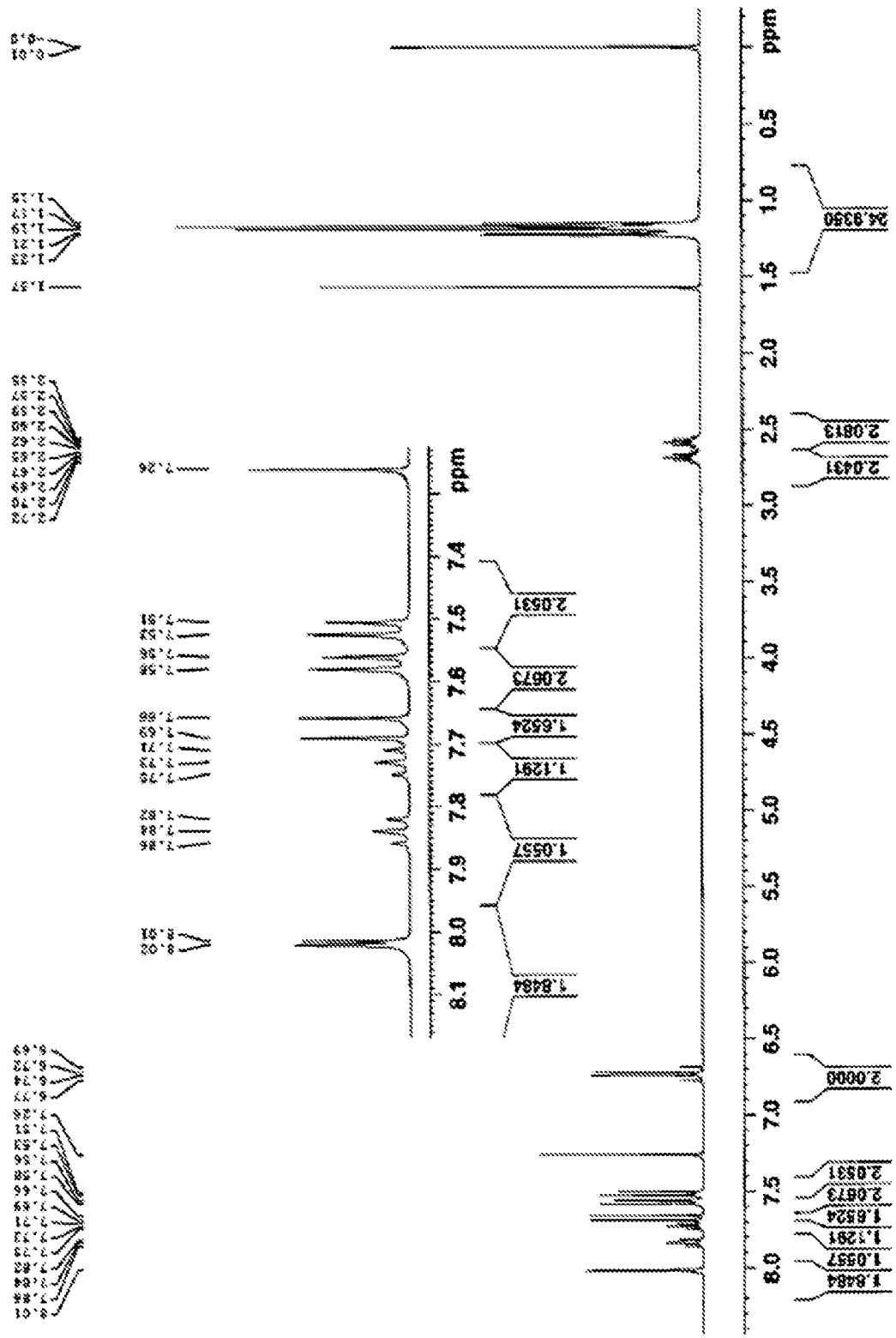
FIG. 17 is a $^1$H NMR chart of a compound (D-26).
Figure 18:
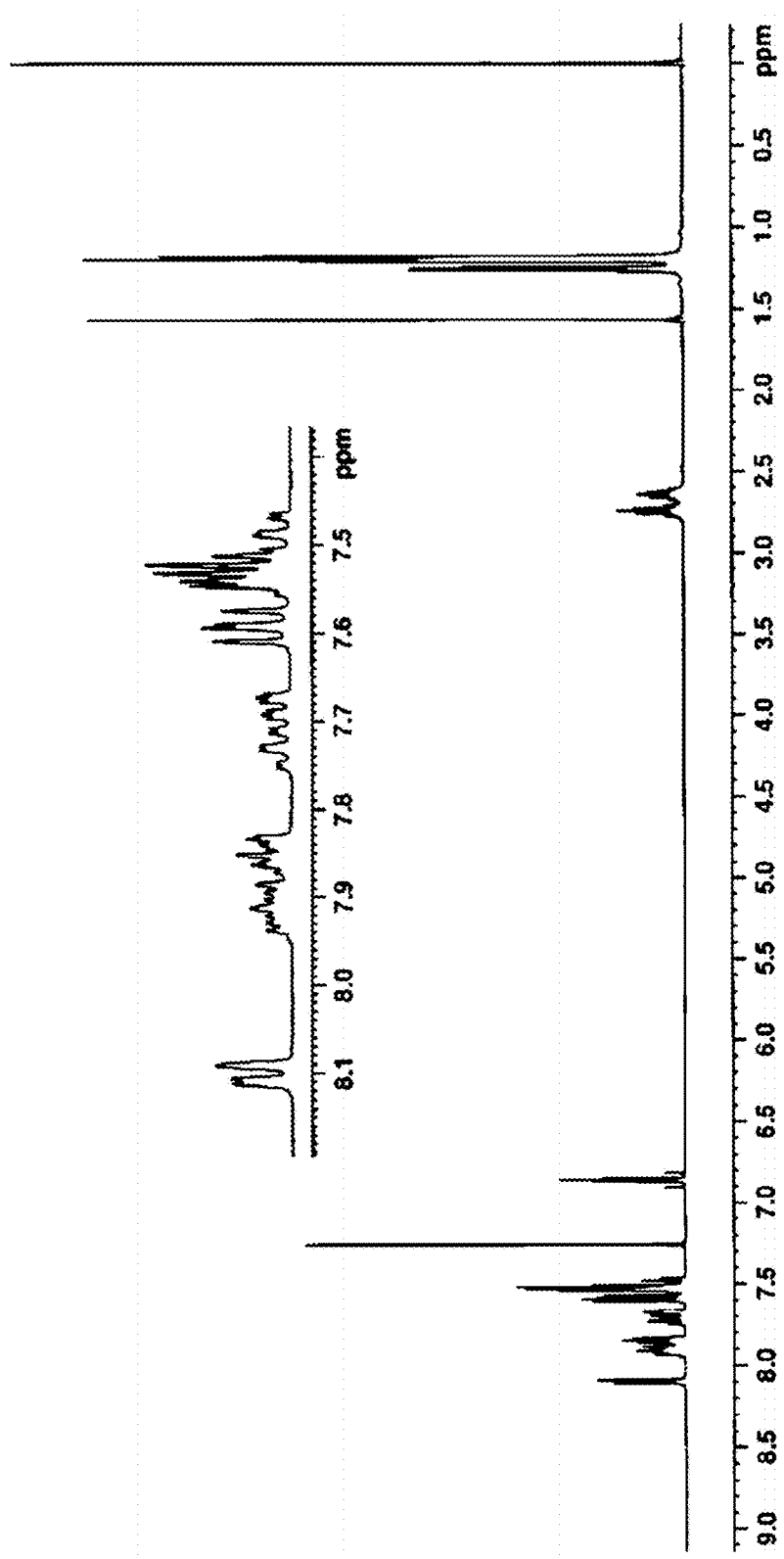
FIG. 18 is a $^1$H NMR chart of a compound (D-27).
Figure 19:
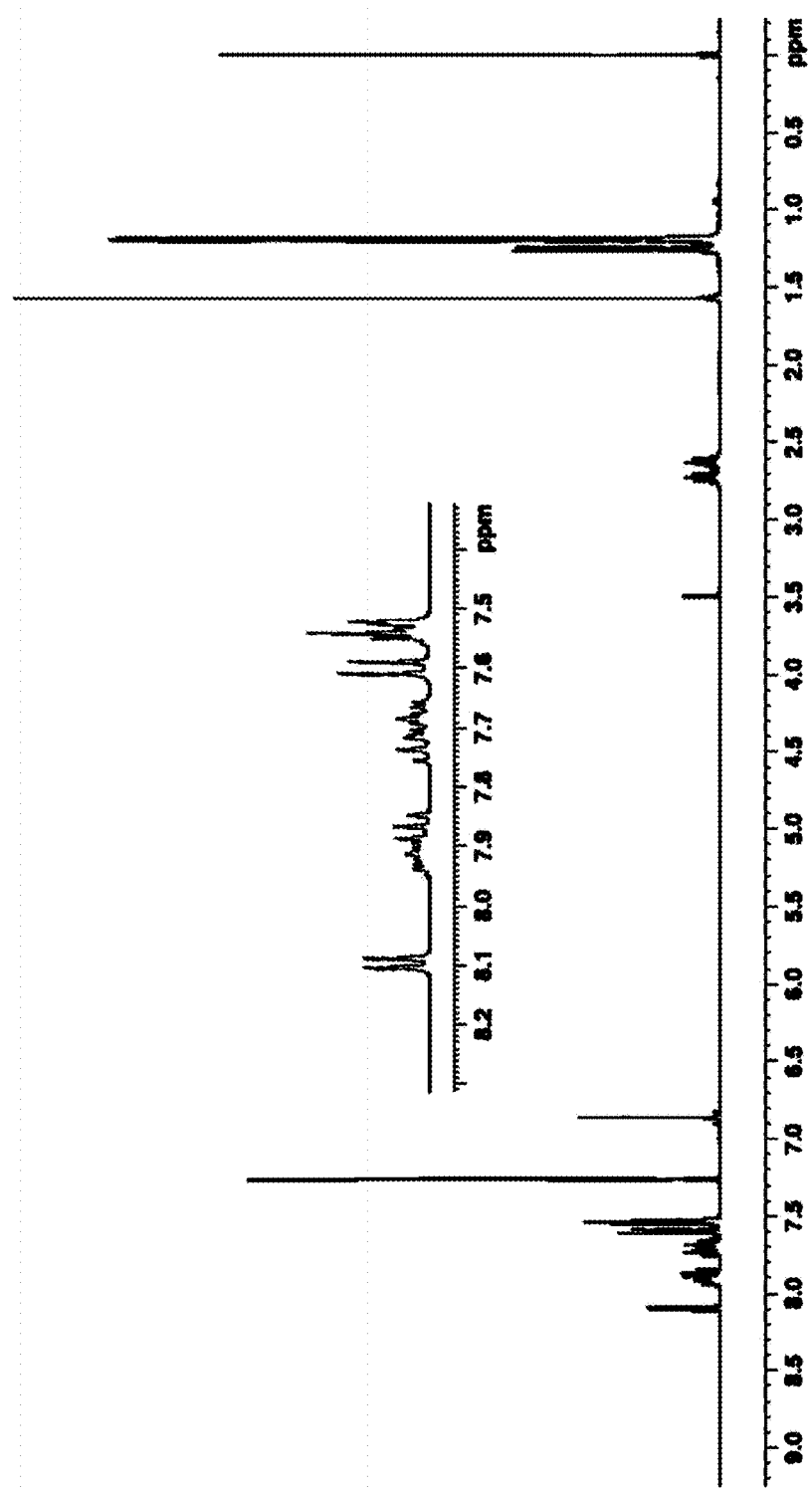
FIG. 19 is a $^1$H NMR chart of a compound (D-28).
Figure 20:
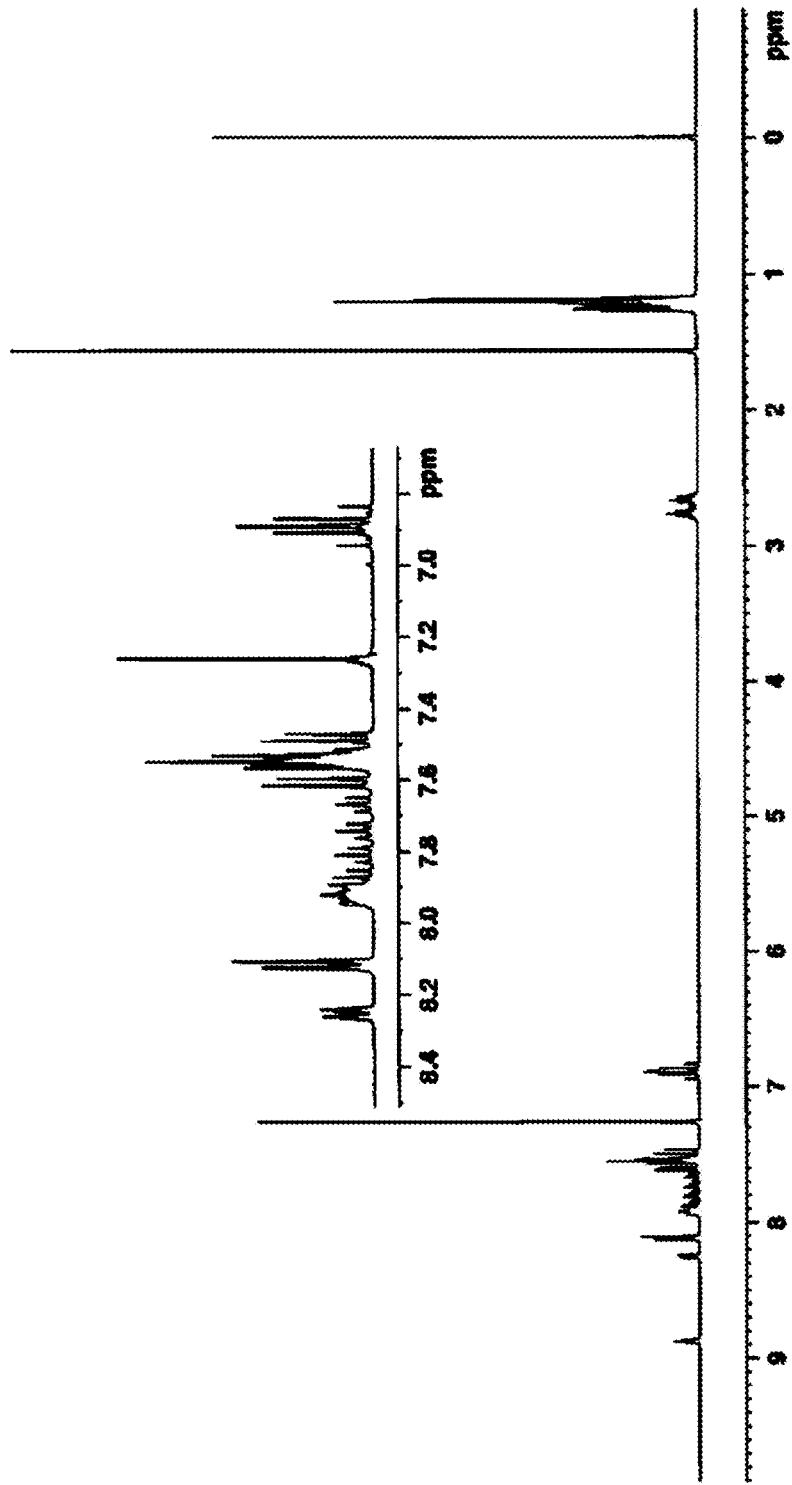
FIG. 20 is a $^1$H NMR chart of a compound (D-29).
Figure 21:
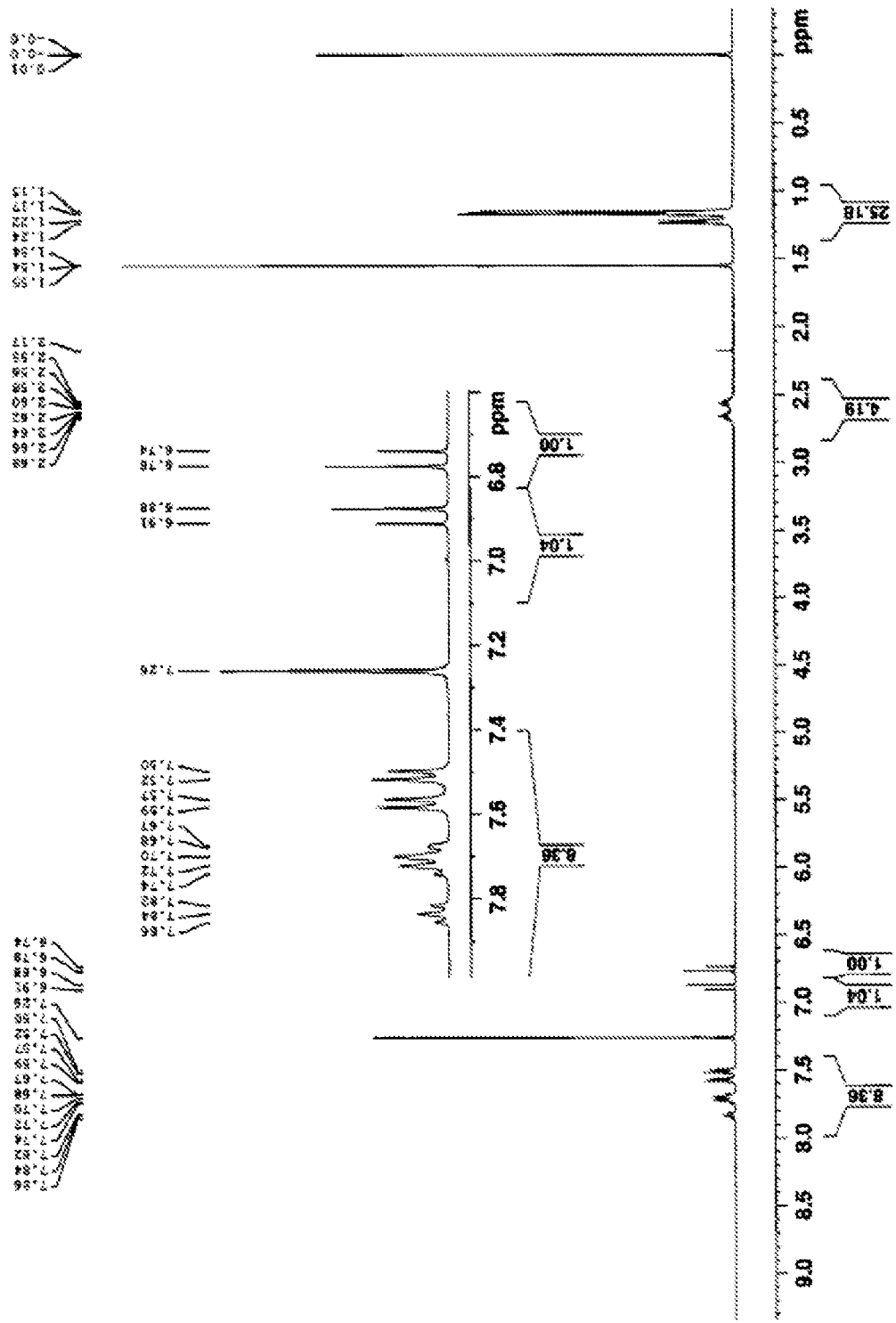
FIG. 21 is a $^1$H NMR chart of a compound (D-31).
Figure 22:
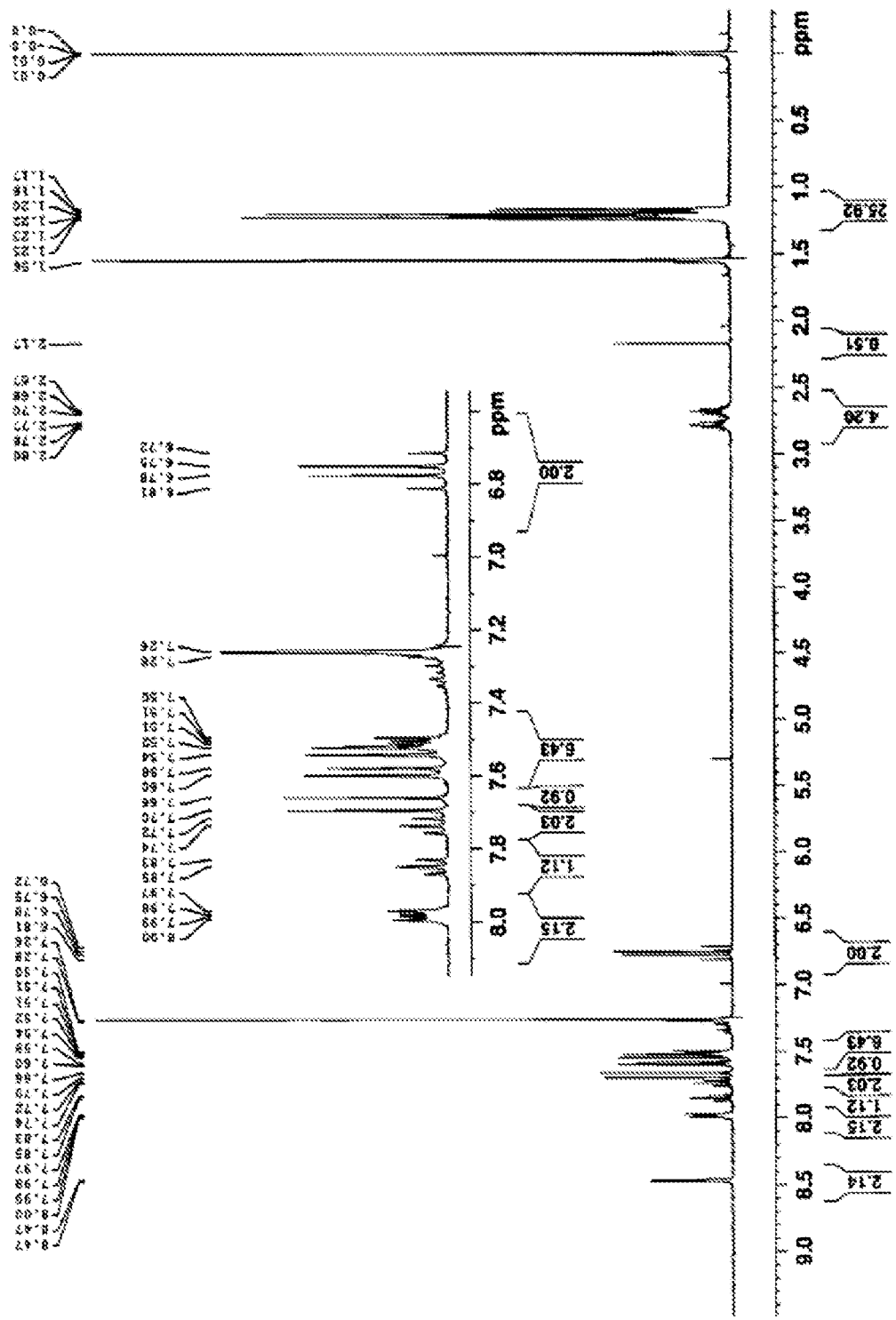
FIG. 22 is a $^1$H NMR chart of a compound (D-32).
Figure 23:
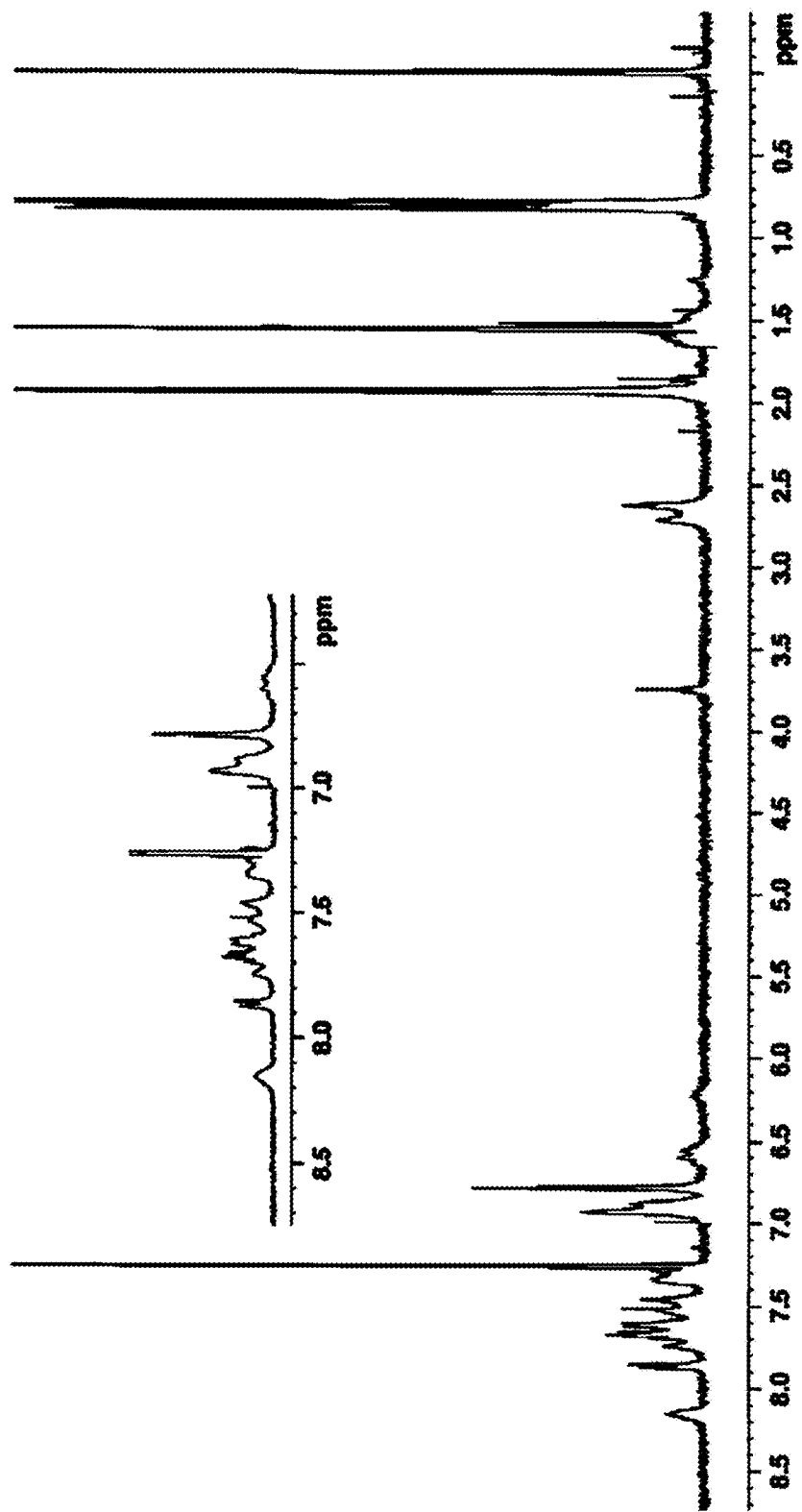
FIG. 23 is a $^1$H NMR chart of a compound (D-34).
Figure 24:
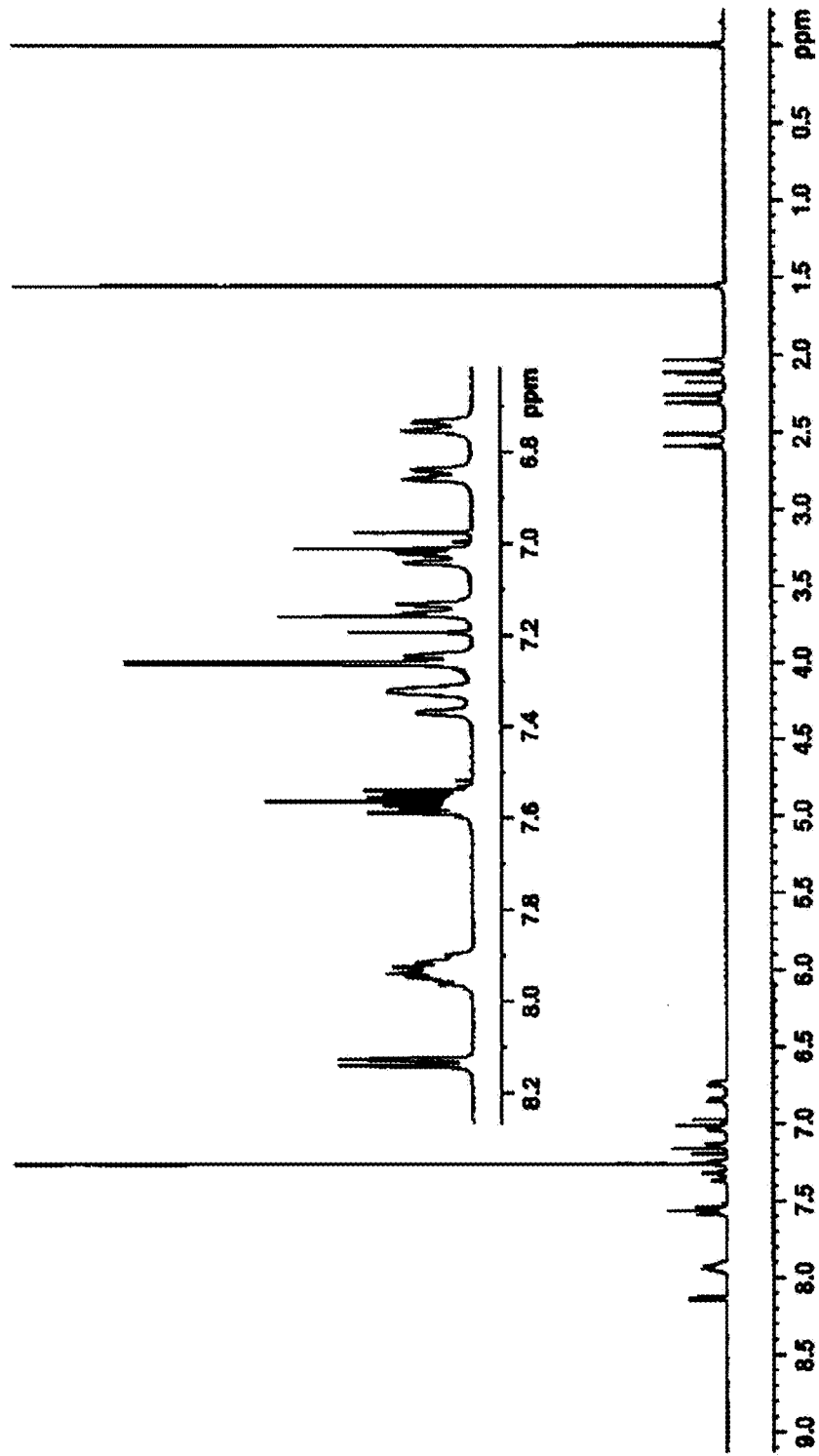
FIG. 24 is a $^1$H NMR chart of a compound (D-35).
Figure 25:
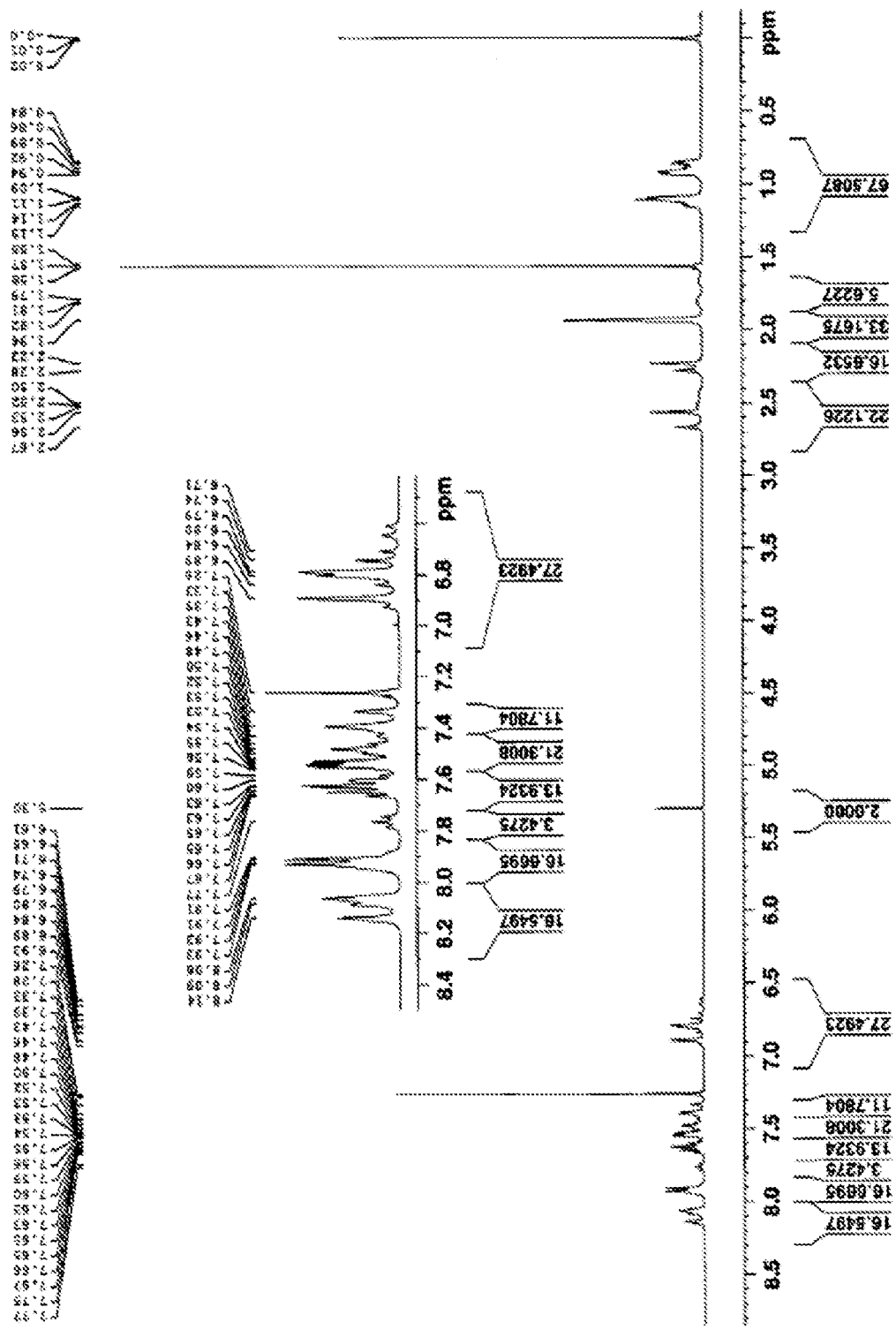
FIG. 25 is a $^1$H NMR chart of a compound (D-37).
Figure 26:
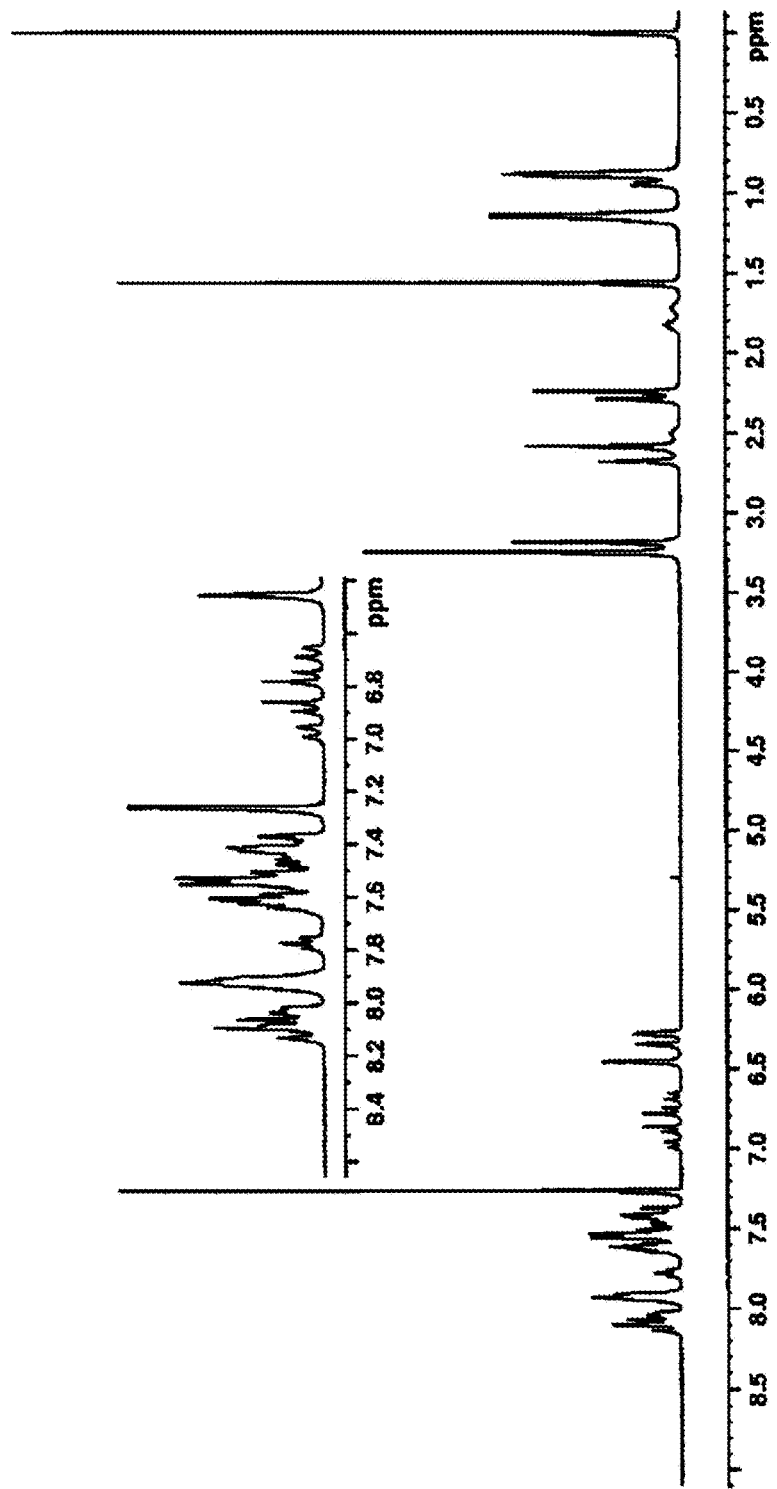
FIG. 26 is a $^1$H NMR chart of a compound (D-38).
Figure 27:
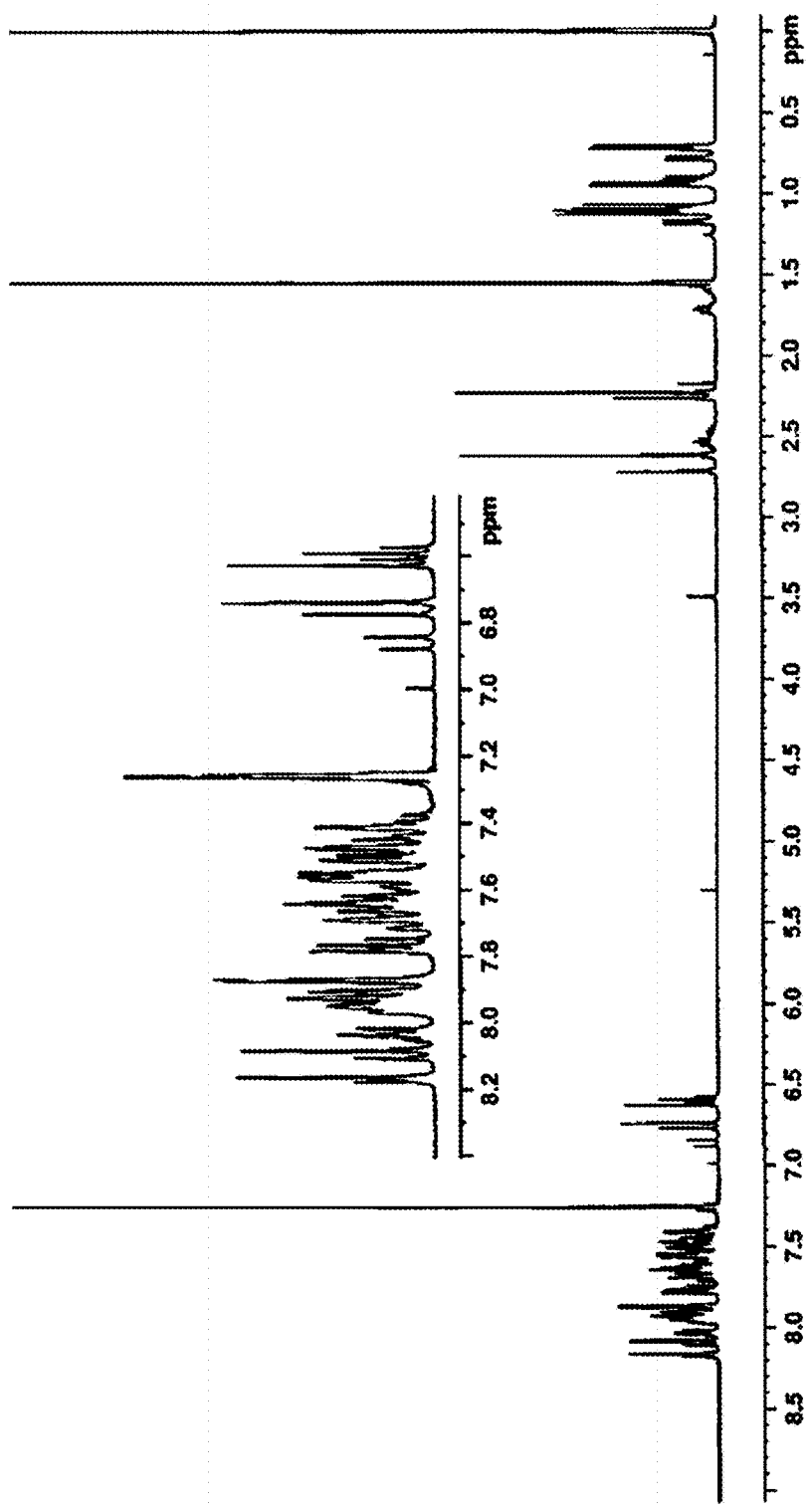
FIG. 27 is a $^1$H NMR chart of a compound (D-39).
Figure 28:
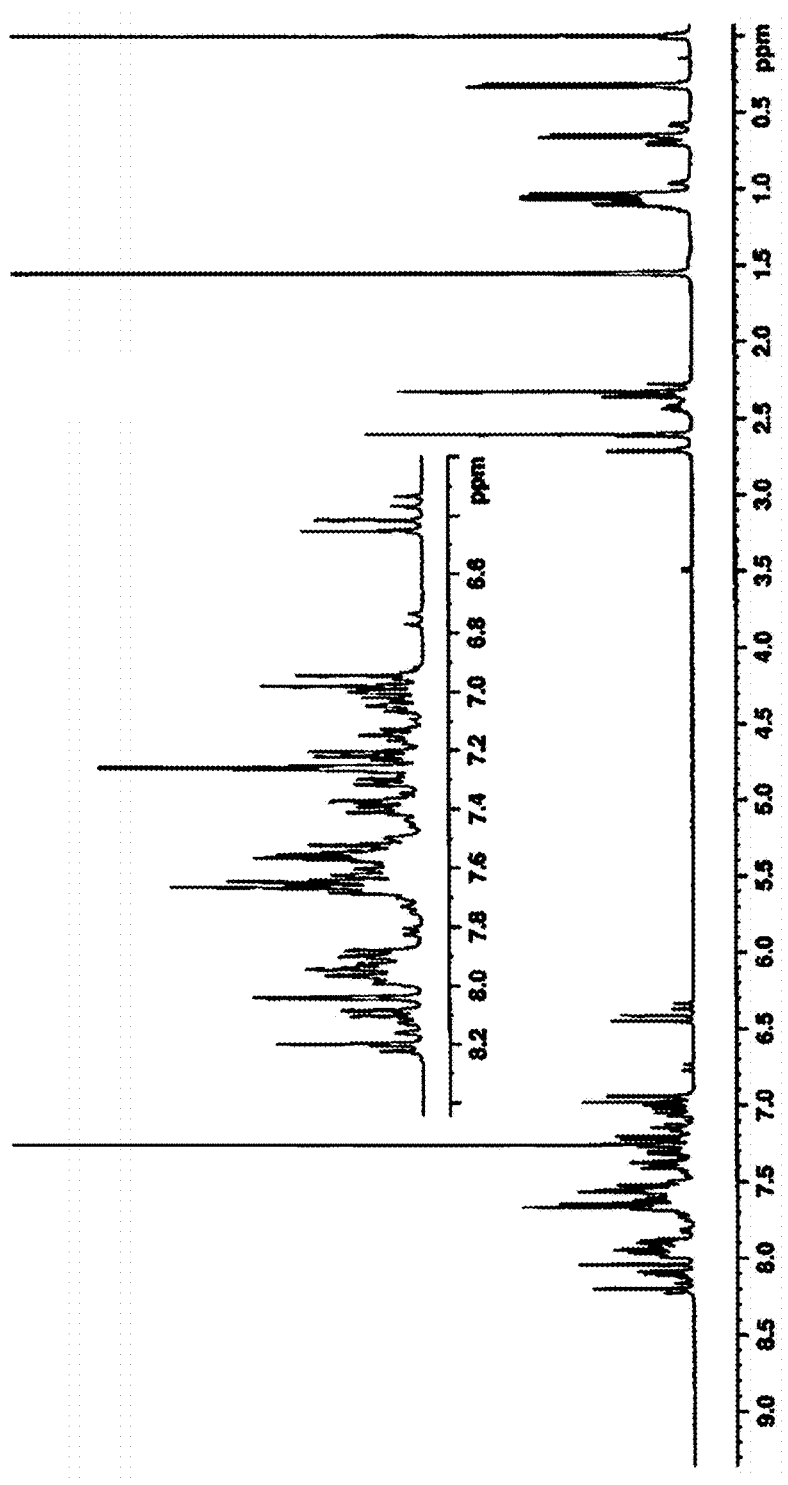
FIG. 28 is a $^1$H NMR chart of a compound (D-40).
Figure 29:
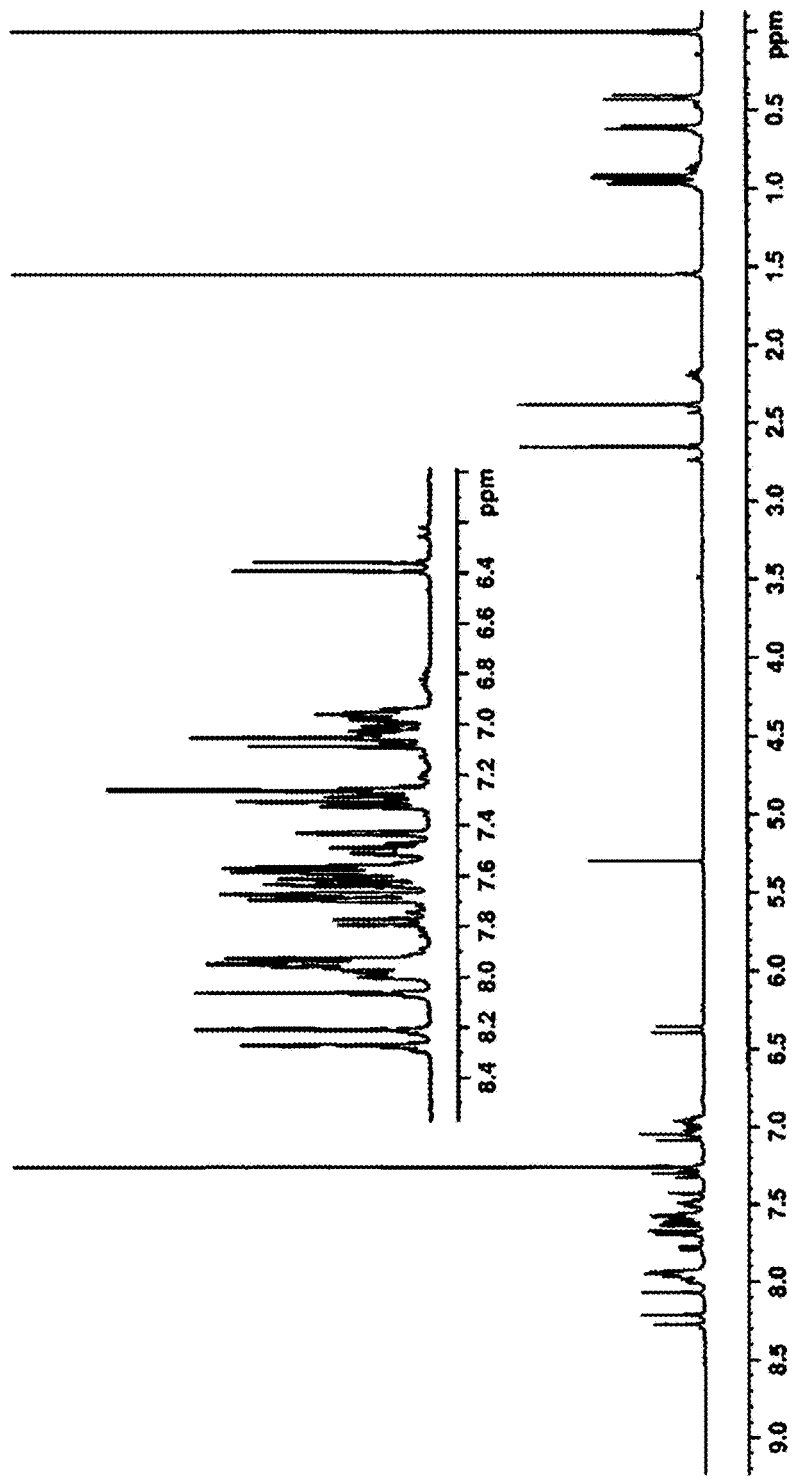
FIG. 29 is a $^1$H NMR chart of a compound (D-41).
Figure 30:
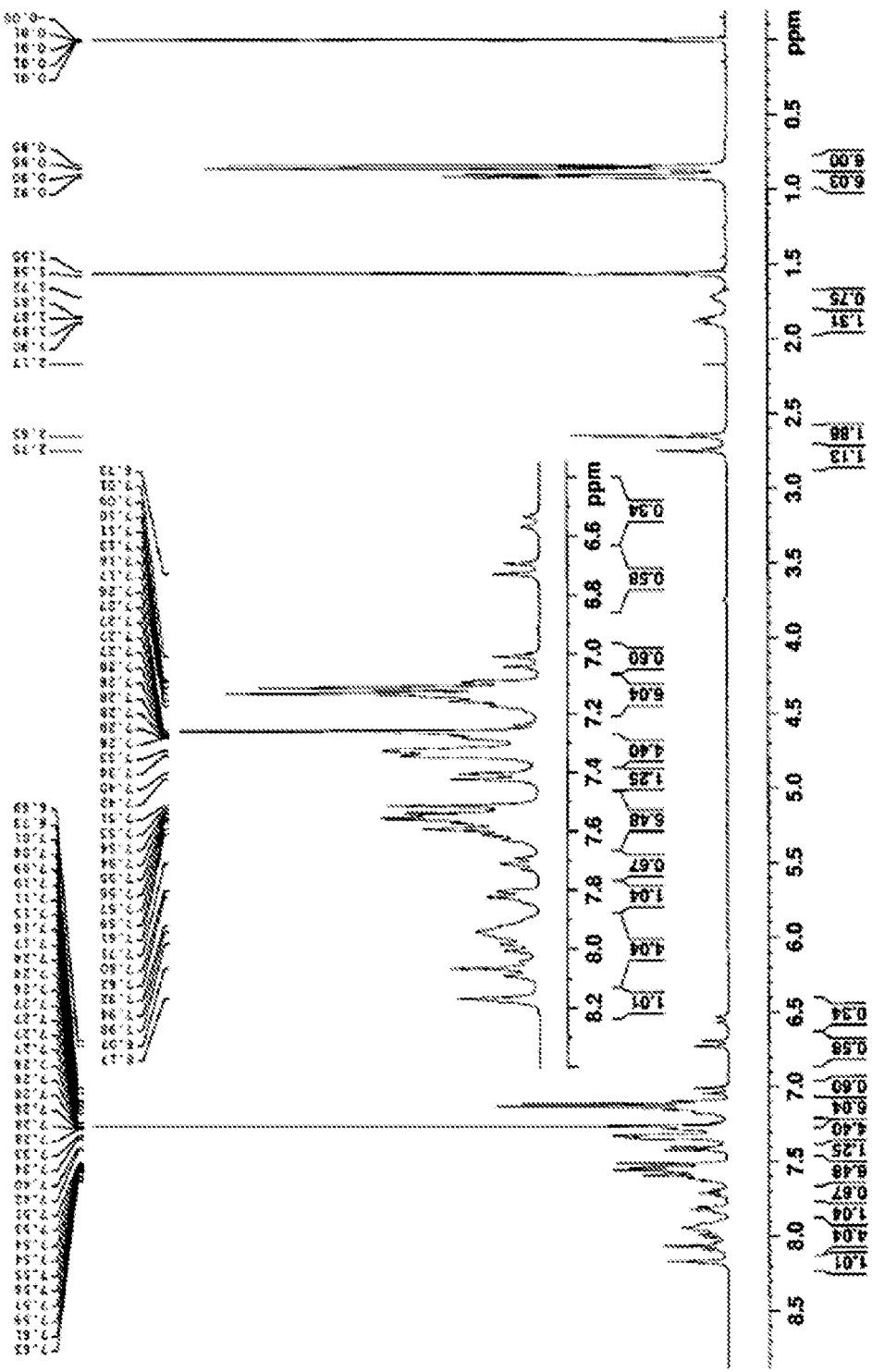
FIG. 30 is a $^1$H NMR chart of a compound (D-45).
Figure 31:
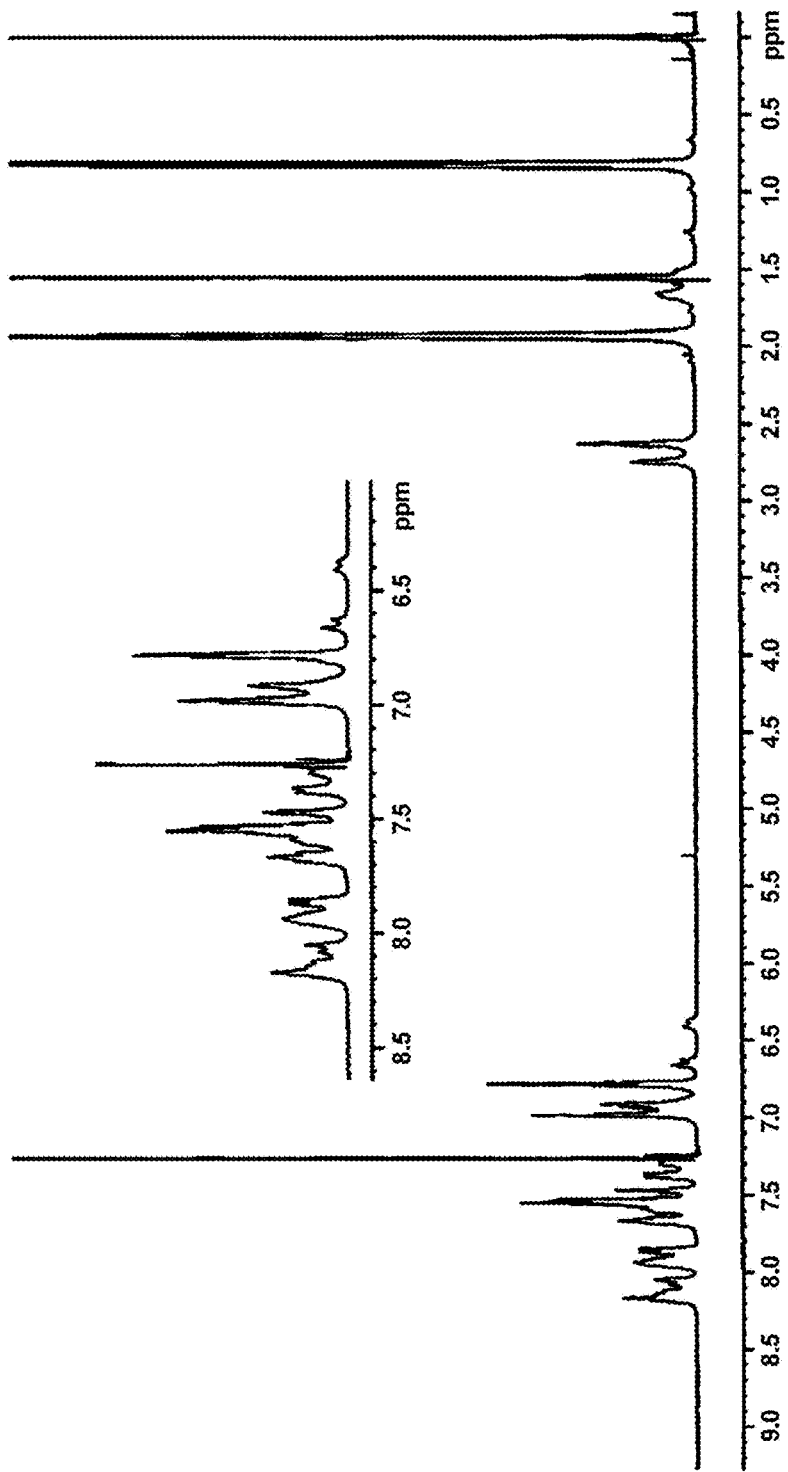
FIG. 31 is a $^1$H NMR chart of a compound (D-46).
Figure 32:
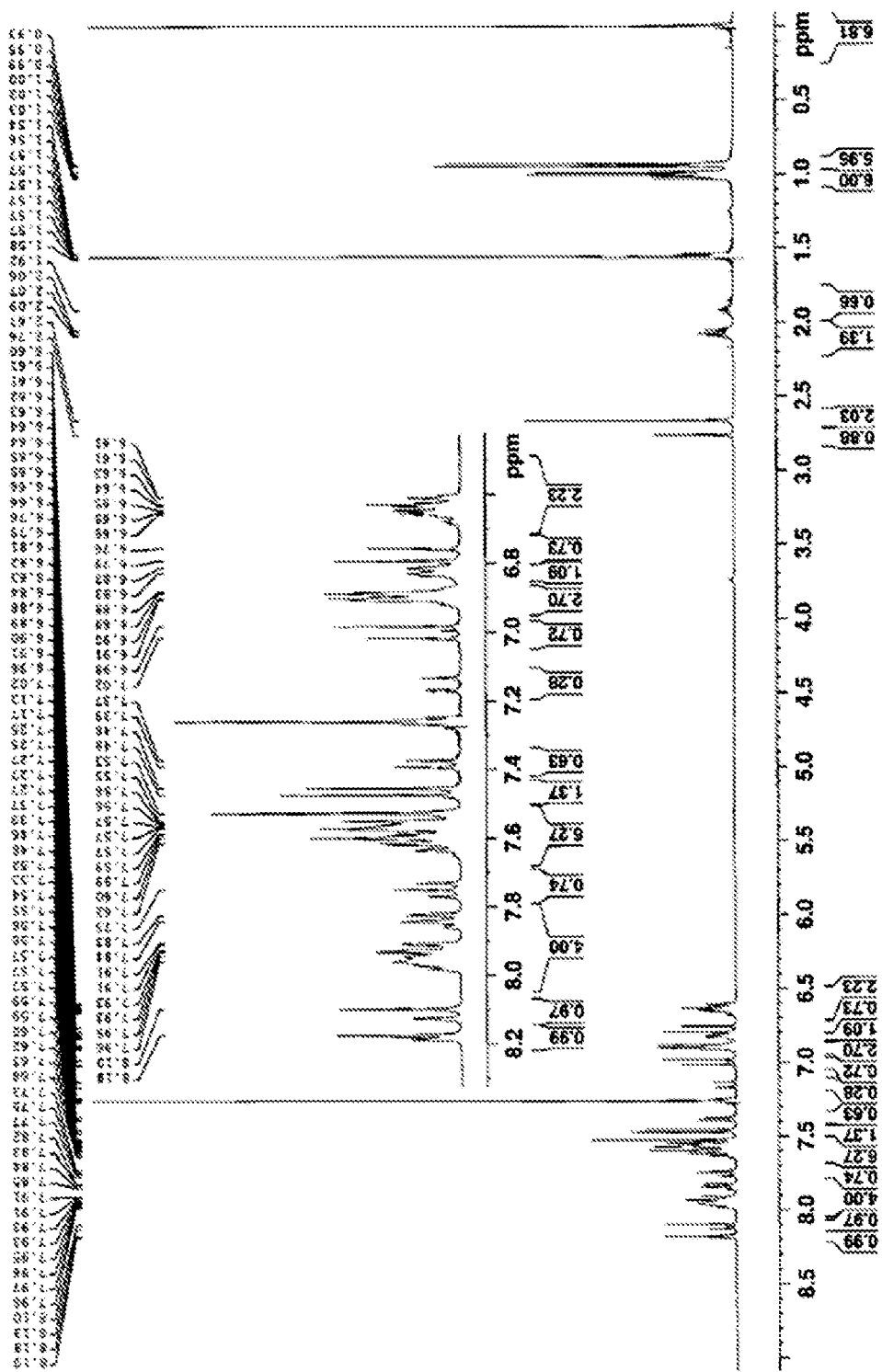
FIG. 32 is a $^1$H NMR chart of a compound (D-47).
Figure 33:
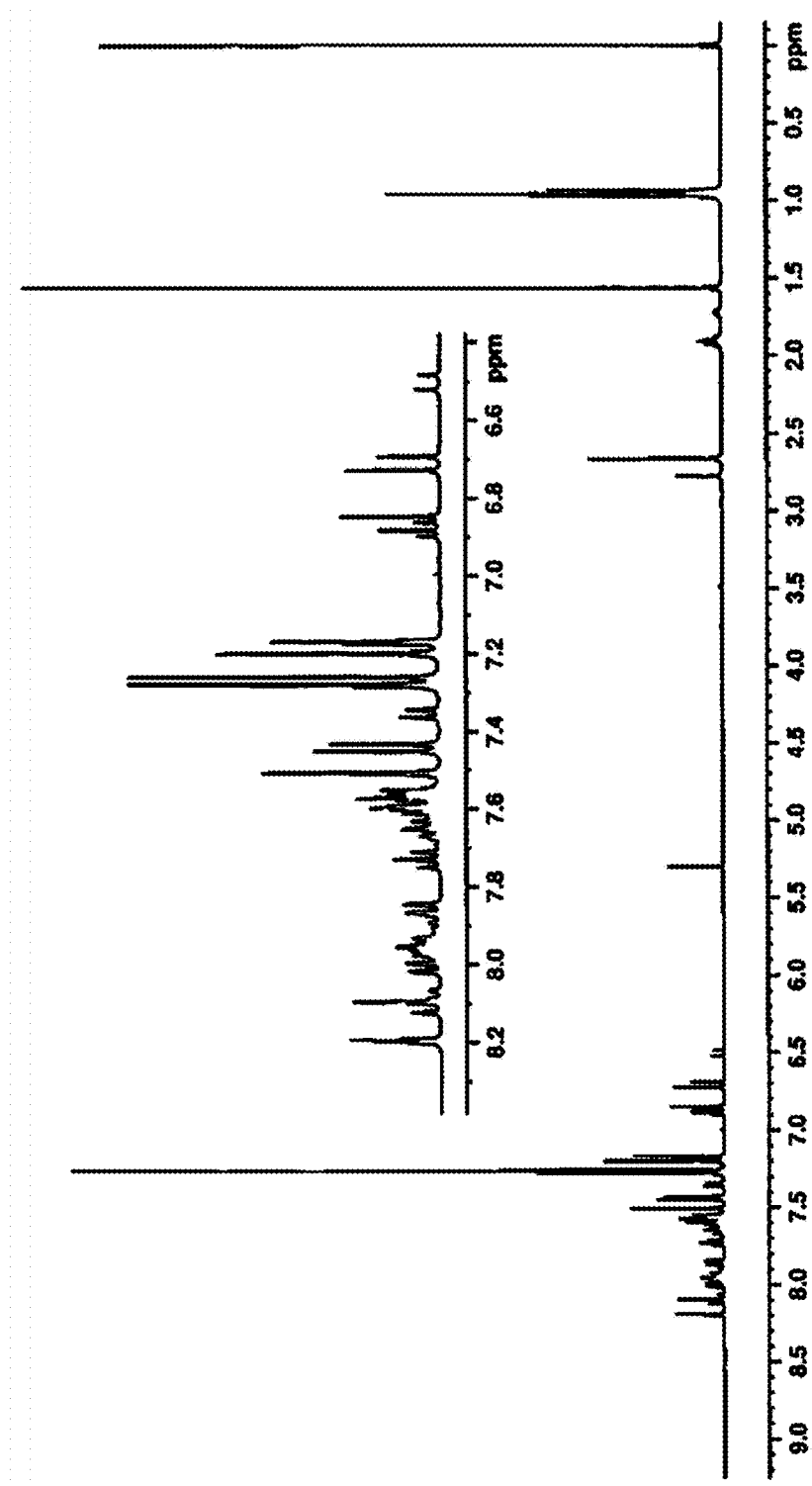
FIG. 33 is a $^1$H NMR chart of a compound (D-48).
Figure 34:
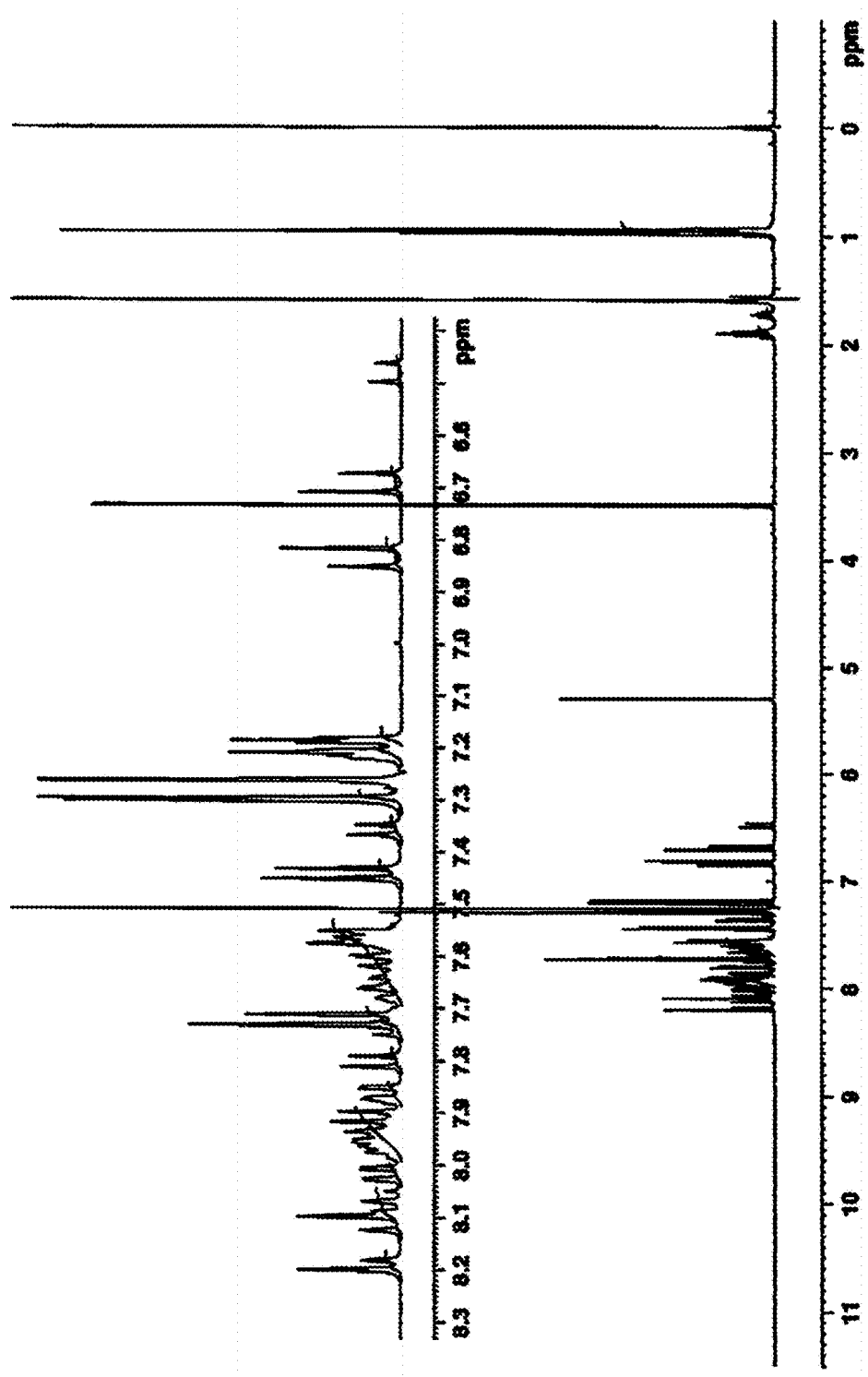
FIG. 34 is a $^1$H NMR chart of a compound (D-59).
Figure 35:
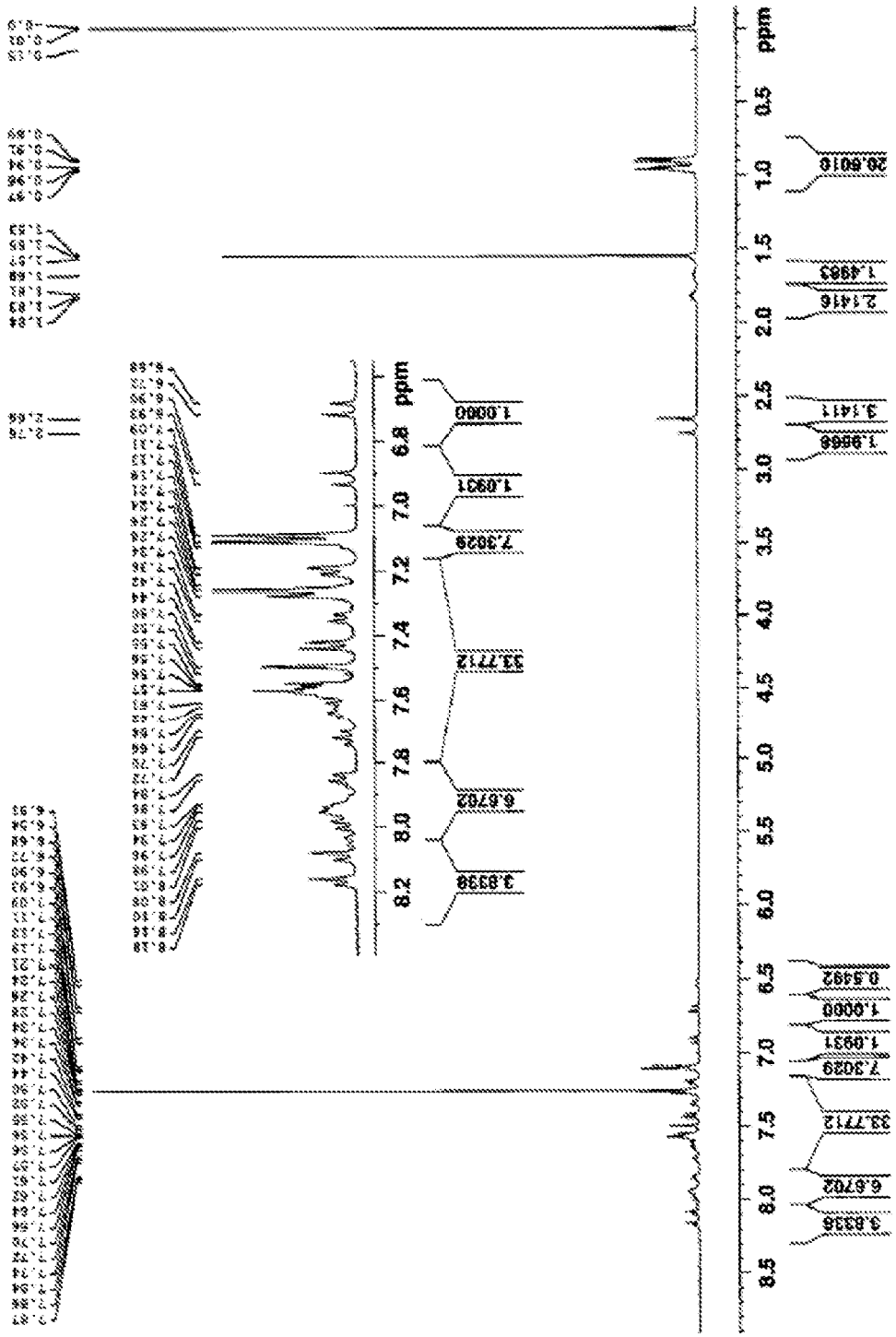
FIG. 35 is a $^1$H NMR chart of a compound (D-69).
Figure 36:
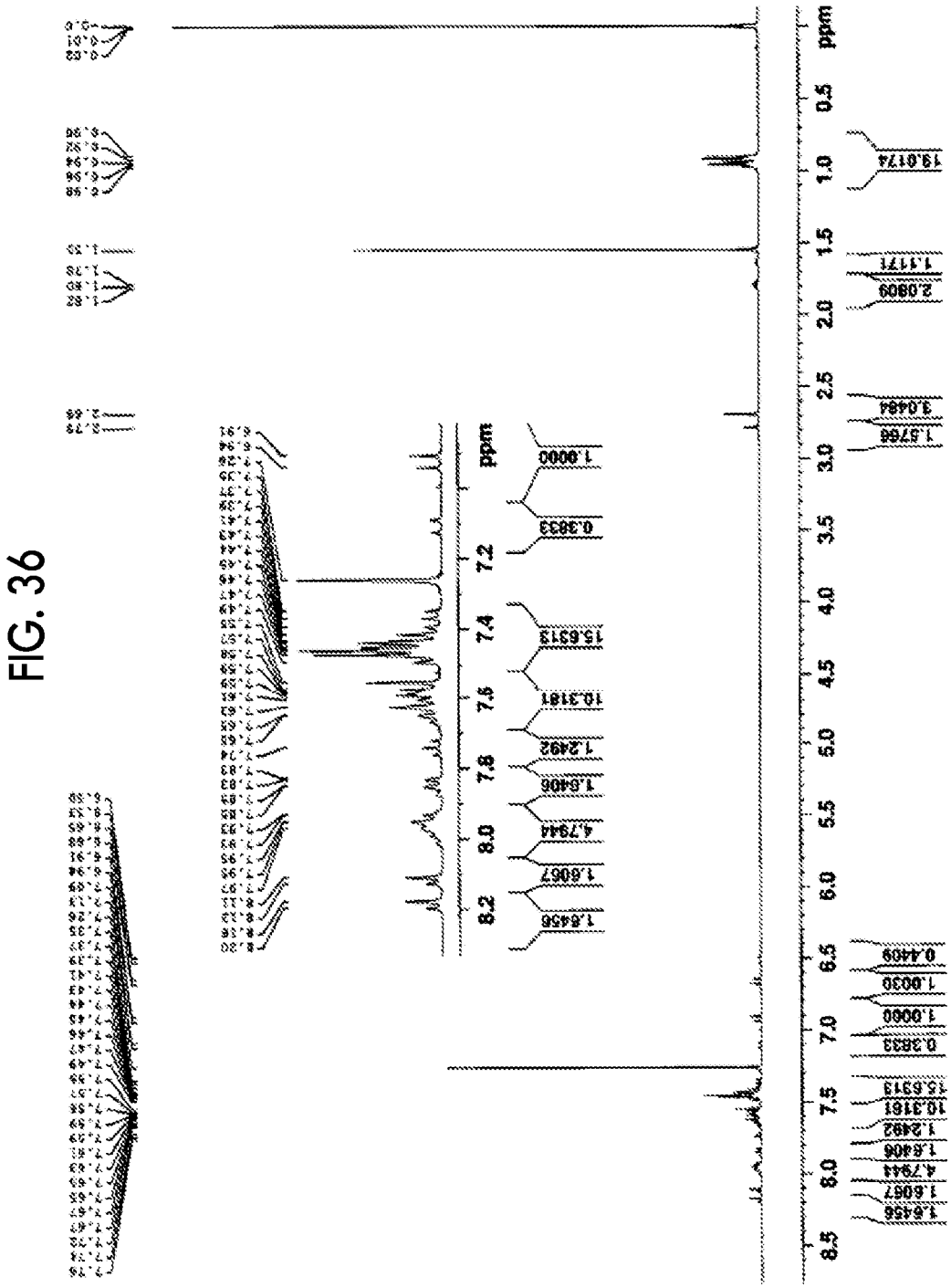
FIG. 36 is a $^1$H NMR chart of a compound (D-71).
Figure 37:
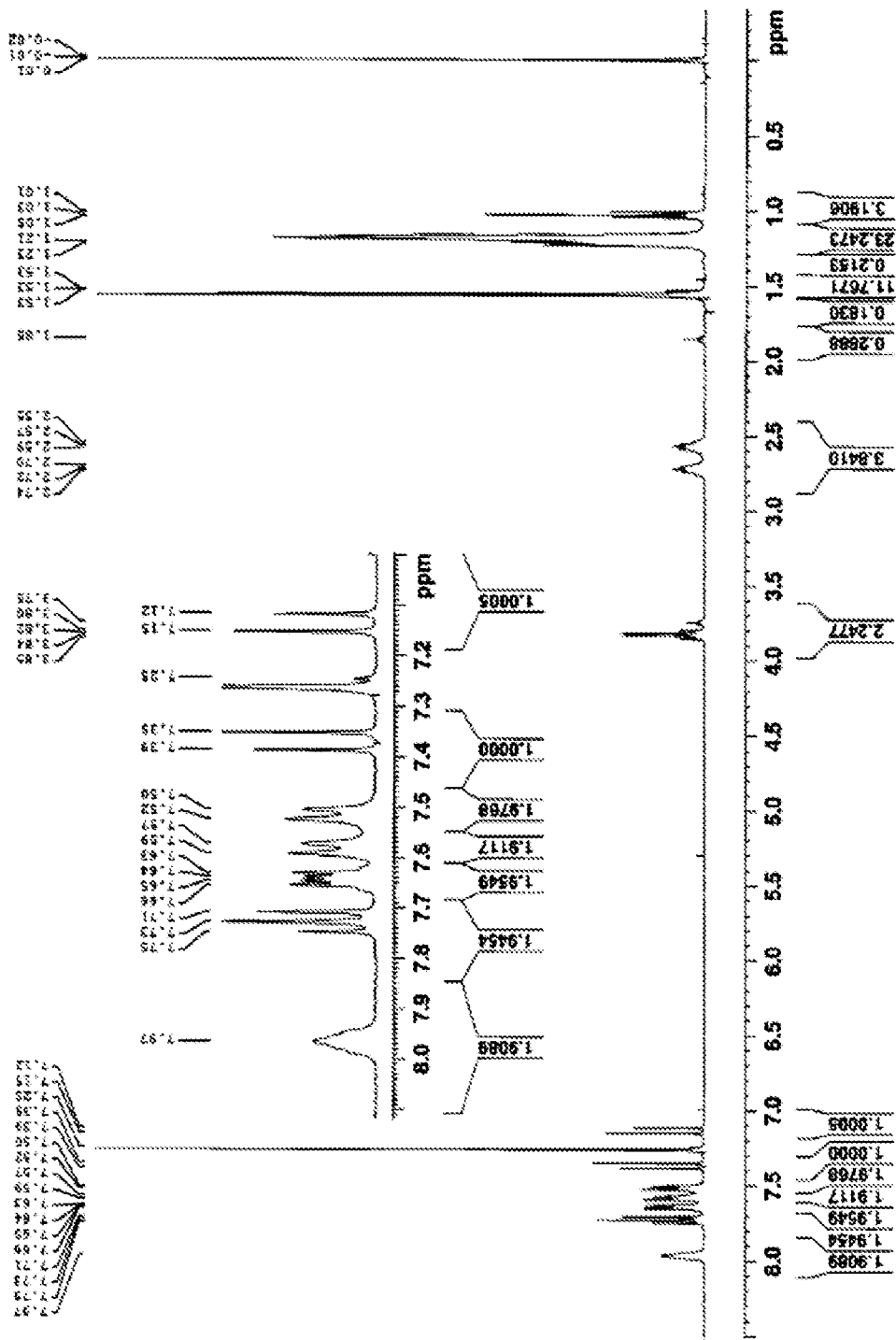
FIG. 37 is a $^1$H NMR chart of a compound (D-75).
Figure 38:
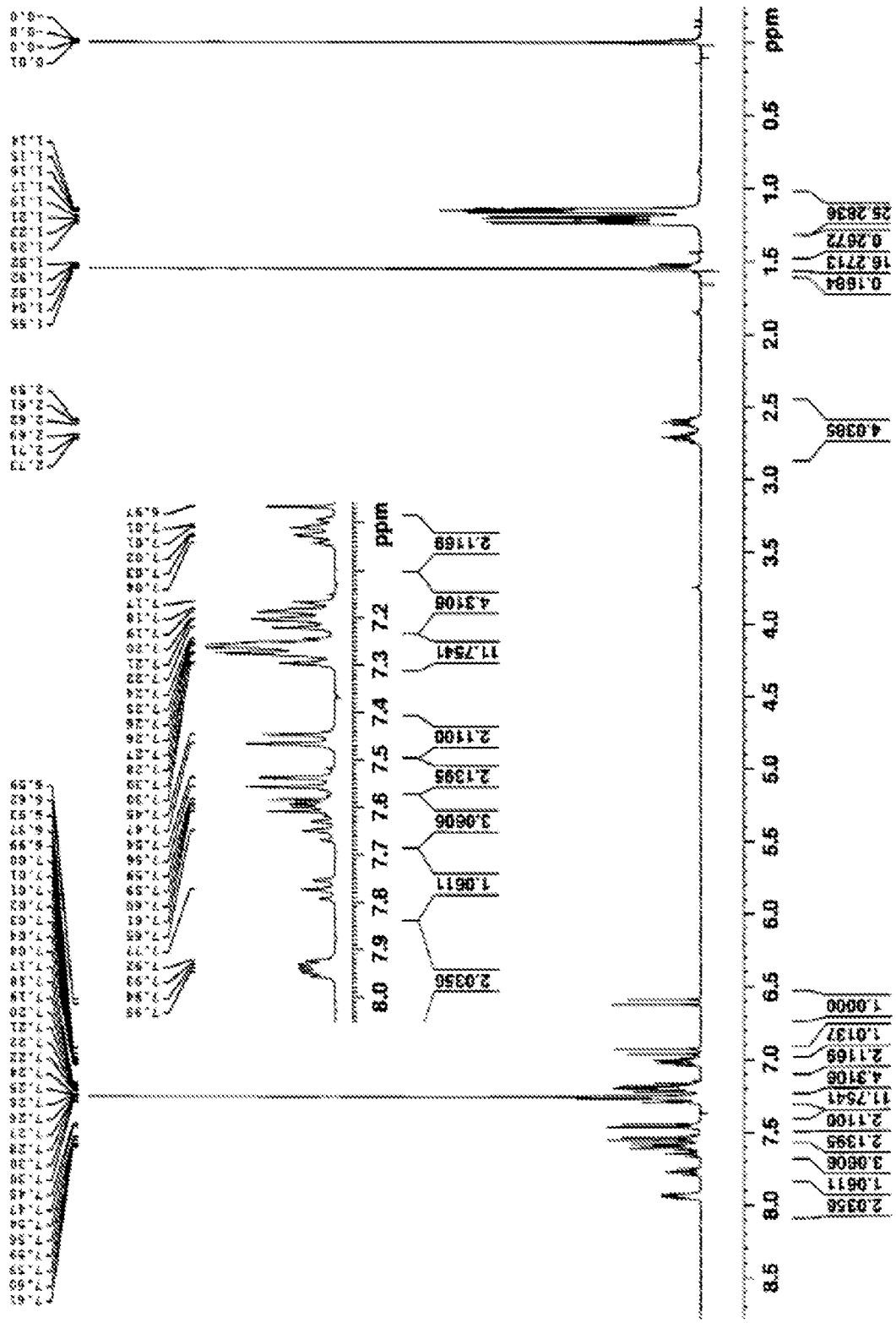
FIG. 38 is a $^1$H NMR chart of a compound (D-76).

¹H NMR spectrum (400 MHz, CDCl₃) is shown in FIG. 5.

¹MS(ESI⁺)m/z: 543.2 ([M+H]⁺)

Compounds (D-2) to (D-78) were synthesized with reference to the synthesis method of the above-described compound (D-1).

¹H NMR spectra (400 MHz, CDCl₃) of compounds (D-2) to (D-5), (D-7), (D-10) to (D-14), (D-16), (D-25) to (D-29), (D-31), (D-32), (D-34), (D-35), (D-37) to (D-41), (D-45) to (D-48), (D-59), (D-69), (D-71), (D-75), and (D-76) are shown in FIGS. 5 to 38.

The compounds (D-1) to (D-78) and comparative compounds (R-1) to (R-6) are shown below.

D-1

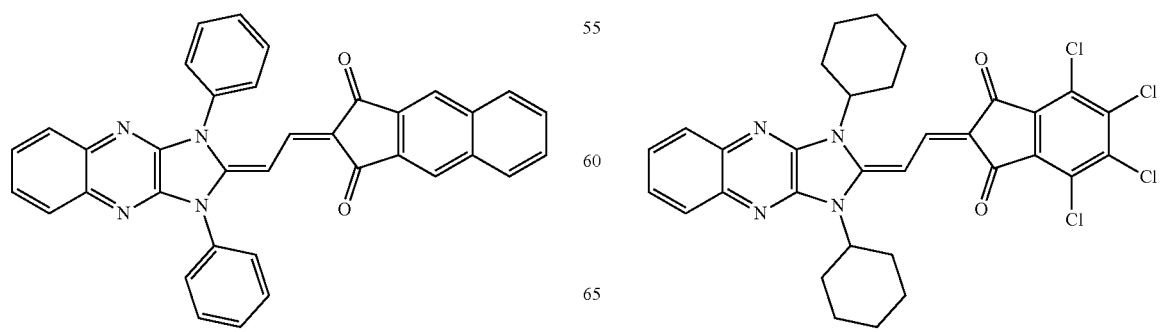

D-2

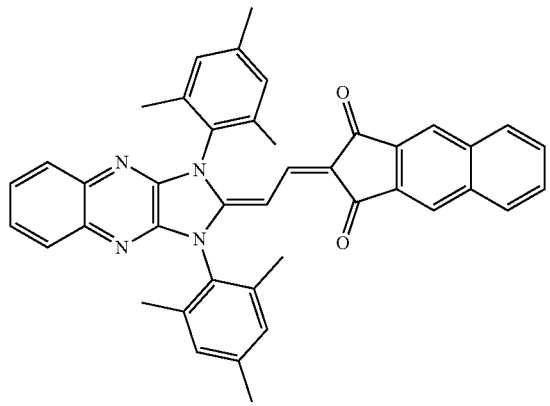

D-3

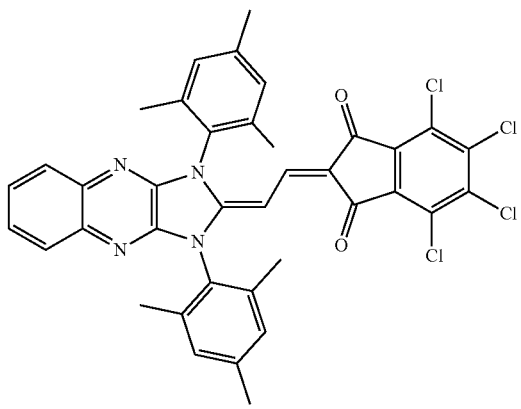

D-4

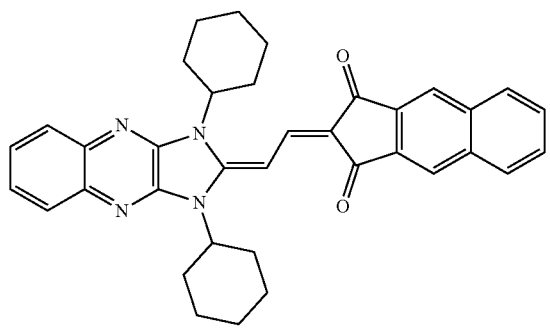

D-5

-continued
D-6
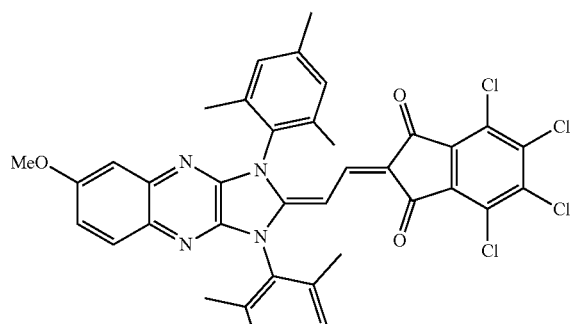
D-7
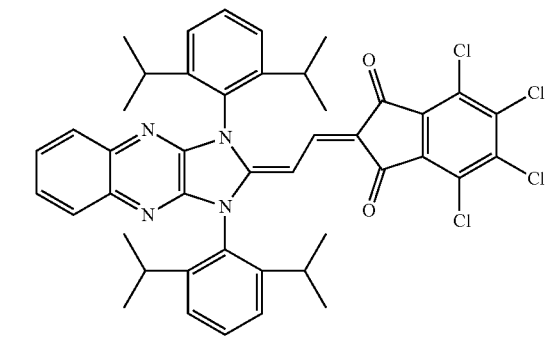
D-8
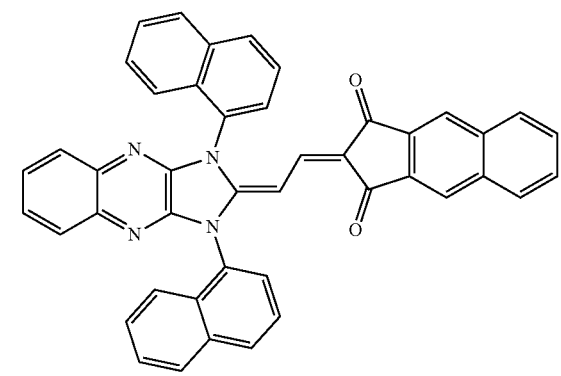
D-9
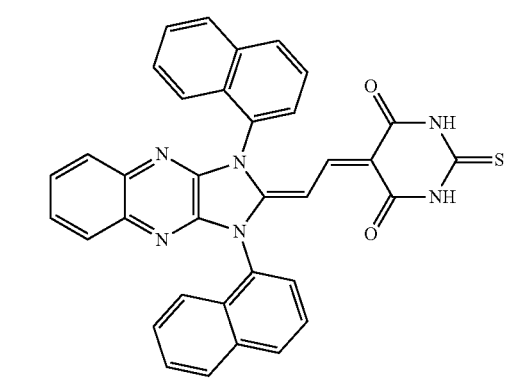
-continued
R-1
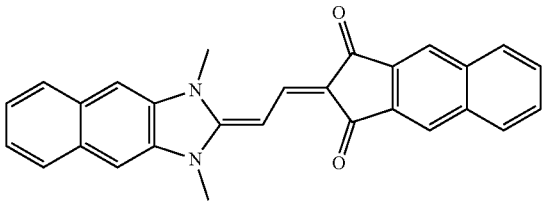
D-10
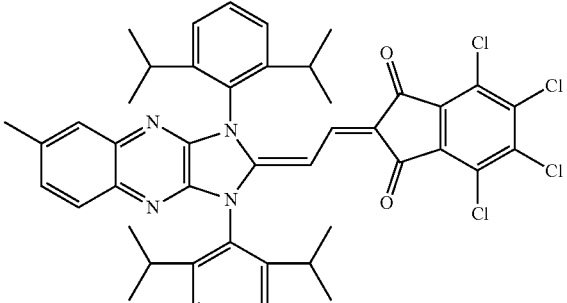
D-11
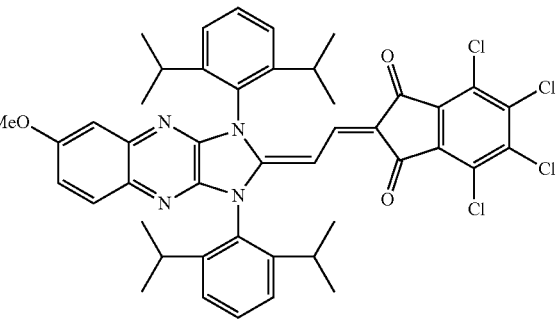
D-12
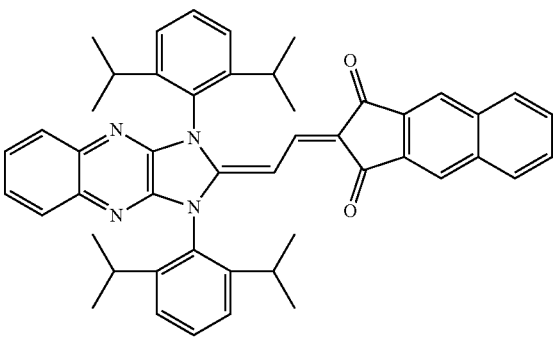
D-13

-continued
D-14
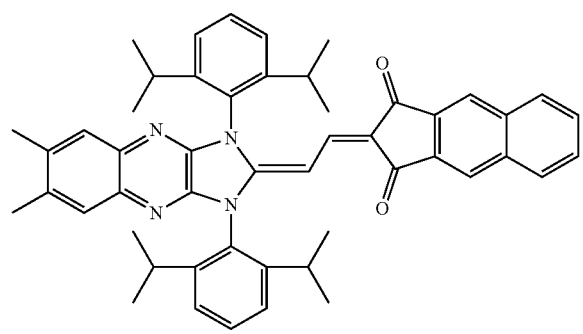
D-15
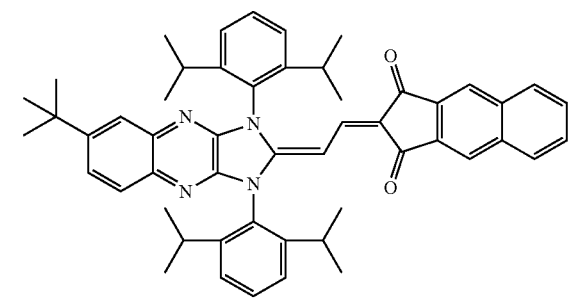
D-16
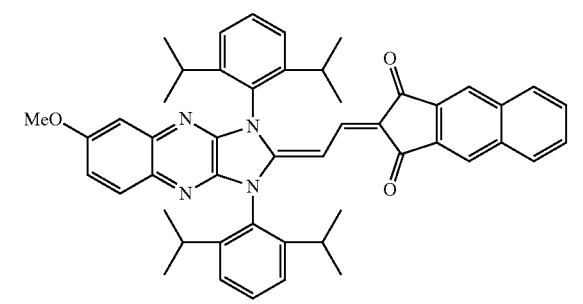
D-17
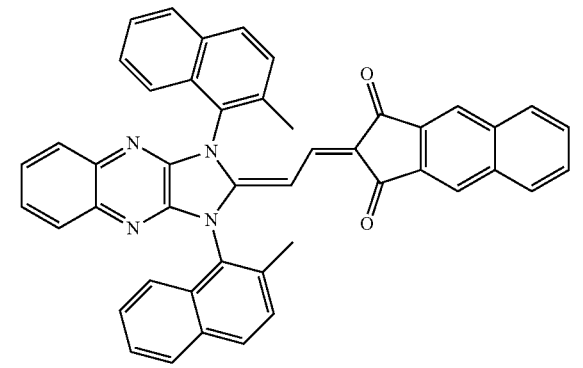
-continued
D-18
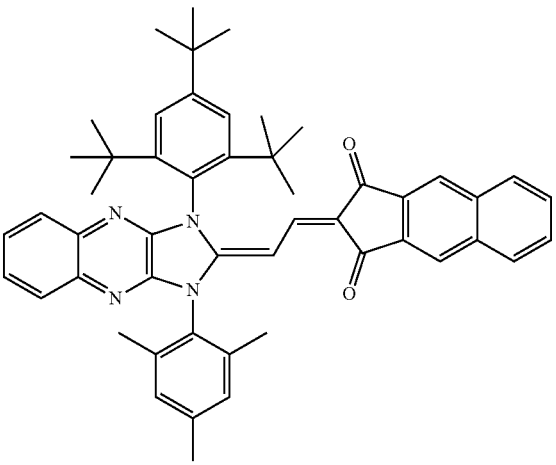
D-19
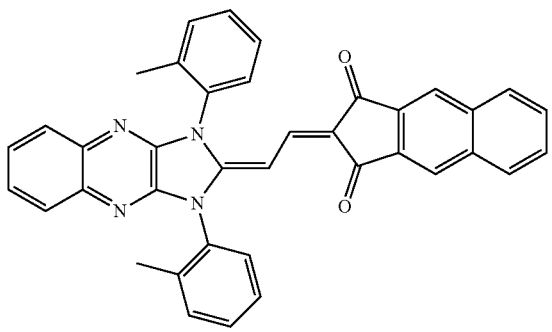
D-20
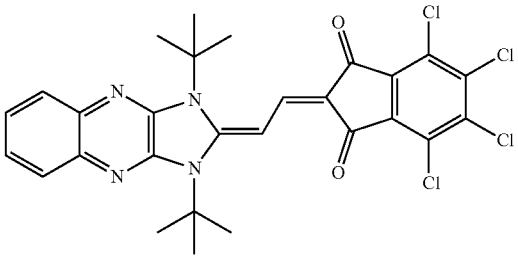
D-21
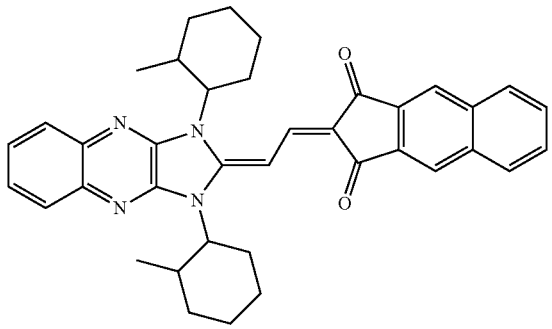

D-22
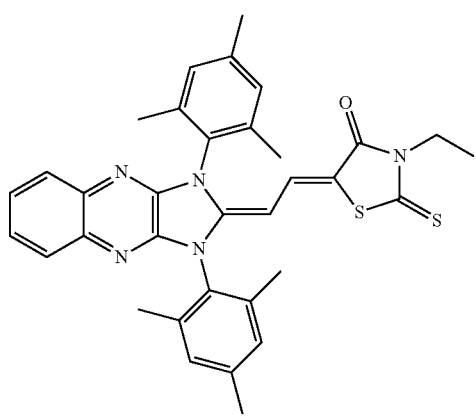
D-23
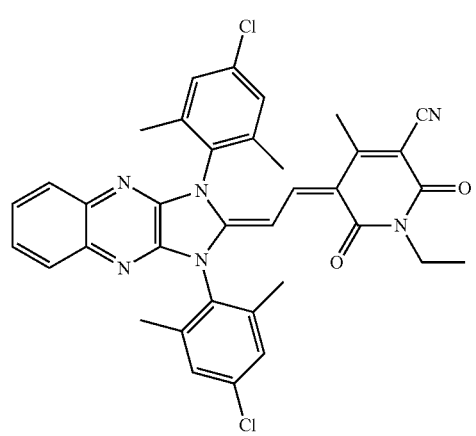
D-24
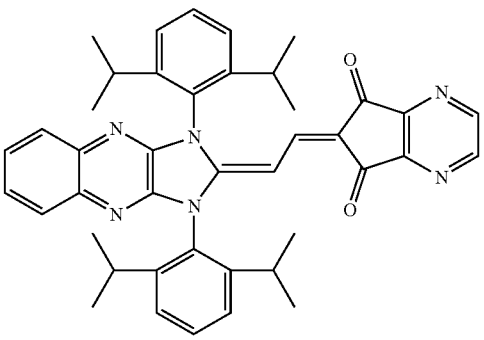
D-25
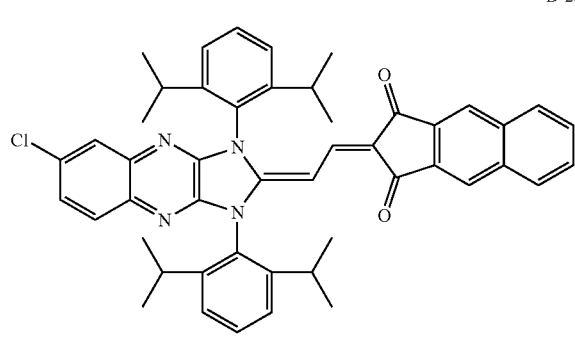
D-26
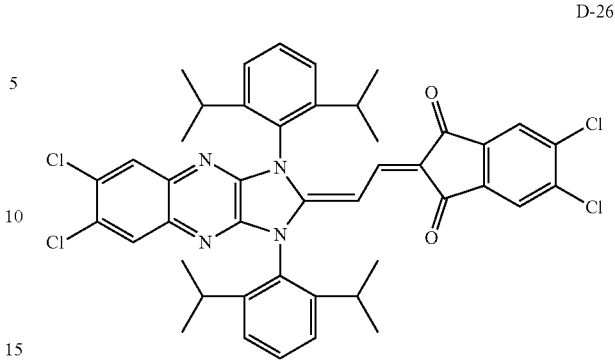
D-27
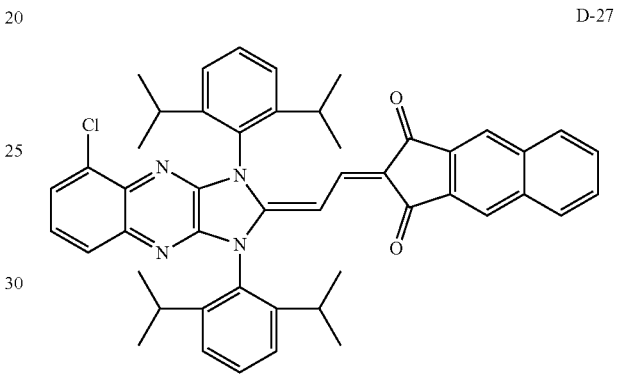
D-28
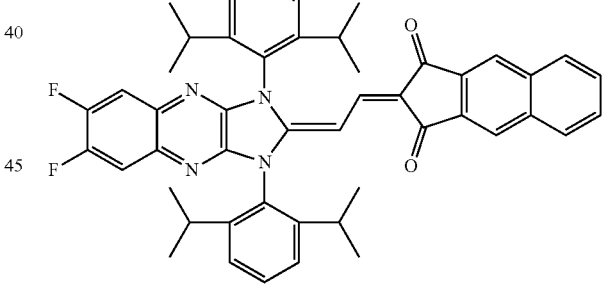
D-29
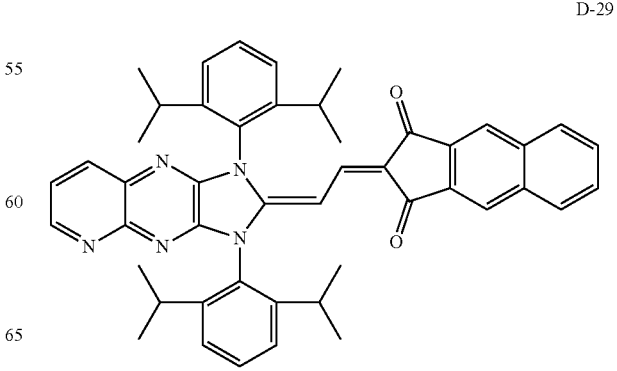

-continued
D-30
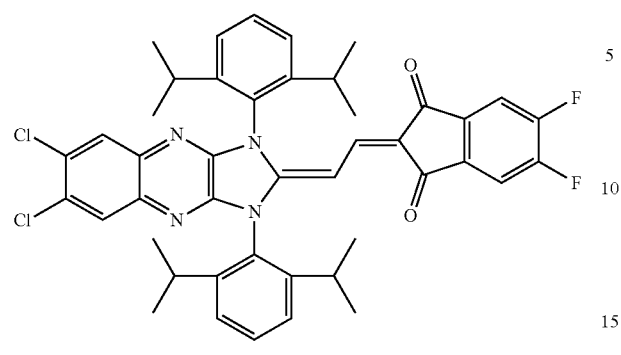
D-31
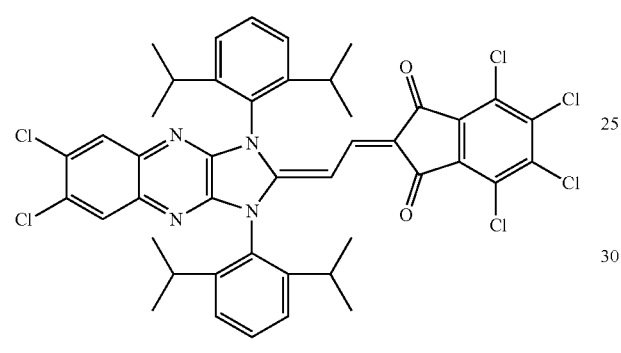
D-32
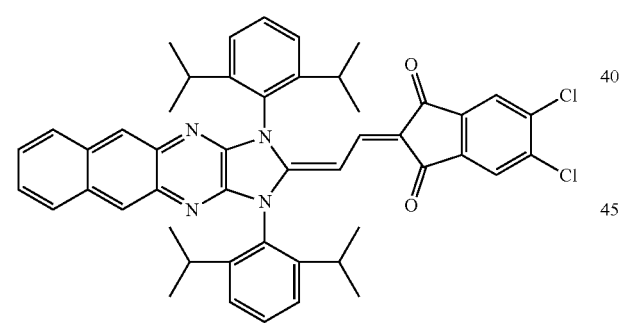
D-33
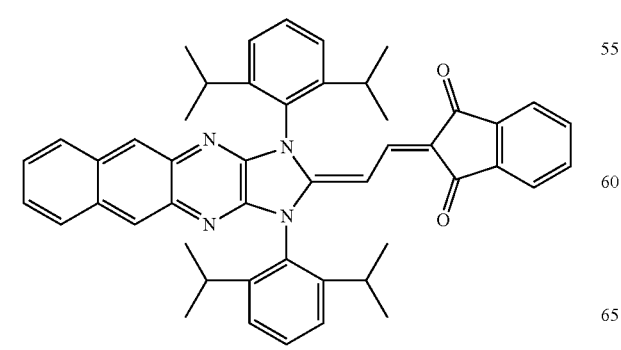
-continued
D-34
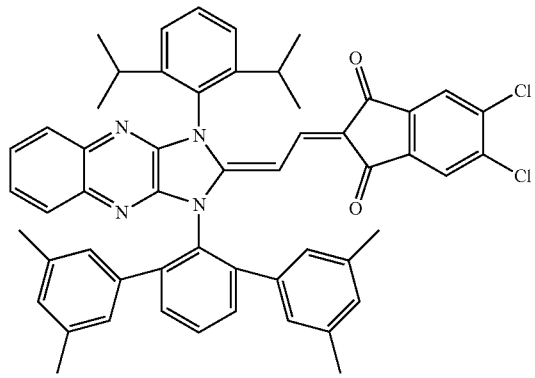
D-35
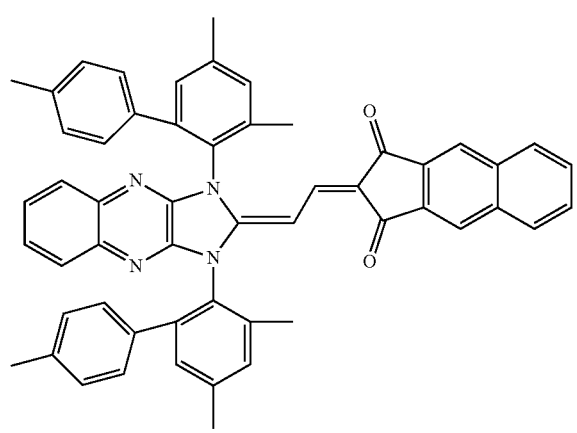
D-36
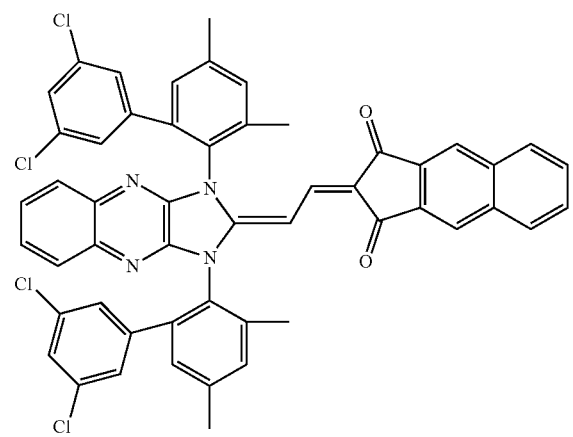

D-37
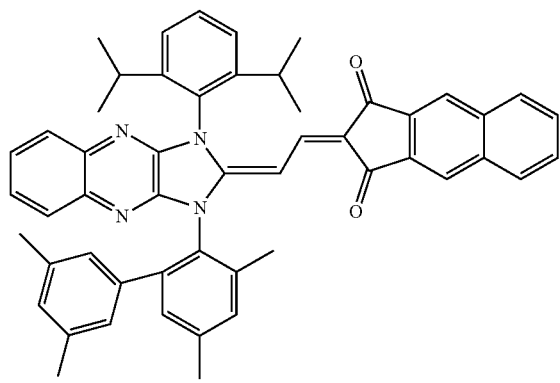
D-38
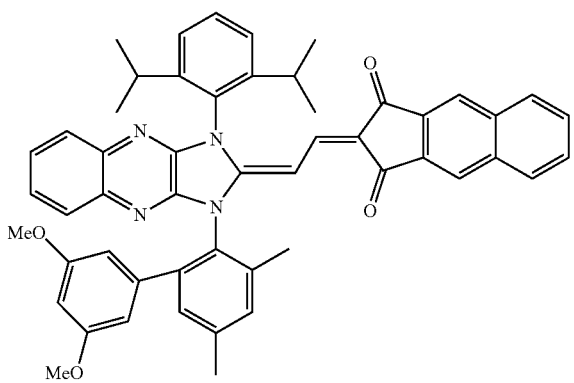
D-39
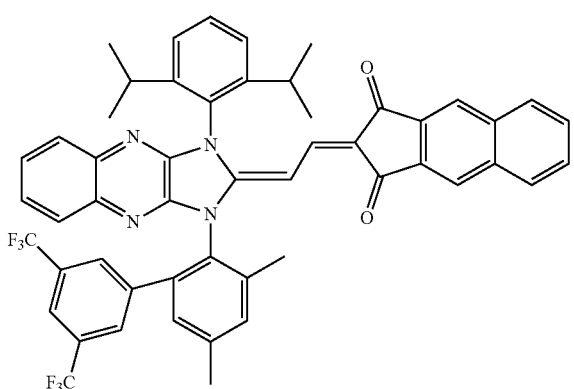
D-40
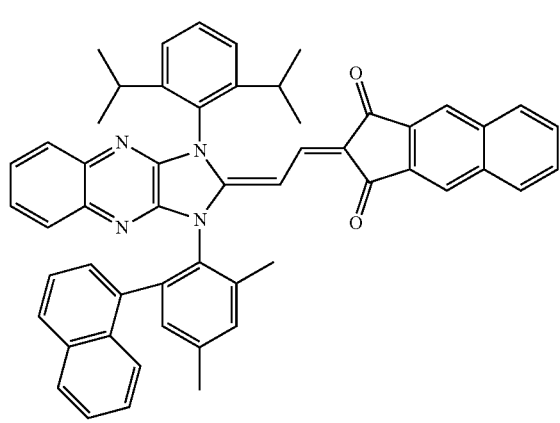
D-41
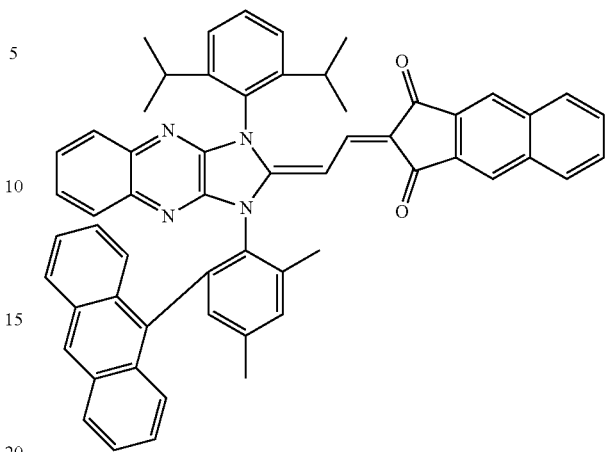
D-42
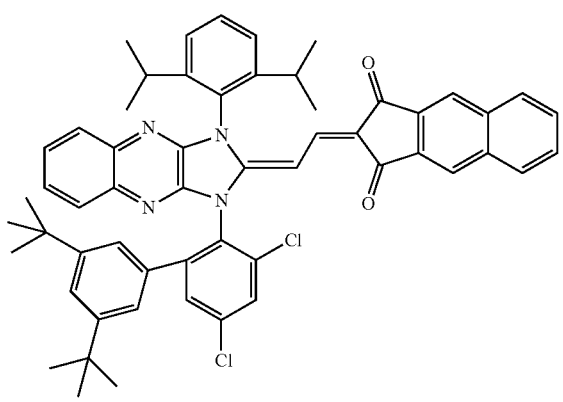
D-43
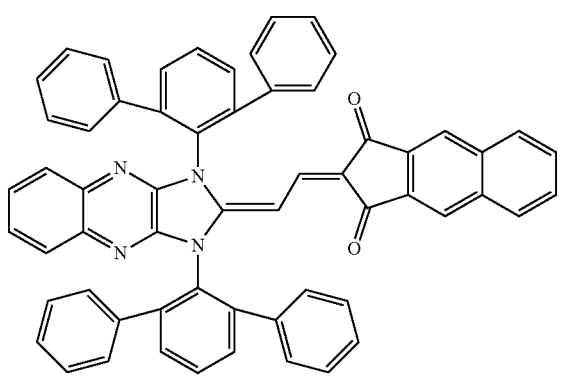

D-44
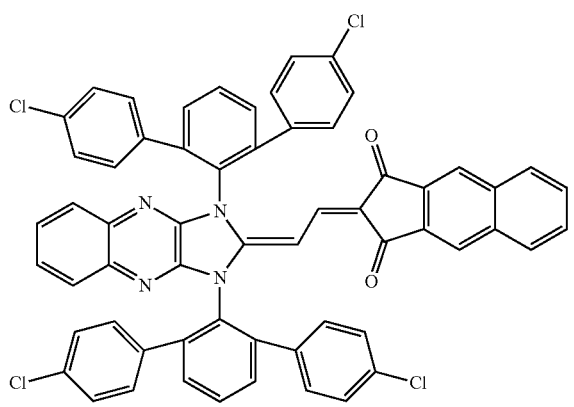
D-45
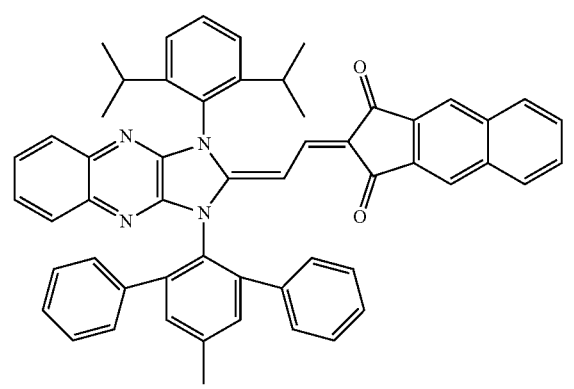
D-46
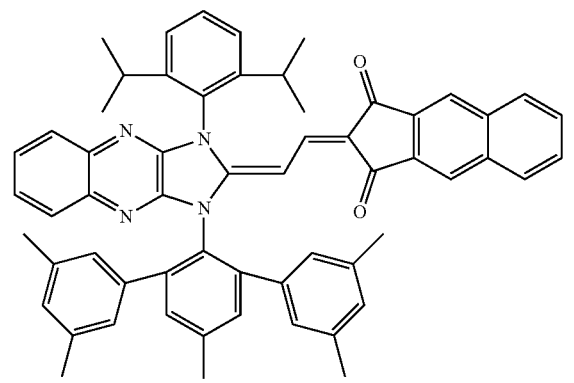
D-47
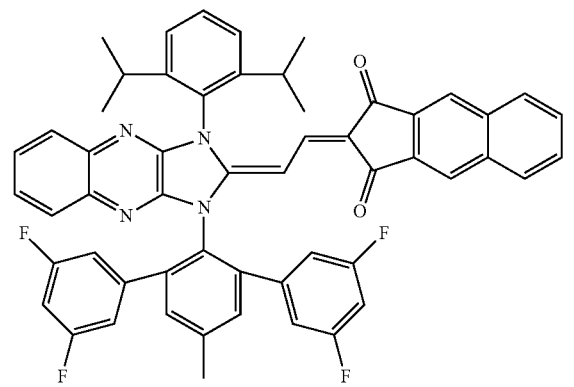
D-48
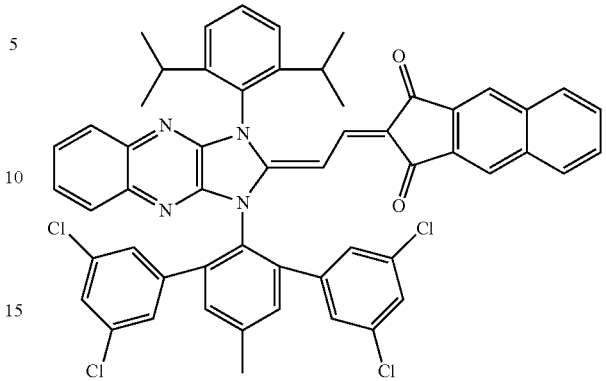
D-49
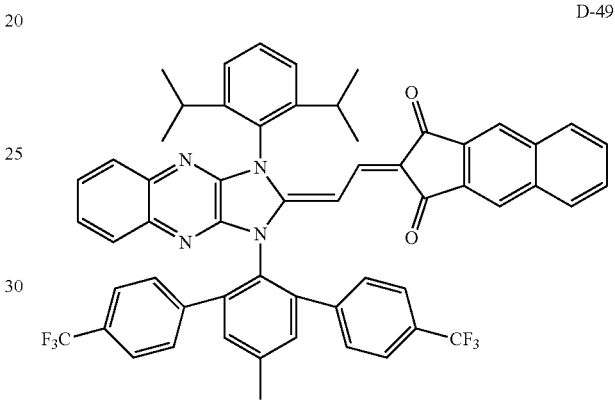
D-50
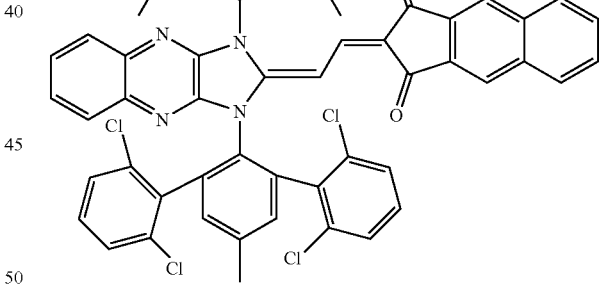
D-50
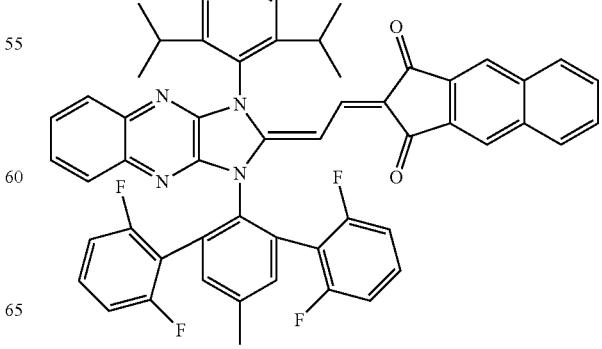

D-51
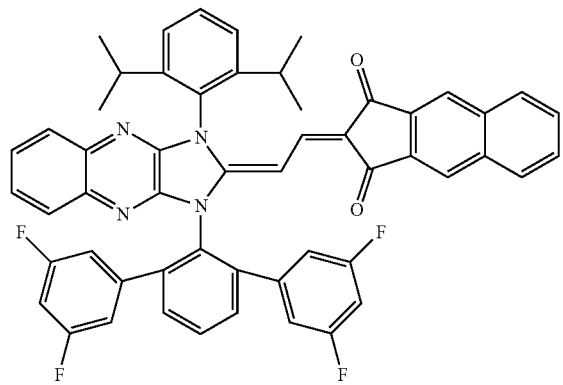
D-52
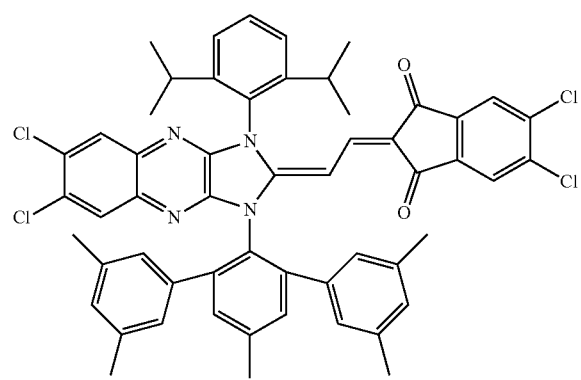
D-53
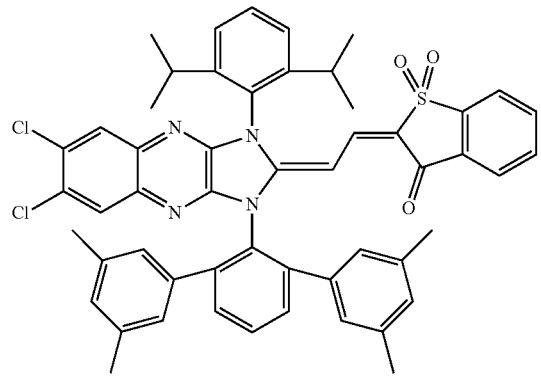
D-55
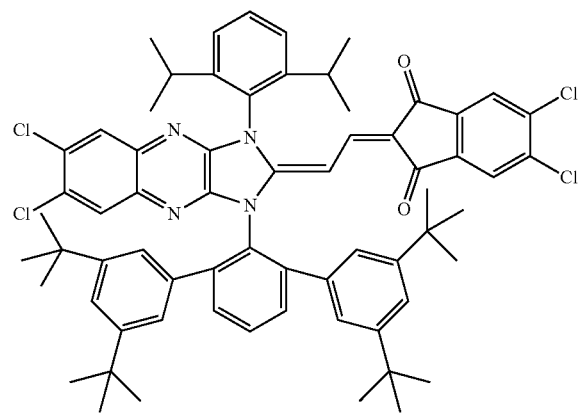
D-56
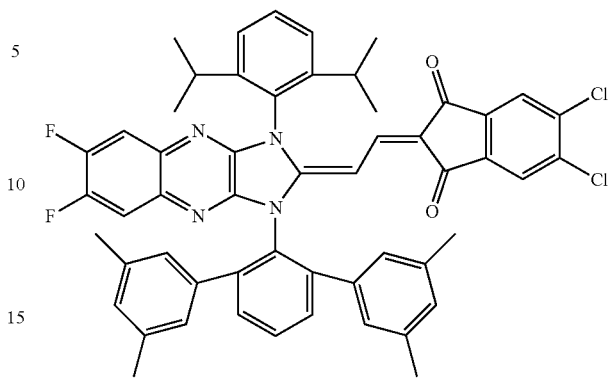
D-57 D-58 D-59
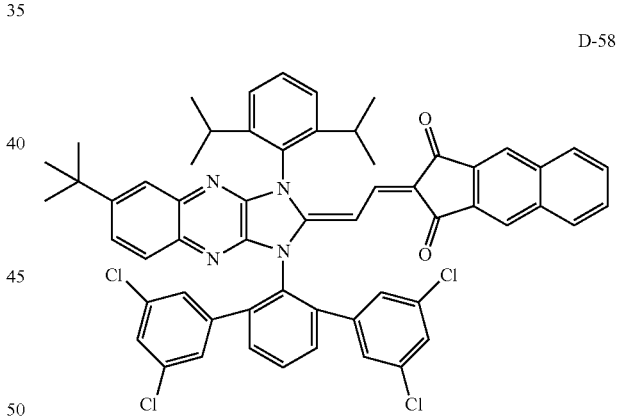
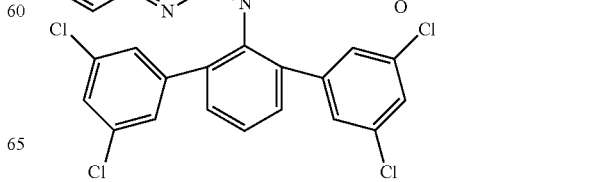

-continued
D-60
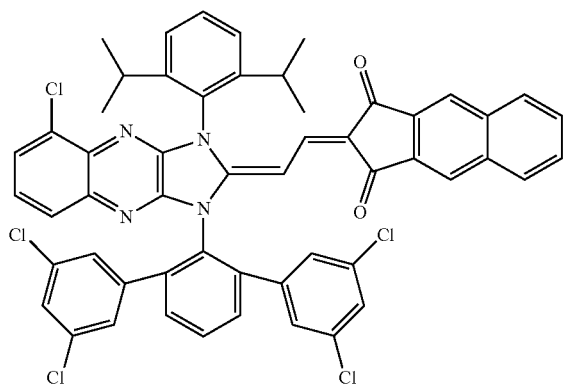
D-61
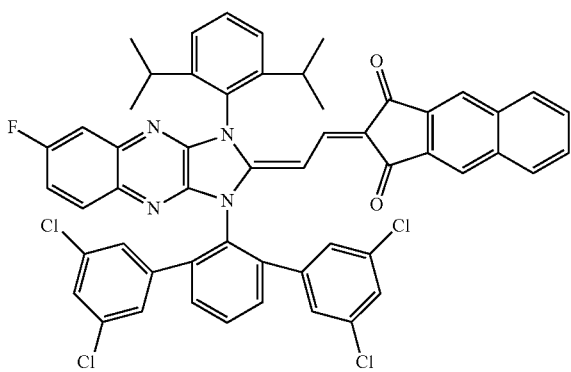
D-62
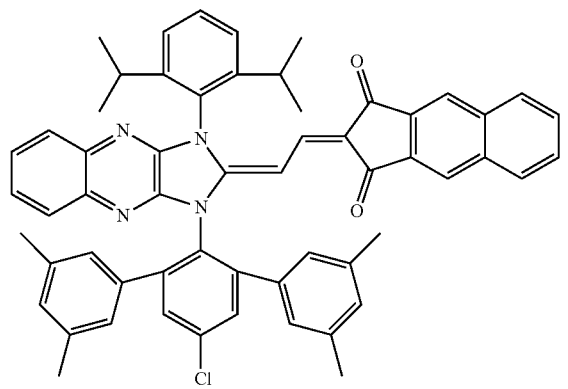
D-63
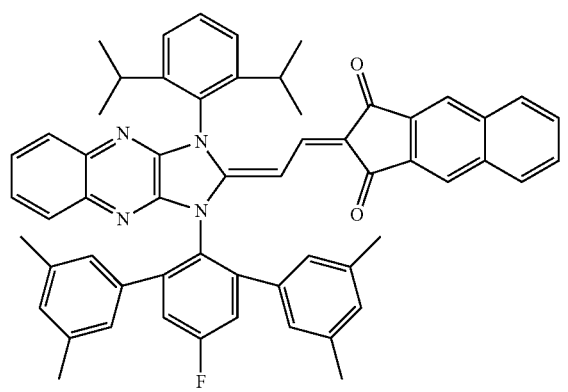
-continued
D-64
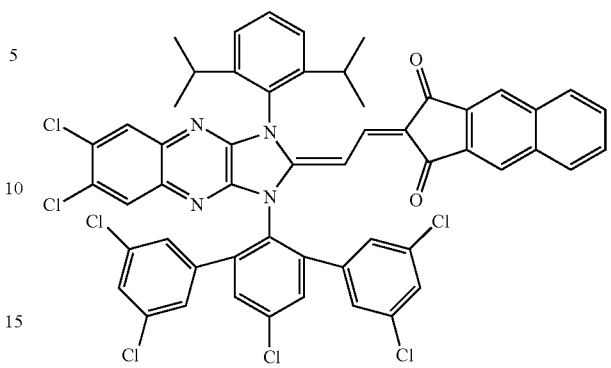
D-65
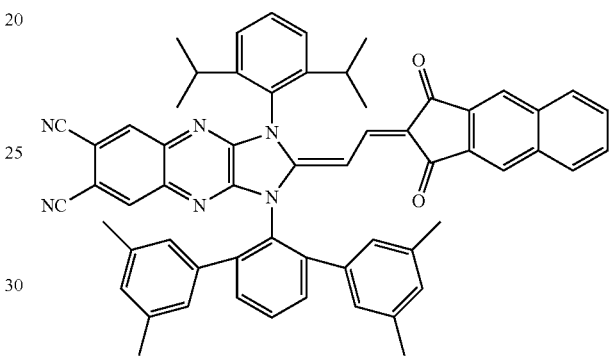
D-66
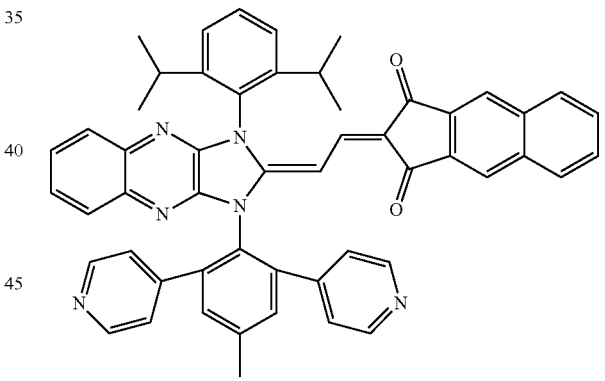
D-67
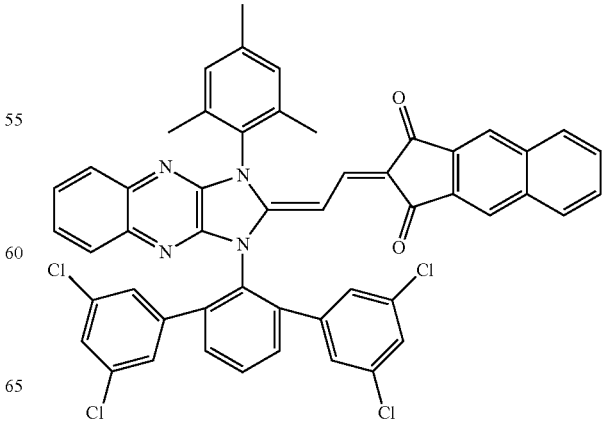

D-68
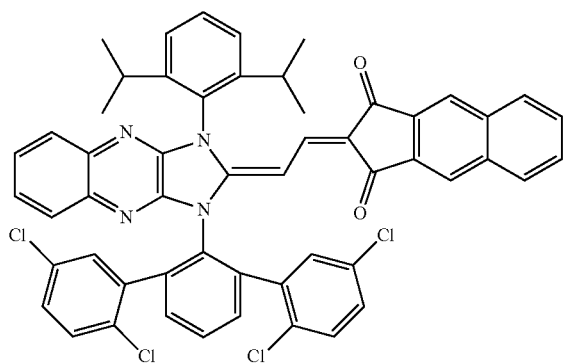
D-73
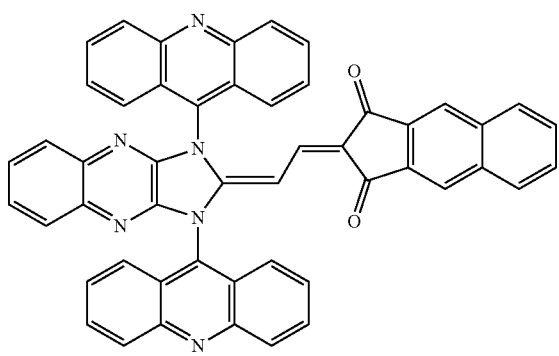
D-69
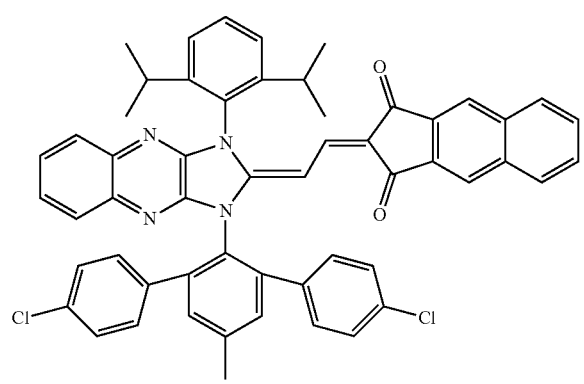
D-73
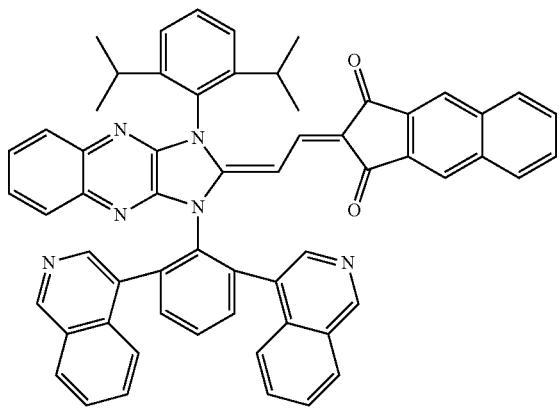
D-70
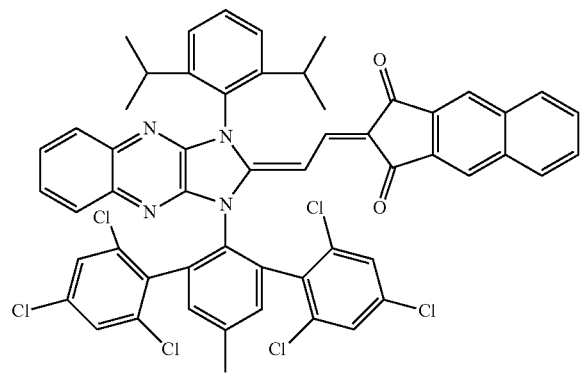
D-74
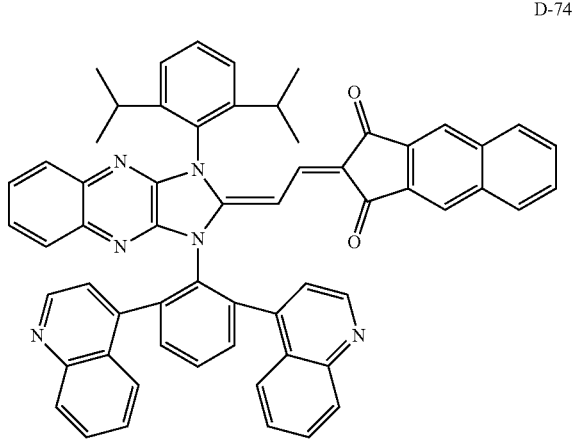
D-71
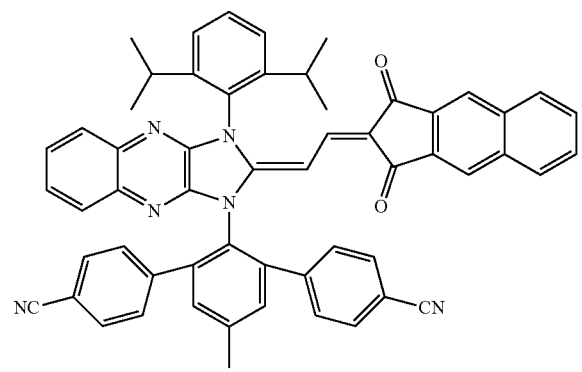
D-75
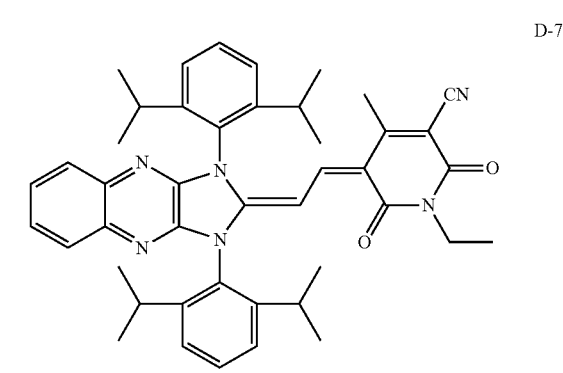

D-76

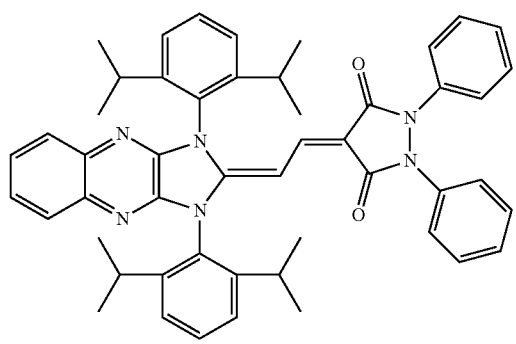

D-77

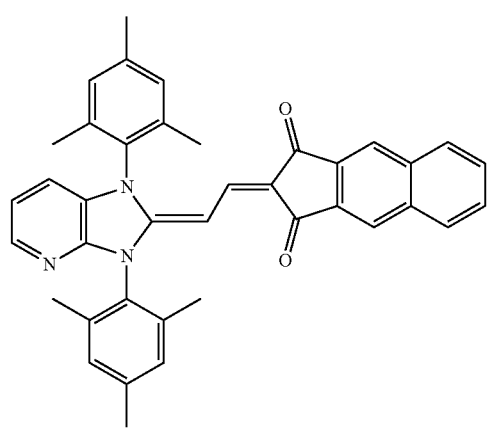

D-78

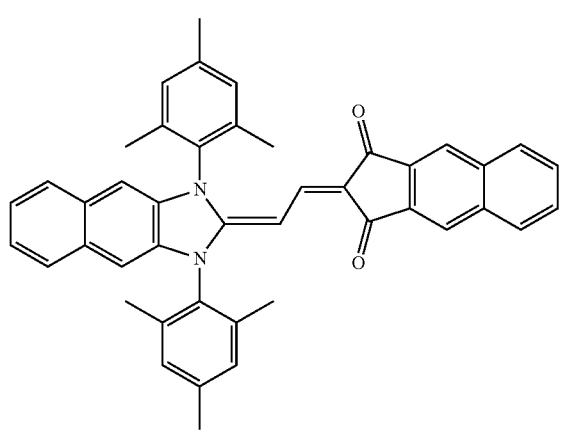

R-2

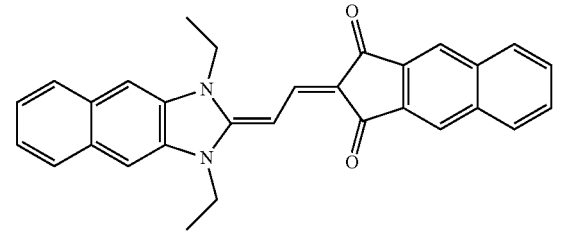

R-3

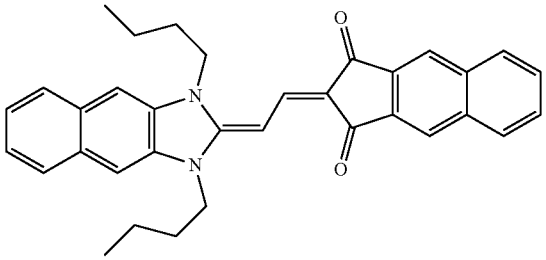

R-4

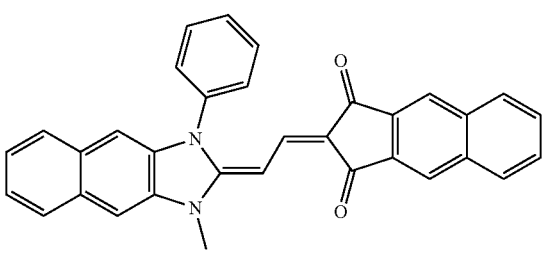

R-5

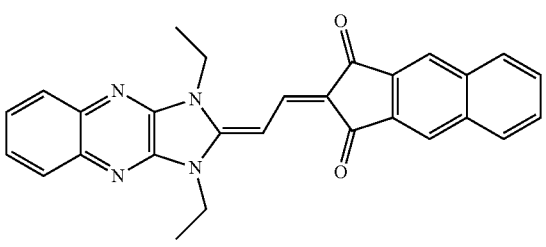

R-6

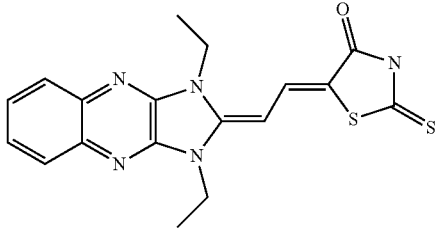

R-7

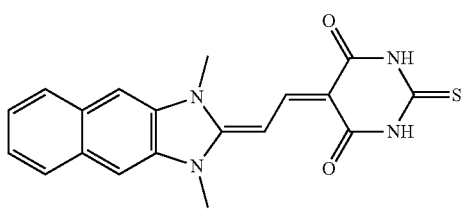

[Evaluation]

<Production of Photoelectric Conversion Element>

The photoelectric conversion element of the form of FIG. 1 was produced using the obtained compound. Here, the photoelectric conversion element includes a lower electrode 11, an electron blocking film 16A, a photoelectric conversion film 12, and an upper electrode 15.

Specifically, an amorphous ITO was formed into a film on the glass substrate by the sputtering method to form the lower electrode 11 (a thickness: 30 nm). Furthermore, the compound (EB-1) was formed into a film on the lower electrode 11 by the vacuum thermal vapor deposition method to form the electron blocking film 16A (a thickness: 30 nm).

Furthermore, the compound (D-1) and the fullerene ($C_{60}$) were subjected to co-vapor deposition by the vacuum evaporation method so as to be respectively 100 nm in terms of single layer on the electron blocking film 16A to form a film in a state where the temperature of the substrate was controlled to 25° C., and the photoelectric conversion film 12 having the bulk hetero structure of 200 nm was formed.

Furthermore, amorphous ITO was formed into a film on the photoelectric conversion film 12 by a sputtering method to form the upper electrode 15 (the transparent conductive film) (the thickness: 10 nm). After the SiO film was formed as the sealing layer on the upper electrode 15 by a vacuum evaporation method, an aluminum oxide ($Al_2O_3$) layer was formed thereon by an atomic layer chemical vapor deposition (ALCVD) method to produce a photoelectric conversion element.

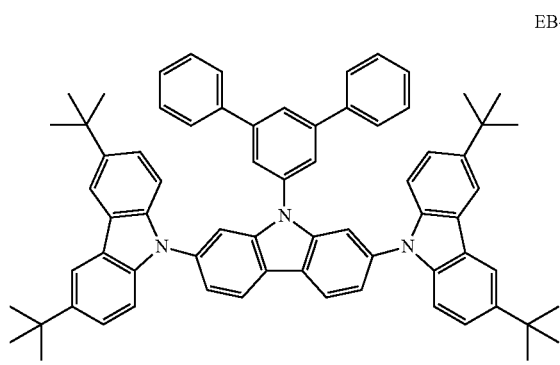

EB-1

Similarly, each of the photoelectric conversion element was produced except that the compounds (D-2) to (D-78) or the compounds (R-1) to (R-7) were used instead of the compound (D-1).

<Driving Confirmation (Dark Current Evaluation)>

The dark current of each of the obtained photoelectric conversion elements was measured by the following method.

A voltage was applied to the lower electrode and the upper electrode of each of the photoelectric conversion elements to have an electric field intensity of $2.5 \times 10^5$ V/cm and current values (dark current) in a dark place was measured. As a result, it was confirmed that all of the photoelectric conversion elements had a dark current of 50 nA/cm² or less, which indicates that all of the photoelectric conversion elements had a sufficiently low dark current.

<Heat Resistance Evaluation>

The heat resistance of each of the obtained photoelectric conversion elements was evaluated according to the following method.

Specifically, each of the obtained photoelectric conversion elements was heated on a hot plate at 180° C. for 30 minutes. A voltage was applied to each of the photoelectric conversion elements after heating so that the electric field intensity was $2.0 \times 10^5$ V/cm, and the dark current at 540 nm was measured by irradiation with light from the upper electrode (transparent conductive film) side. The evaluation was performed using a relative value of the dark current after heating in a case where the dark current before heating was set to 1.

A case where the relative value was 1.5 or less was evaluated as A, a case where the relative value was larger than 1.5 and 3 or less was evaluated as B, a case where the relative value was larger than 3 and 10 or less was evaluated as C, and a case where the relative value was larger than 10 was evaluated as D. In practice, A and B are preferable, and A is more preferable. Table 1 shows the results.

TABLE 11

Table 1-1

| | Used compound | Heat resistance of photoelectric conversion element |
|---|---|---|
| Example A1 | D-1 | B |
| Example A2 | D-2 | A |
| Example A3 | D-3 | A |
| Example A4 | D-4 | A |
| Example A5 | D-5 | A |
| Example A6 | D-6 | A |
| Example A7 | D-7 | A |
| Example A8 | D-8 | A |
| Example A9 | D-9 | B |
| Example A10 | D-10 | A |
| Example A11 | D-11 | A |
| Example A12 | D-12 | A |
| Example A13 | D-13 | A |
| Example A14 | D-14 | A |
| Example A15 | D-15 | A |
| Example A16 | D-16 | A |
| Example A17 | D-17 | A |
| Example A18 | D-18 | A |
| Example A19 | D-19 | A |
| Example A20 | D-20 | A |
| Example A21 | D-21 | A |
| Example A22 | D-22 | B |
| Example A23 | D-23 | B |
| Example A24 | D-24 | A |
| Comparative Example A1 | R-1 | C |

TABLE 12

Table 1-2

| | Used compound | Heat resistance of photoelectric conversion element |
|---|---|---|
| Example A25 | D-25 | A |
| Example A26 | D-26 | A |
| Example A27 | D-27 | A |
| Example A28 | D-28 | A |
| Example A29 | D-29 | A |
| Example A30 | D-30 | A |
| Example A31 | D-31 | A |
| Example A32 | D-32 | A |
| Example A33 | D-33 | A |
| Example A34 | D-34 | A |
| Example A35 | D-35 | A |
| Example A36 | D-36 | A |
| Example A37 | D-37 | A |
| Example A38 | D-38 | A |
| Example A39 | D-39 | A |
| Example A40 | D-40 | A |
| Example A41 | D-41 | A |
| Example A42 | D-42 | A |
| Example A43 | D-43 | A |
| Example A44 | D-44 | A |
| Example A45 | D-45 | A |
| Example A46 | D-46 | A |
| Example A47 | D-47 | A |
| Example A48 | D-48 | A |
| Example A49 | D-49 | A |
| Example A50 | D-50 | A |
| Example A51 | D-51 | A |
| Example A52 | D-52 | A |
| Example A53 | D-53 | A |
| Example A54 | D-54 | B |
| Example A55 | D-55 | A |
| Example A56 | D-56 | A |

TABLE 12-continued

Table 1-2

| | Used compound | Heat resistance of photoelectric conversion element |
|---|---|---|
| Example A57 | D-57 | A |
| Example A58 | D-58 | A |
| Example A59 | D-59 | A |
| Example A60 | D-60 | A |
| Example A61 | D-61 | A |
| Example A62 | D-62 | A |
| Example A63 | D-63 | A |
| Example A64 | D-64 | A |
| Example A65 | D-65 | A |
| Example A66 | D-66 | A |
| Example A67 | D-67 | A |
| Example A68 | D-68 | A |
| Example A69 | D-69 | A |
| Example A70 | D-70 | A |
| Example A71 | D-71 | A |
| Example A72 | D-72 | A |
| Example A73 | D-73 | A |
| Example A74 | D-74 | A |
| Example A75 | D-75 | B |
| Example A76 | D-76 | B |
| Example A77 | D-77 | B |
| Example A78 | D-78 | B |
| Comparative Example A2 | R-2 | D |
| Comparative Example A3 | R-3 | D |
| Comparative Example A4 | R-4 | C |
| Comparative Example A5 | R-5 | C |
| Comparative Example A6 | R-6 | D |
| Comparative Example A7 | R-7 | D |

From the results shown in Tables, it was confirmed that the photoelectric conversion element according to the embodiment of the present invention has excellent heat resistance.

In a case where the specific compound was the compound represented by Formula (4), Formula (4-2), or Formula (5), and $R^{a1}$ and $R^{a2}$ each are a group represented by Formula (X), $-C(R^{L1})(R^{L2})(R^{L3})$, or a polycyclic aryl group which may have a substituent, it was confirmed that the photoelectric conversion element has more excellent heat resistance (results of Examples A1, A9, A22, A23, A54, A75, A76, A77, and A78).

<Production of Imaging Element>

There was no problem in the performance of the imaging element in a case where each of the imaging elements was produced using the photoelectric conversion element produced using the compounds (D-1) to (D-78), which has been subjected to the same heat treatment as in <Heat Resistance Evaluations>

<Evaluation of Absorption Characteristics of Compound>

In a state where the temperature of the glass substrate is controlled at 25° C., each of the vapor deposition films (thickness: 100 nm) formed by using any of the compounds shown in Table 2 was formed on the glass substrate by the vacuum evaporation method.

An absorption shape (absorption spectrum) of each of the obtained vapor deposition films was measured using spectrophotometer U3310 manufactured by Hitachi High-Tech Corporation. In a case where the maximum absorption wavelength of the absorption spectrum and the absorbance at the maximum absorption wavelength were set to 1 from the measurement results, a difference (absorption half-width) between two wavelengths, in which the absorbance was 0.5 was obtained.

In a case where two or more wavelengths each of which has the absorbance of 0.5 exist, the two wavelengths are "a wavelength having an absorbance of 0.5, which exist closest to the maximum absorption wavelength among the wavelengths larger than the maximum absorption wavelength" and "a wavelength having an absorbance of 0.5, which exist closest to the maximum absorption wavelength among the wavelengths smaller than the maximum absorption wavelength".

Table 2 shows the measured absorption half-width and the maximum absorption wavelength of the absorption spectrum.

The results of the absorption half-widths were classified according to the following standard. The smaller the absorption half-width value the more preferable.

A: Absorption half-width is 85 nm or less
B: Absorption half-width is more than 85 nm and 90 nm or less
C: Absorption half-width is more than 90 nm and 95 nm or less
D: Absorption half-width is more than 95 nm and 120 nm or less
E: Absorption half-width is more than 120 nm In Table 2, the column of "$R^{a1}$ and $R^{a2}$" indicates kinds of groups corresponding to $R^{a1}$ and $R^{a2}$ in Formula (1) in the used compounds. "ZB" means the group represented by Formula (ZB). "Polycyclic Ar" means a polycyclic aryl group which may have a substituent. "X" is a group represented by Formula (X), and means a group excluding the group represented by Formula (ZB). "$-C(R^{L1})(R^{L2})(R^{L3})$" means a group represented by the above-described $-C(R^{L1})(R^{L2})(R^{L3})$. "-" means a group that does not correspond to any of the above described groups.

TABLE 13

Table 2

| | Compound | | Absorption half-width | | Maximum absorption wavelength |
|---|---|---|---|---|---|
| | Kind | $R^{a1}$, $R^{a2}$ | (nm) | Result | (nm) |
| Example B1 | D-1 | — | 117 | D | 522 |
| Example B2 | D-2 | ZB | 90 | B | 560 |
| Example B3 | D-3 | ZB | 88 | B | 558 |
| Example B4 | D-7 | ZB | 74 | A | 553 |
| Example B5 | D-10 | ZB | 73 | A | 556 |
| Example B6 | D-12 | ZB | 81 | A | 560 |
| Example B7 | D-13 | ZB | 78 | A | 563 |
| Example B8 | D-16 | ZB | 80 | A | 569 |
| Example B9 | D-17 | Polycyclic Ar | 90 | B | 559 |
| Example B10 | D-19 | X | 95 | C | 561 |
| Example B11 | D-21 | $-C(R^{L1})(R^{L2})(R^{L3})$ | 94 | C | 565 |
| Example B12 | D-25 | ZB | 82 | A | 564 |
| Example B13 | D-26 | ZB | 80 | A | 561 |
| Example B14 | D-27 | ZB | 80 | A | 561 |
| Example B15 | D-28 | ZB | 83 | A | 563 |
| Example B16 | D-31 | ZB | 76 | A | 557 |
| Example B17 | D-33 | ZB | 83 | A | 565 |
| Example B18 | D-34 | ZB | 72 | A | 552 |
| Example B19 | D-35 | ZB | 80 | A | 563 |
| Example B20 | D-37 | ZB | 79 | A | 564 |
| Example B21 | D-38 | ZB | 78 | A | 565 |
| Example B22 | D-39 | ZB | 77 | A | 556 |
| Example B23 | D-40 | ZB | 78 | A | 564 |
| Example B24 | D-41 | ZB | 75 | A | 566 |
| Example B25 | D-43 | ZB | 75 | A | 565 |

145

TABLE 13-continued

Table 2

| | Compound | | Absorption half-width | | Maximum absorption wavelength |
|---|---|---|---|---|---|
| | Kind | $R^{a1}, R^{a2}$ | (nm) | Result | (nm) |
| Example B26 | D-45 | ZB | 74 | A | 565 |
| Example B27 | D-46 | ZB | 73 | A | 565 |
| Example B28 | D-47 | ZB | 74 | A | 559 |
| Example B29 | D-48 | ZB | 72 | A | 559 |
| Example B30 | D-49 | ZB | 72 | A | 558 |
| Example B31 | D-59 | ZB | 73 | A | 558 |
| Example B32 | D-68 | ZB | 72 | A | 560 |
| Example B33 | D-69 | ZB | 72 | A | 562 |
| Example B34 | D-71 | ZB | 72 | A | 560 |
| Example B35 | D-78 | ZB | 92 | C | 510 |
| Comparative Example B1 | R-1 | — | 127 | E | 520 |

It was confirmed that the specific compound had a narrow absorption half-width.

In a case where the specific compound was applied to Formula (1), it was confirmed that the specific compound had a more narrow absorption half-width in a case where $R^{a1}$ and $R^{a2}$ each were the group represented by Formula (X) (preferably the group represented by Formula (ZB)), the polycyclic aryl group which may have a substituent, or —C($R^{L1}$)($R^{L2}$)($R^{L3}$) (results of Examples B2 to B35, and the like).

It was confirmed that the specific compound had a more narrow absorption half-width in a case where the specific compound was a compound represented by Formula (3), Formula (4), Formula (4-2), or Formula (5) (comparison between Examples B2 and B35, and the like)

In a case where the specific compound was applied to Formula (1), it was confirmed that the specific compound had a further narrow absorption half-width in a case where $R^{a1}$ and $R^{a2}$ each were preferably the group represented by Formula (ZB) or the polycyclic aryl group which may have a substituent (results of Examples B2 to B9 and B12 to B34 (results of comparison between Examples in which the specific compound is represented by Formula (3), Formula (4), Formula (4-2), or Formula (5)), and the like).

In Formula (ZB), it was confirmed that the specific compound had a particularly narrow absorption half-width in a case where one or both of $R^{f3}$ and $R^{f4}$ is —CH($R^{d3}$)($R^{d4}$), or an aryl group (results of Examples B4 to B8 and B12 to B34 (results of comparison between Examples in which the specific compound is represented by Formula (3), Formula (4), Formula (4-2), or Formula (5)), and the like).

EXPLANATION OF REFERENCES 10a, 10b: photoelectric conversion element
11: conductive film (lower electrode)
12: photoelectric conversion film
15: transparent conductive film (upper electrode)
16A: electron blocking film
16B: positive hole blocking film
20a: imaging element
22: blue photoelectric conversion element
24: red photoelectric conversion element

146

What is claimed is:

1. A photoelectric conversion element comprising, in the following order:
a conductive film;
a photoelectric conversion film; and
a transparent conductive film,
wherein the photoelectric conversion film contains a compound represented by Formula (2),

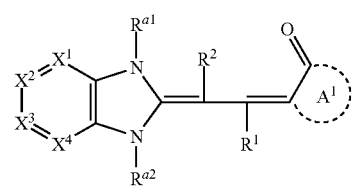

(2)

in Formula (2), A1 represents a ring which contains at least two carbon atoms and may have a substituent;
$R^1$ and $R^2$ each independently represent a hydrogen atom or a substituent;
$R^{a1}$ and $R^{a2}$ each independently represent a group represented by Formula (ZB), and
$X^1$ and $X^4$ each independently represent a nitrogen atom,
$X^2$ and $X^3$ each independently represent a nitrogen atom or —$CR^{c1}$=,
where, $R^{c1}$ represents a hydrogen atom or a substituent, and
in a case where a plurality of $R^{c1}$'s exist, the plurality of $R^{c1}$'s may be bonded to each other to form a ring,

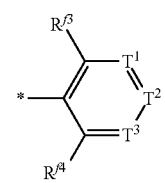

(ZB)

in Formula (ZB), $T^1$ to $T^3$ each independently represent —$CR^{e12}$= or a nitrogen atom, $R^{e12}$ represents a hydrogen atom, an alkyl group, an aryl group, or a heteroaryl group,
$R^{f3}$ and $R^{f4}$ each independently represent an alkyl group, an aryl group, or a heteroaryl group, and
* represents a bonding position.

2. The photoelectric conversion element according to claim 1, wherein the compound represented by Formula (2) is a compound represented by Formula (3),

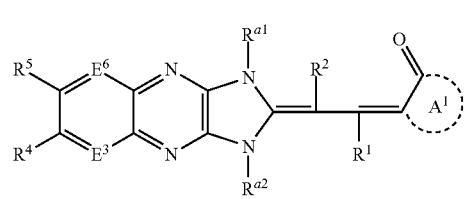

(3)

in Formula (3), A1 represents a ring which contains at least two carbon atoms and may have a substituent;

$E^3$ represents a nitrogen atom or —$CR^3$=;
$E^6$ represents a nitrogen atom or —$CR^6$=,
$R^1$ to $R^6$ each independently represent a hydrogen atom or a substituent;
$R^{a1}$ and $R^{a2}$ each independently represent a group represented by Formula (ZB), and
$R^3$ and $R^4$, $R^4$ and $R^5$, and $R^5$ and $R^6$ each may be independently bonded to each other to form a ring,

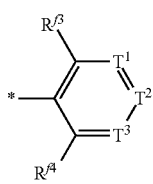

(ZB)

in Formula (ZB), $T^1$ to $T^3$ each independently represent —$CR^{e12}$= or a nitrogen atom, $R^{e12}$ represents a hydrogen atom, an alkyl group, an aryl group, or a heteroaryl group,
$R^{f3}$ and $R^{f4}$ each independently represent an alkyl group, an aryl group, or a heteroaryl group, and
* represents a bonding position.

3. The photoelectric conversion element according to claim 1, wherein the compound represented by Formula (2) is a compound represented by Formula (4),

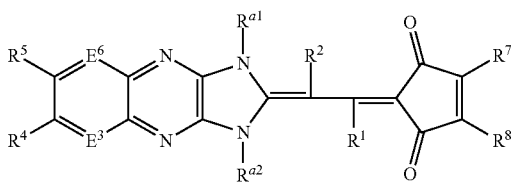

(4)

in Formula (4), $E^3$ represents a nitrogen atom or —$CR^3$=;
$E^6$ represents a nitrogen atom or —$CR^6$=;
$R^1$ to $R^8$ each independently represent a hydrogen atom or a substituent;
$R^{a1}$ and $R^{a2}$ each independently represent a group represented by Formula (ZB), and
$R^3$ and $R^4$, $R^4$ and $R^5$, $R^5$ and $R^6$, and $R^7$ and $R^8$ each may be independently bonded to each other to form a ring,

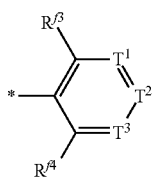

(ZB)

in Formula (ZB), $T^1$ to $T^3$ each independently represent —$CR^{e12}$= or a nitrogen atom, $R^{e12}$ represents a hydrogen atom, an alkyl group, an aryl group, or a heteroaryl group,
$R^{f3}$ and $R^{f4}$ each independently represent an alkyl group, an aryl group, or a heteroaryl group, and
* represents a bonding position.

4. The photoelectric conversion element according to claim 1, wherein the compound represented by Formula (2) is a compound represented by Formula (5),

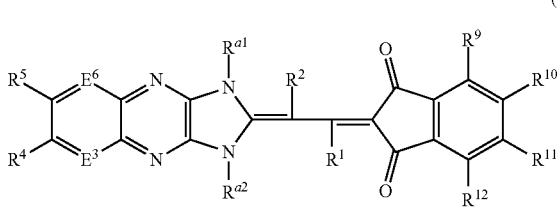

(5)

in Formula (5), $E^3$ represents a nitrogen atom or —$CR^3$=;
$E^6$ represents a nitrogen atom or —$CR^6$=;
$R^1$ to $R^6$, and $R^9$ to $R^{12}$ each independently represent a hydrogen atom or a substituent;
$R^{a1}$ and $R^{a2}$ each independently represent a group represented by Formula (ZB), and
$R^3$ and $R^4$, $R^4$ and $R^5$, $R^5$ and $R^6$, $R^9$ and $R^{10}$, $R^{10}$ and $R^{11}$, and $R^{11}$ and $R^{12}$ each may be independently bonded to each other to form a ring,

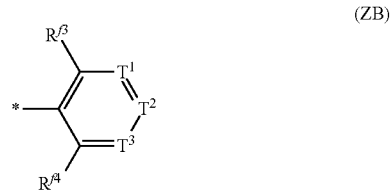

(ZB)

in Formula (ZB), $T^1$ to $T^3$ each independently represent —$CR^{e12}$= or a nitrogen atom, $R^{e12}$ represents a hydrogen atom, an alkyl group, an aryl group, or a heteroaryl group,
$R^{f3}$ and $R^{f4}$ each independently represent an alkyl group, an aryl group, or a heteroaryl group, and
* represents a bonding position.

5. The photoelectric conversion element according to claim 1, further comprising one or more interlayers between the conductive film and the transparent conductive film, in addition to the photoelectric conversion film.

6. An imaging element comprising the photoelectric conversion element according to claim 1.

7. The photoelectric conversion element according to claim 1,
wherein the photoelectric conversion film further includes an n-type organic semiconductor, and
the photoelectric conversion film has a bulk hetero structure formed in a state where the compound represented by Formula (2) and the n-type organic semiconductor are mixed to each other.

8. The photoelectric conversion element according to claim 7, wherein the n-type organic semiconductor contains fullerenes selected from the group consisting of a fullerene and a derivative thereof.

9. An optical sensor comprising the photoelectric conversion element according to claim 1.

10. The imaging element according to claim 6, further comprising another photoelectric conversion element that receives light having a wavelength different from a wavelength of light received by the photoelectric conversion element.

11. The imaging element according to claim 10,
wherein the photoelectric conversion element and the other photoelectric conversion element are laminated, and
at least a part of incident light is transmitted through the photoelectric conversion element and then received by the other photoelectric conversion element.

12. The imaging element according to claim 10,
wherein the photoelectric conversion element is a green photoelectric conversion element, and
the other photoelectric conversion element includes a blue photoelectric conversion element and a red photoelectric conversion element.

\* \* \* \* \*